(12) United States Patent
Rogers et al.

(10) Patent No.: US 10,349,860 B2
(45) Date of Patent: Jul. 16, 2019

(54) CONFORMABLE ACTIVELY MULTIPLEXED HIGH-DENSITY SURFACE ELECTRODE ARRAY FOR BRAIN INTERFACING

(71) Applicants: The Board of Trustees of the University of Illinois, Urbana, IL (US); The Trustees of the University of Pennsylvania, Philadelphia, PA (US)

(72) Inventors: John A. Rogers, Champaign, IL (US); Dae-Hyeong Kim, Urbana, IL (US); Brian Litt, Bala Cynwyd, PA (US); Jonathan Viventi, Philadelphia, PA (US)

(73) Assignees: The Board of Trustees of the University of Illinois, Urbana, IL (US); The Trustees of the University of Pennsylvania, Philadelphia, PA (US)

( * ) Notice: Subject to any disclaimer, the term of this patent is extended or adjusted under 35 U.S.C. 154(b) by 1126 days.

(21) Appl. No.: 14/532,687

(22) Filed: Nov. 4, 2014

(65) Prior Publication Data

US 2015/0080695 A1 Mar. 19, 2015

Related U.S. Application Data

(62) Division of application No. 13/486,726, filed on Jun. 1, 2012, now Pat. No. 8,934,965.
(Continued)

(51) Int. Cl.
*A61B 5/04* (2006.01)
*A61N 1/00* (2006.01)
(Continued)

(52) U.S. Cl.
CPC ........ *A61B 5/0478* (2013.01); *A61B 5/04001* (2013.01); *A61B 5/4094* (2013.01);
(Continued)

(58) Field of Classification Search
CPC .. A61N 1/0531; A61N 1/0539; A61N 1/0529; A61N 1/0534; A61N 1/3606;
(Continued)

(56) References Cited

U.S. PATENT DOCUMENTS

| 3,949,410 A | 4/1976 | Bassous |
| 4,058,418 A | 11/1977 | Lindmayer |

(Continued)

FOREIGN PATENT DOCUMENTS

| CN | 1222758 | 7/1999 |
| CN | 1454045 | 11/2003 |

(Continued)

OTHER PUBLICATIONS

U.S. Appl. No. 11/001,689, filed Dec. 1, 2004, 2006/0286488, Dec. 21, 2006, U.S. Pat. No. 7,704,684, Apr. 27, 2010.
(Continued)

*Primary Examiner* — Joseph A Stoklosa
*Assistant Examiner* — Brian M Antiskay
(74) *Attorney, Agent, or Firm* — Leydig, Voit & Mayer, Ltd.

(57) ABSTRACT

Provided are methods and devices for interfacing with brain tissue, specifically for monitoring and/or actuation of spatio-temporal electrical waveforms. The device is conformable having a high electrode density and high spatial and temporal resolution. A conformable substrate supports a conformable electronic circuit and a barrier layer. Electrodes are positioned to provide electrical contact with a brain tissue. A controller monitors or actuates the electrodes, thereby interfacing with the brain tissue. In an aspect, methods are provided to monitor or actuate spatio-temporal electrical waveforms over large brain surface areas by any of the devices disclosed herein.

18 Claims, 54 Drawing Sheets

Related U.S. Application Data

(60) Provisional application No. 61/492,983, filed on Jun. 3, 2011.

(51) Int. Cl.
*A61B 5/0478* (2006.01)
*A61F 2/72* (2006.01)
*A61M 5/20* (2006.01)
*A61N 1/36* (2006.01)
*A61N 5/06* (2006.01)
*A61B 5/00* (2006.01)
*A61N 1/05* (2006.01)
*A61M 5/31* (2006.01)

(52) U.S. Cl.
CPC .......... *A61B 5/4836* (2013.01); *A61B 5/6868* (2013.01); *A61B 5/7246* (2013.01); *A61B 5/7267* (2013.01); *A61B 5/7282* (2013.01); *A61F 2/72* (2013.01); *A61M 5/20* (2013.01); *A61M 5/31* (2013.01); *A61N 1/0529* (2013.01); *A61N 1/0531* (2013.01); *A61N 1/3606* (2013.01); *A61N 5/0601* (2013.01); *A61B 2562/046* (2013.01); *A61B 2562/125* (2013.01); *A61B 2562/164* (2013.01); *A61N 1/36017* (2013.01); *A61N 1/36025* (2013.01); *A61N 2005/063* (2013.01)

(58) Field of Classification Search
CPC .............. A61N 1/36064; A61B 5/0478; A61B 2018/00434; A61B 5/6868
USPC .................. 600/378, 544–545; 607/115–116
See application file for complete search history.

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,735,208 A | 4/1988 | Wyler et al. |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laermer et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,797,965 A | 8/1998 | Spano et al. |
| 5,817,242 A | 10/1998 | Biebuyck et al. |
| 5,824,186 A | 10/1998 | Smith et al. |
| 5,897,583 A | 4/1999 | Meyer et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gilette et al. |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iverson |
| 6,057,212 A | 5/2000 | Chan et al. |
| 6,061,593 A | 5/2000 | Fischell et al. |
| 6,080,608 A | 6/2000 | Nowak |
| 6,091,979 A | 7/2000 | Madesen |
| 6,097,984 A | 8/2000 | Douglas |
| 6,161,045 A | 12/2000 | Fischell et al. |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 7/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,517,995 B1 | 2/2003 | Jacobson et al. |
| 6,527,964 B1 | 3/2003 | Smith et al. |
| 6,555,408 B1 | 4/2003 | Jacobsen et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |
| 6,780,696 B1 | 8/2004 | Schatz |
| 6,784,450 B2 | 8/2004 | Pan et al. |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |

(56) References Cited

U.S. PATENT DOCUMENTS

| | | |
|---|---|---|
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,120,486 B2 | 10/2006 | Leuhardt et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,521,292 B2 | 4/2009 | Rogers et al. |
| 7,551,951 B1 | 6/2009 | Osorio et al. |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,751,877 B2 | 7/2010 | Flaherty et al. |
| 7,799,699 B2 | 9/2010 | Nuzzo et al. |
| 7,842,780 B2 | 11/2010 | Kaplan et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,562,095 B2 | 10/2013 | Alleyne et al. |
| 8,664,699 B2 | 3/2014 | Nuzzo et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 2001/0003043 A1 | 6/2001 | Metspalu et al. |
| 2002/0021445 A1 | 2/2002 | Boxhevolnyi et al. |
| 2002/0110766 A1 | 8/2002 | Tsai et al. |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0192082 A1 | 9/2004 | Wagner et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0233546 A1 | 1/2005 | Oohata et al. |
| 2005/0038498 A1 | 2/2005 | Dubrow et al. |
| 2005/0082526 A1 | 4/2005 | Bedell et al. |
| 2005/0124712 A1 | 6/2005 | Anderson et al. |
| 2005/0133954 A1 | 6/2005 | Homola |
| 2005/0214962 A1 | 9/2005 | Daniels et al. |
| 2005/0227389 A1 | 10/2005 | Bhattacharya et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0169989 A1 | 8/2006 | Bhattacharya |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0244408 A1 | 10/2007 | Wingeier |
| 2008/0000871 A1 | 1/2008 | Suh et al. |
| 2008/0038236 A1 | 2/2008 | Gimble et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0239755 A1 | 10/2008 | Parker et al. |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2009/0004737 A1 | 1/2009 | Borenstein et al. |
| 2009/0028910 A1 | 1/2009 | Desimone et al. |
| 2009/0124919 A1 | 5/2009 | Ginosar et al. |
| 2009/0132042 A1 | 5/2009 | Hetke et al. |

(56) References Cited

U.S. PATENT DOCUMENTS

| | | |
|---|---|---|
| 2009/0149930 A1 | 6/2009 | Schecnk |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0294803 A1 | 12/2009 | Nuzzo et al. |
| 2009/0312817 A1 | 12/2009 | Hogle et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2011/0054583 A1 | 3/2011 | Litt et al. |
| 2011/0147715 A1 | 6/2011 | Rogers et al. |
| 2011/0170225 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0316120 A1 | 12/2011 | Rogers et al. |
| 2012/0083099 A1 | 4/2012 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0321785 A1 | 12/2012 | Rogers et al. |
| 2013/0036928 A1 | 2/2013 | Rogers et al. |
| 2013/0041235 A1 | 2/2013 | Rogers et al. |
| 2013/0140649 A1 | 6/2013 | Rogers et al. |
| 2013/0333094 A1 | 12/2013 | Rogers et al. |
| 2014/0220422 A1 | 8/2014 | Rogers et al. |

FOREIGN PATENT DOCUMENTS

| | | |
|---|---|---|
| CN | 101772348 | 7/2010 |
| DE | 4241045 | 5/1994 |
| DE | 19748173 | 5/1999 |
| EP | 0 929 097 | 7/1999 |
| EP | 1 357 773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 06-118441 | 4/1994 |
| JP | 06-163365 | 6/1994 |
| JP | 11-026344 | 1/1999 |
| JP | 11-142878 | 5/1999 |
| JP | 2001-007340 | 1/2001 |
| JP | 2002-092984 | 3/2002 |
| JP | 2006-504450 | 2/2006 |
| JP | 2006-186294 | 7/2006 |
| JP | 2007-515391 | 6/2007 |
| JP | 2008-502739 | 1/2008 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| KR | 10-2008-0069553 | 7/2008 |
| TW | 367570 | 8/1999 |
| TW | 494257 | 7/2002 |
| TW | 200836353 | 9/2008 |
| WO | WO 1998/049936 | 11/1998 |
| WO | WO 1999/045860 | 9/1999 |
| WO | WO 2000/046854 | 8/2000 |
| WO | WO 2000/049421 | 8/2000 |
| WO | WO 2000/049658 | 8/2000 |
| WO | WO 2000/055915 | 9/2000 |
| WO | WO 2000/055916 | 9/2000 |
| WO | WO 2001/031082 | 5/2001 |
| WO | WO 2001/033621 | 5/2001 |
| WO | WO 2001/066833 | 9/2001 |
| WO | WO 2001/098838 | 12/2001 |
| WO | WO 2002/027701 | 4/2002 |
| WO | WO 2002/043032 | 5/2002 |
| WO | WO 2002/073699 | 9/2002 |
| WO | WO 2002/092778 | 11/2002 |
| WO | WO 2002/097724 | 12/2002 |
| WO | WO 2004/099068 | 12/2002 |
| WO | WO 2003/030194 | 4/2003 |
| WO | WO 2003/032240 | 4/2003 |
| WO | WO 2003/049201 | 6/2003 |
| WO | WO 2003/063211 | 7/2003 |
| WO | WO 2003/085700 | 10/2003 |
| WO | WO 2003/085701 | 10/2003 |
| WO | WO 2003/092073 | 11/2003 |
| WO | WO 2004/000915 | 12/2003 |
| WO | WO 2004/001103 | 12/2003 |
| WO | WO 2004/003535 | 1/2004 |
| WO | WO 2004/022637 | 3/2004 |
| WO | WO 2004/022714 | 3/2004 |
| WO | WO 2004/023527 | 3/2004 |
| WO | WO 2004/024407 | 3/2004 |
| WO | WO 2004/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |
| WO | WO 2004/100252 | 11/2004 |
| WO | WO 2004/105456 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/054119 | 6/2005 |
| WO | WO 2005/104756 | 11/2005 |
| WO | WO 2002/097708 | 12/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130721 | 12/2006 |

(56) References Cited

FOREIGN PATENT DOCUMENTS

| WO | WO 2007/000037 | 1/2007 |
|---|---|---|
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/018172 | 2/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |

OTHER PUBLICATIONS

U.S. Appl. No. 11/115,954, filed Apr. 27, 2005, 2005/0238967, Oct. 27, 2005, U.S. Pat. No. 7,195,733, Mar. 27, 2007.
U.S. Appl. No. 11/145,574, filed Jun. 2, 2005, 2009/0294803, Dec. 3, 2009, U.S. Pat. No. 7,622,367, Nov. 24, 2009.
U.S. Appl. No. 11/145,542, filed Jun. 2, 2005, 2006/0038182, Feb. 23, 2006, U.S. Pat. No. 7,557,367, Jul. 7, 2009.
U.S. Appl. No. 11/421,654, filed Jun. 1, 2006, 2007/0032089, Feb. 8, 2007, U.S. Pat. No. 7,799,699, Sep. 21, 2010.
U.S. Appl. No. 11/423,287, filed Jun. 9, 2006, 2006/0286785, Dec. 21, 2006, U.S. Pat. No. 7,521,292, Apr. 21, 2009.
U.S. Appl. No. 11/423,192, filed Jun. 9, 2006, 2009/0199960, Aug. 13, 2009, U.S. Pat. No. 7,943,491, May 17, 2011.
U.S. Appl. No. 11/465,317, filed Aug. 17, 2006.
U.S. Appl. No. 11/675,659, filed Feb. 16, 2007, 2008/0055581, Mar. 6, 2008.
U.S. Appl. No. 11/782,799, filed Jul. 25, 2007, 2008/0212102, Sep. 4, 2008, U.S. Pat. No. 7,705,280, Apr. 27, 2010.
U.S. Appl. No. 11/851,182, filed Sep. 6, 2007, 2008/0157235, Jul. 3, 2008, U.S. Pat. No. 8,217,381, Jul. 10, 2012.
U.S. Appl. No. 11/858,788, filed Sep. 20, 2007, 2008/0108171, May 8, 2008, U.S. Pat. No. 7,932,123, Apr. 26, 2011.
U.S. Appl. No. 11/981,380, filed Oct. 31, 2007, 2010/0283069, Nov. 11, 2010, U.S. Pat. No. 7,972,875, Jul. 5, 2011.
U.S. Appl. No. 12/372,605, filed Feb. 17, 2009.
U.S. Appl. No. 12/398,811, filed Mar. 5, 2009, 2010/0002402, Jan. 7, 2010, U.S. Pat. No. 8,552,299, Oct. 8, 2013.
U.S. Appl. No. 12/405,475, filed Mar. 17, 2009, 2010/0059863, Mar. 11, 2010, U.S. Pat. No. 8,198,621, Jun. 12, 2012.
U.S. Appl. No. 12/418,071, filed Apr. 3, 2009, 2010/0052112, Mar. 4, 2010, U.S. Pat. No. 8,470,701, Jun. 25, 2013.
U.S. Appl. No. 12/564,566, filed Sep. 22, 2009, 2010/0072577, Mar. 25, 2010, U.S. Pat. No. 7,982,296, Jul. 19, 2011.
U.S. Appl. No. 12/669,287, filed Jan. 15, 2010, 2011/0187798, Aug. 4, 2011.
U.S. Appl. No. 12/778,588, filed May 12, 2010, 2010/0317132, Dec. 16, 2010, U.S. Pat. No. 8,865,489, Oct. 21, 2014.
U.S. Appl. No. 12/844,492, filed Jul. 27, 2010, 2010/0289124, Nov. 18, 2010, U.S. Pat. No. 8,039,847, Oct. 18, 2011.
U.S. Appl. No. 12/892,001, filed Sep. 28, 2010, 2011/0230747, Sep. 22, 2011.
U.S. Appl. No. 12/916,934, filed Nov. 1, 2010, 2012/0105528, May 3, 2012, U.S. Pat. No. 8,562,095, Oct. 22, 2013.
U.S. Appl. No. 12/947,120, filed Nov. 16, 2010, 2011/0170225, Jul. 14, 2011.
U.S. Appl. No. 12/996,924, filed Dec. 8, 2010, 2011/0147715, Jun. 23, 2011.
U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/120,486, filed Aug. 4, 2011, 2011/0277813, Nov. 17, 2011, U.S. Pat. No. 8,679,888, Mar. 25, 2014.
U.S. Appl. No. 13/228,041, filed Sep. 8, 2011, 2011/0316120, Dec. 29, 2011.
U.S. Appl. No. 13/270,954, filed Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/472,165, filed May 15, 2012, 2012/0320581, Dec. 20, 2012.
U.S. Appl. No. 13/492,636, filed Jun. 8, 2012, 2013/0041235, Feb. 14, 2013.
U.S. Appl. No. 13/549,291, filed Jul. 13, 2012, 2013/0036928, Feb. 14, 2013.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/835,284, filed Mar. 15, 2013, 2014/0220422, Aug. 7, 2014.

(56) References Cited

OTHER PUBLICATIONS

U.S. Appl. No. 13/853,770, filed Mar. 29, 2013, 2013/0333094, Dec. 19, 2013.
Office Action Corresponding to European Patent Application No. 12792485.0, dated May 16, 2017.
Abbaschian et al. (Dec. 2005) "High Pressure-High Temperature Growth of Diamond Crystals Using Split Sphere Apparatus," *Diamond Relat. Mater.* 14(11-12):1916-1919.
Adachi et al (1982) "Chemical Etching of InGaAsP/InP DH Wafer," *J. Electrochem. Soc.* 129:1053-1062.
Adachi et al. (1983) "Chemical Etching Characteristics of (001)GaAs," *J. Electrochem. Soc.* 130:2427-2435.
Adrega et al. (2010) "Stretchable Gold Conductors Embedded in PDMS and Patterned by Photolithography: Fabrication and Electromechanical Characterization," *J. Micromech. Microeng.* 20:055025.
Ago et al. (2005) "Aligned Growth of Isolated Single-Walled Carbon Nanotubes Programmed by Atomic Arrangement of Substrate Surface," *Chem. Phys. Lett.* 408:433-438.
Ago et al. (2006) "Synthesis of Horizontally-Aligned Single-Walled Carbon Nanotubes with Controllable Density on Sapphire Surface and Polarized Raman Spectroscopy," *Chem. Phys. Lett.* 421:399-403.
Ahmed et al. (Web Release Oct. 11, 2005) "Extending the 3ω-Method to the MHz Range for Thermal Conductivity Measurements of Diamond Thin Films," *Diamond Relat. Mater.* 15(2-3):389-393.
Ahn et al. (2007) "Bendable Integrated Circuits on Plastic Substrates by Use of Printed Ribbons of Single-Crystalline Silicon," *Appl. Phys. Lett.* 90:213501.
Ahn et al. (Dec. 15, 2006) "Heterogeneous Three-Dimensional Electronics by Use of Printed Semiconductor Nanomaterials," *Science* 314:1754-1757.
Ahn et al. (Jun. 2006) "High-Speed Mechanically Flexible Single-Crystal Silicon Thin-Film Transistors on Plastic Substrates," *IEEE Electron Dev. Lett.* 27(6):460-462.
Al-Halhouli et al. (2008) "Nanoindentation Testing of SU-8 Photoresist Mechanical Properties," *Microelectronic Eng.* 85:942-944.
Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," *Europace* 11:771-817.
Alivisatos et al. (1996) "Semiconductor Clusters, Nanocrystals, and Quantum Dots," *Science* 271:933-937.
Alivisatos et al. (1998) "From Molecules to Materials: Current Trends and Future Directions," *Adv. Mater.* 10:1297-1336.
Allen et al. (Feb. 20, 2006) "Nanomaterial Transfer Using Hot Embossing for Flexible Electronic Devices," *Appl. Phys. Lett.* 88:083112.
Al-Sarawi et al. (Feb. 1998) "A Review of 3-D Packaging Technology," *IEEE Trans. Comp. Packag. Manufac. Technol. B* 21(1):2-14.
Altman et al. (2003) "Silk-Based Biomaterials," *Biomaterials* 24:401-416.
Amano et al. (Feb. 3, 1986) "Metalorganic Vapor Phase Epitaxial Growth of a High Quality GaN Film Using an AlN Buffer Layer," *Appl. Phys. Lett.* 48(5):353-355.
Ambrosy et al. (1996) "Silicon Motherboards for Multichannel Optical Modules," *IEEE Trans. Compon. Pack. A* 19:34-40.
Amir et al. (2000) "The Influence of Helium-Neon Irradiation on the Viability of Skin Flaps in the Rat," *Br. J. Plast. Surg.* 53:58-62.
Amsden et al. (Nov. 9, 2009) "Spectral Analysis of Induced Color Change on Periodically Nanopatterned Silk Films," *Opt. Express* 17(23):21271-21279.
Amunts et al. (2000) "Brodmann's Areas 17 and 18 Brought Into Stereotaxic Space—Where and How Variable?" *NeuroImage.* 11:66-84.
Andersen et al. (2004) "Selecting the Signals for a Brain—Machine Interface," *Curr. Opin. Neurobiol.* 14:720-726.

Anderson et al. (2007) "Studies of Stimulus Parameters for Seizure Disruption Using Neural Network Simulations," *Biological Cybernetics.* 97:173-94.
Andersson et al. (Oct. 16, 2002) "Active Matrix Displays Based on All-Organic Electrochemical Smart Pixels Printed on Paper," *Adv. Mater.* 14:1460-1464.
Ando et al. (2004) "Self-Aligned Self-Assembly Process for Fabricating Organic Thin-Film Transistors," *Appl. Phys. Lett.* 85:1849-1851.
Angadi et al. (Web Release Jun. 1, 2006) "Thermal Transport and Grain Boundary Conductance in Ultrananocrystalline Diamond Thin Films," *J. Appl. Phys.* 99:114301.
Aoki et al. (2003) "Microassembly of Semiconductor Three Dimensional Photonic Crystals," *Nat. Mater.* 2:117-121.
Arnold et al. (2003) "Field-Effect Transistors Based on Single Semiconducting Oxide Nanobelts," *J. Phys. Chem. B* 107(3):659-663.
Ayón et al. (Jan. 1999) "Characterization of a Time Multiplexed Inductively Coupled Plasma Etcher," *J. Electrochem. Soc.* 146(1):339-349.
Baca et al. (2008) "Semiconductor Wires and Ribbons for High-Performance Flexible Electronics," *Angew. Chem. Int. Ed.* 47:5524-5542.
Bachtold et al. (Nov. 9, 2001) "Logic Circuits with Carbon Nanotube Transistors," *Science* 294:1317-1320.
Bae et al. (Jul. 1, 2002) "Single-Crystalline Gallium Nitride Nanobelts," *Appl. Phys. Lett.* 81(1):126-128.
Ball et al. (2004) "Towards an Implantable Brain-Machine Interface Based on Epicortical Field Potentials," *Biomed. Tech.* 49:756-759.
Balmer et al. (2005) "Diffusion of Alkanethiols in PDMS and Its Implications on Microcontact Printing (μCP)," *Langmuir* 21(2):622-632.
Banerjee et al. (May 2001) "3-D ICs: A Novel Chip Design for Improving Deep-Submicrometerinterconnect Performance and Systems-on-Chip Integration," *Proc. IEEE* 89(5):602-633.
Bao et al. (1997) "High-Performance Plastic Transistors Fabricated by Printing Techniques," *Chem. Mater.* 9:1299-1301.
Bao et al. (1999) "Printable Organic and Polymeric Semiconducting Materials and Devices," *J. Mater. Chem.* 9:1895-1904.
Barquins, M. (1992) "Adherence, Friction and Wear of Rubber-Like Materials," *Wear* 158:87-117.
Bates, F.S. (1991) "Polymer-Polymer Phase Behavior," *Science* 251:898-905.
Battaglia et al. (2003) "Colloidal Two-Dimensional Systems: CdSe Quantum Shells and Wells," Angew. Chem. Int. Ed. 442:5035-5039.
Bauer et al. (2004) "Biological Applications of High Aspect Ratio Nanoparticles," *J. Mater. Chem.* 14:517-526.
Berg et al. (2003) "Tailored Micropatters Through Weak Polyelectrolyte Stamping," Langmuir 19:2231-2237.
Bernard et al. (1998) "Printing Patterns of Proteins," *Langmuir* 14(9):2225—2229.
Besson et al. (2008) "Small Focal Cortical Dysplasia Lesions Are Located at the Bottom of a Deep Sulcus," *Brain: A Journal of Neurology.* 131:3246-55.
Bett et al. (Aug. 1999) "III-V Compounds for Solar Cell Applications," *Appl. Phys. A. Mater. Sci.* 69(2):119-129.
Bhunia et al. (2004) "Free-Standing and Vertically Aligned InP Nanowires Grown by Metalorganic Vapor Phase Epitaxy," *Physica E* 21:583-587.
Bhushan et al. (Nov. 2004) "Multiwalled Carbon Nanotube AFM Probes for Surface Characterization of Micro/Nanostructures," *Microsyst. Technol.* 10(8-9):633-639.
Bietsch et al. (Oct. 1, 2000) "Conformal Contact and Pattern Stability of Stamps Used for Soft Lithography," *J. Appl. Phys.* 88(7):4310-4318.
BIOFLEX—Biocompatible Flexible Electronic Circuits. Available at http://tfcg.elis.ugent.be/projects/bioflex. Accessed Feb. 8, 2012.
Bishay et al. (2000) "Temperature Coefficient of the Surface Resistivity of Two-Dimensional Island Gold Films," *J. Phys. D. Appl. Phys.* 33(18):2218-2222.
Blanchet et al. (2003) "Large Area, High Resolution, Dry Printing of Conducting Polymers for Organic Electronics," *Appl. Phys. Lett.* 82:463-465.

(56) References Cited

OTHER PUBLICATIONS

Blanchet et al. (2003) "Printing Techniques for Plastic Electronics," *J. Imag. Sci. Tech.* 47(4) :296-303.
Blanco et al. (2010) "Unsupervised Classification of High-Frequency Oscillations in Human Neocortical Epilepsy and Control Patients," *Journal of Neurophysiology*.
Blazdell et al. (Nov. 1999) "Preparation of Ceramic Inks for Solid Freeforming Using a Continuous Jet Printer," *J. Mat. Syn. Process.* 7(6):349-356.
Boltau et al. (1998) "Surface-Induced Structure Formation of Polymer Blends on Patterned Substrates," *Nature* 391:877-879.
Boncheva et al. (Mar. 15, 2005) "Magnetic Self-Assembly of Three-Dimensional Surfaces from Planar Sheets," *Proc. Natl. Acad. Sci. USA* 102(11):3924-3929.
Boncheva et al. (Mar. 8, 2005) "Templated Self-Assembly: Formation of Folded Structures by Relaxation of Pre-Stressed, Planar Tapes," *Adv. Mater.* 17(5):553-557.
Bourzac, K. (May/Jun. 2010) "TR10: Implantable Electronics," *Technology Review*, Published by MIT, http://www.technologyreview.com/biomedicine/25086/?a=f.
Bowden et al. (1997) "Self Assembly of Mesoscale Objects into Ordered Two-Dimensional Arrays," *Science* 276:233-235.
Bowden et al. (2001) "Molecule-Mimetic Chemistry and Mesoscale Self-Assembly," *Acc. Chem. Res.* 34:231-238.
Bowden et al. (May 14, 1998) "Spontaneous Formation of Ordered Structures in Thin Films of Metals Supported on an Elastomeric Polymer," *Nature* 393:146-149.
Bracher et al. (2009) "Shaped Films of Ionotropic Hydrogels Fabricated Using Templates of Patterns Paper," *Adv. Mater.* 21:445-450.
Bradley et al. (2003) "Flexible Nanotube Electronics," *Nano Lett.*, vol. 3, No. 10, pp. 1353-1355.
Branco et al. (2003) "Functional Variability of the Human Cortical Motor Map: Electrical Stimulation Findings in Perirolandic Epilepsy Surgery," *Journal of Clinical Neurophysiology*. Society 20:17-25.
Braun et al. (1999) "Electrochemically Grown Photonic Crystals," *Nature* 402:603-604.
Britton et al. (Web Release Oct. 25, 2005) "Microstructural Defect Characterization of a Si:H Deposited by Low Temperature HW-CVD on Paper Substrates," *Thin Solid Films* 501(1-2):79-83.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26:3123-3129.
Brown et al. (Dec. 19, 2001) "Heterogeneous Materials Integration: Compliant Substrates to Active Device and Materials Packaging," *Mater. Sci. Eng. B* 87(3):317-322.
Brown, H.R. (1991) "The Adhesion Between Polymers," *Ann. Rev. Mater. Sci.* 21:463-489.
Brunner et al. (2011) "Rapid Communication with a 'P300' Matrix Speller Using Electrocorticographic Signals (ECoG)," *Frontiers in Neuroscience.* 5:5.
Bruschi et al. (2001) "Micromachined Silicon Suspended Wires With Submicrometric Dimensions," *Microelectron. Eng.* 57-58:959-965.
Buma et al. (2001) "High-Frequency Ultrasound Array Element Using Thermoelastic Expansion in an Elastomeric Film," *Appl. Phys. Lett.* 79:548-550.
Burdinski et al. (2005) "Single Etch Patterning of Stacked Silver and Molybdenum Alloy Layers on Glass Using Microcontat Wave Printing," *J. Am. Chem. Soc.* 127(31):10786-10787.
Burdinski, D. (non-dated) "Soft Lithography and Microcontact Wave Printing," http://www.research.philips.com/technologies/light_dev_microsys/softlitho/index.html, Downloaded May 23, 2007.
Burge et al. (Jun. 25, 1997) "X-Ray Holography for VLSI Using Synthetic Bilevel Holograms," *Proc. Int. Soc. Opt. Eng.* 3183:2-13.
Burgin et al. (2000) "Large Area Submicrometer Contact Printing Using a Contact Aligner," *Langmuir* 16:5371-5375.

Burns et al. (2003) "Printing of Polymer Thin-Film Transistors for Active-Matrix-Display Applications," *J. Soc. Inf. Display* 11:599-604.
Campbell et al. (1991) "A Silicon-Based, Three-Dimensional Neural Interface: Manufacturing Processes for an Intracortical Electrode Array," *IEEE Transactions on Bio-Medical Engineering.* 38:758-68.
Campbell et al. (2000) "Fabrication of Photonic Crystals for the Visible Spectrum by Holographic Lithography," *Nature* 404:53-56.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," *Adv. Funct. Mater.* 16:2355-2362.
Cao et al. (2006) "Highly Bendable, Transparent Thin-Film Transistors That Use Carbon-Nanotube-Based Conductors and Semiconductors with Elastomeric Delectrics," *Adv. Mater.* 18(3):304-309.
Cao et al. (2006) "Transparent flexible organic thin-film transistors that use printed single-walled carbon nanotube electrodes," *Applied Physics Letters* 88:113511.
Cao et al. (Jan. 5, 2009) "Ultrathin Films of Single-Walled Carbon Nanotubes for Electronics and Sensors: A Review of Fundamental and Applied Aspects," *Adv. Mater.* 21(1):29-53.
Cao et al.(Jul 24, 2008) "Medium-Scale Carbon Nanotube Thin-Film Integrated Circuits on Flexible Plastic Substrates," *Nature* 454:495-500.
Cardin et al. (2007) "Stimulus Feature Selectivity in Excitatory and Inhibitory Neurons in Primary Visual Cortex," *Journal of Neuroscience.* 27:10333.
Cardin et al. (2008) "Cellular Mechanisms Underlying Stimulus-Dependent Gain Modulation in Primary Visual Cortex Neurons In Vivo," *Neuron.* 59:150-160.
Carr et al. (1998) "Measurement of Nanomechanical Resonant Structures in Single-Crystal Silicon," *J. Vac. Sci. Technol. B* 16:3821-3824.
Chaudhury et al. (1991) "Direct Measurement of Interfacial Interactions Between Semispherical Lenses and Flat Sheets of Poly(dimethylsiloxane) and their Chemical Derivatives," *Langmuir* 7:1013-1025.
Chamberlain et al. (Aug. 30, 2011) "Millimeter-Scale Epileptiform Patterns and Their Relation to Seizures," *Conf Proc IEEE Eng Med Biol Soc.* 2011:761-4.
Chang et al. (1994) "Process Techniques," "Lithography," and "Device-Related Physics and Principles," In; *GaAs High-Speed Devices: Physics, Technology and Circuit Application*, John Wiley and Sons, New York, pp. 115-278.
Chao et al. (2010) "Long-Term Asynchronous Decoding of Arm Motion Using Electrocorticographic Signals in Monkeys," *Frontiers in Neuroengineering.* 3:3.
Chen et al. (2003) "Characterization of Pd—GaAs Schottly Diodes Prepared by the Electrodes Plating Technique," *Semiconductor. Sci. Technol.* 18:620-626.
Chen et al. (2003) "Electronic Paper: Flexible Active-Matrix Electronics Ink Display," *Nature* 423:136.
Chen et al. (2005) "InGaN Nanorings and Nanodots by Selective Area Epitaxy," *Appl. Phys. Lett.* 87:143111.
Chen et al. (2005) "The Role of Metal-Nanotube Caontact in the Performance of Carbon Nanotube Field-Effect Transistors," *Nano Lett.* 5(7):1497-1502.
Chen et al. (Feb. 27, 2006) "Complementary Carbon Nanotube-Gated Carbon Nanotube Thin-Fim Transistor," *Appl. Phys. Lett.* 88:093502.
Chen et al. (Jun. 2002) Effect of Process Parameters on the Surface Morphology and Mechanical Performance of Silicon Structures After Deep Reactive Ion Etching (DRIE) *J. Microelectromech. Syst.* 11(3):264-275.
Chen et al. (Mar. 2004) "A Family of Herringbone Patterns in Thin Films," *Scr. Mater.* 50(6):797-801.
Chen et al. (Mar. 24, 2006) "An Integrated Logic Circuit Assembled on a Single Carbon Nanotube," *Science* 311:1735.
Chen et al. (Sep. 2004) "Herringbone Buckling Patterns of Compressed Thin Films on Compliant Substrates," *J. Appl. Mech.* 71:597-603.

(56) References Cited

OTHER PUBLICATIONS

Cheng et al. (2005) "Ink-Jet Printing, Self-Assembled Polyelectrolytes, and Electroless Plating: Low Cost Fabrication of Circuits on a Flexible Substrate at Room Temperature," *Macromol. Rapid Commun.* 26:247-264.
Childs et al. (2002) "Decal Transfer Microlithography: A New Soft-Lithographic Patterning Method," *J. Am. Chem. Soc.* 124:13583-13596.
Childs et al. (2005) "Masterless Soft-Lithography: Patterning UV/Ozone-Induced Adhesion on Poly(dimethylsiloxane) Surfaces," *Langmuir* 21:10096-10105.
Childs et al. (Aug. 14, 2004) "Patterning of Thin-Film Microstructures on Non-Planar Substrate Surfaces Using Decal Transfer Lithography," *Adv. Mater.* 16(15):1323-1327.
Choi et al. (2007) "Biaxially Stretchable 'Wavy' Silicon Nanomembranes," *Nano Lett.* 7(6):1655-1663.
Choi et al. (Web Release Jan. 25, 2005) "Simple Detachment Patterning of Organic Layers and Its Applications to Organic Light-Emitting Diodes," *Adv. Mater.* 17(2):166-171.
Chou et al. (2004) "An Orientation-Controlled Pentacene Film Aligned by Photoaligned Polyimide for Organic Thin-Film Transistor Applications," *Adv. Func. Mater.* 14:811-815.
Chou et al. (Jun. 8, 1999) "Micromachining on (111)-Oriented Silicon," *Sens. Actuators A* 75(3):271-277.
Chu et al. (2005) "High-Performance Organic Thin-Film Transistors with Metal Oxide/Metal Bilayer Electrode," *Appl. Phys. Lett.* 87:193508.
Chung et al. (2000) Silicon Nanowire Devices *Appl. Phys. Lett.* 76(15):2068-2070.
Chung et al. (Jul. 1, 2003) "A Study on Formation of Al and $Al_2O_3$ on the Porous Paper by DC Magnetron Sputtering," *Surf. Coat. Technol.* 171(1-3):65-70.
Clerc, L. (1976) "Directional Differences of Impulse Spread in Trabecular Muscle from Mammalian Heart," *J. Physiol.* 255:335-346.
Cohen-Karni et al. (2009) "Flexible Electrical Recording from Cells Using Nanowire Transistor Arrays," *Proc. Natl. Acad. Sci. USA* 106:7309-7313.
Cole et al. (2008) "Patterned Growth and Transfer of ZnO Micro- and Nanocrystals with Size and Location Control," *Adv. Mater.* 20:1474-1478.
Collinso et al. (Apr. 27, 2001) "Engineering Carbon Nanotubes and Nanotube Circuits Using Electrical Breakdown," *Science* 292:706-709.
Corazza et al. (2007) "Photobiomodulation on the Angiogenesis of Skin Wounds in Rats Using Different Light Sources," *Photomedicine Laser Surg.* 25:102-106.
Cox, H. L. (1952) "The Elasticity and Strength of Paper and Other Fibrous Materials," *Br. J. Appl. Phys.* 3:72-79.
Creagh et al. (2003) "Design and Performance of Inkjet Print Heads for Non-Graphic-Arts Applications," *MRS Bull.* 28:807-811.
Crone et al. (Feb. 3, 2000) "Large-Scale Complementary Integrated Circuits Based on Organic Transistors," *Nature* 403:521-523.
Crowder et al. (1998) "Low-Temperature Single-Crystal Si TFTs Fabricated on Si Films Processed via Sequential Lateral Solidification," *IEEE Electron. Dev. Lett.* 19:306-308.
Cui et al. (2001) "Nanowire Nanosensors for Highly Sensitive and Selective Detection of Biological and Chemical Species," *Science* 293:1289-1292.
Dai et al. (2002) "Gallium Oxide Nanoribbons and Nanosheets," *J. Phys. Chem. B* 106(5):902-904.
Dai et al. (2003) "Novel Nanostructures of Functional Oxides Synthesized by Thermal Evaporation," *Adv. Funct. Mater.* 13:9-24.
Davidson et al. (2004) "Supercritical Fluid-Liquid-Solid Synthesis of Gallium Arsenide Nanowires Seeded by Alkanethiol-Stabilized Gold Nanocrystals," *Adv. Mater.* 16:646-649.
De Gans (2004) "Inkjet Printing of Polymers: State of the Art and Future Developments," *Adv. Mater.* 16(3):203-213.
De Sio et al. (Web Release May 18, 2005) "Electro-Optical Response of a Single-Crystal Diamond Ultraviolet Photoconductor in Transverse Configuration," *Appl. Phys. Lett.* 86:213504.
DeBoer et al. (2004) "Organic Single-Crystal Field-Effect Transistors," *Phys. Stat. Sol.* 201:1302-1331.
Deen et al. (2004) "Electrical Characterization of Polymer-Based FETs Fabricated by Spin-Coating Poly(3-alkylthiophene)s," *IEEE Trans. Electron Devices* 51:1892-1901.
Delmerche et al. (1997) "Stability of Molded Polydimethylsiloxane Microstructures," *Adv. Mat.* 9:741-746.
Deruelle et al. (1995) "Adhesion at the Solid-Elastomer Interface: Influence of Interfacial Chains," *Macromol.* 28:7419-7428.
Derycke et al. (Sep. 2001) "Carbon Nanotube Inter- and Intramolecular Logic Gates," *Nano Lett.* 1(9):453-456.
Desai et al. (Feb. 1999) "Nanopore Technology for Biomedical Applications," *Biomed. Microdevices* 2(1):11-40.
Dick et al. (Jun. 2004) "Synthesis of Branched 'Nanotrees' by Controlled Seeding of Multiples Branching Events," *Nat. Mater.* 3:380-384.
Dimroth et al. (Mar. 2007) "High Efficiency Multijunction Solar Cells," *MRS Bull.* 32:230-235.
Ding et al. (Oct. 4, 2004) "Self Catalysis and Phase Transformation in the Formation of CdSe Nanosaws," *Adv. Mater.* 16(19):1740-1743.
Dinsmore et al. (2002) "Colloidosomes: Selectively Permeable Capsules Composed of Colloidal Particles," *Science* 298:1006-1009.
Divliansky et al. (2003) "Fabrication of Three-Dimensional Polymer Photonic Crystal Structures Using Single Diffraction Element Interference Lithography," *Appl. Phys. Lett.* 82(11):1667-1669.
Dodabalapur A. (Apr. 2006) "Organic and Polymer Transistors for Electronics," *Mater Today* 9(4):24-30.
Dodabalapur et al. (1995) "Organic Transistors: Two-Dimensional Transport and Improved Electrical Characteristics," *Science* 268:270-271.
Duan et al. (2000) "General Synthesis of Compound Semiconductor Nanowires," *Adv. Mater.* 12(4):298-302.
Duan et al. (2003) "High-performance Thin-Film Transistors Using Semiconductor Nanowires and Nanoribbons," *Nature* 425:274-278.
Duan X, (2003) "Semiconductor Nanowires: From Nanoelectronics to Macroelectronics," Abstract from a presentation given at the 11$^{th}$ Foresight Conference on Molecular Nanotechnology, Oct. 10-20, Burlingame, CA.
Duboz et al. (1998) "Transistors and Detectors Based on GaN-Related Materials," In; *Group III Nitride Semiconductor Compounds*, Gill, B. ed., Clarendon, Oxford, pp. 343-387.
Duesberg et al. (2000) "Polarized Raman Spectroscopy on Isolated Single-Wall Carbon Nanotubes," *Phys. Rev. Lett.*, vol. 85, No. 25, pp. 5436-5439.
Duffy et al. (1998) "Rapid Prototyping of Microfluidic Systems in Poly(dimethylsiloxane)," *Anal. Chem.* 70:4974-4984.
Dupuis et al. (2008) "History, Development, and Applications of High-Brightness Visible Light-Emitting Diodes," *IEEE J. Lightwave Tech.* 26:1154-1171.
Durkop et al. (2004) "Extraordinary Mobility in Semiconducting Carbon Nanotube," *Nano Lett.* 4(1):35-39.
Eder et al. (Apr. 5, 2004) "Organic Electronics on Paper," *Appl. Phys. Lett.* 84(14):2673-2675.
Edrington et al. (2001) "Polymer-Based Photonic Crystals," *Adv. Mater.* 13:421-425.
Efimenko et al. (Oct. 15, 2002) "Surface Modification of Sylgard-184 Poly(dimethyl Siloxane) Networks by Ultraviolet and Ultraviolet/Ozone Treatment," *J. Colloid Interface Sci.* 254(2):306-315.
Eftekhari, G. (1993) "Variation in the Effective Richardson Constant of Metal—GaAs and Metal—InP Contacta Due to the Effect of Processing Parameters," *Phys. Status Solid A—Appl. Res.* 140:189-194.
Ensell, G. (1995) "Free Standing Single-Crystal Silicon Microstructures," *J. Micromech. Microeng.* 5:1-4.
Exam Report, Written Opinion and Response to Written Opinion, Corresponding to Singapore Patent Application No. 2007/18082-1, dated Jan. 15, 2009.
Examination Report and Response, Corresponding to Malaysian Patent Application No. PI 20062672, dated Aug. 28, 2009.
Examination Report, Corresponding to European Application No. EP 05 756 327.2, dated Jan. 20, 2010.

(56) References Cited

OTHER PUBLICATIONS

Examination Report, Corresponding to Malaysian Patent Application No. PI 20092343, dated Jun. 15, 2010.
Examination Report, Corresponding to Malaysian Patent Publication No. PI 20052553, dated Mar. 13, 2009.
Examination Report, Corresponding to Singapore Patent Application No. 200608359-6, Completed on Aug. 27, 2008.
Examination Report, Response and Search Report, Corresponding to Malaysian Patent Application No. PI 20062537, dated Nov. 20, 2009.
Faez et al. (1999) "An Elastomeric Conductor Based on Poluaniline Prepared by Mechanical Mixing," *Polymer* 40:5497-5503.
Felgner et al. (1996) "Flexural Rigidity of Microtubules Measured with the Use of Optical Tweezers," *J. Cell Sci.* 109:509-516.
Fink et al. (1999) "Block Copolymers as Photonic Bandgap Materials," *J. Lightwave Tech.* 17:1963-1969.
Flewitt et al. (2005) "Low-Temperature Deposition of Hydrogenated Amorphous Silicon in an Electron Cyclotron Resonance Reactor for Flexible Displays," *Proc. IEEE* 93:1364-1373.
Folch et al. (1999) "Wafer-Level In-Registry Microstamping," *J. Microelectromech. Syst.* 8:85-89.
Forment et al. (2004) "Influence of Hydrogen Treatment and Annealing Processes Upon the Schottky Barrier Height of Au/n-GaAs and Ti/n-GaAs Diodes," *Semicond. Sci. Technol.* 19:1391-1396.
Forrest et al. (2004) "The Path to Ubiquitous and Low-Cost Organic Electronic Appliances on Plastic," *Nature* 428:911-918.
Fortunato et al. (2005) "Flexible a-Si: H Position-Sensitive Detectors," *Proc. IEEE* 93:1281-1286.
Fortunato et al. (Sep. 2008) "High-Performance Flexible Hybrid Field-Effect Transistors Based on Cellulose Fiber Paper," *IEEE Electron. Dev. Lett.* 29(9):988-990.
Fox et al. (2001) "Location-Probability Profiles for the Mouth Region of Human Primary Motor-Sensory Cortex: Model and Validation," *NeuroImage.* 13:196-209.
Freeman et al. (2000) "Spatial Spectral Analysis of Human Electrocardiograms Including the Alpha and Gamma Bands," *J. Neurosci. Methods* 95:111-121.
Freire et al. (1999) "Thermal Stability of Polyethylene Terephthalate (PET): Oligomer Distribution and Formation of Volatiles," *Packag. Technol. Sci.* 12:29-36.
Freund, L.B. (2000) "The Mechanics of Electronic Materials," *Int. J. Solids Struct.* 37:185-196.
Friedman et al. (2005) "High-Speed Integrated Nanowire Circuits," *Nature* 434:1085.
Fu et al. (Jan. 10, 2003) "Patterning of Diamond Microstructures on Si Substrate by Bulk and Surface Micromachining," *J. Mater. Process. Technol.* 132(1-3):73-81.
Furneaux et al. (1989) "The Formation of Controlled-Porosity Membranes from Anodically Oxidized Aluminum," *Nature* 337:147-149.
Gais et al. (2002) "Learning-Dependent Increases in Sleep Spindle Density," *The Journal of Neuroscience.* 22:6830-6834.
Gan et al. (2002) "Preparation of Thin-Film Transostros With Chemical Bath Deposited CdSe and CdS Thin Films," *IEEE Trans. Electron. Dev.* 49:15-18.
Gao et al. (Sep. 9, 2005) "Conversion of Zinc Oxide Nanobelts into Superlattice-Structures Nanohelices," *Science* 309:1700-1704.
Garcia et al. (2004) "Etchant Anisotropy Controls the Step Bunching Instability in KOH Etching of Silicon," *Phys. Rev. Lett.* 93(16):166102.
Gardner et al. (1965) "Physical Aspects of the Internal Water Relations of Plant Leaves," *Plant Physiol.* 40:705-710.
Garnier et al. (1994) "All-Polymer Field-Effect Transistor Realized by Printing Techniques," *Science* 265:1684-1686.
Geim et al. (Mar. 2007) "The Rise of Graphene," *Nature Mater.* 6:183-191.
Geissler et al. (2003) "Fabrication of Metal Nanowires Using Microcontact Printing," *Langmuir* 19(15):6301-6311.
Geissler et al. (Jun. 2003) "Selective Wet-Etching of Microcontact-Printed Cu Substrates with Control Over the Etch Profile," *Microelec. Eng.* 67-68:326-332.
Gelinck et al. (2000) "High-Performance All-Polymer Integrated Circuits," *Appl. Phys. Lett.* 77:1487-1489.
Gelinck et al. (2004) "Flexible Active-Matrix Displays and Shift Registers Based on Solution-Processed Organic Transistors," *Nat. Mater.* 3:106-110.
Georgakilas et al. (2002) "Wafer-Scale Integration of GaAs Optoelectronic Devices with Standard Si Integrated Circuits Using a Low-Temperature Bonding Procedure," *Appl. Phys. Lett.* 81:5099-5101.
Givargizov, E.I. (1991) "Applications," In; *Oriented Crystallization on Amorphous Substrates*, Plenum Press, New York, pp. 341-363.
Goetting et al. (1999) "Microcontact Printing of Alkanephosphonic Acids on Aluminum: Pattern Transfer by Wet Chemical Etching," *Langmuir* 15:1182-1191.
Goldman et al. (1996) "Correlation of Buffer Strain Relaxation Modes with Transport Properties of Two-Dimensional Electron Gases," *J. Apple. Phys.* 80:6849-6854.
Goldmann et al. (2004) "Hole Mobility in Organic Single Crystals Measured by a "Flip-Crystal" Field-Effect Technique," *J. Appl. Phys.* 96:2080-2086.
Goldsmith, T.H. (Sep. 1990) "Optimization, Constraint, and History in the Evolution of Eyes," *Quart. Rev. Biol.* 65(3):281-322.
Gratz et al. (1991) "Atomic Force Microscopy of Atomic-Scale Ledges and Etch Pits Formed During Dissolution of Quartz," *Science*, 251:1343-1346.
Gray et al. (Dec. 2001) "Screen Printed Organic Thin Film Transistors (OTFTs) on a Flexible Substrate," *Proc. SPIE* 4466:89-94.
Gray et al. (Mar. 5, 2004) "High-Conductivity Elastomeric Electronics," *Adv. Mater.* 16(5):393-397.
Grayson, T. (2002) "Curved Focal Plane Wide Field of View Telescope Design," *Proc. SPIE* 4849:269-274.
Griffith (2006) "Long-Term Gliosis Around Chronically Implanted Platinum Electrodes in the Rhesus Macaque Motor Cortex," *Neuroscience Letters.* 406:81-86.
Gruen et al. (Mar. 21, 1994) "Fullerenes as Precursors for Diamond Film Growth Without Hydrogen or Oxygen Additions," *Appl. Phys. Lett.* 65(12):1502-1504.
Gudiksen et al. (Web Release Apr. 18, 2001) "Synthetic Control of the Diameter and Length of Single Crystal Semiconductor Nanowires," *J. Phys. Chem. B* 105:4062-4064.
Guo et al. (Aug. 19, 2002) "Metal-Insulator-Semiconductor Electrostatics of Carbon Nanotubes," *Appl. Phys. Lett.* 81(8):1486-1488.
Gur et al. (2005) "Air-Stable All-Inorganic Nanocrystal Solar Cells Processed from Solution," *Science* 310:462-465.
Gurbuz et al. (Jul. 2005) "Diamond Semiconductor Technology for RF Device Applications." *Solid State Electron.* 49(7):1055-1070.
Haisma et al. (2002) "Contact Bonding, Including Direct-Bonding in a Historical and Recent Context of Materials Science and Technology, Physics and Chemistry," *Mater. Sci Eng.* 37:1-60.
Halik et al. (2004) "Low-Voltage Organic Transistors with an Amorphous Molecular Gate Dielectric," *Nature* 431:963-966.
Hamedi et al. (May 2007) "Towards Woven Logic from Organic Electronic Fibres," *Nat. Mater.* 6:357-362.
Hamilton et al. (2004) "Field-Effect Mobility of Organic Polymer Thin-Film Transistors," *Chem. Mater.* 16:4699-4704.
Han et al. (2005) "Template-Free Directional Growth of Single-Walled Carbon Nanotues on a- and r-Plane Sapphire," *J. Am. Chem. Soc.* 127:5294-5295.
Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.
Harkonen et al. (Jun. 8, 2006) "4 W Single-Transverse Mode Vecsel Utilizing Intra-Cavity Diamond Heat Spreader," *Electron Lett.* 42(12):693-694.
Hayase et al. (2001) "Photoangioplasty with Local Motexafin Lutetium Delivery Reduces Macrophages in a Rabbit Post-Balloon Injury Model," *Cardiovascular Res.* 49:449-455.
He et al. (2005) "Si Nanowire Bridges in Microtrenches: Integration of Growth into Device Fabrication," *Adv. Mater.* 17:2098-2102.

(56) References Cited

OTHER PUBLICATIONS

Heffelfinger et al. (1997) "Steps and the structure of the (0001) α-alumina surface," *Surf. Sci.*, 370:L168-L172.
Hillbrog et al. (Web Release Dec. 30, 2003) "Nanoscale Hydrophobic Recovery: A Chemical Force Microscopy Study of UV/Ozone-Treated Cross-Linker Poly(dimethylsiloxane)," *Langmuir* 20(3):785-794.
Hines et al. (2005) "Nanotransfer Printing of Organic and Carbon Nanotube Thin-Film Transistors on Plastic Substrates," *Appl. Phys. Lett.* 86:163101.
Hinton et al. (2006) "Reducing the Dimensionality of Data with Neural Networks," *Science*. 313:504-507.
Hochberg et al. (2006) "Neuronal Ensemble Control of Prosthetic Devices by a Human with Tetraplegia," *Nature*. 442:164-71.
Hollenberg et al. (2006) "A MEMS Fabricated Flexible Electrode Array for Recording Surface Field Potentials," *J. Neurosci. Methods* 153:147-153.
Holmes et al. (Feb. 25, 2000) "Control of Thickness and Orientation of Solution-Grown Silicon Nanowires," *Science* 287:1471-1473.
Horan et al. (Jun. 2005) "In Vitro Degradation of Silk Fibroin," *Biomaterials* 26(17):3385-3393.
Horn et al. (1992) "Contact Electrification and Adhesion Between Dissimilar Materials," *Science* 256:362-364.
Hoyer, P. (1996) "Semiconductor Nanotube Formation by a Two-Step Template Process," *Adv. Mater.* 8:857-859.
Hsia et al. (2005) "Collapse of Stamps for Soft Lithography Due to Interfacial Adhesion," *Appl. Phys. Lett.* 86:154106.
Hsu et al. (2002) "Amorphous Si TFTs on Plastically Deformed Spherical Domes," *J. Non-Crystalline Solids* 299-302:1355-1359.
Hsu et al. (2003) "Nature of Electrical Contacts in a Metal-Molecule-Semiconductor System," *J. Vac. Sci. Technol. B* 21(4):1928-1935.
Hsu et al. (Jan. 15, 2004) "Spherical Deformation of Compliant Substrates with Semiconductor Device Islands," *J. Appl. Phys.* 95(2):705-712.
Hsu et al. (Mar. 2004) "Effects of Mechanical Strain on TFT's on Spherical Domes," *IEEE Trans. Electron Dev.* 51(3):371-377.
Hu et al. (1997) "Using Soft Lithography to Fabricate GaAs/AlGaAs Heterostructure Field Effect Transistors," *Appl. Phys. Lett.* 71:2020-2022.
Hu et al. (1999) Chemistry and Physics in One Dimension: Synthesis and Properties of Nanowires and Nanotubes, *Acc. Chem. Res.* 32:435-445.
Hu et al. (2004) "Percolation in Transparent and Conducting Carbon Nanotube Networks," *Nano Lett.*, vol. 4, No. 12, pp. 2513-2517.
Hu et al. (2009) "Highly Conductive Paper for Energy-Storage Devices," *Proc. Natl. Acad. Sci. USA* 106:21490-21494.
Hu et al. (2010) "Stretchable, Porous, and Conductive Energy Textiles," *Nano Lett.* 10:708-714.
Huang et al. (2001) "Directed Assembly of One-Dimensional Nanostructures into Functional Networks," *Science* 291:630-633.
Huang et al. (2001) "Room-Temperature Ultraviolet Nanowire Nanolasers," *Science* 292:1897-1899.
Huang et al. (2003) "Growth of Millimeter-Long and Horizontally Aligned Single-Walled Carbon Nanotubes on Flat Substrates," *J. Am. Chem. Soc.*, 125:5636-5637.
Huang et al. (2004) "Long and Oriented Single-Walled Carbon Nanotubes Grown by Ethanol Chemical Vapor Deposition," *J. Phys. Chem. B.* 108:16451-16456.
Huang et al. (2004) "Self-Organizing High-Density Single-Walled Carbon Nanotube Arrays from Surfactant Suspensions," *Nanotechnol.* 15:1450-1454.
Huang et al. (2004) "Spiral Waves in Disinhibited Mammalian Neocortex," *The Journal of Neuroscience*. 24:9897-9902.
Huang et al. (2005) "Nanomechanical Architecture of Strained Bilayer Thin Films: From Design Principles to Experimental Fabrication," *Adv. Mater.* 17(23):2860-2864.
Huang et al. (2005) "Nanowires for Integrated Multicolor Nanophotonics," *Small* 1(1):142-147.

Huang et al. (2005) "Nonlinear Analyses of Wrinkles in a Film Bonded to a Compliant Substrate," *J. Mech. Phys. Solids* 53:2101-2118.
Huang et al. (2005) "Stamp Collapse in Soft Lithography," *Langmuir* 21:8058-8068.
Huang et al. (2010) "Spiral Wave Dynamics in Neocortex," *Neuron*. 68, 978-990.
Huang et al. (Jan. 16, 2001) "Catalytic Growth of Zinc Oxide Nanowires by Vapor Transport," *Adv. Mater.* 13(2):113-116.
Huck et al. (2000) "Ordering of Spontaneously Formed Buckles on Planar Surfaces," *Langmuir* 16:3497-3501.
Huie, J.C. (2003) "Guided Molecular Self Assembly: A review of Recent Efforts," *Smart Mater. Struct.* 12:264-271.
Huitema et al. (2001) "Plastic Transistors in Active-Matrix Displays," *Nature* 414:599.
Hur et al. (2005) "Printed thin-film transistors and complementary logic gates that use polymer-coated single-walled carbon nanotube networks," *J. Appl. Phys.*, 98, 114302.
Hur et al. (2005) "Organic Nanodielectrics for Low Voltage Carbon Nanotube Thin Film Transistors and Complementary Logic Gates," *J. Am. Chem. Soc.* 127:13808-13809.
Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.
Hur et al. (Jun. 13, 2005) "Extreme Bendability of Single Walled Carbon Nanotube Networks Transferred From High-Temperature Growth Substrates to Plastic and Their Use in Thin-Film Transistors," *Appl. Phys. Lett.* 243502.
Hutchinson et al. (1992) "Mixed Mode Cracking in Layered Materials," *Adv. Appl. Mech.* 29:63-191.
Imparato et al. (2005) "Excimer Laser Induced Crystallization of Amorphous Silicon on Flexible Polymer Substrates," *Thin Solid Films* 487:58-62.
International Search Report and Written Opinion, Corresponding to International Application No. PCT/US10/50468, dated Jan. 6, 2011.
International Search Report and Written Opinion, Corresponding to International Application No. PCT/US10/60425, dated May 25, 2011.
International Search Report and Written Opinion, Corresponding to International Application No. PCT/2005/014449, dated Jul. 3. 2008.
International Search Report and Written Opinion, Corresponding to International Application No. PCT/US04/40192, dated Jul. 6, 2005.
International Search Report and Written Opinion, Corresponding to International Application No. PCT/US07/74293, dated Jul. 24, 2008.
International Search Report and Written Opinion, Corresponding to International Application No. PCT/US07/77217, dated Jun. 3, 2008.
International Search Report and Written Opinion, Corresponding to International Application No. PCT/US07/82633, dated May 16, 2008.
International Search Report and Written Opinion, Corresponding to International Application No. PCT/US09/47442, dated Sep. 21, 2009.
International Search Report and Written Opinion, Corresponding to International Application No. PCT/US2006/032125, dated Mar. 21, 2008.
International Search Report and Written Opinion, Corresponding to International Application No. PCT/US2009/036192, dated Jul. 6, 2009.
International Search Report and Written Opinion, Corresponding to International Application No. PCT/US2009/058231, dated Nov. 17, 2009.
International Search Report and Written Opinion, Corresponding to International Application No. PCT/US2010/034520, dated Sep. 24, 2010.
International Search Report and Written Opinion, Corresponding to International Application No. PCT/US2010/042585, dated May 25, 2011.
International Search Report and Written Opinion, Corresponding to International Application No. PCT/US2011/028094, dated Jul. 14, 2011.

(56) References Cited

OTHER PUBLICATIONS

International Search Report and Written Opinion, Corresponding to International Application No. PCT/US2012/040482, dated Dec. 6, 2012.
International Search Report and Written Opinion, Corresponding to International PCT Application No. PCT/US05/19354, dated Apr. 18, 2007.
International Search Report and Written Opinion, Corresponding to International PCT Application No. PCT/US2006/021161, dated Feb. 28, 2008.
International Search Report and Written Opinion, Corresponding to International PCT Application No. PCT/US2007/022959, dated Oct. 14, 2008.
International Search Report and Written Opinion, Corresponding to International PCT Application No. PCT/US2007/077759, dated Apr. 11, 2008.
International Search Report and Written Opinion, Corresponding to International PCT Application No. PCT/US2007/079070, dated Apr. 23, 2008.
Isberg et al. (Sep. 6, 2002) "High Carrier Mobility in Single-Crystal Plasma-Deposited Diamond," *Science* 297:1670-1672.
Islam et al. (Jan. 16, 2003) "High Weight Fraction Surfactant Solubilization of Single-Wall Carbon Nanotubes in Water," *Nano Lett.* 3(2):269-273.
Ismach et al. (2004) "Atomic-Step-Templated Formation of Single Wall Carbon Nanotube Patters," *Angew. Chem. Int. Ed.* 43:6140-6143.
Itoh et al. (1991) "Cathodoluminescence Properties of Undoped and Zn-Doped $Al_xGa_{1-x}N$ Grown by Metaloganic Vapor Phase Epitaxy," *Jap. J. Appl. Phys.* 30:1604-1608.
J. Vanfleteren. SWEET: Stretchable and Washable Electronics for Embedding Textiles. Available at ftp://ftp.cordis.europa.eu/pub/ist/docs/mnd/ws-sfit_en.pdf. Accessed Feb. 8, 2012.
Jabbour et al. (2001) "Screen Printing for the Fabrication of Organic Light-Emitting Devices," *IEEE J. Select. Top. Quantum. Electron.* 7:769-773.
Jackman et al. (Aug. 4, 1995) "Fabrication of Submicrometer Features on Curved Substrates by Microcontact Printing," *Science* 269:664-666.
Jacobs et al. (2001) "Submicrometer Patterning of Charge in Thin-Film Electrets," *Science* 291:1763-1766.
Jacobs et al. (2002) "Fabrication of a Cylindrical Display by Patterned Assembly," *Science* 296:323-325.
Jain et al. (2000) "III-Nitrides: Growth, Characterization, and Properties," *J. Appl. Phys.* 87:965-1006.
Jain et al. (2005) "Flexible Electronics and Displays: High-Resolution, Roll-to-Roll, Projection Lithography and Photoblation processing Technologies for Hiogh-Throughput Production," *Proc. IEEE* 93:1500-1510.
James et al. (1998) "Patterned Protein Layers on Solid Substrates by This Stamp Microcontact Printing," *Langmuir* 14:742-744.
Jang et al. (2003) "Lateral Growth of Aligned Multiwalled Carbon Nanotubes Under Electric Fiels," *Solid State Commun.* 126:305-308.
Jang et al. (2006) "Low-Voltage and High-Field-Effect Mobility Organic Transistors with a Polymer Insulator," *Appl. Phys. Lett.* 88:072101.
Javey et al. (2002) "High-κ Dielectrics for Advanced Carbon-Nanotube Transistors and Logic Gates," *Nature Mater.* 1:241-246.
Javey et al. (2005) "High Performance n-Type Carbon Nanotube Field-Effect Transistors with Chemically Doped Contacts," *Nano Lett.*, vol. 5, No. 2, pp. 345-348.
Javey et al. (Aug. 7, 2003) "Ballistic Carbon Nanotube Field-Effect Transistors," *Nature* 424:654-657.
Jenkins et al. (1994) "Gallium Arsenide Transistors: Realization Through a Molecularly Designs Insulator," *Science* 263:1751-1753.
Jeon et al. (1995) "Patterning of Dielectric Oxide Thin Layers by Microcontact Printing of Self-Assembled Monolayers," *J. Mater. Res.* 10:2996-2999.
Jeon et al. (2003) "Structural and Mechanical Properties of Woven Fabrics Employing Peirce's Model," *Textile Res. J.* 73:929-933.
Jeon et al. (2004) "Fabricating Complex Three-Dimensional Nanostructures with High Resolution Conformable Phase Masks," *Proc. Natl. Acad. Sci. USA* 101:12428-12433.
Jeon et al. (Aug. 4, 2004) "Three Dimensional Nanofabrication with Rubber Stamps and Conformable Photomasks," *Adv. Mater.* 16(15):1369-1375.
Jiang et al. (Oct. 2, 2007) "Finite Deformation Mechanics in Buckled Thin Films on Compliant Supports," *Proc. Natl. Acad. Sci. USA* 104(40):15607-15612.
Jiang et al. (1999) "Preparation of Macroporous Metal Films from Colloidal Crystals," *J. Am. Chem. Soc.* 121:7957-7958.
Jiang et al. (2002) "Polymer-on-Polymer Stamping: Universal Approaches to Chemically Patterned Surfaces," *Langmuir* 18:2607-2615.
Jiang et al. (2007) "Mechanical Properties of Robust Ultrathin Silk Fibroin Films," *Adv. Funct. Mater.* 17:2229-2237.
Jin et al. (2004) "Scalable Interconnection and Integration of Nanowire Devices Without Registration," *Nano Lett.* 4:915-919.
Jin et al. (2004) "Soft Lithographic Fabrication of an Image Sensor Array on a Curved Substrate," *J. Vac. Sci. Technol. B* 22(5):2548-2551.
Jin et al. (Aug. 2005) "Water-Stable Silk Films with Reduced β-Sheet Content," *Adv. Funct. Mater.* 15(8):1241-1247.
Jin et al. (Web Release Jan. 23, 2004) "Biomaterial Films of *Bombyx mori* Silk Fibroin with Poly(ethylene oxide)," *Biomacromolecules* 5(3):711-717.
Jiyun, C.H. (2003) "Guided Molecular Self-Assembly: A Review of Recent Efforts," *Smart Mater. Struct.* 12:264-271.
Joachim et al. (Nov. 30, 2000) "Electronics Using Hybrid-Molecular and Mono-Molecular Devices," *Nature* 408:541-548.
Johnson et al. (1999) "Ordered Mesoporous Polymers of Tunable Pore Size from Colloidal Silica Templates," *Science* 283:963-965.
Jones et al. (1992) "A Glass-Silicon Composite Intracortical Electrode Array," *Annals of Biomedical Engineering.* 20:423-437.
Jones et al. (Jul./Aug. 2004) "Stretchable Wavy Metal Interconnects," *J. Vac. Sci. Technol. A* 22(4):1723-1725.
Joo et al. (2006) "Low-Temperature Solution-Phase Synthesis of Quantum Well Structures CdSe Nanoribbons," *J. Am. Chem. Soc.* 128(17):5632-5633.
Jortner et al. (2002) "Nanostructured Advanced Materials Perspectives and Directions," *Pure Appl. Chem.* 74(9):1491-1506.
Joselevich (2002) "Vectorial Growth of Metallic and Semiconducting Single-Wall Carbon Nanotubes," *Nano Lett.*, vol. 2, No. 10, pp. 1137-1141.
Kadish et al. (1988) "Interaction of Fiber Orientation and Direction of Impulse Propagation with Anatomic Barriers in Anisotropic Canine Myocardium," *Circulation.* 78:1478-1494.
Kagan (1999) "Organic-Inorganic Hybrid Materials as Semiconducting Channels in Thin-Film Field-Effect Transistors," *Science* 286:945-947.
Kagan et al. (2001) "Patterning Organic-Inorganic Thin-Film Transistors Using Microcontact Printed Templates," *Appl. Phys Lett.* 79(21):3536-3538.
Kagan et al. (2003) *Thin Film Transistors*, Dekker, New York, pp. 1-34.
Kane et al. (2000) "Analog and Digital Circuits Using Organic Thin-Film Transistors on Polyester Substrates," *IEEE Electron. Dev. Lett.* 21:534-536.
Kang et al. (2007) "Printed Multilayer Superstructures of Aligned Single-Walled Carbon Nanotubes for Electronic Applications," *Nano Lett.* 7(11):3343-3348.
Kang et al. (Apr. 2007) "High-Performance Electronics Using Dnese, Perfectly aligned Arrays of Single-Walled Carbon Nanotubes," *Nat. Nanotechnol.* 2(4):230-236.
Kar et al. (2005) "Controlled Synthesis and Photoluminescence Properties of ZnS Nanowires and Nanoribbons," *J. Phys. Chem. B* 109(8):3298-3302.
Kar et al. (2005) "Synthesis and Optical Properties of CdS Nanoribbons," *J. Phys. Chem B.* 109(41):19134-19138.

(56) References Cited

OTHER PUBLICATIONS

Kar et al. (2006) "Shape Selective Growth of CdS One-Dimensional Nanostructures by a Thermal Evaporation Process," *J. Phys. Chem. B.* 110(10):4542-4547.
Karnik et al. (2003) "Lateral Polysilicon $p^+$-p-$n^+$ and $p^+$-n-$n^+$ Diodes," *Solid-State Electronics* 47:653-659.
Karnik et al. (2003) "Multiple Lateral Polysilicon Diodes as Temperature Sensors for Chemical Microreaction Systems," *Jpn. J. Appl. Phys.* 42:1200-1205.
Kato et al. (2004) The Characteristic Improvement of Si(111) Metal-Oxide-Semiconductor Field-Effect Transistor by Long-Time Hydrogen Annealing, *Jpn. J. Appl. Phys.* 43(10):6848-6853.
Katz et al. (2001) "Synthetic Chemistry for Ultrapure, Processable, and High-Mobility Organic Transistor Semiconductors," *Acc. Chem. Res.* 34:359-369.
Katz, H.E. (2004) "Recent Advances in Semiconductor Performance and Printing Processes for Organic Transistor-Based Electronics," *Chem. Mater.* 16:4748-4756.
Kawata et al. (2001) "Finer Features for Functional Microdevices," *Nature* 412:697-698.
Kellis et al. (2009) "Human Neocortical Electrical Activity Recorded on Nonpenetrating Microwire Arrays: Applicability for Neuroprostheses," *Neurosurg. Focus* 27(1):E9.
Kellis et al. (2010) "Decoding Spoken Words Using Local Field Potentials Recorded from the Cortical Surface," *Journal of Neural Engineering* 7:056007.
Kendall, D.L. (1979) "Vertical Etching of Silicon at Very High Apect Ratios," *Ann. Rev. Mater. Sci.* 9:373-403.
Khakani et al. (2006) "Lateral Growth of Single Wall Carbon Nanotubes on Various Substrates by Means of an 'All-Laser' Synthesis Approach," *Diamond Relat. Mater.* 15:1064-1069.
Khan et al. (1993) "High Electron Mobility Transistor Based on a GaN—$Al_xGa_{1-x}$N Heterojunction," *Appl. Phys. Lett.* 63:1214-1215.
Khang et al. (2006) "A Stretchable Form of Single-Crystal Silicon for High-Performance Electronics on Rubber Substraights," *Science* 311:208-212.
Kilby, J.S. (1976) "Invention of the Integrated Circuit," *IEEE Trans. Electron. Dev.* 23:648-654.
Kilpatrick et al. (2010) "Effects of Synaptic Depression and Adaptation on Spatiotemporal Dynamics of an Excitatory Neuronal Network," *Physica D.* 239:547-560.
Kim et al. (2000) "Field Emission from Carbon Nanotubes for Displays," *Diamond and Related Mater.* 9(3-6):1184-1189.
Kim et al. (2002) "Nanolithography Based on Patterned Metal Transfer and Its Application to Organic Electronic Devices," *Appl. Phys. Lett.* 80:4051-4053.
Kim et al. (2003) "Epitaxial Self-Assembly of Block Copolymers on Lithographically Defined Nanopatterned Substrates," *Nature* 424:411-414.
Kim et al. (2008) "Stretchable Electronics: Materials Strategies and Devices," *Adv. Mater.* 20:4887-4892.
Kim et al. (2009) "Integrated Wireless Neural Interface Based on the Utah Electrode array," *Biomed. Microdevices* 11:453-466.
Kim et al. (2009) "Optimized Structural Designs for Stretchable Silicon Integrated Circuits," *Small* 5(24):2841-2847.
Kim et al. (Apr. 25, 2008) "Stretchable and Foldable Silicon Integrated Circuits," *Science* 320:507-511.
Kim et al. (Dec. 2, 2008) "Materials and Noncoplanar Mesh Designs for Integrated Circuits with Linear Elastic Responses to Extreme Mechanical Deformations," *Proc. Natl. Acad. Sci. USA* 105(48):18675-18680.
Kim et al. (Jan. 2008) "Complementary Logic Gates and Ring Oscillators Plastic Substrates by Use of Printed Ribbons Single-Crystalline Silicon," *IEEE Electron. Dev. Lett.* 29(1):73-76.
Kim et al. (Nov. 15, 1999) "Direct Observation of Electron Emission Site on Boron-Doped Polycrystalline Diamond Thin Films Using an Ultra-High-Vacuum Scanning Tunneling Microscope," *Appl. Phys. Lett.* 75(20):3219-3221.
Kim et al. (Oct. 17, 2010) "Waterproof AlInGaP optoelectronics on stretchable substrates with applications in biomedicine and robotics," *Nature Materials* 9:929-937.
Kim et al. (Oct. 2004) "Organic TFT Array on a Paper Substrate," *IEEE Electron. Dev. Lett.* 25(10):702-704.
Kim et al. (Web Release Apr. 18, 2010) "Dissolvable Films of Silk Fibroin for Ultrathin Conformal Bio-Integrated Electronics," *Nature Materials* 9:511-517.
Kim et al. (Web Release Feb. 29, 2008) "Highly Emissive Self-Assembled Organic Nanoparticles Having Dual Color Capacity for Targeted Immunofluorescence Labeling," *Adv. Mater.* 20(6):1117-1121.
Kim et al. (Web Release Jul. 31, 2008) "Complementary Metal Oxide Silicon Integrated Circuits Incorporating Monolithically Integrated Stretchable Wavy Interconnects," *Appl. Phys. Lett.* 93(4):044102.
Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21(36):3703-3707.
Kim et al. (Web Release Sep. 29, 2009) "Silicon Electronics on Silk as a Path to Bioresorbable, Implantable Devices," *Appl. Phys. Lett.* 95:133701-133703.
Kim, Y.S. (Web Release Aug. 9, 2005) "Microheater-Integrated Single Gas Sensor Array Chip Fabricated on Flexible Polyimide Substrate," *Sens. Actuators B* 114(1),410-417.
Kitzmiller et al. (2007) "Micro-Field Evoked Potentials Recorded from the Porcine Sub-Dural Cortical Surface Utilizing a Microelectrode Array," *Journal of Neuroscience Methods.* 162:155-161.
Klauk et al. (2002) "High-Mobility Polymer Gate Dielectric Pentacene Thin Film Transistors," *J. Appl. Phys.* 92:5259-5263.
Klein-Wiele et al. (2003) "Fabrication of Periodic Nanostructures by Phase-Controlled Multiple-Beam Interference," *Appl. Phys. Lett.* 83(23):4707-4709.
Knipp et al. (2003) "Pentacine Thin Film Transistors on Inorganic Dielectrics: Morphology, Structural Properties, and Electronic Transport," *Appl. Phys. Lett.* 93:347-355.
Ko et al. (2006) "Bulk Quantities of Single-Crystal Silicon Micro-/Nanoribbons Generated from Bulk Wafers," *Nano Lett.* 6(10):2318-2324.
Ko et al. (2010) "Flexible Carbon Nanofiber Connectors with Anisotropic Adhesion Properties," *Small* 6:22-26.
Ko et al. (Aug. 7, 2008) "A Hemispherical Electronic Eye Camera Based on Compressible Silicon Optoelectronics," *Nature* 454:748-753.
Ko et al. (Web Release Oct. 28, 2009) "Curvilinear Electronics Formed Using Silicon Membrane Circuits and Elastomeric Transfer Elements," *Small* 5(23):2703-2709.
Kocabas et al. (2004) "Aligned Arrays of Single-Walled Carbon Nanotubes Generated from Random Networks by Orientationally Selective Laser Ablation," *Nano Lett.*, vol. 4, No. 12, pp. 2421-2426.
Kocabas et al. (2005) "Guided Growth of Large-Scale, Horizontally Aligned Arrays of Single-Walled Carbon Nanotubes and Their Use in Thin-Film Transstors," *Small* 1(11):1110-1116.
Kocabas et al. (2006) "Large Area Aligned Arrays of SWNTs for High Performance Thin Film Transistors," American Physical Society, APS March Meeting, Mar. 13-17, Abstract # W31.004.
Kocabas et al. (2006) "Spatially Selective Guided Growth of High-Coverage Arrays and Random Networks of Single-Walled Carbon Nanotbes and Thir Integration into Electronic Devices," *J. Am. Chem. Soc.* 128:4540-4541.
Kocabas et al. (2007) "Experimental and Theoretical Studies of Transport Through Large Scale, Partially Aligned Arrays of Single-Walled Carbon Nanotubes ni Thin Film Type Transistors," *Nano Lett.* 7(5):1195-1202.
Kocabas et al. (Feb. 5, 2008) "Radio Frequency Analog Electronics Based on Carbon Nanotube Transistors," *Proc. Natl. Acad. Sci. USA* 105(5):1405-1409.
Kodambaka et al. (2006) "Control of Si Nanowire Growth by Oxygen," *Nano Lett.* 6(6):1292-1296.
Koide et al. (2000) "Patterned Luminescence of Organic Light-Emitting Diodes by Hot Microcontact Printing (HuCP) of Self-Assembled Monolayers," *J. Am. Chem. Soc.* 122:11266-11267.

(56) References Cited

OTHER PUBLICATIONS

Konagai et al. (1978) "High Efficiency GaAs Thin Film Solar Cells by Peeled Film Technology," *J. Cryst. Growth* 45:277-280.
Kong et al. (2004) "Single-Crystal Nanorings Formed by Epitaxial Self Coating of Polar Nanobelts," *Science* 303:1348-1351.
Kong et al. (Jan. 28, 2000) "Nanotube Molecular Wires as Chemical Sensors," *Science* 287:622-625.
Kong et al. (Oct. 2003) "Structure of Indium Oxide Nanobelts," *Solid State Commun.* 128(1):1-4.
Kong et al. (Oct. 29, 1998) "Synthesis of Individual Single-Walled Carbon Nonotubes on Patterned Silicon Wafers," *Nature* 395:878-881.
Kudo et al. (Web Release Jun. 13, 2006) "A Flexible and Wearable Glucose Sensor Based on Functional Polymers with Soft-MEMS Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(4):2002-2004.
Kumar et al. (1994) "Patterning Self-Assembled Monolayers: Applications in Materials Science," *Langmuir* 10:1498-1511.
Kumar et al. (2002) "Thermally-Stable Low-Resistance Ti/Al/Mo/Au Multilayer Ohmic Contacts on n-GaN," *J. Appl. Phys.* 92:1712-1714.
Kumar et al. (2005) "Percolating Conduction in Finite Nanotube Networks," *Phys. Rev. Lett.*, 95, 066802.
Kuo et al. (1985) "Effect of Mismatch Strain on Band Gap in III-V Semiconductors," *J. Appl. Phys.* 57:5428-5432.
Kuykendall et al. (Aug. 2004) "Crystallographic Alignment of High Density Gallium Nitride Nanowire Arrays," *Nat. Mater.* 3:524-528.
Lacour et al. (2005) "Stretchable Interconnects for Elastic Electronic Surfaces," *Proc. IEEE* 93:1459-1467.
Lacour et al. (2010) "Flexible and Stretchable Micro-Electrodes for in Vitro and n Vivo Neural Interfaces," *Med. Biol. Eng. Comput.* 48:945-954.
Lacour et al. (Apr. 14, 2003) "Stretchable Gold Conductors on Elastomeric Substrates," *Appl. Phys. Lett.* 82(15):2404-.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14, 2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.
Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-Transistor-Array (MTA) Recording at 7.8 μm Resolution," *Appl. Phys. A* 79:1607-1611.
Landes et al. (2002) "Some Properties of Spherical and Rod-Shaped Semiconductor and Metal Nanocrystals," *Pure Appl. Chem.* 74(9):1675-1692.
Larochelle et al. (2007) "An Empirical Evaluation of Deep Architectures on Problems with Many Factors of Variation," In; The Proceedings of the 24th International Conference on Machine learning—ICML '07. 473-480.
Law et al. (2004) "Semiconductor Nanowires and Nanotubes," *Ann. Rev. Mater. Res.* 34:83-122.
Law et al. (Aug. 27, 2004) "Nanoribbon Waveguides for Subwavelength Photonics Integration," *Science* 305:1269-1273.
Lawrence et al. (2008) "Bioactive Silk Protein Biomaterial Systems for Optical Devices," *Biomacromolecules* 9:1214-1220.
Lay et al. (2004) "Simple Route to Large-Scale Ordered Arrays of Liquid-Deposited Carbon Nanotubes," *Nano Lett.*, vol. 4, No. 4, pp. 603-606.
Leclercq et al. (1998) "III-V Micromachined Devices for Microsystems," *Microelectronics J.* 29:613-619.
Lecomte et al. (Apr. 2006) "Degradation Mechanism of Diethylene Glycol Units in a Terephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24:19-21.
Lee et al. (2004) "Organic Light-Emitting Diodes Formed by Soft Contact Lamination," *Proc. Natl. Acad. Sci. USA* 101(2):429-433.
Lee et al. (2005) "A Printable Form of Single-Crystalline Gallium Nitride for Flexable Optoelectronic Systems," *Small* 1:1164-1168.
Lee et al. (2005) "Large-Area, Selective Transfer of Microstructured Silicon (μs-Si): A Printing-Based Approach to High-Performance Thin0Film Transistors Supported on Flexible Substraights," *Adv. Mater.* 17:2332-2336.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," *Appl. Phys. Lett.* 100:084907/1-7.
Lee et al. (Apr. 2005) "Fabrication of Stable Metallic Patterns Embedded in Poly(dimethylsiloxane) and Model Applications in Non-Planar Electronic and Lab-on-a-Chip Device Patterning," *Adv. Funct. Mater.* 15(4):557-566.
Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.
Lee et al. (Feb. 2001) "Application of Carbon Nanotubes to Field Emission Displays," *Diamond and Related Mater.* 10(2):265-270.
Lee et al. (Feb. 2005) "Weave Patterned Organic Transistors on Fiber for E-Textiles," *IEEE Trans. Electron. Dev.* 52(2):269-275.
Leong et al. (2009) "Tetherless Thermobiochemicall Actuated Microgrippers," *Proc. Natl. Acad. Sci. USA* 106:703-709.
Létant et al. (Jun. 2003) "Functionalized Silicon Membranes for Selective Bio-Organisms Capture," *Nat. Mater.* 2:391-395.
Li et al. (2002) "High-Resolution Contact Printing with Dendrimers," *Nano Lett.* 2(4):347-349.
Li et al. (2003) "Ultrathin Single-Crystalline-Silicon Cantilever Resonators: Fabrication Technology and Significant Specimen Size effect on Young's Modulus," *Appl. Phys. Lett.* 83:3081-3083.
Li et al. (2004) "Electrospinning of Nanofibers: Reinventing the Wheel," *Adv. Mater.* 16(14):1151-1170.
Li et al. (2006) "Catalyst-Assisted Formation of Nanocantilever Arrays on ZnS Nanoribbons by Post-Annealing Treatment," *J. Phys. Chem. B* 110(13):6759-6762.
Li et al. (Dec. 2005) "Compliant Thin Film Patterns of Stiff Materials as Platforms for Stretchable Electronics," *J. Mater. Res.* 20(12):3274-3277.
Li et al. (Jul. 1, 2002) "ZnO Nanobelts Grown on Si Substrate," *Appl. Phys. Lett.* 81:144-146.
Lieber, C. (2001) "The Incredible Shrinking Circuit," *Sci. Am.* 285(3):58-64.
Lieber, C.M. (2003) "Nanoscale Science and Technology: Building a Bog Future from Small Things," *MRS. Bull.* 28:486-491.
Lim et al. (2005) "Flexible Membrane Pressure Sensor," *Sens. Act. A* 119:332-335.
Lima et al. (2007) "Creating Micro- and Nanostructures on Tubular and Spherical Surfaces," *J. Vac. Sci. Technol. B* 25(6):2412-2418.
Lin et al. (Sep. 2005) "High-Performance Carbon Nanotube Field-Effect Transistor With Tunable Polarities," *IEEE Trans. Nano* 4(5):481-489.
Linder et al. (1994) "Fabrication Technology for Wafer Through-Hole Interconnections and Three-Dimensional Stacks of Chips and Wafers," *Proc. IEEE Micro. Electro Mech. Syst.* 349-354.
Ling et al. (2004) "Thin Film Deposition, Patterning, and Printing in Organic Thin Film Transistors," *Chem. Mater.* 16:4824-4840.

(56) References Cited

OTHER PUBLICATIONS

Liu et al. (1999) "Controlled deposition of individual single-walled carbon nanotubes on chemically functionalized templates," *Chem. Phys. Lett.*, 303:125-129.

Llinás et al. (1999) "Thalamocortical Dysrhythmia: A Neurological and Neuropsychiatric Syndrome Characterized by Magnetoencephalography," *Proc. Nat. Acad. Sci. USA*. 96:15222-15227.

Long et al. (1990) "Heterostructure FETs and Bipolar Transistors," In; *Gallium Arsenide Digital Integrated Circuit Design*, McGraw-Hill, New York, pp. 58-69.

Loo et al. (2002) "Additive, Nanoscale Patterning of Metal Films with a Stamp and A Surface Chemistry Mediated Transfer Process: Applications in Plastic Electronics," *Appl. Phys. Lett.* 81:562-564.

Loo et al. (2002) "High-Resolution Transfer Printing on GaAs Surfaces Using Alkane Dithiol Monolayers," *J. Vac. Sci. Technol. B* 20(6):2853-2856.

Loo et al. (2002) "Interfacial Chemistries for Nanoscale Transfer Printing," *J. Am. Chem. Soc.* 124:7654-7655.

Loo et al. (2002) "Soft, Conformable Electrical Contacts for Organic Semiconductors: High-Resolution Plastic Circuits by Lamination," *Proc. Natl. Acad. Sci. USA* 99(16):10252-10256.

Loo et al. (2003) "Electrical Contacts to Molecular Layers by Nanotransfer Printing," *Nano Lett.* 3(7):913-917.

Lopes et al. (Sep. 2004) "Thermal Conductivity of PET/(LDPE/Al) Composites Determined by MDSC," *Polym. Test.*23(6):637-643.

Lu et al. (Apr. 2010) "Water-Insoluble Silk Films with Silk I Structure," *Acta Biomater.* 6(4):1380-1387.

Lu et al. (Dec. 2006) "Electronic Materials-Buckling Down for Flexible Electronics," *Nat. Nanotechnol.* 1:163-164.

Lu et al. (Jul. 19, 2005) "One Dimensional Hole Gas in Germanium/Silicon Nanowire Heterostructures," *Proc. Nat. Acad. Sci. USA* 102(29):10046-10051.

Lu et al. (Nov. 2008) "Nanowire Transistor Performance Limits and Applications," *IEEE Trans Electron Dev.* 55(11):2859-2876.

Luan et al. (1992) "An Experimental Study of the Source/Drain Parasitic Resistance Effects in Amorphous Silicon Thin Film Transistors," *J. Appl. Phys.* 72:766-772.

Ma et al. (2004) "Single-Crystal CdSe Nanosaws," *J. Am. Chem. Soc.* 126(3):708-709.

Mack et al. (2006) "Mechanically Flexible Thin-Film Transistors that Use Ultrathin Ribbons of Silicon Derived from Bulk Wafers," *Appl. Phys. Lett.* 88:213101.

Madou, M. (1997) "Etch-Stop Techniques," In; *Fundamentals of Microfabrication*, CRC Press, New York, pp. 193-199.

Maikap et al. (2004) "Mechanically Strained-Si NMOSFETs," *IEEE Electron. Dev. Lett.* 25:40-42.

Maldovan et al. (2004) "Diamond-Structured Photonic Crystals," *Nature Materials* 3:593-600.

Mandlik et al. (Aug. 2006) "Fully Elastic Interconnects on Nanopatterned Elastomeric Substrates," *IEEE Electron Dev. Lett.* 27(8):650-652.

Manna et al. (Web Release May 25, 2003) "Controlled Growth of Tetrapod-Branched Inorganic Nanocrystals," *Nat. Mater.* 2:382-385.

Margalit (2003) "Visual and Electrical Evoked Response Recorded from Subdural Electrodes Implanted Above the Visual Cortex in Normal Dogs Under Two Methods of Anesthesia," *Journal of Neuroscience Methods*. 123:129-137.

Markovich et al. (1999) "Architectonic Quantum Dot Solids," *Acc. Chem. Res.* 32:415-423.

Marquette et al. (2004) "Conducting Elastomer Surface Texturing: A Path to Electrode Spotting Application to the Biochip Production," *Biosens. Bioelectron.* 20:197-203.

Martensson et al. (2004) "Nanowire Arrays Defined by Nanoimprint Lithography," *Nano Lett.* 4:699-702.

Martin, C.R. (1995) "Template Synthesis of Electronically Conductive Polymer Nanostructures," *Acc. Chem. Res.* 28:61-68.

Mas-Torrent et al. (2006) "Large Photoresponsivity in High-Mobility Single-Crystal Organic Field-Effect Phototransistors," *ChemPhysChem* 7:86-88.

Masuda et al. (2000) "Fabrication of Ordered Diamonds/Metal Nanocomposite Structures," *Chem. Lett.* 10:1112-1113.

Matsunaga et al. (2003) "An Improved GaAs Device Model for the Simulation of Analog Integrated Circuit," *IEEE Trans. Elect. Dev.* 50:1194-1199.

Maynard (1997) "The Utah Intracortical ELECTRODE Array: A Recording Structure for Potential Brain-Computer Interfaces," *Electroencephalography and Clinical Neuropgysiology*. 102:228-239.

McAlpine et al. (2003) "High-Performance Nanowire Electronics and Photonics on Glass and Plastic Substrates," *Nano Lett.* 3:1531-1535.

McAlpine et al. (2005) "High-Performance Nanowire Electronics and Photonics and Nanoscale Patterning on Flexible Plastic Substrates," *Proc. IEEE* 93:1357-1363.

McCaldin et al. (1971) "Diffusivity and Solubility of Si in the Al Metallization of Integrated Circuits," *Appl. Phys. Lett.* 19:524-517.

Mehring C. et al. (2003) Inference of hand movements from local field potentials in monkey motor cortex. *Nature Neurosci.* 6, 1253-1254.

Meisel et al. (2004) "Three-Dimensional Photonic Crystals by Holographic Lithography Using the Umbrella Configuration: Symmetries and Complete Photonic Band Gaps," *Phys. Rev. B*. 70:165101:1-10.

Meitl et al. (2004) "Solution Casting and Transfer Printing Single-Walled Carbon Nanotube Films," *Nano Lett.* 4:1643-1947.

Meitl et al. (2006) "Transfer Printing by Kinetic Control of Adhesion to an Elastomeric Stamp," *Nat. Mater.* 5:33-38.

Meitl et al. (Web Release Feb. 22, 2007) "Stress Focusing for Controlled Fracture in Microelectromechanical Systems," *Appl. Phys. Lett.* 90:083110.

Melosh et al. (2003) "Ultrahigh-Density Nanowire Lattices and Circuits," *Science* 300:112-115.

Menard et al. (2004) "A Printable Form of Silicon for High Performance Thin Film Transistors on Plastic Substrates," *Appl. Phys. Lett.* 84:5398-5400.

Menard et al. (2004) "Improved Surface Chemistries, Thin Film Deposition Techniques, and Stamp Designs for Nanotransfer Printing," *Langmuir* 20:6871-6878.

Menard et al. (2004) "High-Performance n- and p-Type Single-Crystal Organic Transistors with Free-Space Gate Dielectrics," *Adv. Mat.* 16:2097-2101.

Menard et al. (2005) "Bendable Single Crystal Silicon Thin Film Transistors Formed by Printing on Plastic Substrates," *Appl. Phys. Lett.* 86(093507):1-3.

Menard et al. (2007) "Micro- and Nanopatterning Techniques for Organic Electronic and Optoelectronic Systems," *Chem. Rev.* 107:1117-1160.

Miao et al. (2003) "Micromachining of Three-Dimensional GaAs Membrane Structures Using High-Energy Nitrogen Implantation," *J. Micromech. Microeng.* 13:35-39.

Michalske et al. (1985) "Closure and Repropagation of Healed Cracks in Silicate Glass," *J. Am. Ceram. Soc.* 68:586-590.

Michel et al. (2001) Printing Meets Lithography: Soft Approaches to High-Resolution Printing, *IBM J. Res. Dev.* 45:697-719.

Miller et al. (2002) "Direct Printing of Polymer Microstructures on Flat and Spherical Surfaces Using a Letterpress Technique," *J. Vac. Sci. Technol. B* 20(6):2320-2327.

Milliron et al. (2004) "Colloidal Nanocrystal Heterostructures with Linear and Branched Topology," *Nature* 430:190-195.

Min, G. (Apr. 4, 2003) "Plastic Electronics and Their Packaging Technologies," *Syn. Metals*. 135:141-143.

Minev et al. (2010) "Impedance Spectroscopy on Stretchable Microelectrode Arrays," *Appl. Phys. Lett.* 97:043707.

Mirkin et al. (2001) "Emerging Methods for Micro- and Nanofabrication," *MRS Bulletin* 26(7):506-507.

Misewich et al. (May 2, 2003) "Electronically Induced Optical Emission from a Carbon Nanotube FET," *Science* 300:783-786.

Mishra et al. (2002) "AlGaN/GaN HEMTs—an Overview of Device Operation and Applications," *Proc. IEEE* 90:1022-1031.

(56) References Cited

OTHER PUBLICATIONS

Mitzi et al. (2004) "High-Mobility Ulltrathin Semiconducting Films Prepared by Spin Coating," *Nature* 428:299-303.
Moon et al. (2002) "Ink-Jet Printing of Binders for Ceramic Components," *J. Am. Ceram. Soc.* 85:755-762.
Moore et al. (Sep. 9, 2003) "Individually Suspended Single-Walled Carbon Nanotubes in Various Surfactants," *Nano Lett.* 3(10):1379-1382.
Morales et al. (Jan. 9, 1998) "A Laser Ablation Method for the Synthesis of Crystalline Semiconductor Nanowires," *Science* 279:208-211.
Morent et al. (2007) "Adhesion Enhancement by a Dielectric Barrier Discharge of PDMS used for Flexible and Stretchable Electronics," *J. Phys. D. Appl. Phys.* 40:7392-7401.
Mori et al. (1978) "A New Etching Solution System, $H_3PO_4$—$H_2O_2$—$H_2O$, for GaAs and Its Kinetics," *J. Electrochem. Soc.* 125:1510-1514.
Morimoto et al. (2004) "Kindling and Status Epilepticus Models of Epilepsy: Rewiring the Brain," *Progress in Neurobiology.* 73:1-60.
Morkoc et al. (1995) "High-Luminosity Blue and Blue-Green Gallium Nitride Light-Emitting Diodes," *Science* 267:51-55.
Morkved et al. (1994) "Mesoscopic Self-Assembly of Gold Islands on Diblock-Copolymer Films," *Appl. Phys. Lett.* 64:422-424.
Morra et al. (1990) "On the Aging of Oxygen Plasma-Treated Polydimthylsiloxane Surfaces," *J. Colloid Interface Sci.* 137:11-24.
Murakami et al. (2005) "Polarization Dependence of the Optical Absorption of Single-Walled Carbon Nanotubes," *Phys. Rev. Lett.*, 94, 087402.
Murphy et al. (2008) "Modification of Silk Fibroin Using Diazonium Coupling Chemistry and the Effects on hMSC Proliferation and Differentiation," *Biomaterials* 29:2829-2838.
Namazu et al. (2000) "Evaluation of Size Effect on Mechanical Properties of Single Crystal Silicon by Nanoscale Bending Test Using AFM," *J. MEMS* 9:450-459.
Nath et al. (2002) "Nanotubes of the Disulfides of Groups 4 and 5 Metals," *Pure Appl. Chem.* 74(9):1545-1552.
Nathan et al. (2000) "Amorphous Silicon Detector and Thin Film Transistor Technology for Large-Area Imaging of X-Rays,." *Microelectron J.* 31:883-891.
Nathan et al. (2002) "Amorphous Silicon Technology for Large Area Digital X-Ray and Optical Imaging," *Microelectronics Reliability* 42:735-746.
Newman et al. (2004) "Introduction to Organic Thin Film Transistors and Design of n-Channel Organic Semiconductors," *Chem. Mater.* 16:4436-4451.
Nirmal et al. (1999) "Luminescence Photophysics in Semiconductor Nanocrystals," *Acc. Chem. Res.* 32:407-414.
Noda et al. (1996) "New Realization Method for Three-Dimensional Photonic Crystal in Optical Wavelength Region," *Jpn. J. Appl. Phys.* 35:L909-L912.
Nomura et al. (2004) "Room-Temperature Fabrication of Transparent Flexible Thin-Film Transistors Using Oxide Semiconductors," *Nature* 432:488-492.
Nordhausen et al. (1994) "Optimizing Recording Capabilities of the Utah Intracortical Electrode Array," *Brain Research.* 637:27-36.
Novoselov et al. (Oct. 22, 2004) "Electric Field Effect in Atomically Thin Carbon Films," *Science* 306:666-669.
O'Connell et al. (Jul. 26, 2002) "Bang Gap Fluorescence from Individual Single-Walled Caarbon Nanotubes," *Science* 297:593-596.
O'Riordan et al. (2004) "Field Configured Assembly: Programmed Manipulation and Self-Assembly at the Mesoscale," *Nano Lett.* 4:761-765.
Odom et al. (2002) "Improved Pattern Transfer in Soft Lithography Using Composite Stamps," *Langmuir* 18(13):5314-5320.
Office Action and Response, Corresponding to Malaysian Patent Publication No. PI 20052553, dated Mar. 13, 2009 and Dec. 8, 2009.
Office Action and Response, Corresponding to U.S. Appl. No. 11/423,287, dated Feb. 13, 2008.
Office Action and Response, Corresponding to U.S. Appl. No. 11/421,654, dated Sep. 29, 2009.
Office Action and Response, Corresponding to U.S. Appl. No. 11/858,788, dated Jan. 28, 2011.
Office Action Corresponding to Chinese Patent Application No. 200780041127.6, dated Apr. 8, 2011.
Office Action Corresponding to Chinese Patent Application No. 200780049982.1, dated May 12, 2010.
Office Action Corresponding to Chinese Patent Application No. 201010519400.5 dated Nov. 3, 2011.
Office action Corresponding to Korean Patent Application No. 10-2006-7010632, Completed Nov. 22, 2007.
Office Action Corresponding to U.S. Appl. No. 11/851,182, dated Apr. 1, 2010.
Office Action, Corresponding to Chinese Patent Application No. 200780048002.6, dated Apr. 13, 2010.
Office Action, Corresponding to Chinese Patent Application No. 200580013574.1, dated May 11, 2010.
Office Action, Corresponding to Taiwan Patent Application No. 095121212, dated May 7, 2010.
Office Actions and Responses, Corresponding to U.S. Appl. No. 11/145,542, dated between Apr. 5, 2007 and Dec. 23, 2008.
Office Actions and Responses, Corresponding to U.S. Appl. No. 11/981,380, dated Sep. 23, 2010.
Office Actions Corresponding to Chinese Patent Application No. 200480035731.4, dated Mar. 27, 2009 and Dec. 3, 2010.
Office Actions, Corresponding to Chinese Patent Application No. 200580018159.5, dated Jan. 23, 2009 and Feb. 12, 2010.
Ohzono et al. (2004) "Ordering of Microwrinkle Patterns by Compressive Strain," *Phys. Rev. B* 69(13):132202.
Ohzono et al. (Web Release Jul. 7, 2005) "Geometry-Dependent Stripe Rearrangement Processes Induced by Strain on Preordered Microwrinkle Patterns," *Langmuir* 21(16):7230-7237.
Omenetto et al. (2008) "A New Route for Silk," *Nature Photon.* 2:641-643.
Ong et al. (2004) "High-Performance Semiconducting Poolythiophenes for Organic Thin-Film Transistors," *J. Am. Chem. Soc.* 126:3378-3379.
Ong et al. (2005) "Design of High-Performance Regioreular Polythiophenes for Organic Thin-Film Transistors," *Proc. IEEE* 93:1412-1419.
Origin Energy (May 2004) "Fact Sheet—Sliver Cells," www.orginenergy.com.au/sliver.
Ouyang et al. (2002) "High-Performance, Flexible Polymer Light-Emitting Diodes Fabricated by a Continuous Polymer Coating Process," *Adv. Mat.* 14:915-918.
Ouyang et al. (2008) "High Frequency Properties of Electro-Textiles for Wearable Antenna Applications," *IEEE Trans. Antennas Propag.* 56(2):381-389.
Ouyang et al. (Web Release Mar. 20, 2000) "Conversion of Some Siloxane Polymers to Silicon Oxide by UV/Ozone Photochemical Processes," *Chem. Mater.* 12(6):1591-1596.
Overholt et al. (2005) "Photodynamic Therapy for Esophageal Cancer using a 180° Windowed Esophageal Balloon," *Lasers in Surg. Med.* 14:27-33.
Padnick et al. (1999) "Properties of the Flash Visual Evoked Potential Recorded in the Cat Primary Visual Cortex," *Vision Research.* 39:2833-2840.
Pan et al. (2001) "Nanobelts of Semiconducting Oxides," *Science* 291:1947-1949.
Panev et al. (2003) "Sharp Excitation from Single InAs Quantum Dots in GaAs Nanowires," *Appl. Phys. Lett.* 83:2238-2240.
Pardo et al. (2000) "Application of Screen Printing in the Fabrication of Organic Ligh-Emitting Devices," *Adv. Mater.* 12(17):1249-1252.
Park et al. (1997) "Block Copolymer Lithography: Periodic Arrays of ~$10^{11}$ Holes in 1 Square Centimeter," *Science* 276:1401-1404.
Park et al. (1998) "Fabrication of Three-Dimensional Macroporous Membranes with Assemblies of Microspheres as templates," *Chem. Mater.* 10:1745-1747.
Park et al. (Aug. 2009) "Printed Assemblies of Inorganic Light-Emitting Diodes for Deformable and Semitransparent Displays," *Science* 325:977-981.

(56) References Cited

OTHER PUBLICATIONS

Park et al. (Web Release Feb. 22, 2009) "Biodegradable Luminescent Porous Silicon Nanoparticles for in Vivo Applications," *Nature Mater.* 8:331-336.
Parker et al. (2009) "Biocompatible Silk Printed Optical Waveguides," *Adv. Mater.* 21:2411-2415.
Patolsky et al. (2006) "Stimulation, and Inhibition of Neuronal Signals with High-Density Nanowire Transistor Arrays," *Science* 313:1100-1104.
Patton et al. (Mar. 1998) "Effect of Diamond like Carbon Coating and Surface Topography on the Performance of Metal Evaporated Magnetic Tapes," *IEEE Trans Magn.* 34(2) :575-587.
Paul et al. (Apr. 2003) "Patterning Spherical Surfaces at the Two Hundred Nanometer Scale Using Soft Lithography," *Adv. Func. Mater.* 13(4):259-263.
Paullet et al. (1994) "Stable Rotating Waves in Two-Dimensional Discrete Active Media," *SIAM Journal on Applied Mathematics.* 54:1720.
Pearton et al. (1999) "GaN: Processing, Defects, and Devices," *J. Appl. Phys.* 86:1-78.
Peng et al. (Mar. 2, 2000) "Shape Control of CdSe Nanocrystals," *Nature* 404:59-61.
Perry et al. (2008) "Nano- and Micropatterning of Optically Transparent, Mechanically Robust, Biocompatible Silk Fibroin Films," *Adv. Mater.* 20:3070-3072.
Phongphanphanee et al. (2008) "Spatiotemporal Profiles of Field Potentials in Mouse Superior Colliculus Analyzed by Multichannel Recording," *The Journal of Neuroscience.* 28:9309-9318.
Piazza et al. (2005) "Protective Diamond-Like Carbon Coatings for Future Optical Storage Disks," *Diamond Relat. Mater.* 14:994-999.
Pimparkar et al. (Feb. 2007) "Current-Voltage Characteristics of Long-Channel Nanobundle Thin-Film Transistors: A 'Bottom-Up' Perspective," *IEEE Electron Dev. Lett.* 28(2):157-160.
Podzorov et al. (2005) "Hall Effect in the Accumulation Layers on the Surface of Orgaic Semiconductors," *Phys. Rev. lett.* 95:226601.
Polikov (2005) "Response of Brain Tissue to Chronically Implanted Neural Electrodes," *Journal of Neuroscience Methods.* 148:1-18.
Prechtl et al. (1997) "Visual Stimuli Induce Waves of Electrical Activity in Turtle Cortex," *Proc. Nat. Acad. Sci. USA.* 94:7621-7626.
Pushpa et al. (2002) "Stars and Stripes. Nanoscale Misfit Dislocation Patterns on Surfaces," *Pure Appl. Chem.* 74(9):1663-1671.
Qian et al. (2006) "Scaling Effects of Wet Adhesion in Biological Attachment Systems," *Acta Biomaterialia* 2:51-58.
Quake et al (2000) "From Micro- to Nanofabrication with Soft Materials," *Science* 290:1536-1540.
Radtke et al. (Feb. 5, 2007) "Laser-Lithography on Non-Planar Surfaces," *Opt. Exp.* 15(3):1167-1174.
Raman et al. (1989) "Study of Mesa Undercuts Produced in GaAs with $H_3PO_4$-Based Etchants," *J. Electrochem. Soc.* 136:2405-2410.
Randall et al. (2005) "Permeation-driven flow in poly(dimethylsiloxane) microfluidic devices," *Proc. Nat. Acad. Sci. USA* 102(31):10813-10818.
Rao et al. (2003) "Large-scale assembly of carbon nanotubes," *Nature,* 425:36-37.
Razavi et al. (2009) "Three Dimensional Nanopillar Array Photovoltaics on Low Cost and Flexible Substrates," *Nature Materials* 8:648-653.
Razeghi et al. (1994) "High-Power Laser Diode Based on in GaAsP Alloys," *Nature* 369:631-633.
Razouk et al. (Sep. 1979) "Dependence of Interface State Density on Silicon Thermal Oxidation Process Variables," *J. Electrochem. Soc.* 126(9):1573-1581.
Reuss et al. (Jul. 2005) "Macroelectronics: Perspectives on Technology and Applications," *Proc. IEEE* 93(7):1239-1256.
Reuss et al. (Jun. 2006) "Macroelectronics," *MRS Bull.* 31:447-454.
Ribas et al. (1998) "Bulk Micromachining Characterization of 1.2 µm HEMT MMIC Technology for GaAs MEMS Design," *Mater. Sci. Eng. B* 51:267-273.

Ridley et al. (1999) "All-Inorganic Field Effect Transistors Fabricated by Printing," *Science* 286:746-749.
Roberts et al. (1979) "Looking at Rubber Adhesion," *Rubber Chem. Technol.* 52:23-42.
Roberts et al. (Mar. 2006) "Elastically Relaxed Free-Standing Strained-Silicon Nanomembranes," *Nat. Mater.* 5:388-393.
Robinson et al. (1983) "GaAs Readied for High-Speed Microcircuits," *Science* 219:275-277.
Roelkens et al. (Dec. 2005) "Integration of InP/InGaAsP Photodetectors onto Silicon-on-Insulator Waveguide Circuits," *Optics Express* 13(25):10102-10108.
Rogers et al. (1997) "Using an Elastomeric Phase Mask for Sub-100 nm Photolithography in the Optical Near Field," *Appl. Phys. Lett.* 70:2658-2660.
Rogers et al. (1998) "Generating ~90 Nanometer Features Using Near Field Contact Mode Photolithography with an Elastomeric Phase Mask," *J. Vac. Sci. Technol.* 16(1):59-68.
Rogers et al. (1998) "Quantifying Distortions in Soft Lithography," *J. Vac. Sci. Technol.* 16:88-97.
Rogers et al. (1998) "Using Printing and Molding Techniques to Produce Distributed Feedback and Bragg Reflector Resonators for Plastic Lasers," *Appl. Phys. Lett.* 73:1766-1768.
Rogers et al. (1999) "Printing Process Suitable for Reel-to-Reel Production of High-Performance Organic Transistors and Circuits," *Adv. Mater.* 11(9):741-745.
Rogers et al. (2002) "Paper-Like Electronic Displays: Large-Area Rubber-Stamped Plastic Sheets of Electronics and Microencazpsulated Electrophoretic Inks," *Proc. Nat. Acad. Sci. USA* 98:4835-4840.
Rogers et al. (2002) "Printed Plastic Electronics and Paperlike Displays," *J. Polym. Sci. Part A. Polym. Chem.* 40:3327-3334.
Rogers et al. (Mar. 2000) "Organic Smart Pixels and Complementary Inverter Circuits Formed on Plastic Substrates by Casting and Rubber Stamping," *IEEE Electron Dev. Lett.* 21(3):100-103.
Rogers, J. (Jul. 9, 2010) "Farewell to Flatland," *Science* 329:138-139.
Rogers, J.A. (2001) "Rubber Stamping for Plastic Electronics and Fiber Optics," *MRS Bulletin* 26(7):530-534.
Rogers, J.A. (2001) "Toward Paperlike Displays," *Science* 291:1502-1503.
Rosenblatt et al. (2002) "High Performance Electrolyte Gated Carbon Nanotube Transistors," *Nano Lett.* 2(8):869-872.
Rotkin et al. (2003) "Universal Description of Channel Conductivity for Nanotube and Nanowire Transistors," *Appl. Phys. Lett.* 83:1623-1625.
Roundy et al. (2003) "Photonic Crystal Structure with Square Symetry within Each Layer and a Three-Dimensional Band Gap," *Appl. Phys Lett.* 82:3835-3837.
Rubehn et al. (2009) "A MEMS based Flexible Multichannel ECoG-Electrode Array," *J. Neural Eng.* 6:036003.
Ruchehoeft et al. (2000) "Optimal Strategy for Controlling Linewidth on Spherical Focal Surface Arrays," *J. Vac. Sci. Technol. B* 18(6):3185-3189.
Ryu et al. (2009) "Human Cortical Prostheses: Lost in Translation?" *Neurosurg Focus* 27(1):E5.
Samuelson et al. (2004) "Semiconductor Nanowires for Novel One-Dimensional Devices," *Physica E* 21:560-567.
Sangwal et al. (1997) "Nature of multilayer steps on the {100} cleavage planes of MgO single crystals," *Surf. Sci.,* 383:78-87.
Santin et al. (1999) "In vitro Evaluation of the Inflammatory Potential of the Silk Fibroin," *J. Biomed. Mater. Res.* 46:382-389.
Sanyal et al. (2002) "Morphology of Nanostructures Materials," *Pure Appl. Chem.* 74(9):1553-1570.
Sazonov et al. (2005) "Low-Temperature Materials and Thin-Film Transistors for Flexible Electronics," *Proc. IEEE* 93:1420-1428.
Scherlag et al. (1969) "Catheter Technique for Recording His Bundle Activity in Man," *Circulation* 39:13-18.
Schermer et al. (Web Release Apr. 28, 2005) "Thin-Film GaAs Epitaxial Lift-Off Solar Cells for Space Applications," *Prog. Photovoltaics: Res. Applic.* 13:587-596.
Schermer et al. (Web Release Jan. 19, 2006) "Photon Confinement in High-Efficiency, Thin-Film III-V Solar Cells Obtained by Epitaxial Lift-Off," *Thin Solid Films* 511-512:645-653.

(56) References Cited

OTHER PUBLICATIONS

Schevon et al. (2008) "Microphysiology of Epileptiform Activity in Human Neocortex," *Journal of Clinical Neurophysiology.* 25:321-330.
Schindl et al. (2003) "Direct Stimulatory Effect of Low-Intensity 670-nm Laser Irradiation on Human Endothelial Cell Proliferation," *Br. J. Dermatol.* 148:334-336.
Schlegel et al. (2002) "Structures of quartz (1010)- and (1011)-water interfaces determined by X-ray reflectivity and atomic force microscopy of natural growth surfaces," *Geochim. Cosmochim. Acta*, vol. 66, No. 17, pp. 3037-3054.
Schmid et al. (2003) "Preparation of metallic Films on Elastomeric Stamps and Their Application on Contact Processing and Contact Printing," *Adv. Funct. Mater.* 13:145-153.
Schmid et al. (Mar. 25, 2000) "Siloxane Polymers for High-Resolution, High-Accuracy Soft Lithography," *Macromolecules* 33(8):3042-3049.
Schmid et al. (May 11, 1998) "Light Coupling Masks for Lensless, Sub-wavelength Optical Lithography," *Appl. Phys. Lett.* 72(19):2379-2381.
Schmidt et al. (1993) "Biocompatibility of Silicon-Based Electrode Arrays Implanted in Feline Cortical Tissue," *Journal of Biomedical Materials Research.* 27:1393-1399.
Schmidt et al. (Mar. 8, 2001) "Thin Solid Films Roll up into Nanotubes," *Nature* 410:168.
Schneider et al. (2008) "Mechanical Properties of Silicones for MEMS," *J. Micromech. Microeng.* 18:065008.
Schon et al. (1995) "Ambipolar Pentacene Field-Effect Transistors and Inverters," *Science* 287:1022-1023.
Schrieber et al. (1998) "The Effectiveness of Silane Adhesion Promotors in the Performance of Polyurethane Adhesives," *J. Adhesion* 68:31-44.
Schnable et al. (1969) "Aluminum Metallization; Advantages and Limitations for Integrated Circuit Applications," *IEEE* 57:1570-1580.
Scorzoni et al. (Oct. 4, 2004) "On the Relationship Between the Temperature coefficient of Resistance and the Thermal Conductance of Integrated Metal Resistors," *Sens Actuators A* 116(1):137-144.
Search and Examination Report, Corresponding to Singapore Application No. 200904208-6, dated Dec. 17, 2010.
Search Report and Examination Report Corresponding to Singapore Patent Application No. 200901178-4, Completed Mar. 13, 2010.
Search Report and First Written Opinion, Corresponding to Singapore Patent Application No. 200902530-5, dated Jun. 10, 2010.
Search Report and Written Opinion, Corresponding to Singapore Application No. 200901451-5, dated Dec. 22, 2010.
Search Report Corresponding to Singapore Patent Application No. SG 200607372-0, dated Oct. 17, 2007.
Search Report Corresponding to Taiwanese Patent Application No. 095121212, Completed Oct. 8, 2010.
Search Report, Corresponding to Republic of China (Taiwan) Patent Application No. 094118507, dated Feb. 24, 2007.
Seidel et al. (2004) "High-Current Nanotube Transistors," *Nano Lett.*, vol. 4, No. 5, pp. 831-834.
Sekitani et al. (2005) "Bending Experiment on Pentacene Fiield-Effect Transistors on Plastic Films," *Appl. Phys. Lett.* 86:073511.
Sekitani et al. (2007) "A Large-Area Wireless Power-Transmission Sheet Using Printed Organic Transistors and Plastic MEMS Switches," *Nat. Materials.* 6:413-417.
Sekitani et al. (2009) "Stretchable Active-Matrix Organic Light-Emitting Diode Display Using Printable Elastic Conductors," *Nature Mater.* 8:494-499.
Sekitani et al. (Sep. 12, 2008) "A Rubberlike Stretchable Active Matrix Using Elastic Conductors," *Science* 321:1468-1472.
Sen et al. (2002) "Nonequilibrium Processes for Generating Silicon Nanostructures in Single-Crystalline Silicon," *Pure Appl. Chem.* 74(9):1631-1641.
Serikawa et al. (May 1, 2000) "High-Mobility Poly-Si Thin Film Transistors Fabricated on Stainless-Steel Foils by Low-Temperature Processes Using Sputter-Depositions," *Jpn. J. Appl. Phys.* 39:L393-L395.
Servanti et al. (2005) "Functional Pixel Circuits for Elastic AMOLED displays," *Proc. IEEE* 93:1257-1264.
Service, R.F. (Aug. 15, 2003) "Electronic Textiles Charge Ahead," *Science* 301:909-911.
Shan et al. (2004) "From Si Source Gas Directly to Positioned, Electrically Contained Si Nanowires: The Self-Assembling 'Grow-in-Place' Approach," *Nano Lett.* 4(11):2085-2089.
Sharp et al. (2003) "Holographic Photonic Crystals with Diamond Symmetry," *Phys. Rev. B* 68:205102/1-205102/6.
Sheraw et al. (2002) "Organic Thin-Film Transistor-Driven Polymer-Dispersed Liquid Crystal Displays on Flexible Polymeric Substrates," *Appl. Phys. Lett.* 80:1088-1090.
Shetty et al. (2005) "Formation and Characterization of Silicon Films on Flexible Polymer Substrates," *Mater. Lett.* 59:872-875.
Shi et al. (2001) "Free-Standing Single Crystal Silicon Nanoribbons," *J. Am. Chem. Soc.* 123(44):11095-11096.
Shi et al. (Sep. 2000) "Synthesis of Large Areas of Highly Oriented, Very Long Silicon Nanowires," *Adv. Mater.* 12(18):1343-1345.
Shin et al. (2003) "PDMS-Based Micro PCR Chip with Parylene Coating," *J. Micromech. Microeng.* 13:768-774.
Shtein et al. (Oct. 15, 2004) "Direct Mask-Free Patterning of Molecular Organic Semiconductors Using Organic Vapor Jet Printing," *J. Appl. Phys.* 96(8):4500-4507.
Shull et al. (1998) "Axisymmetric Adhesion Tests of Soft Materials," *Macromol. Chem. Phys.* 199:489-511.
Siegel et al. (2009) "lightweight, Foldable Thermochromic Displays on Paper," *Lab Chip* 9:2775-2781.
Siegel et al. (2010) "Foldable Printed Circuit Boards on Paper Substrates," *Adv. Funct. Mater.* 20:28-35.
Siegel et al. (Web Release Feb. 7, 2007) "Microsolidics: Fabrication of Three-Dimensional Metallic Microstructures in Poly(dimethylsiloxane)," *Adv. Mater.* 19(5):727-733.
Sim et al. (1993) "An Analytical Back-Gate Bias Effect Model for Ultrathin SOI CMOS Devices," *IEEE Trans. Elec. Dev.* 40:755-765.
Sirringhaus et al. (2003) "Inkjet Printing of Functional Materials," *MRS Bull.* 28:802-806.
Sirringhaus et al. (Dec. 15, 2000) "High-Resolution Inkjet Printing of All-Polymer Transistor Circuits," *Science* 290:2123-2126.
Sirringhaus, H. (2005) "Device Physics of Solution-Processed Organic Field-Effect Transistors," *Adv. Mater.* 17:2411-2425.
Smay et al. (2002) "Colloidal Inks for Directed Assembly of 3-D Periodic Structures," *Langmuir* 18:5429-5437.
Smith et al. (2000) "Electric-Field Assisted Assembly and Alignment of Metallic Nanowires," *Appl. Phys. Lett.* 77(9):1399-1401.
Snow et al. (2003) "Random networks of carbon nanotubes as an electronic material," *Appl. Phys. Lett.*, vol. 82, No. 13, pp. 2145-2147.
Snow et al. (2005) "High-mobility carbon-nanotube transistors on a polymeric substrate," *Appl. Phys. Lett.*, 86, 033105.
So et al. (2008) Organic Light-Emitting Devices for Solid-State Lighting, *MRS Bull.* 33:663-669.
Sofia et al. (2001) "Functionalized Silk-Based Biomaterials for Bone Formation," *J. Biomed. Mater. Res.* 54:139-148.
Someya et al. (2005) "Conformable, Flexible, Large-Area Networks of Pressure and Thermal Sensors with Organic Transistor Active Matrixes," *Proc. Nat. Acad. Sci. USA* 102:12321-12325.
Someya et al. (2005) "Integration of Organic FETs with Organic Photodiodes for a Large Area, Flexible, and Lightweight Sheet Image Scanners," *IEEE Trans. Electron Devices* 52:2502-2511.
Someya et al. (Jul. 6, 2004) "A Large-Area, Flexible, Pressure Sensor Matric with Organic Field-Effect Transistors for Artificial Skin Applications," *Proc. Nat. Acad. Sci. USA* 101(27):9966-9970.
Someya, T. (Aug. 7, 2008) "Electronic Eyeballs," *Nature* 454:703-704.
Soole et al. (Mar. 1991) "InGaAs Metal-Semiconductor-Metal Photodetectors for Long Wavelength Optical Communications," *IEEE J. Quantum Electron.* 27(3):737-752.

(56) References Cited

OTHER PUBLICATIONS

Soong et al. (1984) "Adverse Reactions to Virgin Silk Sutures in Cataract Surgery," *Ophthalmology* 91:479-483.
Srinivasan et al. (Web Release Mar. 26, 2007) "Piezoelectric/Ultrananocrystalline Diamond Heterostructures for High-Performance Multifunctional Micro/Nanoelectromechanical Systems," *Appl. Phys. Lett.* 90:134101.
Stafford et al. (Aug. 2004) "A Buckling-Based Metrology for Measureing the Elastic Moduli of Polymeric Thin Films," *Nature Mater.* 3:545-550.
Star et al. (2004) "Nanotube Optoelectric Memory Devices," *Nano Lett.*, vol. 4, No. 9, pp. 1587-1591.
Stead et al. (2010) "Microseizures and the Spatiotemporal Scales of Human Partial Epilepsy," *Brain: A Journal of Neurology.* 133:2789-2797.
STELLA Project-Stretchable Electronics for Large-Area Applications. Available at www.stella-project.de. Accessed Feb. 8, 2012.
Stieglitz (2001) "Flexible Biomedical Microdevices with Double-Sided Electrode Arrangements for Neural Applications," *Sensor. Actuat. A: Phys.* 90:203-211.
Stieglitz. (2002) "Flexible BIOMEMS with Electrode Arrangements on Front and Back Side as Key Component in Neural Prostheses and Biohybrid Systems," Sensors and Actuators B: Chemical 83, 8-14(2002).
Storm et al. (Aug. 2003) "Fabrication of Solid-State Nanopores with Single-Nanometre Precision," *Nat. Mater.* 2:537-540.
Streetman et al. (2000) "Intrinsic Material," In; *Solid State Electronic Devices*, 5$^{th}$ Ed., Prentice Hall; Upper Saddle River, NJ; pp. 74-75.
Strukov et al. (2005) "CMOL FPGA: A Reconfigurable Architecture for Hybrid Digital Circuits with Two-Terminal Nanodevices," *Nanotechnology* 16:888-900.
Su et al. (2000) "Lattice-Oriented Growth of Single-Walled Carbon Nanotubes," *J. Phys. Chem. B* 104(28):6505-6508.
Sum et al. (2009) "Near-Infrared Spectroscopy for the Detection of Lipid Core Coronary Plaques," *Curr. Cardiovasc. Imag. Rep.* 2:307-315.
Sumant et al. (Apr. 2005) "Toward the Ultimate Tribological Interface: Surface Chemistry and Nanotribology of Ultrananocrystalline Diamond," *Adv. Mater.* 17(8):1039-1045.
Sun et al. (2004) "Fabricating Semiconductor Nano/Microwires and Transfer Printing Ordered Arrays of Them onto Plastic Substrates," *Nano Lett.* 4:1953-1959.
Sun et al. (2005) "Advances in Organic Field-Effect Transistors," *J. Mater. Chem.* 15:53-65.
Sun et al. (2005) "Bendable GaAs Metal-Semiconductor Field-Effect Transistors Formed with a Printed GaAs Wire Arrays on Plastic Substrates," *Appl. Phys. Lett.* 87:083501.
Sun et al. (2005) "Photolithographic Route to the Fabrication of Micro/Nanowires of III-V Semiconductors," *Adv. Fuct. Mater.* 15:30-40.
Sun et al. (2007) "Controlled Buckling of Semiconductor Nanoribbons for Stretchable Electronics," *Nat. Nanotechnol.* 1:201-207.
Sun et al. (2007) "Inorganic Semiconductors for Flexible Electronics," *Adv. Mater.* 19:1897-1916.
Sun et al. (2007) "Structural Forms of Single Crystal Semiconductor Nanoribbons for High-Performance Stretchable Electronics," *J. Mater Chem.* 17:832-840.
Sun et al. (Aug. 2007) "Inorganic Semiconductors for Flexible Electronics," *Adv. Mater.* 19(15):1897-1916.
Sun et al. (Nov. 2006) "Buckled and Wavy Ribbons of GaAs for High-Performance Electronics on Elastomeric Substrates," *Adv. Mater.* 18(21):2857-2862.
Sundar et al. (2004) "Elastomeric Transistor Stamps: Reversible Probing of CHaarge Transport in Organic Crystals," *Science* 303:1644-1646.
Suo et al. (Feb. 22, 1999) "Mechnics of Rollable and Foldable Film-on-Foil Electronics," *Appl. Phys. Lett.* 74(8):1177-1179.
Supplementary European Search Report Corresponding to European Patent Application No. 07 84 1968, Completed Mar. 31, 2011.
Supplementary European Search Report Corresponding to European Patent Application No. 12 79 2485, Completed Sep. 25, 2014; dated Oct. 2, 2014.
Supplementary European Search Report, Corresponding to European Application No. 04 81 2651, Completed Oct. 19, 2010.
Supplementary European Search Report, Corresponding to European Application No. 05 75 6327, Completed Sep. 25, 2009.
Supplementary European Search Report, Corresponding to European Application No. 10 84 2518, Completed Aug. 9, 2013.
Swain et al. (2004) "Curved CCD Detector Devices and Arrays for Multi-Spectral Astrophysical Application and Terrestrial Stereo Panoramic Cameras," *Proc. SPIE* 5499:281-301.
Sze et al. (1985) *Semiconductor Devices, Physics and Technology*, 2$^{nd}$ ed., Wiley, New York, pp. 190-192.
Sze, S. (1985) *Semiconductor Devices: Physics and Technology*, New York: Wiley, pp. 428-467.
Sze, S. (1988) *VLSI Technology*, Mcgraw-Hill, 327-374, 566-611.
Sze, S. (1994) *Semiconductor Sensors*, John Wiley and Sons: New York, pp. 17-95.
Takamoto et al. (Jan. 20, 1997) "Over 30% Efficient InGaP/GaAs Tandem Solar Cells," *Appl. Phys. Lett.* 70(3):381-383.
Talapin et al. (Oct. 7, 2005) "PbSe Nanocrystal Solids for n- and p-Channel Thin Film Field-Effect Transistors," *Science* 310:86-89.
Tamminen et al. (2010) "Sleep Spindle Activity is Associated with the Integration of New Memories and Existing Knowledge," *Journal of Neuroscience.* 30:14356-14360.
Tan et al. (Apr. 12, 2004) "Performance Enhancement of InGaN Light Emitting Diodes by Laser-Lift-off and Transfer from Sapphire to Copper Substrate," *Appl. Phys. Lett.* 84(15):2757-2759.
Tanase et al. (2002) "Magnetic Trapping and Self-Assembly of Multicomponent Nanowires," *J. Appl. Phys.* 91:8549-8551.
Tang et al. (2005) "One-Dimensional Assemblies of Nanoparticles: Preparation, Properties, and Promise," *Adv. Mater.* 17:951-962.
Tao et al. (2003) "Langmuir-Blodgett Silver Nanowire Monolayers for Molecular Sensing Using Surface-Enhanced Raman Spectroscopy," *Nano Lett.* 3:1229-1233.
Tate et al. (2000) "Anodization and Microcontact Printing on Electroless Silver: Solution-Based Fabrication Procedures for Low-Voltage Electronic Systems with Organic Active Components," *Langmuir* 16:6054-6060.
Taylor et al. (2004) "Reassessment of Brain Elasticity for Analysis of Biomechanisms of Hydrocephalus," *Journal of Biomechanics.* 37:1263-1269.
Teshima et al. (2001) "Room-Temperature Deposition of High-Purity Silicon Oxide Films by RF Plasma-Enhanced CVD," *Surf. Coat. Technol.* 146-147:451-456.
Theiss et al. (1998) "PolySilicon Thin Film Transistors Fabricated at 100° C on a Flexible Plastic Substrate," *IEDM* 98:257-260.
Thompson et al. (2004) "A 90-nm Logic Technology Featuring Strained-Silicon. IEEE Transactions on Electron Devices," 51:1790-1797.
Thornwood et al. (Oct. 1, 1990) "Utilizing Olptical Lithography in the Sub-Micron Dimensional Regime," *IBM Tech. Disc. Bull.* 33(5):187-188.
Tibshirani et al. (2001) "Estimating the Number of Clusters in a Data Set via the Gap Statistic," Journal of the Royal Statistical Society: Series B 63:411-423.
Timko et al. (2009) "Electrical Recording from Hearts with Flexible Nanowire Device Arrays," *Nano Lett.* 9:914-918.
Toader et al. (2004) "Photonic Band Gap Architectures for Holographic Lithography," *Phy. Rev. Lett.* 043905/1-043905/4.
Toader et al. (2004) "Photonic Band Gaps Based on Tetragonal Lattices of Slanted Pores," *Phys. Rev. Lett.* 90:233901/1-233901/4.
Tong (1999) *Semiconductor Wafer Bonding: Science and Technology*, John Wiley; New York, pp. 187-221.
Trau et al. (1997) "Microscopic Patterning of Orientated Mesoscopic Silica Through Guided Growth," *Nature* 390:674-676.
Trentler et al. (1995) "Solution-Liquid-Solid Growth of Crytalline III-V Semiconductors: An Analogy to Vapor-Liquid-Solid Growth," *Science* 270:1791-1794.
Tseng et al. (Web Release Dec. 19, 2003) "Monolithic Integration of Carbon Nanotube Devices with Silicon MOS Technology" *Nano Lett.* 4(1):123-127.

(56) References Cited

OTHER PUBLICATIONS

Tusa et al. (1979) "Retinotopic Organization of Areas 18 and 19 in the Cat," *The Journal of Comparative Neurology.* 185:657-78.
Ucjikoga, S. (2002) "Low-Temperature Polycrystalline Silicon Thin-Film Transistor Technologies ofr System-on-Glass Displays," *MRS Bull.* 27:881-.
Urruchi et al. (2000) "Etching of DLC Films Using a Low Intensity Oxygen Plasma Jet," *Diamond Relat. Mater.* 9:685-688.
Van Essen et al. (1984) "The Visual Field Representation in Striate Cortex of the Macaque Monkey: Asymmetries, Anisotropies, and Individual Variability," *Vision Research.* 24, 429-48.
Vanhollenbeke et al. (2000) "Compliant Substrate Technology: Integration of Mismatched Materials for Opto-Electronic Applications," *Prog. Cryst. Growth Charact. Mater.* 41(1-4):1-55.
Velev et al. (1997) "Porous silica via colloidal crystallization," *Nature* 389:447-448.
Vepari et al. (Aug. Sep. 2007) "Silk as a Biomaterial," *Prog. Polym. Sci.* 32(8-9):991-1007.
Vilan et al. (2000) "Molecular Control Over Au/GaAs Diodes," *Nature* 404:166-168.
Vinck et al. (2003) "Increased Fibroblast Proliferation Induced by Light Emitting Diode and Low Power Laser Irradiation," *Lasers Med. Sci.* 18:95-99.
Viventi et al. (Mar. 2010) "A Conformal, Bio-Interfaced Class of Silicon Electronics for Mapping Cardiac Electrophysiology," *Sci. Trans. Med.* 2(24):24ra22.
Viventi et al. (published online Nov. 13, 2011) "Flexible, Foldable, Actively Multiplexed, High-Density Electrode Array for Mapping Brain Activity In Vivo," *Nature Neuroscience.* 14:1599-1605.
Vlasov et al. (2001) "On-Chip Natural Assembly of Silicon Photonic Bandgap Crystals," *Nature* 414:289-293.
Voss, D. (2000) "Cheap and Cheerful Circuits," *Nature* 407:442-444.
Wagner et al. (2003) "Silicon for Thin-Film Transistors," *Thin Solid Films* 430:15-19.
Wagner et al. (2005) "Electronic Skin: Architecture and Components," *Physica E* 25:326-334.
Wagner et al. (Mar. 1, 1964) "Vapor-Liquid-Solid Mechanism of Single Crystal Growth," *Appl. Phys. Lett.* 4(5):89-90.
Waksman et al.(2008) "Photopoint Photodynamic Therapy Promotes Stabilization of Atherosclerotic Plaques and Inhibits Plaque Progression," *J. Am. Coll. Cardiol.* 52:1024-1032.
Wang et al. (2003) "A Solution-Phase, Precursor Route to Polycrystalline $SnO_2$ Nanowores that can be Used for Gas Sensing under Ambient Conditions," *J. Am. Chem. Soc.* 125:16176-16177.
Wang et al. (2005) "Electronically Selective Chemical Functionalization of Carbon Nanotubes: Correlation between Raman Spectral and Electrical Responses," *J. Am. Chem. Soc.*, 127:11460-11468.
Wang et al. (2005) "Oxidation Resistant Germanium Nanowires: Bulk Synthesis, Long Chain Alkanethiol Functionalization, and Langmuir-Blodgett Assembly," *J. Am. Chem. Soc.* 127(33):11871-11875.
Wang et al. (2006) "Direct Synthesis and Characterization of CdS Nanobelts," *Appl. Phys. Lett.* 89:033102.
Wang et al. (Aug.-Sep. 2008) "In Vivo Degradation of Three-Dimensional Silk Fibroin Scaffolds," *Biomaterials* 29(24-25):3415-3428.
Waxman et al. (2009) "In vivo Validation of a Catheter-Based Near-Infrared Spectroscopy System for Detection of Lipid Core Coronary Plaques: Initial Results of the Spectacl Study," *J. Am. Coll. Cardiol. Img.* 2:858-868.
Waxman, S. (2008) "Near-Infrared Spectroscopy for Plaque Characterization," *J. Interv. Cardiol.* 21:452-458.
Weber et al. (Jan. 2004) "A Novel Low-Cost, High Efficiency Micromachined Silicon Solar Cell," *IEEE Electron Device Lett.* 25(1):37-39.
Wen et al. (Web Release Dec. 4, 2004) "Controlled Growth of Large-Area, Uniform, Vertically Aligned Arrays of $\alpha$-$Fe_2O_3$ Nanobelts and Nanowires," *J. Phys. Chem. B* 109(1):215-220.

Whang et al. (2003) "Large-Scale Hierarchical Organization of Nanowire Arrays for Integrated Nanosystems," *Nano Lett.* 3(9):1255-1259.
Williams et al. (Oct. 2006) "Growth and Properties of Nanocrystalline Diamond Films," *Phys. Stat. Sol. A* 203(13):3375-3386.
Williams et al. (Web Release Jan. 23, 2006) "Comparison of the Growth and Properties of Ultranocrystalline Diamond and Nanocrystalline Diamond," *Diamond Relat. Mater.* 15:654-658.
Willner et al. (2002) "Functional Nanoparticle Architectures for Senoric, Optoelectronic, and Bioelectronic Applications," *Pure Appl. Chem.* 74(9):1773-1783.
Wilson et al. (2006) "ECoG Factors Underlying Multimodal Control of a Brain-Computer Interface," *IEEE Trans. Neural Syst. Rehabil. Eng.* 14:246-250.
Wind et al. (May 20, 2002) "Vertical Scaling of Carbon Nanotube-Field-Effect Transistors Using Top Gate Electrodes," *Appl. Phys. Lett.* 80(20):3871-3819.
Wise et al. (Jul. 2008) "Microelectrodes, Microelectronics, and Implantable Neural Microsystems," *Proc. IEEE* 96(7):1184-1202.
Witkowski et al. (1998) "Spatiotemporal Evolution of Ventricular Fibrillation," *Nature.* 392:78-82.
Won et al. (2004) "Effect of Mechanical and Electrical Stresses on the Performance of an a-Si:H TFT on Plastic Substrate," *J. Electrochem. Soc.* 151:G167-G170.
Wong-Riley et al. (2005) "Photobiomodulation Directly Benefits Primary Neurons Functionally Inactivated by Toxins," *J. Biol. Chem.* 280:4761-4771.
Woodburn et al. (1996) "Phototherapy of Cancer and Atheromatous Plaque with Texaphyrins," *J. Clin. Laser Med. Surg.* 14:343-348.
Worrell et al. (2008) "High-Frequency Oscillations in Human Temporal Lobe: Simultaneous Microwire and Clinical Macroelectrode Recordings," *Brain: A Journal of Neurology.* 131:928-37.
Wu et al. (2001) "Amorphous Silicon Crystallization and Polysilicon Thin Film Transistors on SiO2 Passivated Steel Foil Substrates," *Apple. Surf. Sci* 175-176:753-758.
Wu et al. (2001) "Direct Observation of Vapor-Liquid-Solid Nanowire Growth," *J. Am. Chem. Soc.* 123(13):3165-3166.
Wu et al. (2001) "Thermal Oxide of Polycrystalline Silicon on Steel Foil as a Thin-Film Transitor Gate Dielectric," *Appl. Phys. Lett.* 78:3729-2731.
Wu et al. (2002) "Block-by-Block Growth of Single-Crystalline Si/SiGe Superlattice Nanowires," *Nano Lett.* 2(2):83-86.
Wu et al. (2002) "Growth of Au-Catalyzed Ordered GaAs Nanowire Arrays by Molecular-Beam Epitaxy," *Appl. Phys. Lett.* 81:5177-5179.
Wu et al. (2002) "Inorganic Semiconductor Nanowires: Rational Growth, Assembly, and Novel Properties," *Chem. Eur. J.* 8(6):1261-1268.
Wu et al. (2003) "Growth, Branching, and Kinking of Molecular-Beam Epitaxial (110) GaAs Nanowires," *Appl. Phys. Lett.* 83:3368-3370.
Wu et al. (Jul. 1, 2004) "Single-Crystal Metallic Nanowires and Metal/Semiconductor Nanowire Heterostructures," *Nature* 430:61-65.
Wu et al. (Nov. 2002) "Complementary Metal-Oxide-Semiconductor Thin-Film Transistor Circuits from a High-Temperature Polycrystalline Silicon Process on Steel Foil Substrates," *IEEE Trans. Electr. Dev.* 49(11):1993-2000.
Xia (1998) "Soft Lithography" *Angew. Chem. Int. Ed.* 37:551-575.
Xia et al. (1996) "Shadowed Sputtering of Gold on V-Shaped Microtrenches Etched in Silicon and Applications in Microfabrication," *Adv. Mater.* 8(9):765-768.
Xia et al. (1998) "Soft Lithography," *Annu. Rev. Mater. Sci.* 28:153-184.
Xia et al. (1999) "Unconventional Methods for Fabricating and Patterning Nanostructures," *Chem. Rev.* 99:1823-1848.
Xia et al. (2003) "One-Dimensional Nanostructures: Synthesis, Characterization and Applications," *Adv. Mater.* 15:353-389.
Xia et al. (Jul. 19, 1996) "Complex Optical Surfaces Formed by Replica Molding Against Elastomeric Masters," *Science* 273:347-349.
Xiang et al. (Mar. 25, 2006) "Ge/Si Nanowire Heterostructures as High-Performance Field-Effect Transistors," *Nature* 441:489-493.

(56) References Cited

OTHER PUBLICATIONS

Xiao et al. (2003) "High-mobility thin-film transistors based on aligned carbon nanotubes," *Appl. Phys. Lett.*, vol. 83, No. 1, pp. 150-152.
Xie et al. (May 2003) "Polymer-Controlled Growth of $Sb_2Se_3$ Nanoribbons via a Hydrothermal Process," *J. Cryst. Growth* 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26(16):3123-3129.
Yanagisawa et al. (2009) "Neural Decoding Using Gyral and Intrasulcal Electrocorticograms," *NeuroImage*. 45:1099-1106.
Yang et al. (1997) "Mesoporous Silica with Micrometer-Scale Desgns," *Adv. Mater*. 9:811-814.
Yang et al. (2000) "Stability of Low-Temperature Amorphous Silicon Thin Film Transistors Formed on Glass and Transparent Plastic Substrates," *J. Vac. Sci. Technol. B* 18:683-689.
Yang et al. (2002) "Creating Periodic Three-Dimensional Structures by Multibeam Interface of Visible Laser," *Chem. Mater*. 14:2831-2833.
Yang et al. (Dec. 2007) "RFID Tag and RF Structures on a Paper Substrate Using Inkjet-Printing Technology," *IEEE Trans. Microw. Theory Tech*. 55(12):2894-2901.
Yang, P. (2005) "The Chemistry and Physics of Semiconductor Nanowires," *MRS Bull*. 30:85-.
Yanina et al. (2002) "Terraces and ledges on (001) spinel surfaces," *Surf. Sci*., 513:L402-L412.
Yao et al. (2008) "Seeing Molecules by Eye: Surface Plasmon Resonance Imaging at Visible Wavelengths with High Spatial Resolution and Submonolayer Sensitivity," *Angew. Chem*. 47:5013-5017.
Yao et al. (2010) "Functional Nanostructured Plasmonic Materials," *Adv. Mater*. 22:1102-1110.
Yao et al. (Mar. 2000) "High-Field Effect Electrical Transport in Single-Walled Carbon Nanotubes," *Phys. Rev. Lett*. 84(13):2941-2944.
Yeager et al. (Aug. 30, 2008) "Characterization of Flexible ECoG Electrode Arrays for Chronic Recording in Awake Rats," *J. Neurosci. Methods* 173(2):279-285.
Yeh et al. (1994) "Fluidic Self-Assembly for the Integration of GaAs Light Emitting Diodes on Si Substrates," *IEEE Photon. Techn. Lett*. 6:706-708.
Yin et al. (2000) "A Soft Lithography Approach to the Fabrication of Nanostructures of Single Crystalline Silicon with Well-Defined Dimensions and Shapes," *Adv. Mater*. 12:1426-1430.
Yin et al. (2005) "Colloidal Nanocrystal Synthesis and the Organic-Inorganic Interface," *Nature* 437:664-670.
Yoon et al. (2005) "Low-Voltage Organic Field-Effect Transistors and Inverters Enabled by Ultrathin Cross-Linked Polymers as Gate Dielectrics," *J. Am. Chem. Soc*. 127:10388-10395.
Yu et al. (2000) "Silicon Nanowires: Preparation, Device Fabrication, and Transport Properties," *J. Phys. Chem. B* 104(50):11864-11870.
Yu et al. (2003) "Solution-Liquid-Solid Growth of Soluble GaAs Nanowires," *Adv. Mater*. 15:416-419.
Yu et al. (2003) ,, Two-Versus Three-Dimensional Quantum Confinement in Indium Phosphide Wires and Dots, *Nat. Mater*. 2:517-520.
Yu et al. (2004) "The Yield Strength of Thin Copper Films on Kapton," *J. Appl. Phys*. 95:2991-2997.
Yu et al. (2009) "Monitoring Hippocampus Electrical Activity In Vitro on an Elastically Deformable Microelectrode Array," *Journal of Neurotrauma*. 26:1135-1145.
Yuan et al. (2006) "High-Speed Strained-Single-Crystal-Silicon Thin-Film Transistors on Flexible Polymers," *J. Appl. Phys*. 100:013708.
Yurelki et al. (Jul. 24, 2004) "Small-Angle Neutron Scattering from Surfactant-Assisted Aqueous Dispersions of Carbon Nanotubes," *J. Am. Chem. Soc*. 126(32):9902-9903.
Zakhidov et al. (1998) "Carbon Structure with Three-Dimensional Periodicity at Optical Wavelengths," *Science* 282:897-901.
Zaumseil et al. (2003) "Nanoscale Organic Transistors that use Source/Drain Electrodes Supported by High Resolution Rubber Stamps," *Appl. Phys. Lett*. 82(5):793-795.
Zaumseil et al. (2003) "Three-Dimensional and Multilayer Nanostructures Formed by Nanotransfer Printing," *Nano Lett*. 3(9):1223-1227.
Zhang et al. (2001) "Electric-field-directed growth of aligned single-walled carbon nanotubes," *Appl. Phys. Lett*., vol. 79, No. 19. pp. 3155-3157.
Zhang et al. (2005) "Low-Temperature Growth and Photoluminescence Property of ZnS Nanoribbons," *J. Phys. Chem. B* 109(39):18352-18355.
Zhang et al. (2006) "Anomalous Coiling of SiGe/Si and SiGe/Si/Cr Helical Nanobelts," *Nano Lett*. 6(7):1311-1317.
Zhang et al. (Apr. 2003) "Oxide-Assisted Growth of Semiconducting Nanowires," *Adv. Mater*. 15(7-8):635-640.
Zhang et al. (Apr. 5, 2004) "Structure and Photoiluminescence of ZnSe Nanoribbons Grown by Metal Organic Chemical Vapor Deposition," *Appl. Phys. Lett*. 84(14):2641-2643.
Zhang et al. (Feb. 9, 2006) "Electronic Transport in Nanometre-Scale Silicon-on-Insulator Membranes," *Nature* 439:703-706.
Zhao et al. (Mar. 2007) "Improved Field Emission Properties from Metal-Coated Diamond Films," *Diamond Relat Mater*. 16(3):650-653.
Zheng et al. (1998) "Sudden Cardiac Death in the United States, 1989 to 1998," *Circulation* 104, 2158-2163 (1998.
Zheng et al. (2004) "Shape-and Solder-Directed Self-Assembly to Package Semiconductor Device Segments," *Appl. Phys. Lett*. 85:3635-3637.
Zheng et al. (Aug. 31, 2004) "Sequential Shape-and-Solder-Directed Self Assembly of Functional Microsystems," *Proc. Natl. Acad. Sci. USA* 101(35):12814-12817.
Zhou et al. (2002) "An Efficient Two-Photon-Generated Photoacid Applied to Positive-Tone 3D Microfabrication," *Science* 296:1106-1109.
Zhou et al. (2004) "p-Channel, n-Channel Thin Film Transistors and p-n Diodes Based on Single Wall Carbon Nanotube Networks," *Nano Lett*. 4:2031-2035.
Zhou et al. (2005) "Band Structure, Phonon Scattering, and the Performance Limit of Single-Walled Carbon Nanotube Transistors," *Phys. Rev. Lett*. 95:146805.
Zhou et al. (2005) "Mechanism for Stamp Collapse in Soft Lithography," *Appl. Phys. Lett*. 87:251925.
Zhu et al. (2005) "Spin on Dopants for High-Performance Single Crystal Silicon Transistors on Flexible Plastic Substrates," *Appl. Phys. Lett*. 86(133507)1-3.
Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," *Circulation* 114:385-484.

Fig. 2A
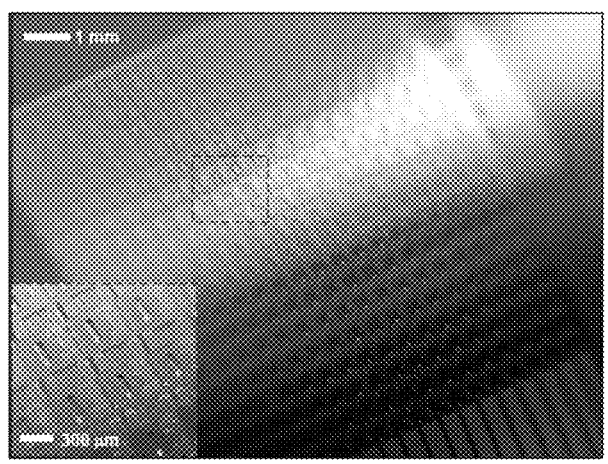
Fig. 2B
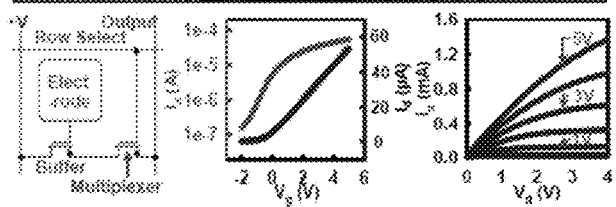
Fig. 2C
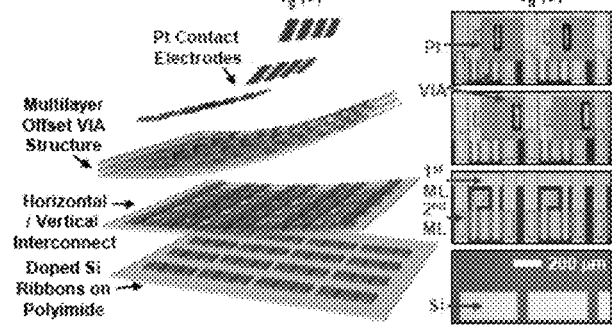
Fig. 2D
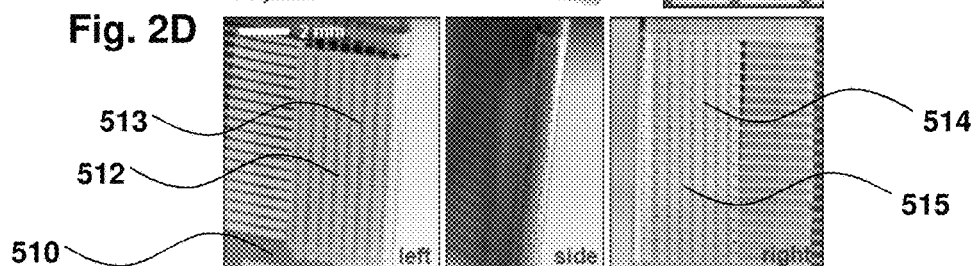
Fig. 2E
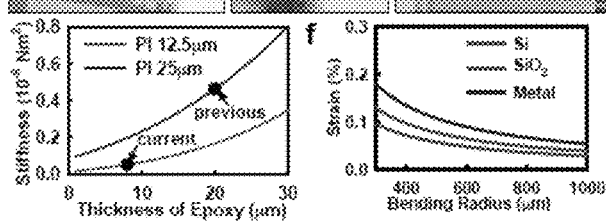
Fig. 2F 65 ms ▬▬▬▬▬▬▬ 145 ms ☐ = Prediction Incorrect
▨ = Prediction off by 1 square
■ = Prediction Correct Fig. 6B Right Angle Wave

I

-3.0 mV ▬▬▬ 3.0 mV    Frame interval 10.8 ms

Clockwise Spiral

II

-0.5 mV ▬▬▬ 1.7 mV    Frame interval 14.4 ms

Planar Wave L→R

III

-1.0 mV ▬▬▬ 3.4 mV    Frame interval 10.8 ms

Counterclockwise Spiral

IV

-0.8 mV ▬▬▬ 1.7 mV    Frame interval 25.2 ms

Planar Wave L←R

V

-2.4 mV ▬▬▬ 3.4 mV    Frame interval 10.8 ms

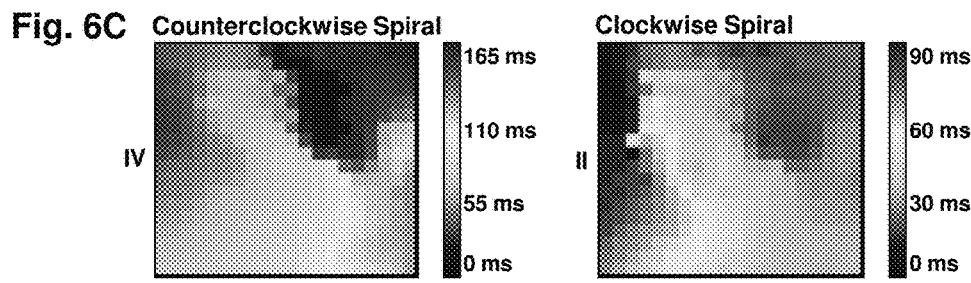
Fig. 6C Counterclockwise Spiral
Fig. 6D Clockwise Spiral
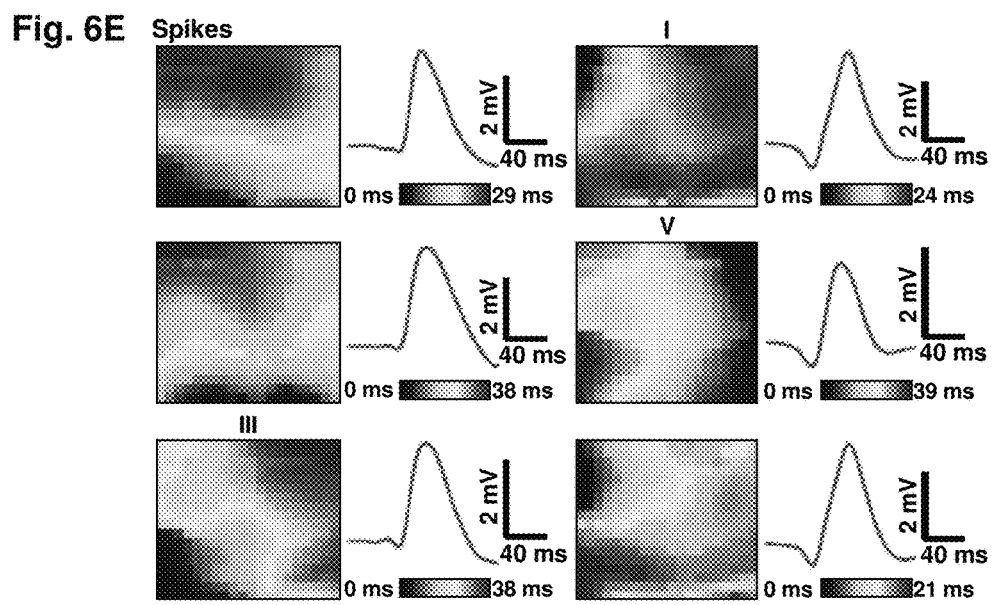
Fig. 6E Spikes
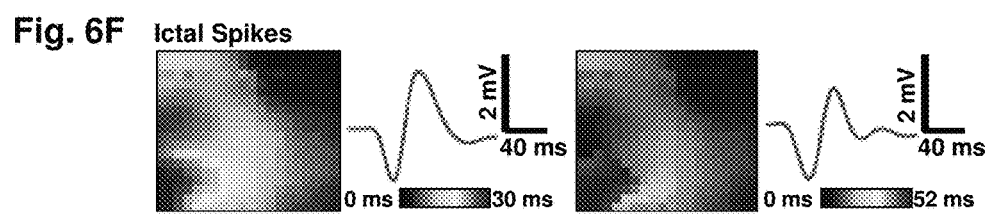
Fig. 6F Ictal Spikes

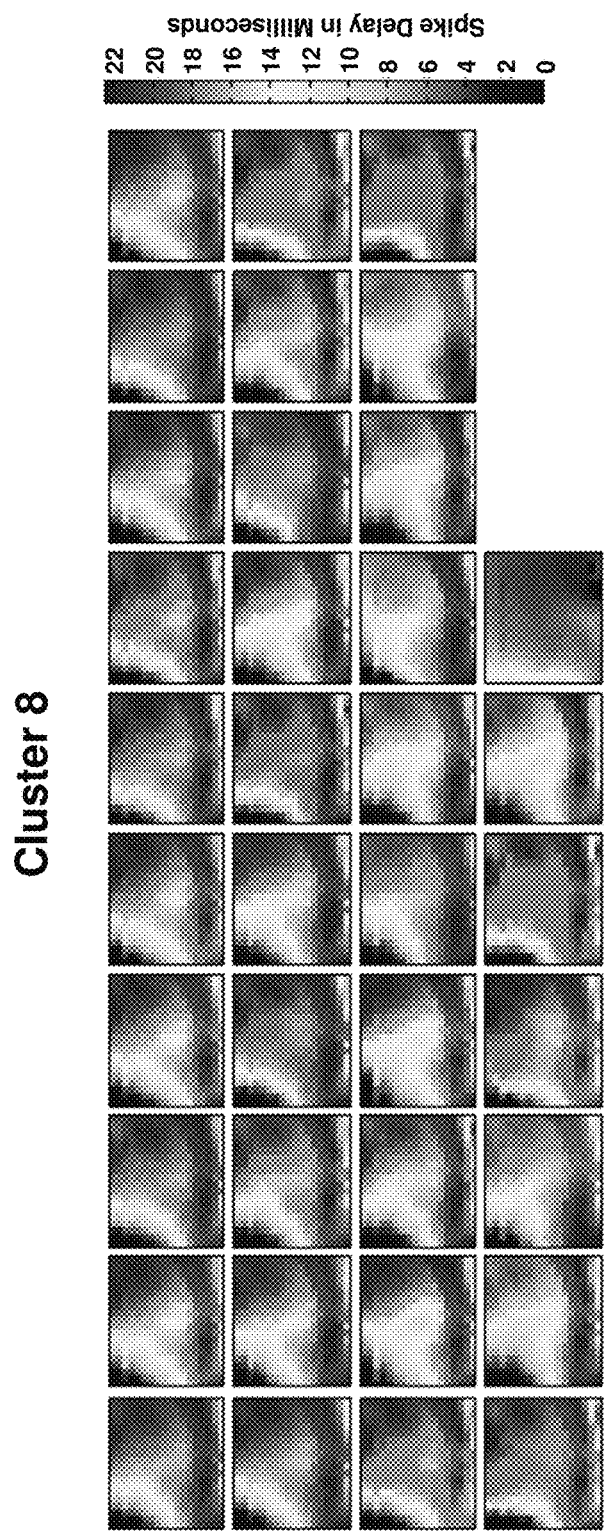

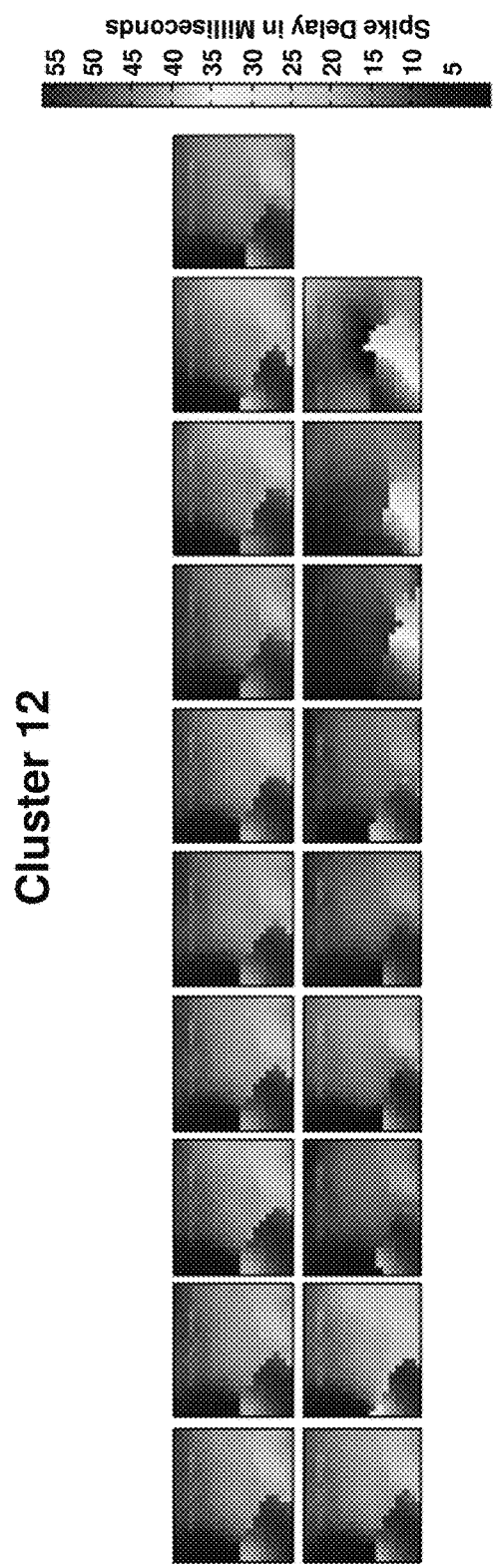

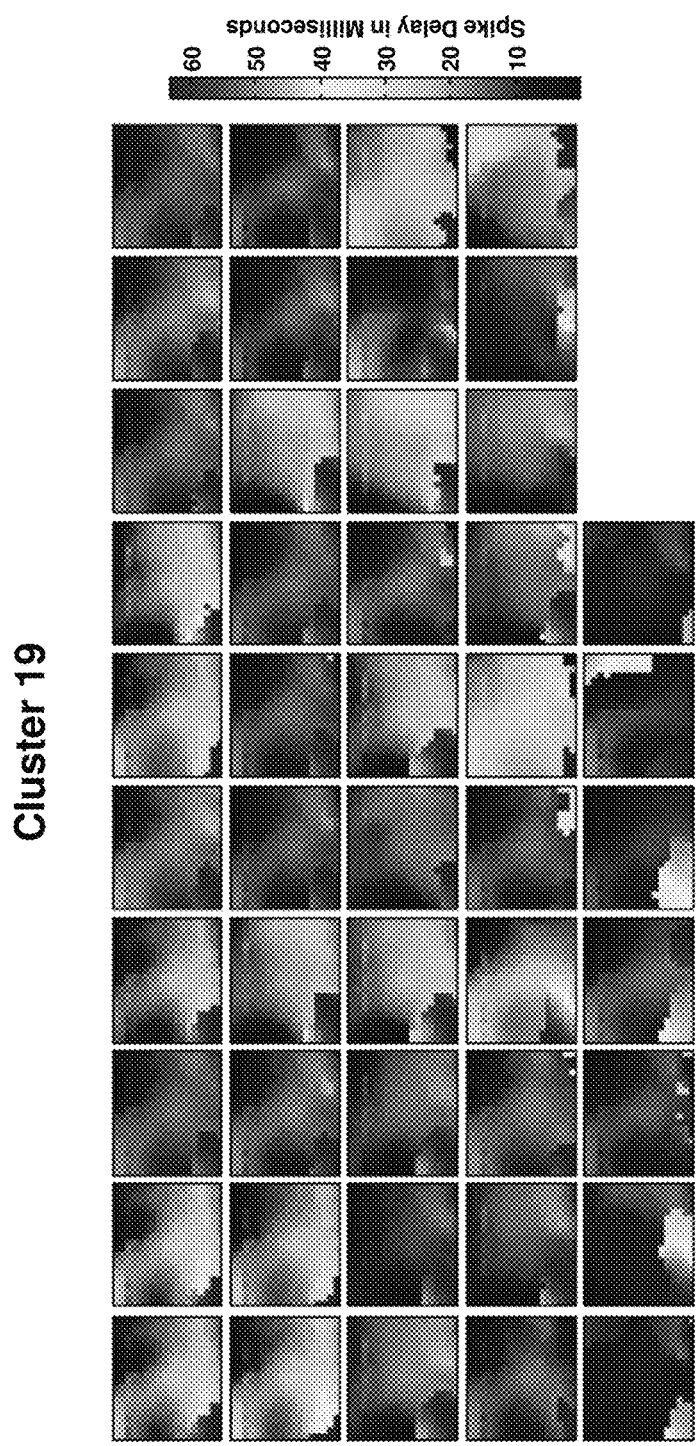

Fig. 30

CONFORMABLE ACTIVELY MULTIPLEXED HIGH-DENSITY SURFACE ELECTRODE ARRAY FOR BRAIN INTERFACING

CROSS-REFERENCE TO RELATED APPLICATIONS

This application is a divisional of U.S. patent application Ser. No. 13/486,726, filed Jun. 1, 2012, which claims the benefit of priority of U.S. Provisional Patent Application No. 61/492,983, filed Jun. 3, 2011, each of which is hereby incorporated by reference herein to the extent not inconsistent with the present application.

STATEMENT REGARDING FEDERALLY SPONSORED RESEARCH OR DEVELOPMENT

This invention was made with government support under DMI-0328162 awarded by the National Science Foundation, DE-FG02-07ER46471 awarded by the U.S. Department of Energy, NINDS RO1-NS041811, NINDS R01 NS 48598 and 2T32HL007954 awarded by the National Institutes of Health. The government has certain rights in the invention.

BACKGROUND OF INVENTION

Provided herein are methods and devices related to electrophysiological measurement over a complex-shaped biological surface, such as the brain. Specially configured devices are conformable and provide the ability to measure complex spatio-temporal waveforms over relatively large areas of the brain, including in areas requiring high device bendability such as between brain hemispheres.

SUMMARY OF THE INVENTION

Provided herein are biomedical devices and methods of making and using biomedical devices for tissue sensing and actuation applications. For example, flexible and/or stretchable biomedical devices are provided including electronic devices useful for establishing in situ conformal contact with a tissue in a biological environment. The invention includes implantable electronic devices and devices administered to the surfaces(s) of a target tissue, for example, for obtaining electrophysiology data from a tissue such as brain tissue. Also disclosed are methods of sensing and making measurements in a biological environment, including methods of making in vivo electrophysiology measurements.

In one aspect, the invention provides devices for interfacing with a tissue in a biological environment including conformable devices. Devices of this aspect are useful, for example, for sensing and/or actuating a tissue in a biological environment. When placed in a biological environment, devices of an aspect of the invention optionally establish conformal contact with a target tissue(s), thereby providing contact useful for sensing or actuation of the tissue. Further, devices of this aspect optionally maintain conformal contact and/or electrical contact and/or optical communication with the surface of a tissue as the tissue moves and/or as the device is moved across a surface of the tissue. One specific advantage of the devices and methods provided herein is that the conformable aspect of the device establishes good electrical contact over relatively large surface areas, without the drawbacks inherent in various penetrating electrode devices and methods. For example, trauma to the brain is avoided, and concerns related to brain infection and adverse immune response is avoided.

In an aspect, the invention is a method for spatio-temporally electrically interfacing with a brain tissue by providing any of the devices disclosed herein. In an aspect, provided is a conformable device for interfacing with brain tissue in a biological environment, where the device comprises a deformable substrate and a deformable array of electrodes comprising a plurality of electrodes in electrical communication with a plurality of deformable electrical interconnects. A barrier layer encapsulates at least a portion of the deformable electrical interconnects, wherein the deformable substrate, deformable array of electrodes and the barrier layer provide a net bending stiffness of the device low enough that the device establishes conformal contact with the brain tissue in the biological environment, wherein the deformable array of electrodes is supported by the barrier layer. At least a portion of the plurality of electrodes is electrically contacted with the brain tissue in the biological environment by conformally contacting the conformable device with a surface of the brain tissue in the biological environment and spatio-temporally interfacing the brain tissue with the conformable device to monitor or actuate a spatio-temporal profile over the surface of the brain tissue in electrical contact with the plurality of electrodes. In an aspect, the brain tissue is a human brain. In an aspect, the brain tissue is a non-human brain. In an aspect, the biological environment is in vivo.

In an embodiment, the interfacing step further comprises monitoring or actuating the electric potential of the brain tissue at a plurality of individual brain surface locations over a plurality of different time points. In an aspect, temporally adjacent time points are separated by a time period that is greater than or equal to 30 µs and less than or equal to 1 second. In an aspect, the plurality of different time points span a total time period selected from a range that is greater than or equal to 1 second and less than or equal to 80 years or for the remaining lifetime of the patient in which the device is implanted. For example, for acute monitoring or an acute treatment, such as during a surgical procedure, the total time period may be relatively short. In contrast, for chronic monitoring and/or treatment, the total time period may be relatively longer, on the order of days or up to the patient's lifetime. In particular, in aspects where the device is implanted, the monitoring may be continuous over extended periods, or intermittently continuous over select time periods.

In an embodiment, the number of individual brain surface locations is selected from a range that is greater than or equal to 10 and less than or equal to 10,000. In an aspect, the number of locations is selected depending on the application of interest. For example, where detailed information about electrical waveform activity in the brain is desired, monitoring may occur over a larger number of locations, thereby increasing spatial resolution. Similarly, applications requiring precise generation of specific waveforms that may have a complex shape or spatial pattern will correspondingly require a larger number of brain surface electrical contact locations. In contrast, where more simple information, such as an average electrical potential over a large region of the brain, is desired, the number of electrical contact locations is relaxed.

Similarly, the spacing between adjacent brain surface electrical contact locations can be selected depending on the application. In effect, spacing between adjacent brain surface electrical contact locations is governed by spacing between adjacent electrodes in the electrode array. In an embodiment, the adjacent individual brain surface locations are separated from each other by a range that is greater than or equal to 50 μm and less than or equal to 5 mm. There is a relationship between the contact area footprint between the conformable device, the number of electrodes and the electrode spacing (separation distance between adjacent brain surface locations). Interface with an area of the brain requires at least a corresponding contact area footprint and, if detailed information is required, a larger number of electrodes with a small separation distance between adjacent electrodes.

In an aspect, any of the methods provided herein relate analyzing the monitored electric potential spatio-temporal profile to identify an electrical waveform. This aspect is particularly useful for identifying potential abnormalities in brain function, such as may arise from disorders associated with defects in particular areas of the brain. In an embodiment, the analyzing step comprises pattern recognition, a clustering algorithm; machine learning, or a combination thereof. For example, the machine learning relate to monitoring brain activity in a certain location, corresponding to an individual's state, such as a normal state sleeping, awake, restful, active, Similarly, the activity at the location may correspond to an adverse event such as a seizure, Parkinson's tremor, depression. In this fashion, waveforms identified as normal or abnormal for that individual at that location are quantified or "learned". This information can then be used in various numerical or other algorithms to identify waveform state under conditions that are not controlled.

In an aspect, the analyzing step comprises monitoring the magnitude of electric potential at each brain surface location, a time course of electric potential change at each brain surface location, or both. In this fashion, detailed information about the waveform is obtained, including an electrical waveform that changes over time and space. In another aspect, the analyzing step further comprises calculating the relative delay of a spike in electrical potential at a brain surface location, wherein a spike is identified for any brain surface location having an electric potential that is greater than 50% of a peak root-mean-square value over all brain surface locations. Alternatively, the spike is calculated on the basis of exceeding an average value at that specific location, such as the average value under normal brain activity conditions.

In an embodiment, the method further comprises encoding a magnitude and/or speed and direction of the waveform from the relative delay and electric potential at each brain surface location. The speed and direction can be calculated using any number of algorithms. For example, if delay times are determined, delay times at various locations can be used to calculate speed and direction of the electric depolarization over the brain surface. Similarly, recording the magnitude of potential at different locations at different times allows one to determine the speed and direction of the electrical waveform and, accordingly, identification of the waveform as abnormal or normal. Accordingly, another embodiment of the invention relates to analyzing the encoded waveform and identifying the waveform as abnormal or normal.

The analyzing step may further comprise any number of techniques known in the art. In an aspect, the analyzing step further comprises principal components analysis (PCA) to reduce the computational requirement of the analyzing step.

Any of the methods provided herein optionally further comprise the step of actuating a spatio-temporal electrical profile over the surface of the brain tissue to disrupt the abnormal waveform. The actuation of a profile over the surface of the brain comprises energizing the plurality of electrodes so that a voltage pattern is generated over the electrode array. In an aspect, each electrode is capable of energization in a time-dependent fashion. In this manner, because there is an electrical connection between each electrode and each brain surface location underlying the electrode, complex spatio-temporal waveforms can be generated on the brain surface from the corresponding time-dependent energization of electrodes. Given the device can have a large number of electrodes, closely spaced, with a high temporal resolution control, extremely fine voltage profiles that can rapidly change with time are obtained, thereby providing high-spatial and temporal spatio-temporal electrical waveforms along the brain surface and underlying regions thereof. The energizing refers to independently energizable electrodes in the electrode array. "Independently" refers to both the magnitude of voltage and the time-dependency of voltage magnitude being independently controlled for each electrode.

In an aspect, the actuating step comprises energizing the plurality of electrodes with a pattern of electric potential having a stimulation profile that stimulates the brain in a pre-emptive manner to cause the neural tissue to be in a refractory state prior to the arrival of the next wave. This prevents the continuation of an ongoing seizure pattern. Other useful actuating steps relate to energization of electrodes to generate a region of high frequency stimulation or depolarization sufficient to at least partially terminate propagation of the abnormal waveform, or to generate a polarity profile corresponding to a waveform of normal brain activity.

In an embodiment, any of the methods are useful for taking action when an abnormal waveform is detected. In an embodiment, this action is energizing the electrodes to generate a voltage profile or a spatio-temporal voltage waveform on the brain surface as discussed above. Another action relates to activating a therapeutic device when an abnormal waveform is identified, wherein the therapeutic device applies a therapeutic intervention to the brain. This therapeutic intervention may be distinct from energization of the plurality of electrodes. For example, the therapeutic device and therapeutic intervention may be one or more of: a penetrating electrode to provide electrical stimulation; a micro-syringe to inject a chemical compound onto or into the brain; or an optical fiber to optically stimulate the brain surface or brain interior.

In another aspect, any of the methods relate to detection or actuation of specific waveform types, such as identifying as abnormal a waveform comprising a plane wave propagating in a first direction that bends and subsequently propagates in a reentrant spiral loop having a preferential direction that is clockwise or counter-clockwise. Furthermore, the abnormal waveform may be identified as having multiple distinct waveforms, such as a second plane wave that changes the direction of the reentrant spiral loop waveform. One advantage of the devices and methods provided herein is that these different waveforms can be detected with a sensitivity that even permits detection of multiple distinct waveforms over the brain surface that interact with each other. Conventional techniques, in contrast, may not be able to distinguish such waveforms, and certainly not a waveform consisting of a plurality of distinct waveforms.

Depending on the waveform monitored by the device, appropriate counter-action may be taken, such as spatio-temporally energizing the plurality of electrodes to actuate the brain tissue surface with a traveling wave of electric potential to terminate a reentrant spiral loop. Given the device is useful for both monitoring and actuation of brain spatio-temporal waveforms, repeated monitoring and actuation may be taken with different actuation waveforms if an initial actuation waveform does not elicit a satisfactory response in the brain (e.g., termination of an undesirable waveform and generation of a normal brain state as reflected by brain activity monitored by the device).

Other spatio-temporal profiles of interest correspond to an interictal or an ictal state, a cluster of spikes, a spindle oscillation that is punctate and temporally coherent, a waveform that is at least partially a substantially planar wave having a preferential propagation direction, and/or a waveform that is a spiral wave.

In an embodiment, any of the methods may be used to detect a spiral wave waveform, thereby providing indication of ictal onset, including warning of a potential seizure episode.

In an aspect, the interfacing step further comprises identifying the spatio-temporal profile as a spiral waveform and actuating electrical activity over the brain surface with an output spatio-temporal profile from the deformable array of electrodes to disrupt or terminate the spiral waveform. This is particularly useful for applications wherein the spiral waveform disruption prevents, attenuates, or stops a seizure.

In an aspect, any of the methods provided herein relate to implanting the conformable device in a patient. In an aspect, the patient is a human. In an aspect, the patient is not a human.

The ability to provide conformable devices having good foldability provides methods wherein at least a portion of the conformable device is inserted into a sulcus or a groove of the brain tissue without penetrating through brain tissue. This aspect acknowledges that the brain surface has a number of invaginations where it may be desired to measure electrical waveforms within the invagination so that, although the device is inserted in brain invaginations (e.g., groove, sulcus), the outer-most membrane defining the brain surface is itself not penetrated. In this aspect, the conformable device can be two-sided to monitor or actuate two spatio-temporal profiles, a first spatio-temporal profile from one side of the sulcus or groove, and a second spatio-temporal profile from a second side of the sulcus or groove. In an embodiment, the two sided device is made by folding the conformable device to provide the two-sides from a single deformable device.

The conformable nature of the device provides access to interfacing with very different locations of the brain surface simultaneously, for example within invaginations and outside the invaginations. Accordingly, an aspect of the invention relates to electrical contact by conformal contact with at least a portion of a sulcus or groove of the brain tissue and at least a portion of a gyrus of the brain tissue.

In an aspect, any of the methods provided herein relate to both monitoring and actuating brain tissue. The configuration of the device and electrodes of the device permit sensing or monitoring of electric potential over the brain surface by the electrodes and/or actuation of electric potential over the brain surface by energization of the electrodes.

In an embodiment, any of the methods further comprise connecting the conformable device to a neuroprosthetic device. This embodiment has particular applications for individuals suffering a neurological disorder or a paralysis where signal from the brain is disrupted. In this case, the nerve-conduction signal between the brain and corresponding body part controlled by the brain can be bypassed with brain output sensed by the conformable device and used to send a corresponding signal to the neuroprosthetic device. Alternatively, the brain signals can be decoded and directly used as an input system for a computer or a communication device. For example, a cursor can be controlled that allows a paralyzed patient to read and write such as email. The devices and methods provided herein are particularly suited to these applications given their relatively high information transfer rates. Examples of neuroprosthetic devices include the BrainGate™ Neural Interface System.

In an aspect, conformal contact comprises physical contact with a surface of the brain tissue, without penetrating the brain tissue.

Any of the devices used in the method may be further characterized by a number of physical parameters. In an aspect, the conformable device is bendable, stretchable, or both bendable and stretchable. The bendable aspect is particularly relevant for applications where the conformable device is at least partially inserted into a brain surface invagination and where the device is folded over a support material to provide two-sided interfacing capability.

Other relevant physical parameters relate to methods having a certain spatial and/or temporal resolution. In an aspect, the spatial resolution is selected from a range that is greater than or equal to 50 μm and less than or equal to 5 mm; and the temporal resolution selected from a range that is greater than or equal to 30 μs and less than or equal to 1 second. Spatial resolution is selected by adjusting the spacing or separation distance between adjacent electrodes, such as center-to-center distance or edge-to-edge distance. Temporal resolution is selected by adjusting the frequency at which the electrodes are monitored and/or energized.

In an embodiment, any of the methods provided herein interface with a large area of brain tissue, as reflected by the large conformable contact area footprint with the brain surface. In an aspect, the conformable contact area footprint is selected from a range that is greater than or equal to 10 mm$^2$ and less than or equal to 100 cm$^2$.

In an aspect, the barrier layer limits a net leakage current from the deformable array of electrodes to the tissue to an amount that does not adversely affect the tissue.

In an aspect of the invention, barrier layers include moisture barriers. In one embodiment, the barrier layer is configured to limit a net leakage current from the electronic device to the biological environment to less than 10 μA, optionally for some applications less than 5 μA and optionally for some applications less than 1 μA, and optionally for some applications less than 0.1 μA. In some embodiments, the barrier layer prevents leakage current from being concentrated to small areas so to prevent tissue damage caused by current leakage from the device. In an embodiment, for example, the barrier layer is configured to limit leakage current from the device to the biological environment to 0.1 μA/cm$^2$; less, and for some applications 0.01 μA/cm$^2$ or less, and for some applications 0.001 μA/cm$^2$ or less. In some embodiments, barrier layers of the invention have an electrical resistivity of $10^{14}$ Ω·m or greater, for example an electrical resistivity selected over the range of $10^{15}$ to $10^{17}$ Ω·m. In some embodiments, the barrier layer prevents the rate at which charge is leaked from the electronic device; for example, one barrier layer embodiment limits electrical discharge from a device to 10 μC or less over a period of 1 second or 10 μA. In some embodiments, the barrier layer limits leakage current or average leakage current from the device to 10 μA or less or 5 μA or less over a long period of time, such as 3 hours or more or 5 hours or more. In an embodiment, any of the devices or methods provided herein relates to monitoring net leakage current, and if the net leakage current exceeds a specified maximum value, the device is shut down. In an embodiment, the maximum value corresponds to a total charge value, such as 10 μA or greater over any 1 second interval. Similarly, the maximum value may correspond to a lower current, but over a greater time interval, such as a sustained leakage of 1 μA over 1 minute, or 0.1 μA over one hour. The maximum value can be selected to correspond to a value above which tissue is adversely affected, including a permanent or a temporary affliction.

In some embodiments, a barrier layer is configured to prevent moisture from reaching the flexible or stretchable electronic circuit and limit leakage current therefrom, for example to less than 10 μA optionally for some applications less than 5 μA and optionally for some applications less than 1 μA. Useful moisture barriers, for example, include those configured for protecting tissue in contact with electronic device embodiments from damage due to leakage current. Further, useful moisture barriers include those configured for protecting electronic devices from damage due to leakage current.

In an embodiment, the barrier layer is patterned so as to selectively modulate physical, thermal, optical, electromagnetic and/or electrical contact and/or communication between flexible semiconductor circuit elements and the tissue in the biological environment. Optionally, a barrier layer comprises multiple layers. For example, a barrier layer comprises at least one organic polymer layer and at least one inorganic dielectric layer. In specific embodiments, the net thickness of a barrier layer comprising multiple layers is selected over the range of 1 μm to 25 μm or over the range of 1 μm to 100 μm.

In some embodiments, the barrier layer includes one or more vertical interconnect access (via) structures. As used herein, a via structure refers to a recessed region which is at least partially filled with a conducting material. Via structures are useful in a barrier layer for providing electrical communication between electronic circuit components encapsulated by a barrier layer (e.g., semiconductor device such as a transistor, amplifier or multiplexer) and electronic circuit components not encapsulated by a barrier layer and in contact with the tissue or fluid in contact with the tissue (e.g., an electrode). In a specific embodiment, the barrier layer comprises multiple layers and includes multiple offset via structures; for example, one via structure in a lower barrier layer and one via structure in an upper barrier layer in electrical communication with the first via structure. In embodiments, barrier layers including multiple layers with offset via structures are useful as moisture barriers.

Depending on the application, the barrier layer can have a variable thickness; that is, for certain applications, the barrier layer has a thickness that is spatially variable (i.e., relatively thicker in some regions and relatively thinner in other regions). In embodiments where a sensing element does not need to be exposed and/or in direct contact with or electrical communication with a tissue in a biological environment, barrier layers of spatially varying thickness are useful; for example, when a sensing element is positioned close to the surface (e.g., within 5 μm or less) of the barrier layer but still encapsulated by the barrier layer.

Also provided herein are devices. In an aspect, the device is useful in performing any of the methods disclosed herein. In an embodiment, the device is for spatio-temporally electrically interfacing with a brain in a biological environment. In an aspect, any of the devices or methods provided herein are used to monitor a spatio-temporal waveform on the brain surface, including identifying waveforms considered abnormal and, optionally, taking action to abrogate such abnormal waveforms.

In an embodiment, the device comprises a conformable substrate and a conformable electronic circuit comprising a deformable array of electrodes in electrical communication with a plurality of deformable electrical interconnects. The deformable array of electrodes are supported by the conformable substrate, such as by an intervening layer that is a barrier layer that is itself supported by the conformable substrate. The barrier layer encapsulates at least a portion of the deformable electrical interconnects, wherein the conformable substrate, conformable electronic circuit and the barrier layer provide a net bending stiffness of the device low enough that the device establishes, or is capable of establishing, conformal contact with brain tissue in the biological environment. A controller is connected to the conformable electrical circuit to monitor or actuate a spatio-temporal profile over the surface of the brain in electrical contact with the plurality of electrodes. In this aspect, each electrode is independently addressable, to provide independent electrical stimulation.

In an aspect, each electrode is electrically connected to a pair of transistors, wherein the transistors comprise a multiplexing transistor and a buffer transistor. In this aspect, a unit cell of the device comprises an electrode and two transistors, with electrical interconnects electrically connecting the electrode to the transistors in series, and electrical interconnects connecting the transistors to power, ground and to the controller. In an embodiment, each pair of transistors is electrically connected to a common constant current source and a current mirror. In an aspect, the constant current source and current mirror are considered components of the controller, where the controller portion is "off-chip" and away from the conformable substrate. The controller may include analog amplification or buffering, filtering and analog to digital conversion. The controller may also include digital signal processing, pattern recognition and programmable stimulation. In an embodiment, the pair of transistors are matched transistors. In an embodiment, the pair of transistors are not matched transistors.

In an aspect, the transistors are flexible and comprise single-crystal silicon.

In an embodiment, adjacent electrodes are separated from each other by a separation distance selected from a range that is greater than or equal to 100 μm and less than or equal to 1 mm. The separation distance may be described in terms of center-to-center distance or edge-to-edge distance of adjacent electrodes. In an aspect, the separation distance is constant. In an aspect, the separation distance varies, such as lower separation distance in a central region of the device (e.g., where high spatial resolution is desired) and higher separation distances around the edges (where high spatial resolution may not be required, but large-area monitoring is desired). In an aspect, the separation distance may be described in terms of an average separation distance, with minimum and maximum separation distances that vary less than or equal to 100% of average, less than or equal to 50% of average, or within about 20% of average.

In an aspect, the device is characterized in terms of an electrode surface area. In an embodiment of this aspect, each electrode has an electrode surface area that is less than or equal to 0.1 $mm^2$, and optionally, greater than or equal to 0.01 $mm^2$.

In an embodiment, the deformable array of electrodes is supported by a top surface of the barrier layer. In an aspect, the electrode is partially embedded in the barrier layer, such that a top surface of the electrode is not covered by the barrier layer. In an aspect, the electrodes are coated with an electrode coating layer, such as an electrode coating layer comprising platinum. In an aspect, the electrode, electrode coating layer and barrier layers are biologically inert, in that the materials do not illicit a significant immune response.

In an aspect, the device is described in terms of a thickness. In an embodiment, the thickness is less than or equal to 30 µm, or less than about 25 µm. Such small thicknesses are particularly relevant given the surface geometry of the brain comprises multiple folds, grooves and invaginations requiring the conformable device to have large bendability or foldability.

Any of the devices provided herein may further comprise a support material having a first surface and a second surface opposed to the first surface, wherein a first portion of the electrodes are supported by the first surface, and a second portion of the electrodes are supported by the second surface. Such a device is particularly suited for insertion between brain hemispheres, or other invaginations or grooves, where an interface is desired with both surfaces simultaneously.

In an aspect, any of the devices, as well as methods, are particularly suited for therapeutic applications beyond electrical waveform actuation by the electrodes of the device. In an embodiment, the device further comprises a therapeutic device operably connected to the controller and a receiving passage through the conformable substrate for receiving at least a portion of the therapeutic device. In this aspect, the controller is configured to actuate the therapeutic device to provide a therapeutic intervention to the brain. For example, in response to detection of an abnormal waveform or other abnormality, the controller may send a signal to the therapeutic device to provide a therapeutic intervention. The therapeutic intervention may itself be a physical parameter such as an electrical stimulation or shock, heat, or electromagnetic radiation. Alternatively, the therapeutic intervention may be chemical in nature, such as by selected application of a chemical or biological agent to a select region of the brain. In an aspect, the therapeutic device is a penetrating electrode, a micro-syringe, or an optical fiber. Other examples of therapies include ablation therapy, such as by locally applied temperature variation (e.g., hypothermic or hyperthermic), electrical stimulation, optical stimulation and radiofrequency (RF).

In an embodiment, the receiving passage is centered at a center point of the conformable substrate, and the receiving passage has a cross-sectional area selected from a range that is greater than or equal to 100 µm$^2$ and less than or equal to 1 cm$^2$. In an aspect, multiple receiving passages are provided through the device, thereby providing the ability to selectively adjust the position at which the therapeutic is delivered.

In another aspect of the invention, provided is a method of identifying an abnormal spatio-temporal brain waveform in a subject using any of the devices provided herein. The spatio-temporal electrical brain waveform is monitored with any of the devices provided herein that are in conformal and electrical contact with a brain surface of the subject. The monitoring comprises detecting the electric potential of a plurality of individual brain surface locations beneath each electrode of the array of electrodes at a plurality of different time points. The monitored electric potential is encoded to obtain an encoded spatio-temporal electrical brain waveform. For example, useful encoded parameters include brain electrical potential as a function of time over the brain surface locations underlying the plurality of electrodes. The encoding may be on-chip or may be transmitted to a recording device or display for further analysis. In an aspect, the encoded waveform provides information about parameters useful for identifying a waveform to provide classification as to brain state, including abnormalities. Examples of useful parameters include waveform speed, direction, intensity, and brain locations thereof. From the encoded waveform, and parameters calculated therefrom, analysis as to abnormality can occur. For example, the analyzing step can be analyzing the encoded waveform to identify an abnormal spatio-temporal brain profile.

In an aspect, the abnormal spatio-temporal brain profile is identified from a waveform that is a spiral waveform.

Optionally, the method further comprises actuating the array of electrodes with a spatio-temporal electric potential profile and generating a waveform of electric potential to the brain surface from the actuated array of electrodes to disrupt or terminate the abnormal spatio-temporal brain profile. For example, the abnormal waveform may comprise a spiral waveform, and the termination may relate to electrode actuation with a counter-stimulus to cancel the unwanted spatial pattern, thereby disrupting the abnormal waveform. Alternatively, select regions of the brain may be stimulated to counter-act physical symptoms associated with an abnormal waveform, such as a seizure.

In an embodiment, the method further comprises the step of implanting the device in the subject by conformally contacting the device with the brain surface without physical penetration of brain tissue. Such an implantation may be endoscopically, especially given the device is conformable, foldable, bendable and stretchable. The monitoring with the device may be acute, such as during an operative procedure or a test (e.g., on the order of 12 hours or less), or may be chronic, such as over a time period that is greater than 12 hours.

In an aspect, any of the methods provided herein are directed to a method to obtain data, such as electrical spatio-temporal waveform over brain tissue. In this aspect, the technique of applying the device against brain may be considered a minor intervention, involving a safe, routine technique of conformal application of an electrode array over a patient, with a device monitoring brain waveform activity, without any physical disruption to the brain. Accordingly, for any of the methods provided herein that recite a surgical treatment step, the surgical treatment step is optionally disclaimed, including in jurisdictions that consider such surgical treatment steps to be prohibited patentable subject matter. In an aspect, any of the devices provided herein are used to measure or monitor electrical activity over a biological surface, such as the brain surface.

The devices and methods provided herein facilitate significantly higher information transfer rates between the brain surface and the device conformally contacted thereto than is possible with current state-of-the art devices. This provides unique capabilities with respect to brain-machine interfaces. Accordingly, any of the devices and methods provided herein may be further characterized in terms of a minimum data transfer rate or "sampling transfer", such as a rate determined by the size of the array and the sampling and/or actuation frequency. In an aspect, the minimum data transfer rate is described in terms of the number of samples per second, with each sample corresponding to a value at one electrode at one point in time. For a 360 electrode array, with a temporal resolution of 0.5 ms, this would correspond to a data transfer rate of 720,000 samples per second. In this aspect, the minimum data transfer rate is optionally, greater than or equal to 90,000 samples per second, greater than or equal to 360,000 samples per second, or greater than or equal to 3,600,000 samples per second.

The capacity for such high rates of data transfer and bandwidth provides access to a brain diagnostic tool that provides information at a rate that is greater than or equal to 90,000, 360,000 or 3,600,000 samples per second. In an embodiment, this information is electric potential of the electrodes in the electrode array, corresponding to the electric potential of the brain surface at a location matched to the electrode that overlies that brain surface location.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DESCRIPTION OF THE DRAWINGS

FIG. 2A-2F. Flexible, high-resolution multiplexed electrode array. FIG. 2A, Photograph of a 360 channel high density active electrode array. The electrode size and spacing (center-to-center) is 300 μm×300 μm and 500 μm, respectively. (inset) A closer view showing a few unit-cells. FIG. 2B Schematic circuit diagram of single unit-cell containing two matched transistors (left) (labeled buffer and multiplexer), transfer characteristics of drain-to-source current (Ids) from a representative flexible transistor on linear and logarithmic scales as gate to source voltage ($V_{gs}$) is swept from −2 to +5 V, demonstrating the threshold voltage ($V_t$) of the transistor (center). Current-voltage characteristics of a representative flexible silicon transistor (right). $I_{ds}$ is plotted as a function of drain-to-source voltage ($V_{ds}$). $V_{gs}$ is varied from 0 to 5 V in 1-V steps. FIG. 2C, Schematic exploded view (left) and corresponding microscope image of each layer: doped silicon nanoribbons (right frame, bottom), after vertical and horizontal interconnection with arrows indicating the 1st and 2nd metal layers (ML) (right frame, 2nd from bottom), after water-proof encapsulation ("barrier layer") (right frame, 3rd from bottom) and after platinum electrode deposition (right frame, top). Green dashed lines illustrate the offset via structure, critical to preventing leakage current while submerged in conductive fluid. FIG. 2D, Images of folded electrode array around low modulus Polydimethylsiloxane (PDMS) insert. FIG. 2E, bending stiffness of electrode array for varying epoxy thicknesses and two different PI substrate thicknesses. A nearly 10-fold increase in flexibility between the current device and our prior work is shown. FIG. 2F, Induced strain in different layers depending on the change in bending radius.

FIG. 3A, A flexible, high-density, active electrode array placed on the visual cortex. (inset) The same electrode array inserted into the interhemispheric fissure. FIG. 3B, Folded electrode array before insertion into the interhemispheric fissure (left). Flat electrode array inserted into the interhemispheric fissure (right).

FIG. 4A, A typical spindle recorded from a representative channel. Negative is plotted up by convention. Arrows point to individual spikes of the spindle (I-IV) further analyzed in the following panel. FIG. 4B, Root-mean-square (RMS) value of the zero-meaned signal of individual sharply contoured waves comprising the spindle demonstrate high sensitivity of the electrode array and the spatially-localized nature of spindles (left column) as well as the high degree of temporal synchronization indicated by the relative time to peak across the array (right column). Data are anatomically orientated as shown in the inset of FIG. 5B.

FIG. 5A, 64 color maps, each showing the response (root-mean-square (RMS) value of the zero-meaned signal within the response window) of the entire 360 channel electrode array. The color maps are arranged in the same physical layout as the stimuli are presented on the monitor, i.e. the image map in the upper left hand corner of the figure represents the neural response across the entire array to a flashing box presented in the upper left hand corner of the monitor. The color scale is constant over all 64 image maps and is saturated at the 1st and 99th percentile respectively to improve the visual display. FIG. 5B, 64 color maps generated from the same response data as in a, but plotting the response latency in ms. Channels that did not show a strong response, as determined by exceeding 50% of the maximum evoked response, were excluded and are colored white. (inset) Exploded view illustrates the anatomical orientation of the electrode array on the brain and approximate location of Brodmann's areas (grey numbers and dashed lines). FIG. 5C, Performance results achieved after subjecting a test set of data to a deep belief net classifier in accurately determining each originating location on the screen of respective stimuli. 23 of the 64 screen locations (36%) were predicted exactly correct (black boxes), significantly better than chance (1.6%). 41 of 64 (64%) screen locations were predicted correctly within one neighboring square (grey boxes, distance≤√2, chance level 14.1%).

FIG. 6A-6F. Detailed 2-dimensional data from electrographic seizures in feline neocortex. FIG. 6A, μECoG signal from a representative channel of the electrode array during a short electrographic seizure. Negative is plotted up by convention. Labelled segments correspond to movie frames below. FIG. 6B, Movie frames showing varied spatial-temporal μECoG voltage patterns from all 360 electrodes during the labeled time intervals from FIG. 6A. The frame interval and color scale are provided for each set of 8 movie frames and the color scale is saturated at the 2nd and 98th percentile respectively over 8 frames to improve the visual display. Data are anatomically orientated as shown in the inset of FIG. 5B. FIG. 6C, Relative delay map for the 4 to 8 Hz band-pass filtered data from 3 seconds of continuous counter-clockwise spiral rotations (FIG. 6B, waveform IV) illustrating a clear phase singularity and counter clockwise rotation. FIG. 6D, Relative delay map for narrow band-pass filtered data from ~0.5 seconds of clockwise spiral rotations (FIG. 6B, waveform II) illustrating clockwise rotation, but a less clear singularity. FIG. 6E, Representative delay image maps from six different spike clusters are shown to illustrate the differences between clusters (left columns). The average waveform for the corresponding spike (red traces, right columns) illustrates that complicated spatial patterns at the micro scale (0.5 mm) can be indistinguishable at the current clinical scale (~10 mm). Numerals I, III and V indicate the clusters that the corresponding waves in FIG. 6B belong to. FIG. 6F, Representative delay image maps from two clusters that occurred almost exclusively during seizures, illustrating striking differences in spatial-temporal micro scale patterns during seizures.

FIG. 7A, Microscope images of each fabrication step. FIG. 7B, schematic cross-sectional information, dotted line shows the location of a neutral mechanical plane (NMP).

FIG. 8A, Spatial distribution of the visual evoked response, as determined by the root-mean-square (RMS) value of the zero-meaned signal within the 40 ms to 160 ms window after the stimulus. Data are anatomically orientated as shown in the inset of FIG. 5B. FIG. 8B, Individual visual evoked responses shown for the 49 electrodes located in the bottom, left-hand corner of the electrode array, as highlighted by the dashed box above. This is an example of a spatio-temporal profile over 49 separate locations. Similar profiles can be obtained over the entire device footprint (e.g., 360 locations in an 18×20 electrode array).

FIGS. 10A-19B and 20. Delay maps for all of the spikes in each cluster indicated a strong similarity within clusters. The spikes in clusters 2, 4, 12, 14, and 19 appeared to occur almost exclusively during seizures, while spikes in the other clusters appeared to occur uniformly throughout the record.

FIG. 22A, Photograph of custom circuit board that implements the off array constant current sinks, buffering and high-pass filtering. FIG. 22B, Photograph of custom data acquisition interface circuit board that generates row select signals and provides another stage of buffering (top) and FIG. 22C, (bottom).

Figure 30:
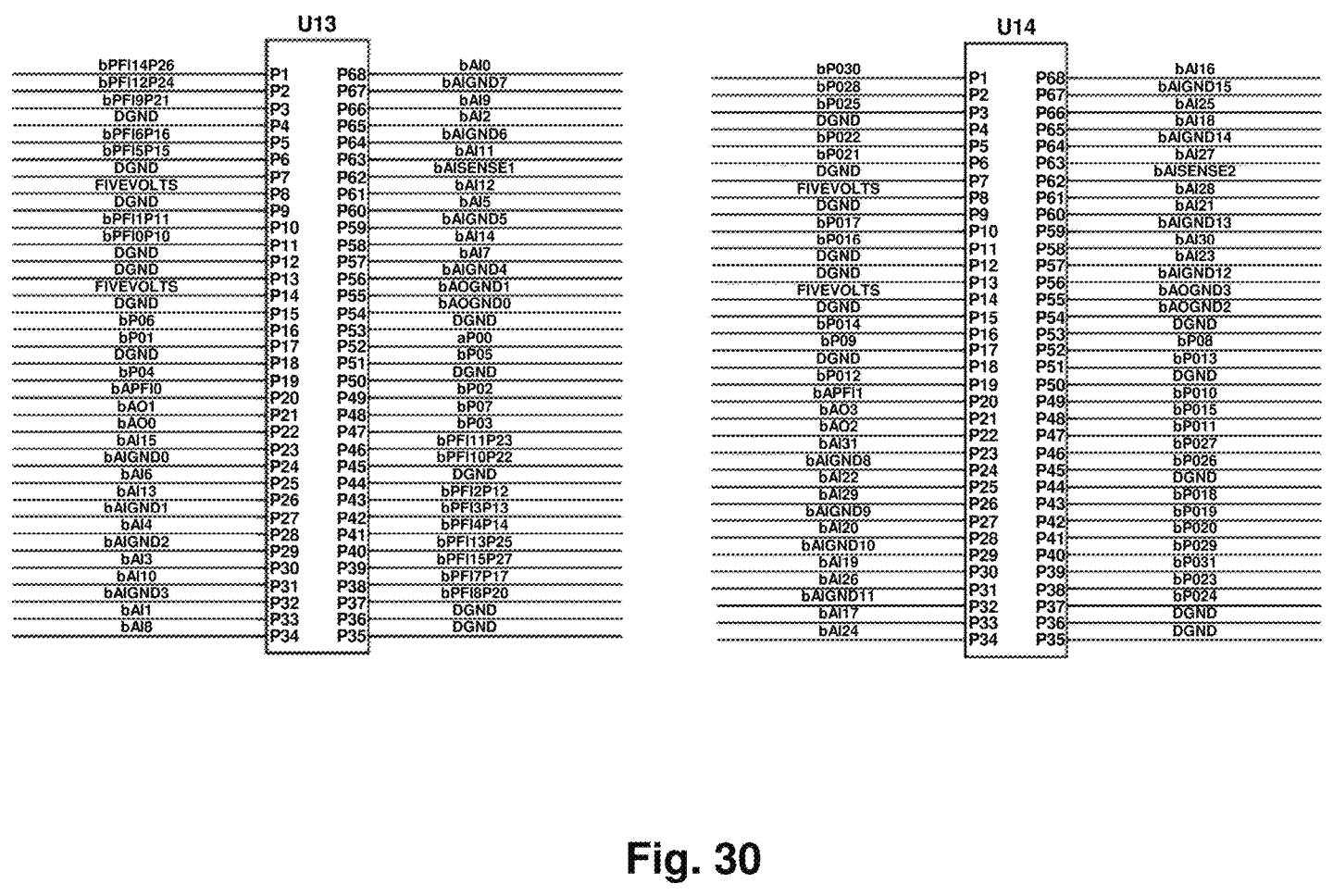

FIGS. 24-31. Schematics of the custom data acquisition interface circuit board.

FIG. 32A, A diagram that shows parameter definitions for insertion model of folded electrode array. FIG. 32B, Strain induced in the brain during insertion of the folded electrode array for two different brain hemisphere spacings.

DETAILED DESCRIPTION OF THE INVENTION

Figure 1A:
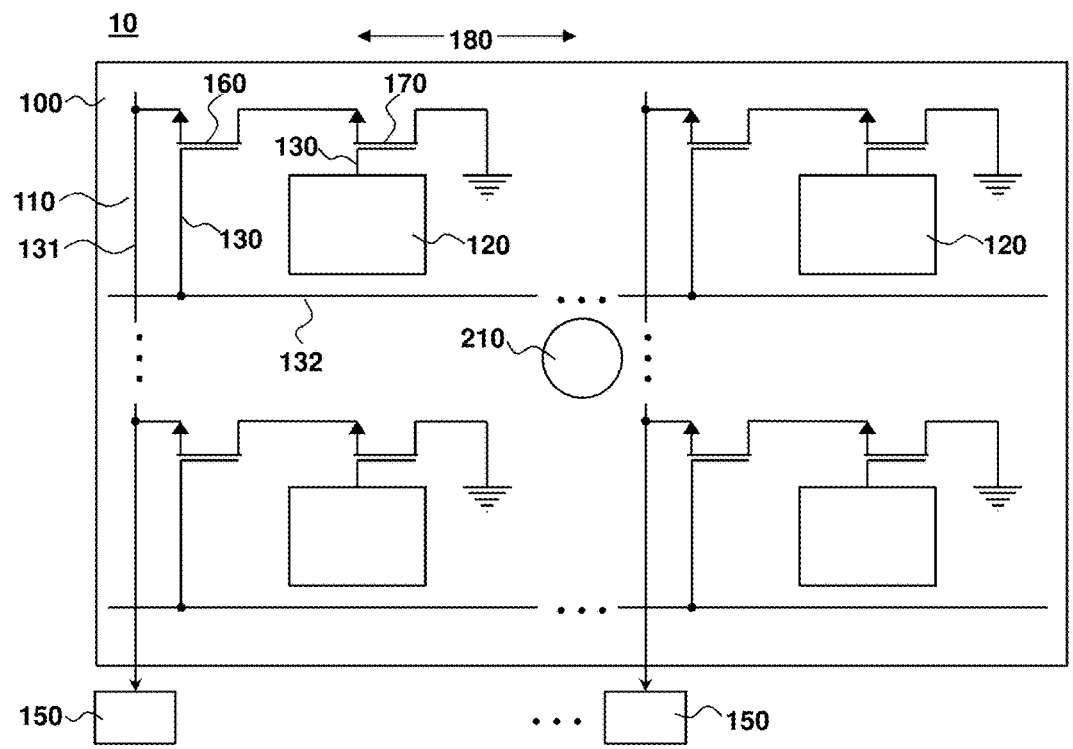
FIG. 1A is a top view schematic of a device for spatiotemporally electrically interfacing with a brain.

In general, the terms and phrases used herein have their art-recognized meaning, which can be found by reference to standard texts, journal references and contexts known to those skilled in the art. The following definitions are provided to clarify their specific use in the context of the invention.

"Spatio-temporally" or "spatio-temporal" refers to a parameter having a spatial pattern which may change over time. For example, electric potential over the brain surface changes with time, with different regions of the brain generating or propagating an electric potential under various conditions. A sleeping patient will have a different spatio-temporal waveform than an active person. A patient having a brain-generated seizure has a different spatio-temporal waveform than a patient not seizing. Accordingly, "spatio-temporally electrically interfacing" refers to spatial and temporal electrical connection between a device and a brain tissue, so that the spatio-temporal monitoring and/or actuation of the brain can occur.

"Electrically interfacing" refers to the ability to monitor and/or generate electrical waveforms on the brain surface in regions underlying the device electrodes.

"Brain tissue" refers to brain in the in vivo, in vitro, or the ex vitro environment. The brain may be from a human or a non-human, such as an animal.

"Conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue. "Deformable" is used similar to conformable, and refers to a device, material or substrate can flex, bend, or conform without undue induced strain during deformation, specifically an induced strain below that required to induce mechanical fracture or permanent fatigue. In particular, the element is considered deformable if any induced stress associated with deformation is below the ultimate tensile stress or the yield stress.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

"Electrical communication" refers to an arrangement of two components of a device wherein electrical signal (e.g., current, potential) is passed between the two components. For example, each electrode in the array is electrically connected to a pair of transistors, and the transistors are connected to a current source or sink, and specifically, to a controller. The parts of the device that convey the electrical signal between the electrical components are herein referred to as "interconnects".

A "component" is used broadly to refer to a material or individual component used in a device. An "interconnect" is one example of a component and refers to an electrically conducting material capable of establishing an electrical connection with a component or between components. In particular, an interconnect may establish electrical contact between components that are separate and/or can move with respect to each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a ""bulk" or "average" bending stiffness for the entire layer of material. A material made up of a plurality of components, e.g., substrate and barrier layers, electrical circuit, may be described in terms of a "net bending stiffness", which is a compilation and average of each component's bending stiffness.

"Conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface. Conformal contact includes large area conformal contact, for example, wherein conformal contact between a tissue and device component is over an area greater than or equal to 1000 $mm^2$, and optionally greater than or equal to 10,000 $mm^2$. In an aspect, the tissue is brain tissue. Conformal contact may also be described in terms of the maximum separation distance between the device and the underlying brain tissue that the device is interfaced with, such as a distance that is less than or equal to 1 mm. In addition, the tissue may have an intervening thin film of brain fluid between the brain tissue and the device. Accordingly, physical contact with brain tissue includes physical contact between the device and any biological film, including brain fluid, surrounding the brain, so long as electrical contact between the device and brain is maintained.

Devices and methods provided herein are useful for "monitoring" or "actuating" electrical spatio-temporal waveforms over the brain surface. Monitoring refers to measuring, and optionally encoding, spatio-temporal electrical waveform on the brain surface. Actuating refers to the electrodes of the device interacting with, stimulating, controlling, or otherwise affecting brain tissue, or a material (e.g., skull, skin) or fluid (e.g., cerebral fluid) in electrical contact therewith.

"Temporally adjacent time points" is a measure of the time resolution of the device. The ability to electrically detect changes in electrical potential in a brain location is constrained by how often the electrical measurement is made or the delay time between measurements. The ability to stimulate brain waveform change is similarly constrained.

"Electrical waveform" refers to a pattern of electric potential over the brain surface. A single waveform snapshot provides only limited information about the waveform at one single instance in time. Accordingly, a spatio-temporal profile requires monitoring of the waveform over a period of time. This provides information about the direction of travel of the waveform, how it initiates, propagates and terminates. That information is required to further identify a waveform as "abnormal" or "normal".

The methods and devices provided herein are particularly useful in detecting various types of waveforms, including waveforms that are associated with abnormal brain states such as during a seizure. A "reentrant spiral loop" refers to a pathway that can generate a sustained spiral wave when stimulated. A "spindle oscillation" is associated with a sleep state and having a waveform that is highly synchronous ("temporally coherent"). Identifying waveforms can provide classification as to whether the patient is in an "interictal" (between seizure/convulsions) or an "ictal" (seizure/convulsions) state.

"Substantially planar" refers to a waveform having a preferential propagation direction that is linear in nature, and includes a plane wave where electrical potential increases or spikes travels geographically from one side of the device toward another side. In contrast, a "spiral loop" refers to a waveform that is non-linear in nature in that the electrical potential spikes spiral about a central point, at least for a certain time period. A "traveling wave" is used to refer to a pattern of electric potential whose position depends on time and, accordingly, may include planar waves, substantially planar waves, spiral loops, and combinations thereof such as a planar wave that transitions to a spiral loop for a certain time period that may either dissipate or transition back to a substantially planar wave geometry. "Preferential propagation direction" Algorithms may be employed to classify a "preferential propagation direction" such as by calculating the position of a weighted potential average over the entire monitored brain surface with time. For situations where the resultant position plot is generally linear, such as by calculating a regression or correlation coefficient that is within a user-specified range, the waveform may be classified as substantially planar or planar. Similarly, for situations where there is a spiral relation, the waveform may be classified, at least in part, as a spiral waveform. Further refinement, such as separately classifying waveforms that are geographically distinct, provides capability of classifying multiple waveforms at any given timepoint. Current devices and methods having large footprints and fine spatial and temporal resolution are particularly compatible with this aspect.

"Principal components analysis" is a mathematical procedure known in the art to transform the number of original variables into principal components by an orthogonal linear transformation and is considered a form of eigenvector-based multivariate analyses. Other methodologies known in the art may be used in the analyzing step, including for example, pattern recognition (where the detected waveform is compared against known waveforms), clustering algorithms, and machine learning.

"Spatial resolution" refers to the ability to spatially resolve electric potential between brain locations, and is dependent on the electrode spacing in the device as the device is in conformal contact with the brain tissue. The spatial resolution may relate to monitoring a waveform or actuating a waveform.

"Temporal resolution" refers to the sampling rate of the device, or the time between samples. The sampling rate determines the highest resolvable frequency content of the sampled signal through the Nyquist-Shannon sampling theorem.

"Conformable contact area footprint" refers to the area over which interfacing takes place between the conformable device and the brain tissue. This footprint generally corresponds to the area defined by the outermost electrodes in the electrode array, or at least for those electrodes in electrical contact with the brain surface.

"Controller" refers to the portion of the device that controls electrode energization for waveform actuation and collection of data related to monitoring of spatio-temporal electrical waveform profile over the brain surface. In addition, the controller may encompass circuitry used to actuate therapeutic devices that are operably connected to the conformable device.

Figure 1B:
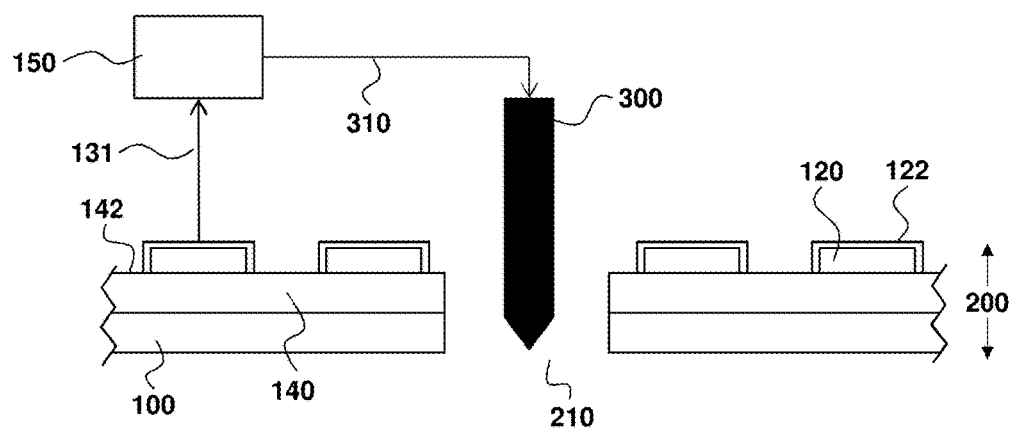
FIG. 1B is a side view.

FIG. 1 illustrates one embodiment of the conformable device 10 comprising a conformable substrate 100 that supports a conformable electronic circuit 110. FIG. 1A is a top view, with four unit cells shown and with the dots indicating that any number of unit cells may be incorporated into the circuit. The circuit 110 comprises a deformable array of electrodes 120 in electrical communication with a plurality of deformable interconnects 130. In the embodiment illustrated in FIG. 1A, the electrodes 120 are connected via interconnects 130 to a pair of transistors 160 (multiplexing transistor) 170 (buffer transistor) in series. Interconnects also provide one row select line 132 per row of the electrode array (shown as the horizontal lines running below the unit cells) which enables the electrodes in that particular row to drive the shared output line 131 (shown as vertical lines to the left of the unit cell) when that particular row is selected. Subsequently, a different row is selected and all of the others de-selected. In this manner, all of the electrodes on the array can be sampled sequentially. The multiplex output from the circuit 110 is provided to controller 150. FIG. 1A shows separate controllers connected to each of interconnect lines 131. In an aspect, the lines 131 are connected to a single controller 150. Controller 150 may comprise an adjustable current source, current mirror, band-pass filters and operational amplifiers, as summarized in FIG. 23. Passage 210 is formed through the device 10, including substrate 100 to provide access to brain tissue underlying conformable device 10, as explained further in FIG. 1B.

FIG. 1B is a side view of a device 10 having a thickness 200. Electrodes 120 are supported by barrier layer 140, such as a top surface 142 of barrier layer 140, which in turn is supported by substrate 100. The electrodes are optionally coated with an electrode coating layer 122. In this embodiment, controller 150 is in operable communication or connection 310 with a therapeutic device 300. Passage 210 is configured to receive at least a portion of therapeutic device 300. Therapeutic device 300 is any device capable of delivering a therapy to brain tissue, such as delivery vessel for a biological or chemical agent (e.g., microsyringe), a penetrating electrode, or an optical fiber for delivering electromagnetic radiation.

Figure 1C:
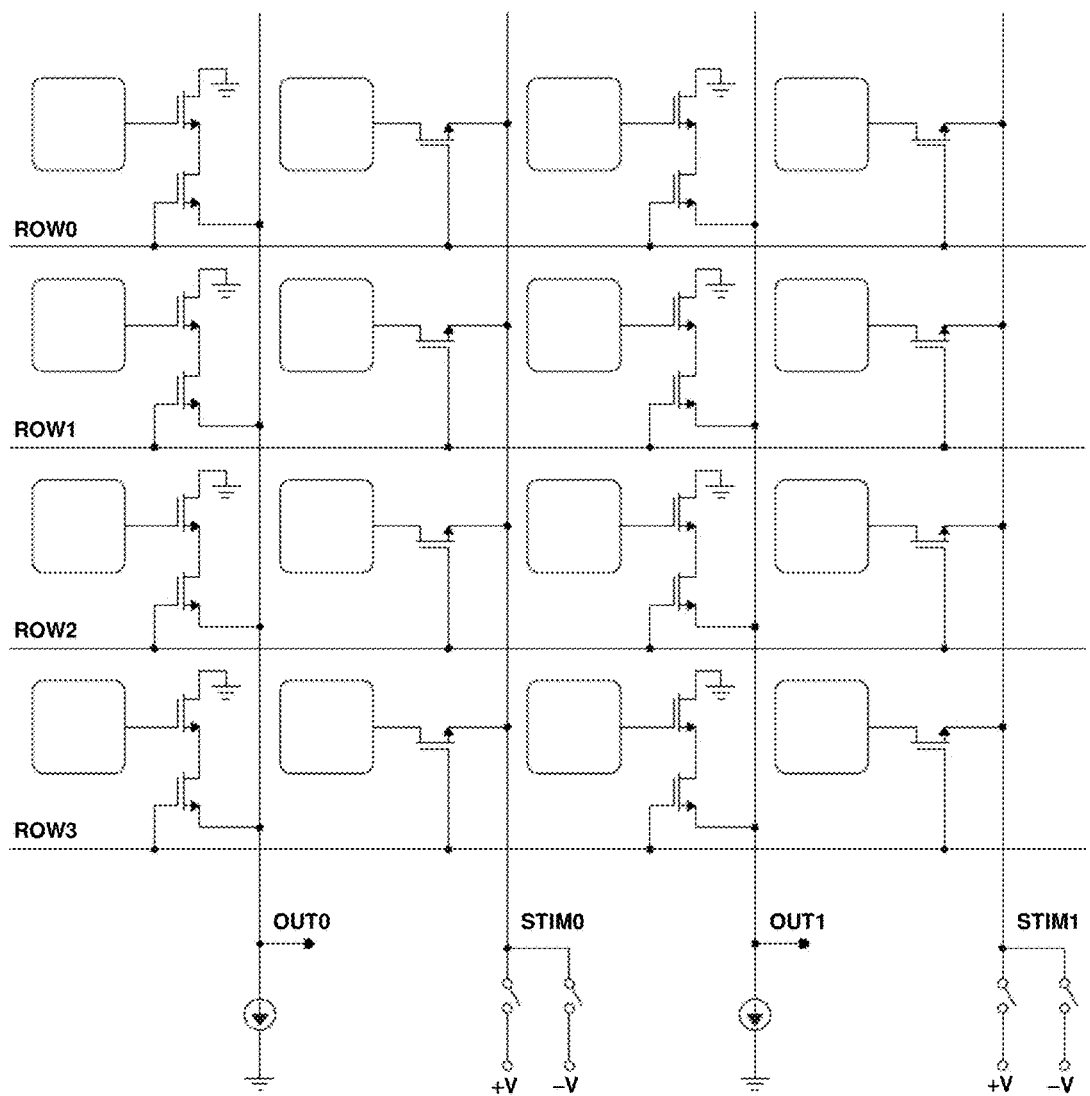
FIG. 1C is a device for monitoring and actuating brain tissue.

FIG. 1C is another embodiment of a device for spatio-temporally interfacing with brain tissue. The device in FIG. 1C is configured so that one-half of the electrode array is used to monitor electrical activity and the other half of the electrode array for electrical stimulation of the brain. The general design is based on the one illustrated in FIG. 1A, but with one transistor removed from unit cells in alternating columns. Removing this transistor enables that column to be used as a multiplexed stimulating electrode. Therefore, half of the electrode array is dedicated to recording only (columns OUT0 . . . OUTN) and half of the electrode array is dedicated to stimulation (columns STIM0 . . . STIMN).

In this example, the device array comprises ten columns for recording, ten columns for stimulation, with eighteen total rows. This yields 360 total electrodes: 180 recording electrodes and 180 stimulating electrodes.

The stimulation is provided from off of the array using a controller, similar to 150, except that it is selectively connected to a positive or negative voltage or current source at a specified time to enable stimulation. Two switches per column (off of the array, but shown on the attached diagram, or as a part of controller 150) are used for this function. If both switches are left open, the device does not stimulate. To stimulate, one of the switches is closed at the same time the desired row or rows are selected. When both switches are closed, the selected rows and columns are stimulated. To balance the overall charge delivered, a second stimulation pulse can be subsequently delivered with opposite polarity. Balancing the delivered charge prevents electrode damage.

The stimulation delivered in the device illustrated in FIG. 1C is shown as constant voltage (as indicated by the labels +V and −V), but by substituting constant current sources in the place of the +V and −V connections, the stimulation can be constant current stimulation.

FIG. 2D shows the device 10 folded over a support material 510, having a first surface 512 and a second surface 514. In this configuration, a first portion 513 of the electrodes is supported by first surface 512 and a second portion 515 of the electrodes is supported by first surface 514. In this configuration, the folded device 10 is inserted into an invagination so that electrodes 513 interface with one surface of the invagination and electrodes 515 interface with a second surface of the invagination opposed to the first surface.

Figure 38:
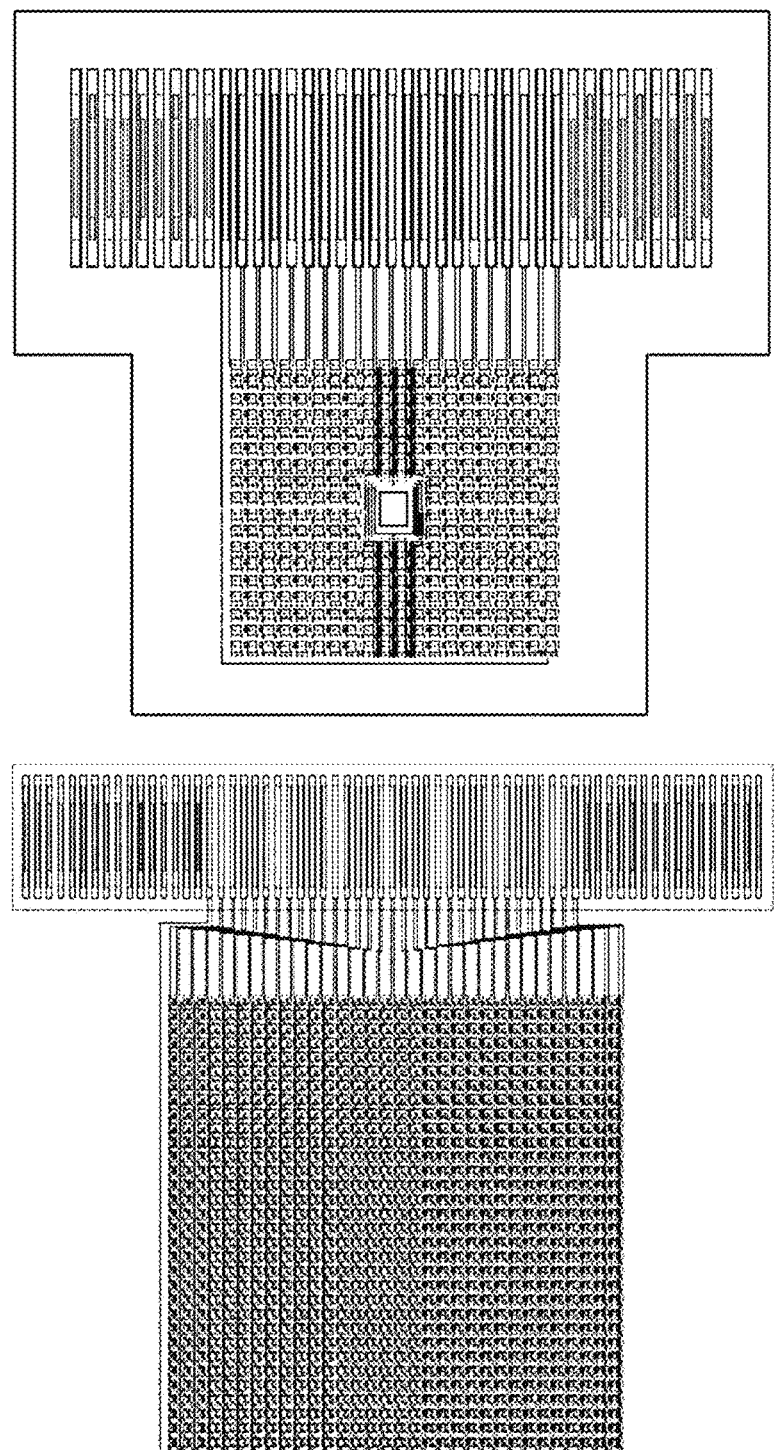
FIG. 38. Top panel shows a high density neural (HDN) sensor array with a passage for receiving a therapeutic device. The array has 500 μm electrode spacing with a 9 mm by 10 mm area coverage. The bottom panel is a large area HDN array comprising 32 by 32 unit cells (1024 total cells) with a 16.2 mm×16.2 mm area coverage.

FIG. 38 summarizes additional applications of high density neural (HDN) arrays. In the top panel, a passage 210 (see FIG. 1), in a central portion of the device provides access to a therapeutic device. For example, a sharp external stimulation device such as a penetrating electrode. The penetrating electrode may be short for action potential mapping or shallow electrical stimulation, or long for deep brain mapping or electrical stimulation. A micropositioner may also be electronically controlled to provide precise penetration depth. Another example is a micro-syringe for surface or penetrating injection of a chemical or biologic, such as injection of various medicaments onto the brain surface, in shallow penetration or deep into brain. The therapeutic device may be an optical fiber to provide optical stimulation, such as optical stimulation for genetically modified neuron, wherein the optical source may be a laser, such as a commercially-available laser diode. The bottom panel is a large area HDN array (32×32), for interfacing with larger areas of neural tissue. This system is conducive for conducting a range of experiments, such as measuring sleep spindles, visual stimulation, epilepsy mapping, task related potential mapping. The larger area coverage is suitable for sensor and/or motor cortex evaluation and can be used for larger brain sizes (e.g., monkey, pig, human).

EXAMPLE 1

Flexible, Foldable, Actively Multiplexed, High-Density Surface Electrode Array for Mapping Brain Activity In Vivo with Single Trial Resolution Arrays of electrodes for recording and stimulating the brain are used throughout clinical medicine and basic neuroscience research, yet are unable to sample large areas of the brain while maintaining high spatial resolution because of the need to individually wire each passive sensor at the electrode-tissue interface. To overcome this constraint, we have developed new devices integrating ultrathin and flexible silicon nanomembrane transistors into the electrode array, enabling new dense arrays of thousands of amplified and multiplexed sensors connected using many fewer wires. We use this system to record novel spatial properties of brain activity in vivo, including sleep spindles, single-trial visual evoked responses, and electrographic seizures. Our electrode array allowed us to discover that seizures are manifest as recurrent spiral waves which propagate in the neocortex. The developments reported here herald a new generation of diagnostic and therapeutic brain-machine interface (BMI) devices.

The conventional electrode arrays in use today can either sample broad regions of the brain (~80 mm×~80 mm) at low spatial resolution (~10 mm spacing), or small regions of brain (~4 mm×~4 mm) at high spatial resolution (~400 μm spacing)[1], with both requiring N wires for N electrodes. Here we show a 360-channel active electrode array capable of sampling a 5-fold larger region of brain (10 mm×9 mm) than prior work[1], with high spatial resolution (500 μm spacing) and high temporal resolution (>10 kS/s) while reducing the number of wires 9-fold. This technology offers the spatial resolution of voltage sensitive dyes, with greatly improved temporal resolution and signal to noise ratio, with the ability to record from non-optically accessible areas and in a potentially fully implantable, non-toxic, clinical-scale system. This technology can be rapidly scaled to clinical sizes (~80 mm×~80 mm), enabling elucidation of microscale brain dynamics in human normal brain activity and disease.

The utility of high-resolution neural recordings from the cortical surface for basic research and clinical medicine has been shown for a wide range of applications. Spatial spectral analysis of electrocorticograms (ECoG) from the superior temporal gyrus and motor cortex demonstrate that electrode spacing should be 1.25 mm or closer in humans to sufficiently capture the rich spatial information available[2]. Motor control signals[3] and spoken words[4] can be decoded with substantially improved performance utilizing electrodes spaced 1 mm apart or less. In occipital cortex, arrays with 500 μm spacing have demonstrated micro-field evoked potentials that can distinguish ocular dominance columns[5]. The spatial scale for some pathologic signals is also sub-millimeter, based on observations of microseizures, microdischarges and high frequency oscillations in epileptic brain[6,7].

Yet the subdural electrodes in use clinically, for example, in the diagnosis and treatment of epilepsy, are much larger (~3 mm diameter) and have large interspacing (~10 mm) because of the clinical need to record from large areas of the brain surface (80 mm×80 mm) in order to accurately localize seizure generating brain regions. Large area electrode arrays with high spatial resolution are also needed in BMI applications to account for variability in the location of brain functions, which can vary by ~5 mm across subjects[8-11]. High-resolution interface over a large area has previously been impossible due to the infeasibility of connecting thousands of wires in the small intracranial space.

Much of the existing research in electrode technology has focused on penetrating electrode arrays, such as the Utah array[1], which can provide a high-resolution interface to a small area of cortex and enable high-performance neuromotor prostheses[12]. However, arrays of penetrating microelectrodes may only function 6-12 months[13] before the signal quality on most electrodes is substantially diminished. These devices can also cause hemorrhage and inflammatory tissue responses from the immediate insertion[14,15] and over long periods of time, possibly due to the inability of the rigid penetrating electrodes to flex and move as the brain pulses, swells and contracts[16].

Highly flexible arrays of subdural electrodes have unique advantages over penetrating microelectrode arrays in that they are able to maintain signal quality over extended periods of time with minimized irritation and injury to brain tissues[17-20]. Further, the micro-electrocorticographic (μECoG) signal recorded from flexible arrays of non-penetrating electrodes with high-resolution can provide comparable information content to the spiking activity recorded by penetrating microelectrodes in some applications, such as BMI[21-26].

Electrode array fabrication and testing: To access high-resolution interface with large areas of the brain, we have developed an array of flexible, non-penetrating electrodes using novel flexible silicon electronics technology. The array is composed of 720 silicon nanomembrane transistors (FIG. 2A). The active matrix circuit design contains two transistors per unit-cell (FIG. 2B, left frame and FIG. 1). The buffer transistor 170 connected to the electrode 120 provides buffering of the biological signals, while the multiplexing transistor 160 allows all of the electrodes in the same column to share a single output wire 131. Flexible transistors are fabricated using high-quality single-crystal silicon, yielding a mobility of ~350 $cm^2/Vs$ and an on/off ratio>$10^3$, calculated from the slopes of the transfer curves and the ratio of maximum and minimum current outputs (FIG. 2B, center and right frames) by using standard field-effect transistor models[26]. This capability enables high speed multiplexing (<5 μs) and sampling rates >10 kS/s per electrode[27].

Figure 7A:
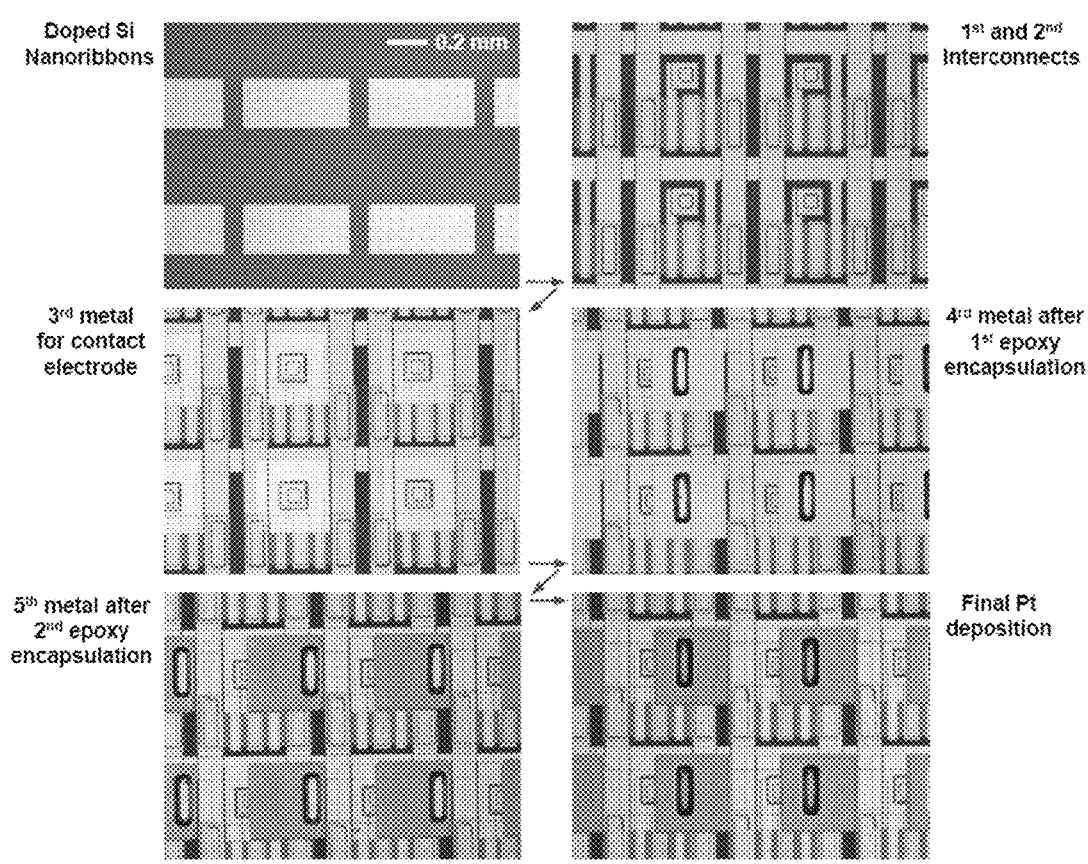
FIG. 7A-7B.

Active electrode arrays are fabricated using a multi-layer process, schematically illustrated in the exploded view in FIG. 2C (see also U.S. Pat. App. No. 12968637 filed Dec. 15, 2010 and PCT App. No. PCT/US10/60425 filed Dec. 15, 2010; which are hereby specifically incorporated by reference). Doped silicon nano-ribbons (~260 nm) are located in the first layer through the use of transfer printing technology. Subsequent horizontal and vertical metal interconnect layers are insulated using layers of polyimide (PI, ~1.2 μm, Sigma Aldrich, USA). Additional polymeric encapsulation layers (PI and epoxy, ~1.2 μm and ~4 μm) with an offset vertical interconnect access (VIA) structure (FIG. 2C, right panels) prevent electrical leakage currents when the device is immersed in highly conductive bio-fluids. As a final step, platinum (Pt, ~50 nm) is evaporated and deposited onto the surface electrodes to reduce their impedance (~20 kOhm at 1 kHz). Detailed fabrication procedures, corresponding microscope images and a cross-sectional schematic can be found in the Methods section and in FIG. 7.

Conventional electrode technology is technically limited in its ability to record from inside of sulci. However, implanting even a few electrodes in sulci such as the central sulcus, has shown that the signals obtained carry more information for BMI applications than signals recorded from the traditional gyral surface[28]. Electrical recording from inside sulci may also be important for clinical applications, as studies of brain pathology have demonstrated that focal cortical dysplasias are preferentially located at the bottom of sulci[29]. Some devices have attempted to address this by exposing a small number of passive electrodes on both surfaces of the device[30,31], but only achieved limited spatial sampling.

The extreme flexibility of our device allows it to be folded around a substrate, such as a silicone rubber substrate that is about 700 μm thick, forming a unique, high-resolution, double-sided recording device that allows access to rarely explored cortical areas, such as the interior of sulci or the medial aspects of the cerebral hemispheres (FIG. 2D). To minimize induced strain in the silicon, silicon dioxide and metal interconnection layers during folding, the overall array thickness has been reduced from our previous efforts, 76 μm[27], to 25 μm, resulting in a nearly 10-fold reduction in bending stiffness. This is accomplished by reducing the PI substrate thickness from 25 μm (FIG. 2E, blue trace) to 12.5 μm (FIG. 2E, red trace), and by reducing the epoxy encapsulation thickness from 20 μm to 8 μm (FIG. 2E, arrows). The induced strain in each layer during folding is estimated via analytical modeling (FIG. 2F) and is maintained well below the mechanical fracture strain of each inorganic material (~1% for Si and $SiO_2$[32]).

Figure 3A:
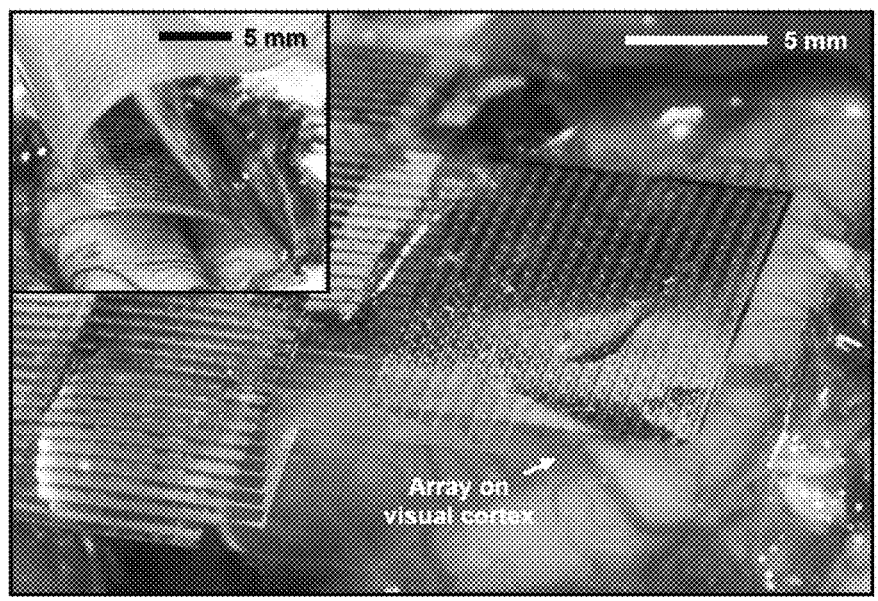
FIG. 3A-3B. Animal experiment using feline model.
Figure 3B:
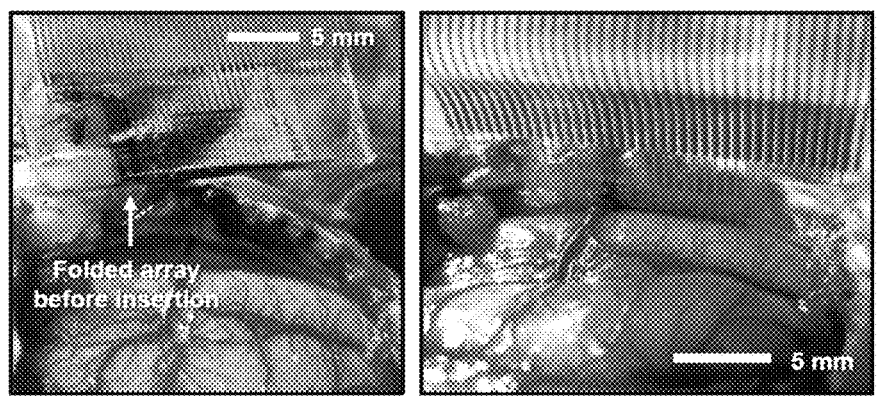

In vivo experiments: We use our flexible electrode device to map neural activity at high resolution, on the surface of visual cortex of 10 cats in vivo (FIG. 3A). An initial craniotomy and durotomy exposed a 2×3 cm region of cortex. Eyes were focused on a monitor that subtended 28°×22° of space. The electrode arrays are either placed on the brain (FIG. 3A) or inserted into the interhemispheric fissure, as shown in the inset of FIG. 3A and FIG. 3B, right frame. Given the high flexibility of the electrode array, it can be placed in between the two hemispheres of the brain without causing damage to tissue. In this configuration, the recording surface is facing the left hemisphere. Alternately, the folded electrode array can be inserted in the same location as the flat electrode array (FIG. 3B, left frame), simultaneously recording from both hemispheres, with the right hemisphere filtered through the dura. Accordingly, an aspect of the invention relates to simultaneous monitoring of both hemispheres of a brain with one device.

Figure 4A:
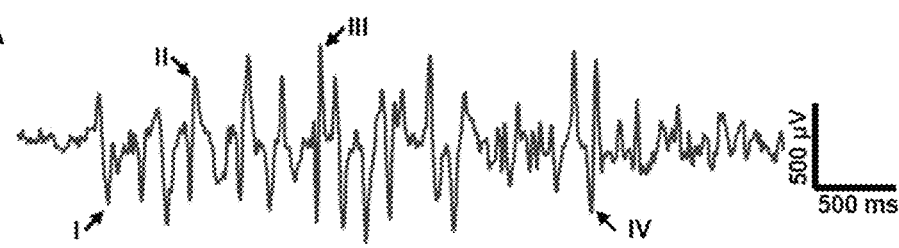
FIG. 4A-4B. Spontaneous barbiturate-induced sleep spindles.
Figure 4B:
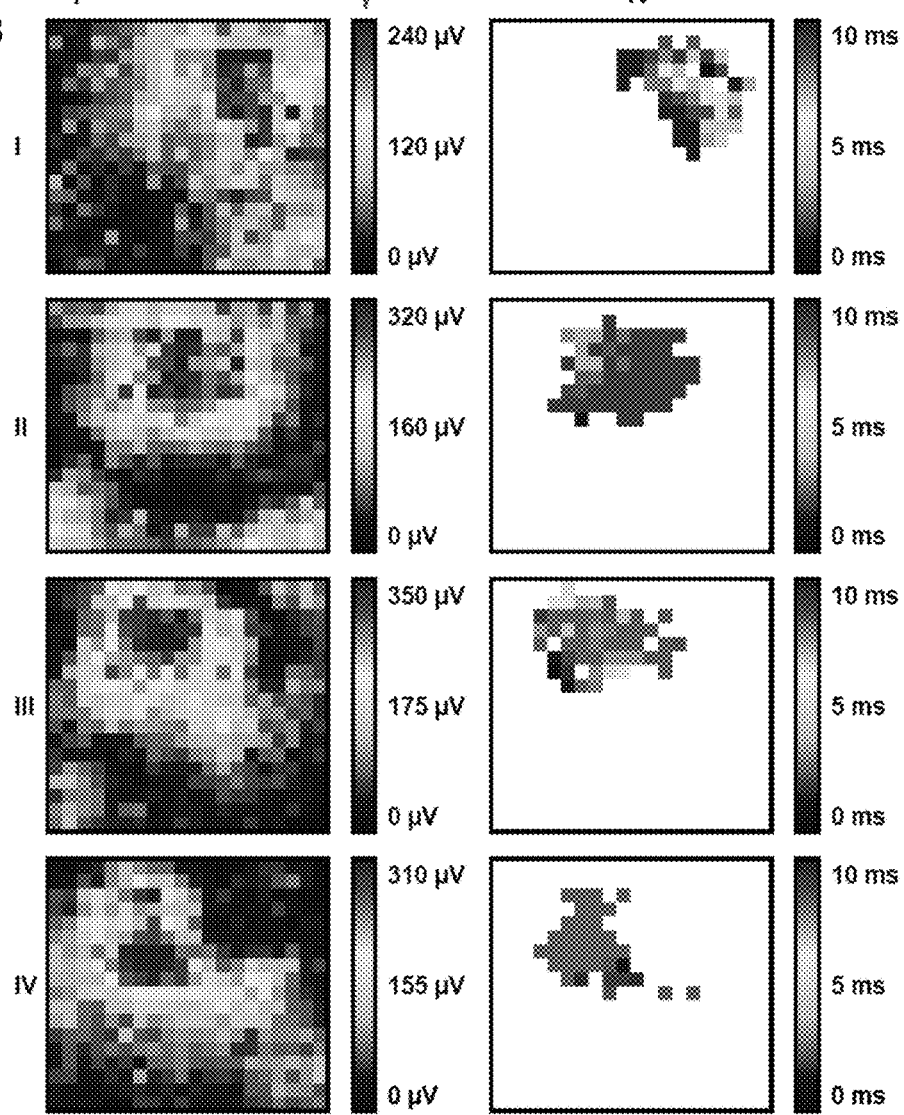

Sleep spindles: Spontaneous spindles during barbiturate anesthesia are recorded in the μECoG signal. Spindle oscillations consisted of waves repeating at 5-7 Hz, lasting 1-2 seconds and repeating every 6-10 seconds. Due to the large number of channels on the electrode array, and the large number of spindles recorded, data from a representative channel is shown for a typical spindle (FIG. 4A). The signal amplitude of ~1.2 mV agrees with earlier published reports[33]. The unfiltered noise level of 30 μV RMS is greatly improved from our previous report[27]. Individual waves within spindle oscillations are identified by a detector triggered on a threshold of two standard deviations above or below the mean. For four of these waves, the root-mean-square (RMS) value of the zero-meaned signal in the 30 ms window before and after the peak is plotted on the array map (FIG. 4B, I-IV, left column). For each channel in the array with >50% of the maximum RMS value, the time to the peak of the wave is plotted (FIG. 4B, I-IV, right column). Individual spindle waves are observed to be spatially confined to a small region of brain (<5 mm×5 mm) and did not move. They are highly synchronous, peaking within a few milliseconds in all of the channels involved.

Figure 8A:
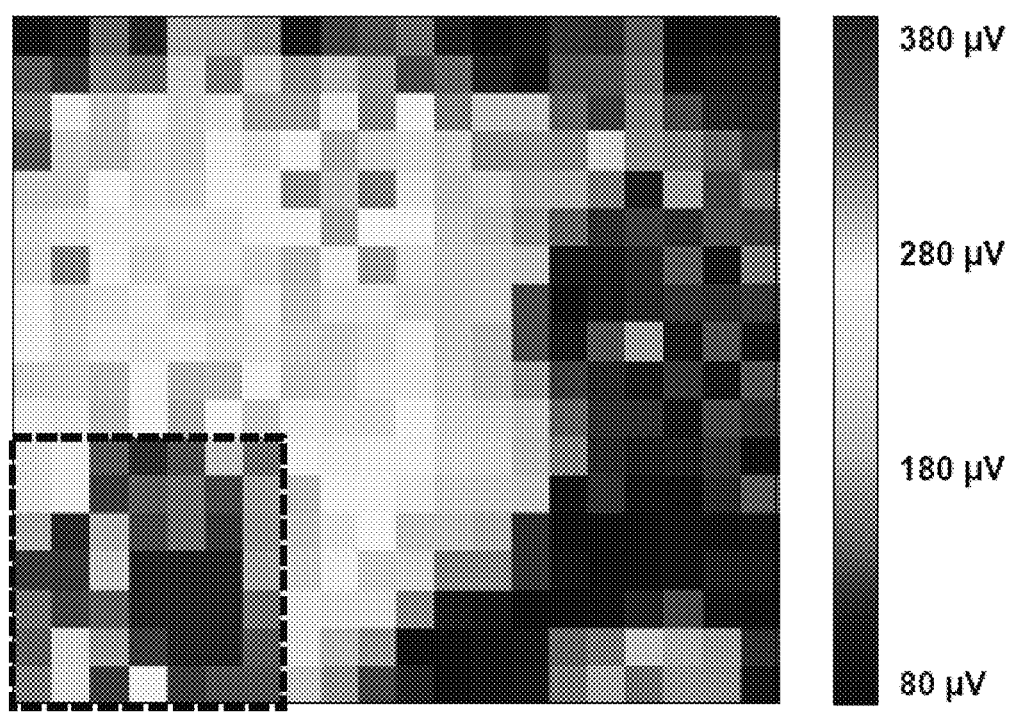
FIG. 8A-8B. A single-trial visual evoked potential from a full-field drifting grating.
Figure 8B:
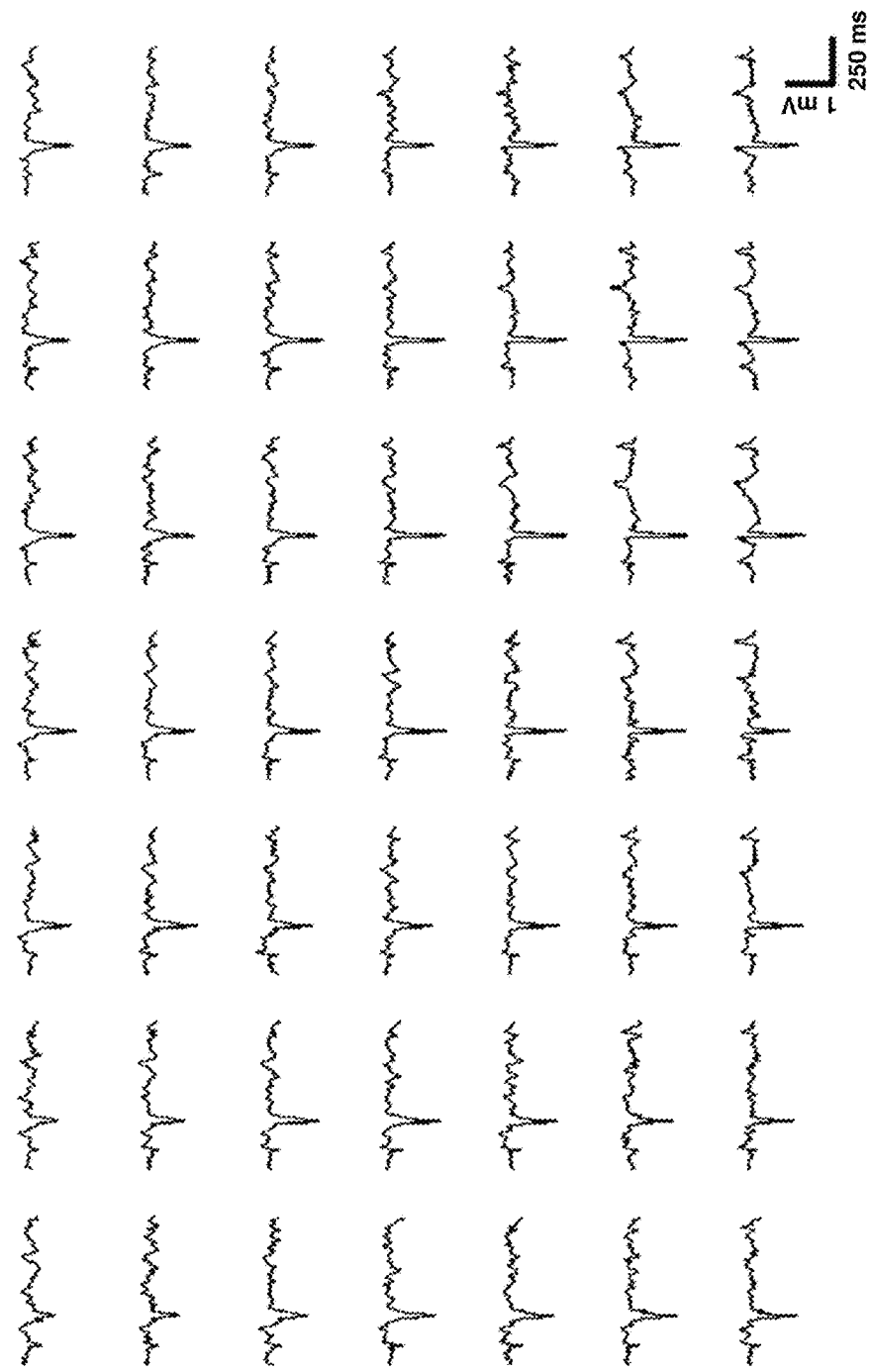

Visual evoked responses: Visual stimuli consisting of full-field drifting gratings are presented for 504 ms at 2 Hz with a spatial frequency of 0.5 cycles per degree. Single-trial visual evoked potentials[34] are visible on many channels of the electrode array. A small subset of these potentials is shown, without averaging, to illustrate the quality of the electrode array recordings (see FIG. 8).

Figure 5A:
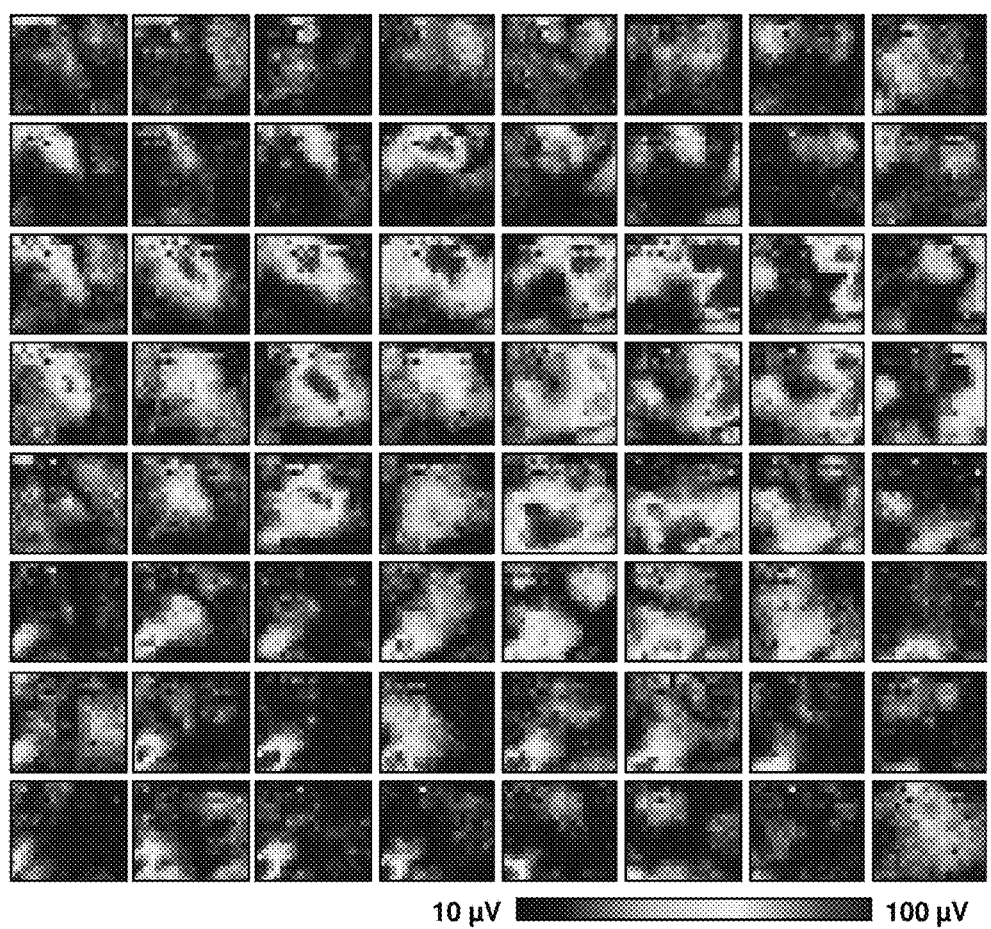
FIG. 5A-5C. Visual evoked response analysis to a 2-dimensional sparse noise visual stimulus.

A second visual stimulus consists of flashing white boxes at pseudorandom locations within an 8 by 8 grid are presented in order to measure the retinotopic organization of the recorded cortical area. The duration of each flash is 200 ms, followed by a 64 ms blank time. Stimuli are presented 15 times at each location, for a total of 960 stimulus presentations. Responses from the 15 trials are averaged. The response strength for the 64 different stimulus locations is determined for each of the 360 electrode array channels by calculating the RMS value of the zero-meaned signal within the 40 ms to 160 ms window after presentation of the visual stimulus, to capture the majority of the visual evoked potential[34]. Response strengths are plotted in FIG. 5A as 64 color maps, each showing the response of the entire 360 channel electrode array. Color maps are arranged in the same physical layout as the stimuli are presented in the visual field, i.e. the image map in the upper left hand corner of the figure represents the neural response recorded from all 360 channels to a flashing box presented in the upper left hand corner of the monitor. The color scale is constant over all 64 image maps and is saturated at the $1^{st}$ and $99^{th}$ percentile of recorded response strength, respectively, to improve the visual display. The responses indicate that distinct regions of the brain respond to distinct areas of the visual field, as expected. The electrode color map data is oriented such that the bottom left-hand corner of the electrode array is approximately located over Brodmann area 18, the bottom right-hand corner over area 17, the middle region over areas 18 and 19, the upper right-hand corner over area 21 and upper left-hand corner over area 7 (inset, FIG. 5B).

Figure 5B:
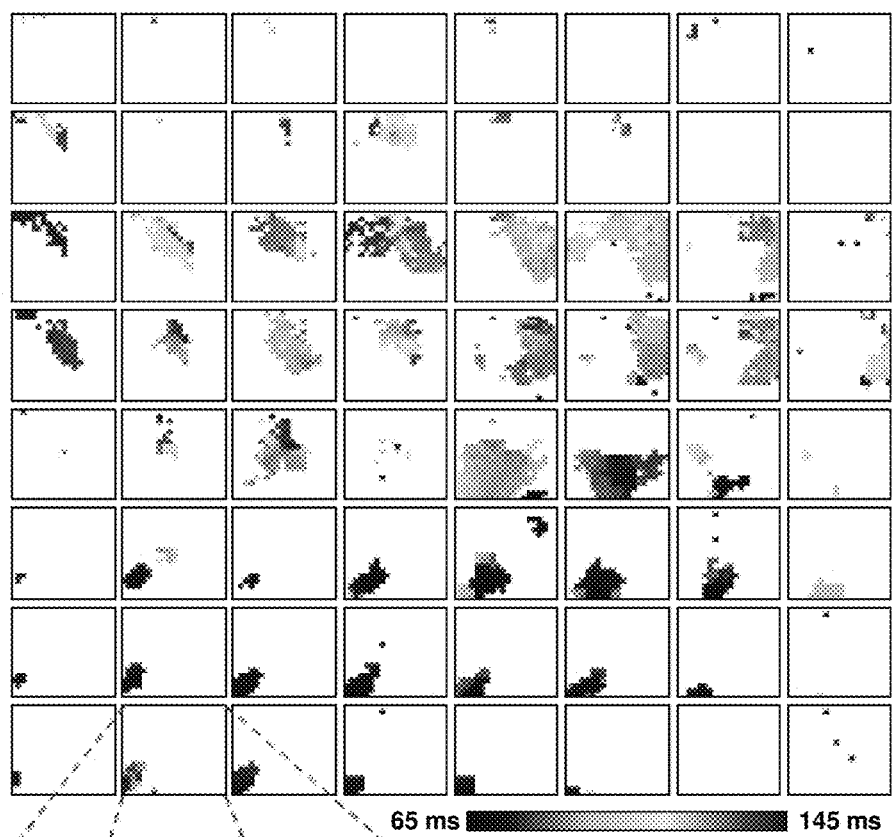
Figure 5B:
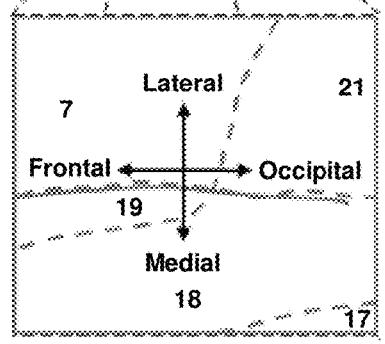

For each channel in the array with a response >50% of the peak RMS value (as calculated above), the delay to the peak of the evoked response is determined (FIG. 5B). Channels below threshold are shown as white. A few general observations are visible in the data. Stimuli presented in the lower and left areas of the screen appear to activate small areas of the lower left-hand corner of the electrode array and these responses occur earliest, consistent with early visual cortical areas[35]. Stimuli presented in middle to upper-middle areas of the visual field appear to elicit responses in large areas of the upper middle areas of the electrode array and these activations occur later, consistent with visual association cortex. The upper two rows of the screen appear to be outside of the visual field covered by the array.

Figure 5C:
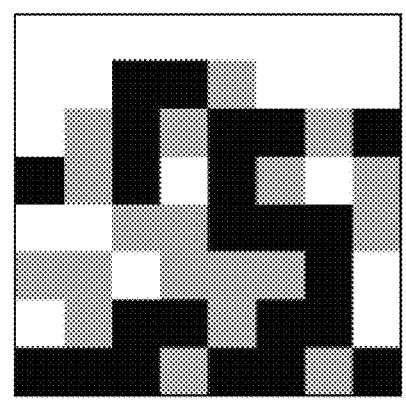

As a more rigorous test of the ability of the electrode array to resolve the visual field, the evoked response data is used to train a deep belief net (DBN) classifier[36,37]. A training set is generated by randomly selecting 10 out of the 15 trials, averaging the evoked responses and repeating this process 100 times for each of the 64 screen locations to yield 6400 total samples. The evoked response feature vectors are calculated as in FIGS. 5A and 5B, and concatenated, giving 720 feature dimensions in each of the 6400 samples. The trained deep belief net is tested on a separate dataset of 10 trials, averaged together, from the same animal and recording day. The prediction performance is illustrated as image map of the visual field in FIG. 5C. 23 of the 64 screen locations (36%) are predicted exactly correct (black boxes), significantly better than chance (1.6%). 41 of 64 (64%) screen locations are predicted correctly within 1 neighboring square (grey boxes, distance≤√2, chance level 11.8%).

Figure 6A:
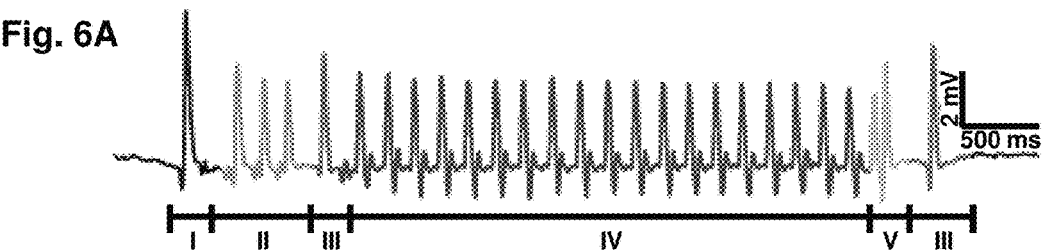
Figure 6A:
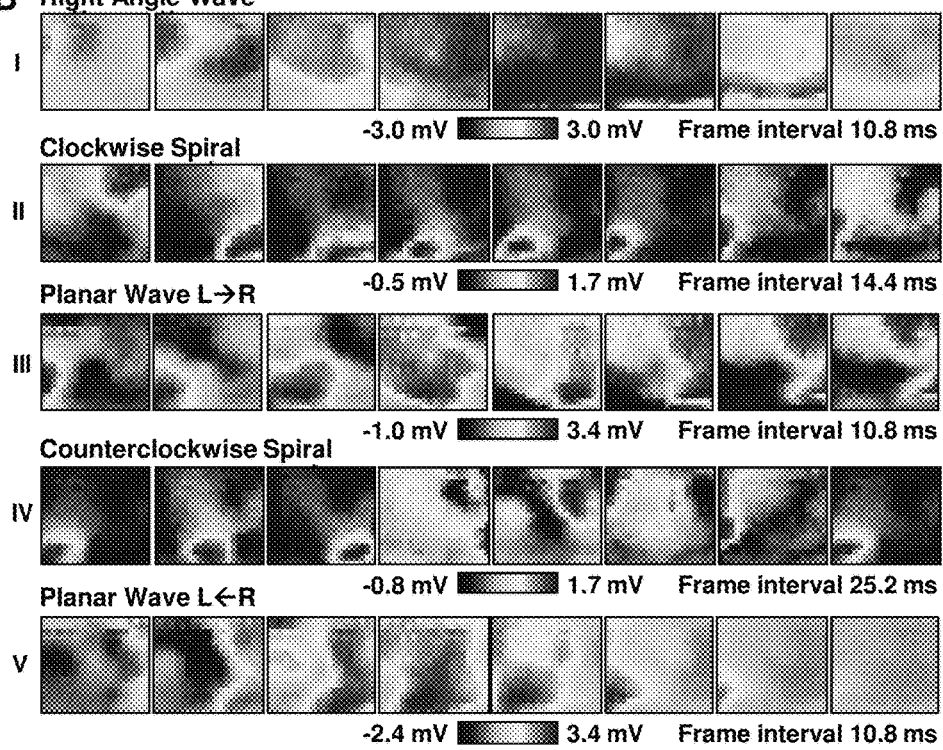

Electrographic seizures: As a third demonstration of this new technology, seizures are induced in the feline model using local administration of picrotoxin. The drug is placed directly on the brain, adjacent to the electrode array on the frontal-medial corner. In one of the animal experiments, the electrode array records four spontaneous electrographic seizures and hundreds of interictal spikes over ~1 hr. The μECoG signal from a single channel of the electrode array during a short electrographic seizure (FIG. 6A) demonstrates large amplitude (6.6 mV), low noise (45 μV RMS) and high signal-to-noise ratio (SNR, 34 dB).

The array recorded spatial patterns never previously observed during seizures. At the ictal onset, there is a plane wave (I) coming from the upper left which encounters a phase anisotropy, bends to the right, and anticipates the subsequent clockwise spiral (wave II). This spiral pattern (wave II) rotates for 3 cycles. A second incoming plane wave (III) changes the direction of rotation of the spiral. The ensuing counterclockwise spiral (wave IV) rotates for 19 cycles and is terminated by a plane wave (V) coming from the right.

Based upon these observations, it is possible that neocortical seizures are initiated by interictal spikes diverted asymmetrically around regional anisotropies, resulting in sustained reentrant loops. Seizures may be terminated by mutual annihilation of a rotating spiral with a traveling wave, which has implications for electrical stimulation to disrupt seizures[38]. Analogous anisotropies and colliding waves have been observed in the genesis and termination of cardiac arrhythmias[39].

Figure 9:
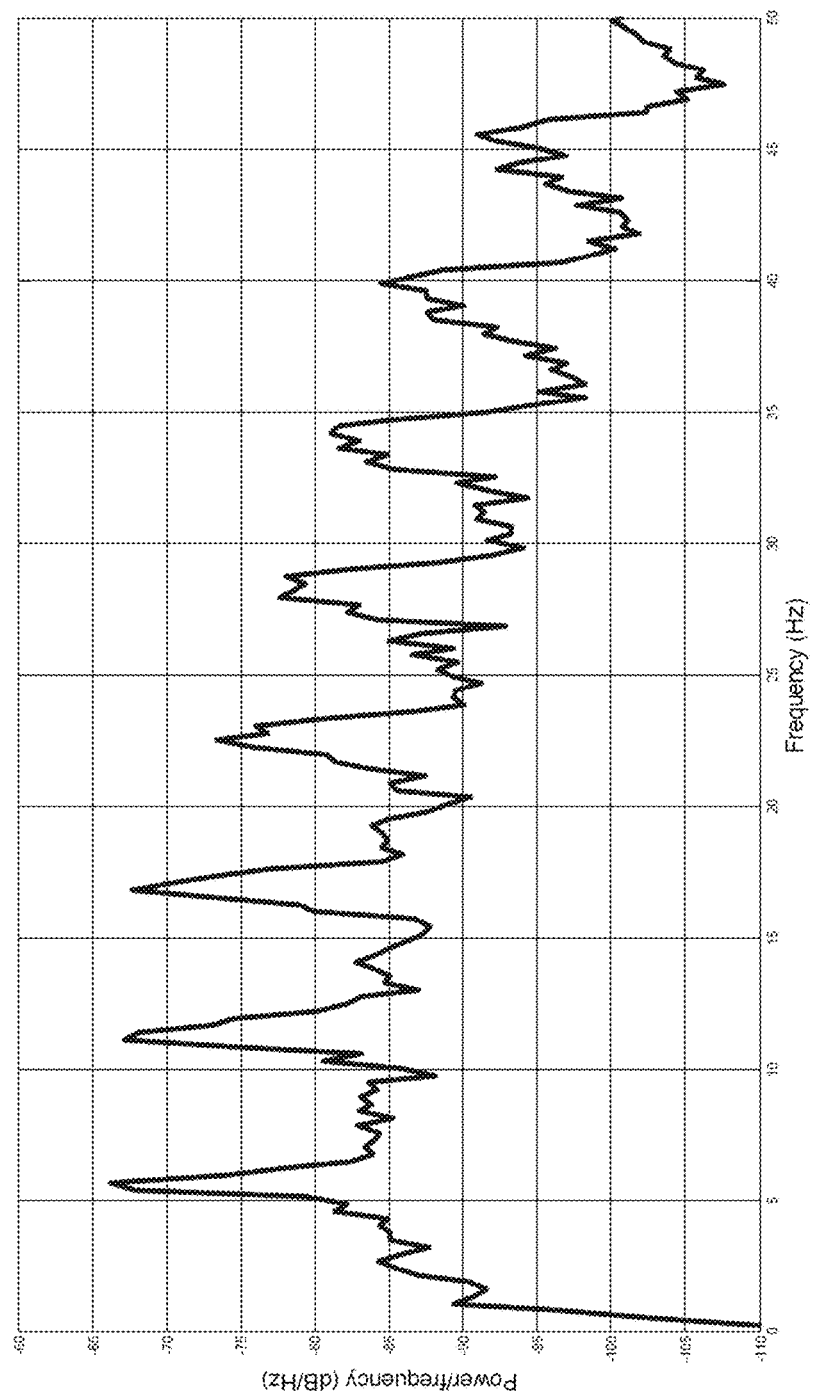
FIG. 9. Analysis of the frequency content of a sustained, counter-clockwise spiral during a short seizure. The primary frequency component was 6 Hz. The power spectral density is calculated using 'pwelch' with a window size of 1024 on each channel of the electrode array individually. The resulting power spectra are averaged to produce a single overall power spectral density.
Figure 10A:
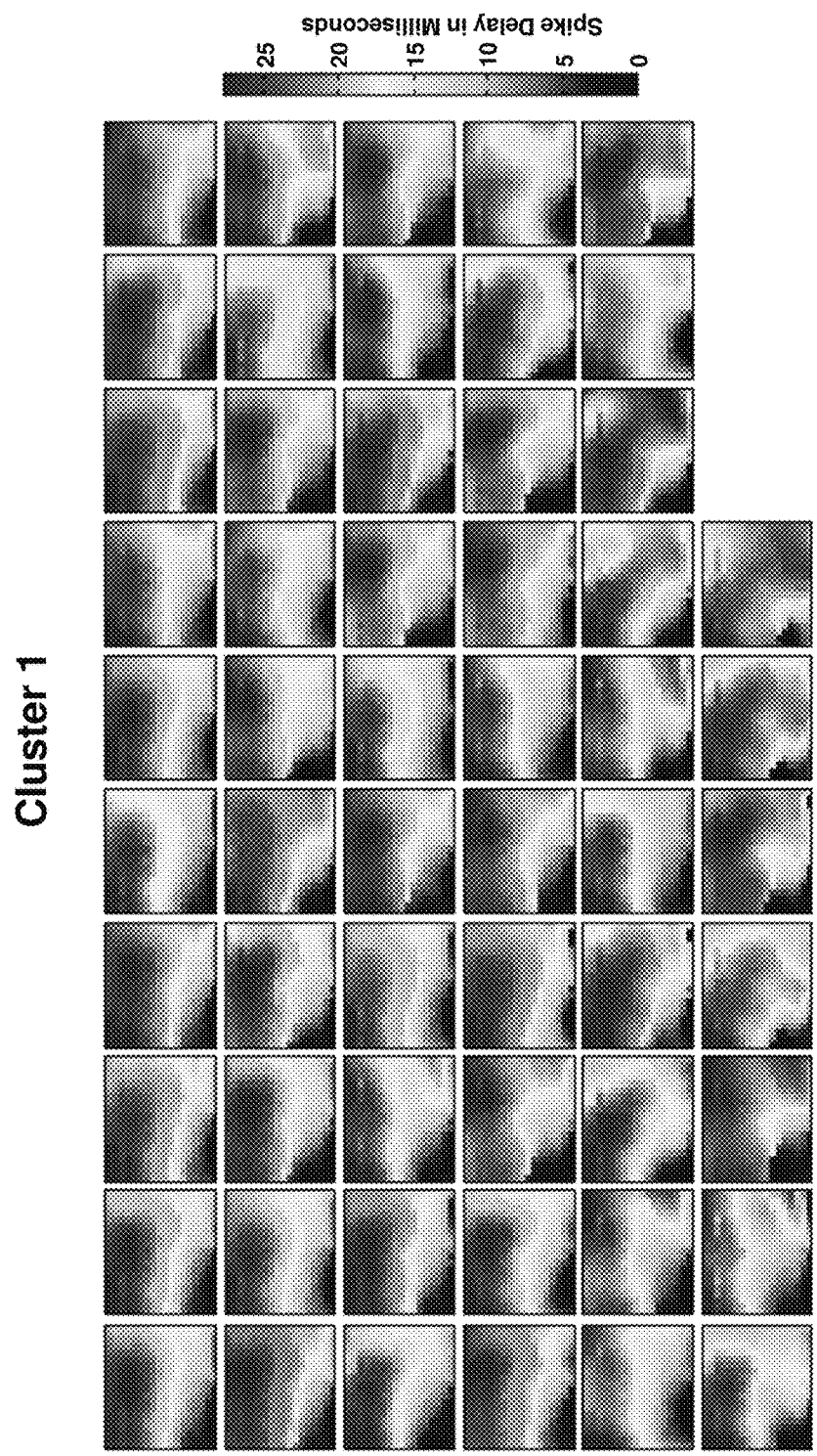
Figure 10B:
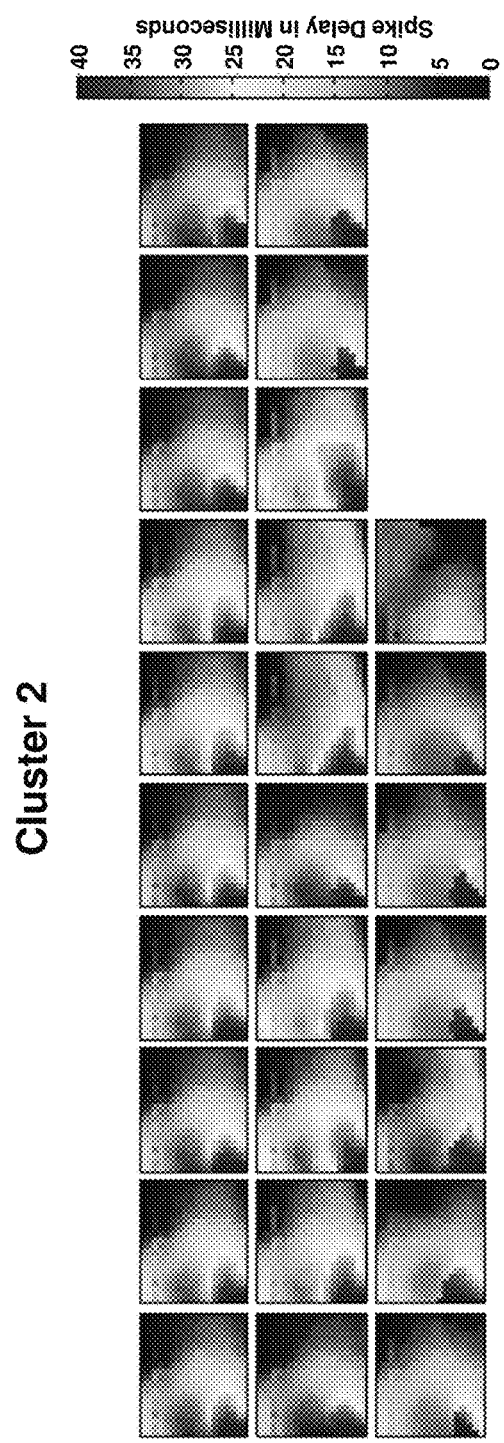
Figure 11A:
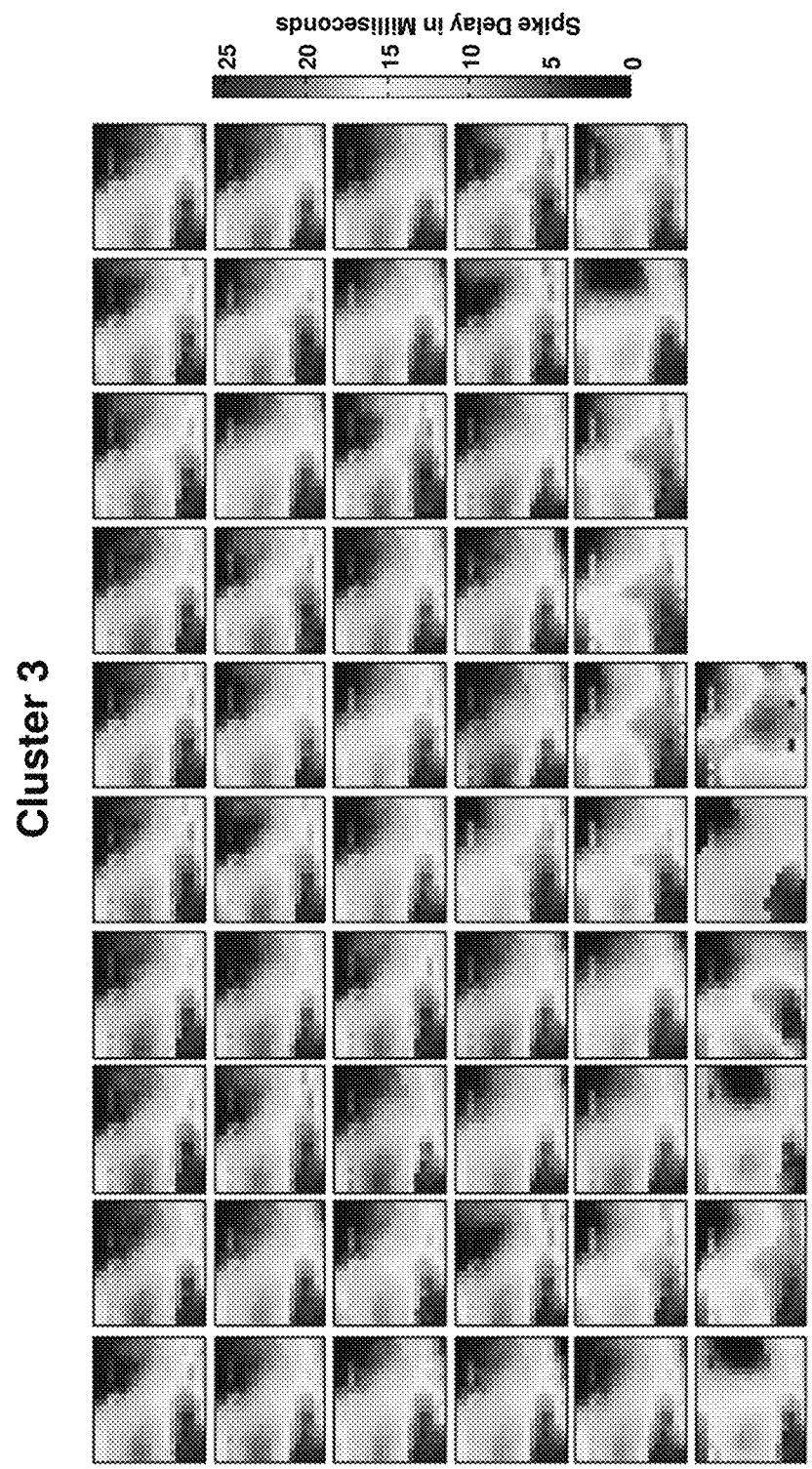
Figure 11B:
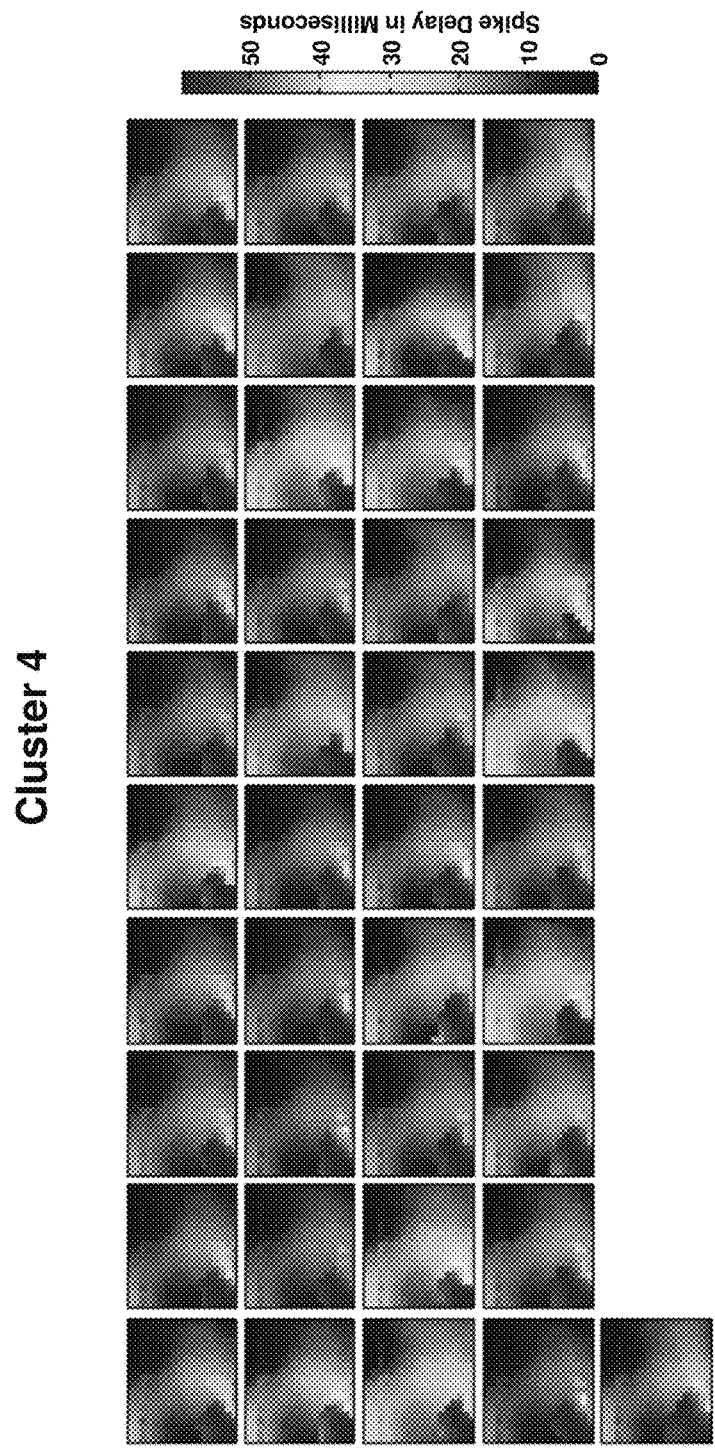
Figure 12A:
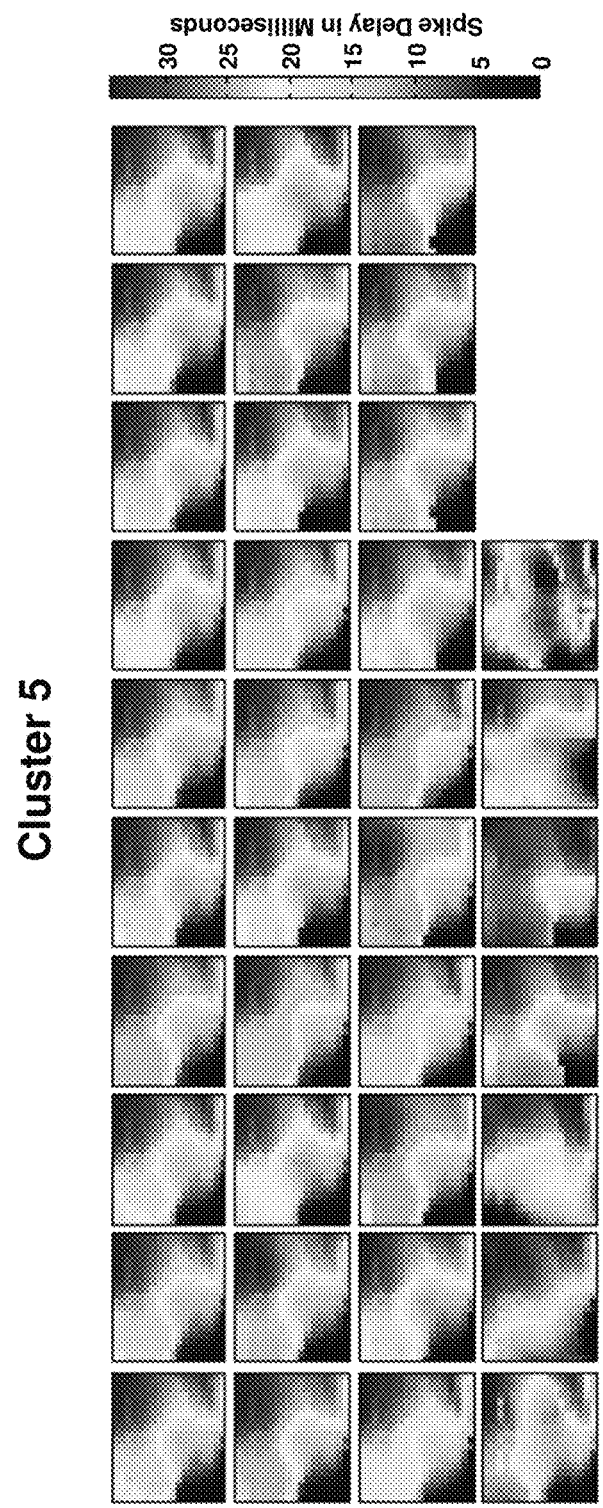
Figure 12B:
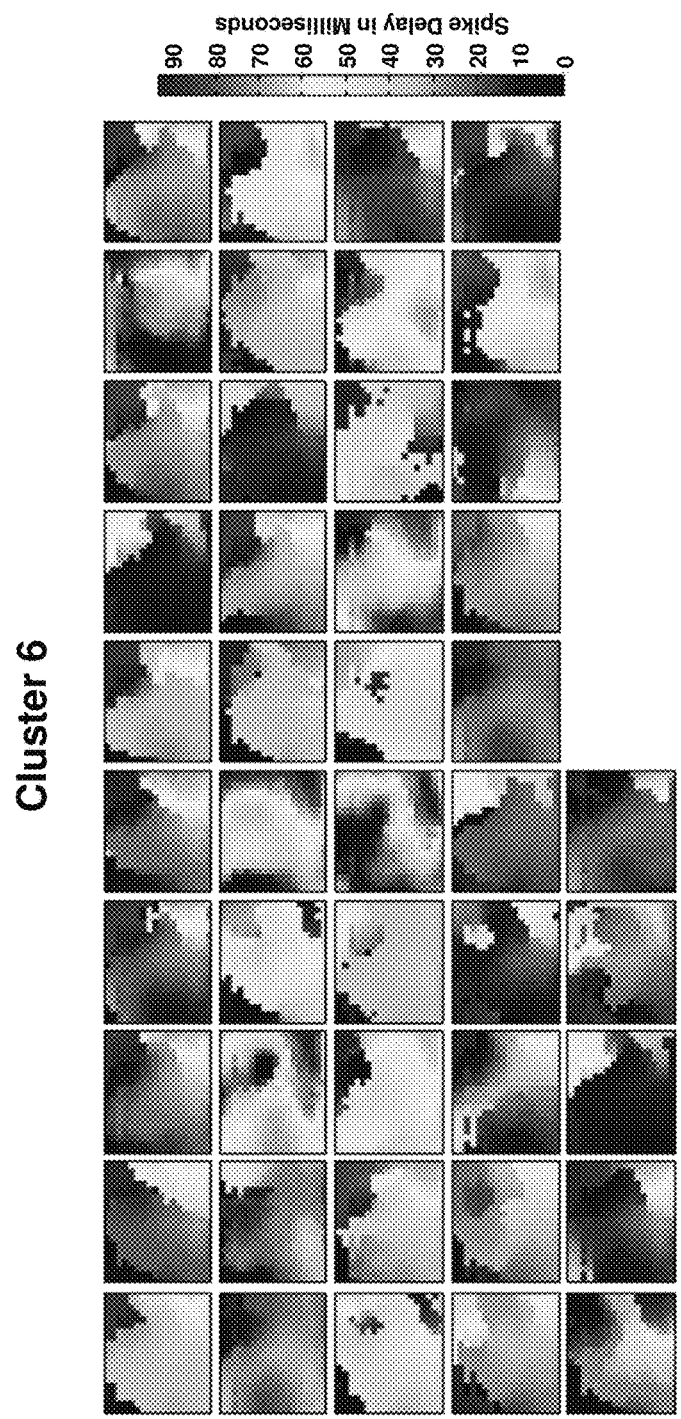
Figure 13A:
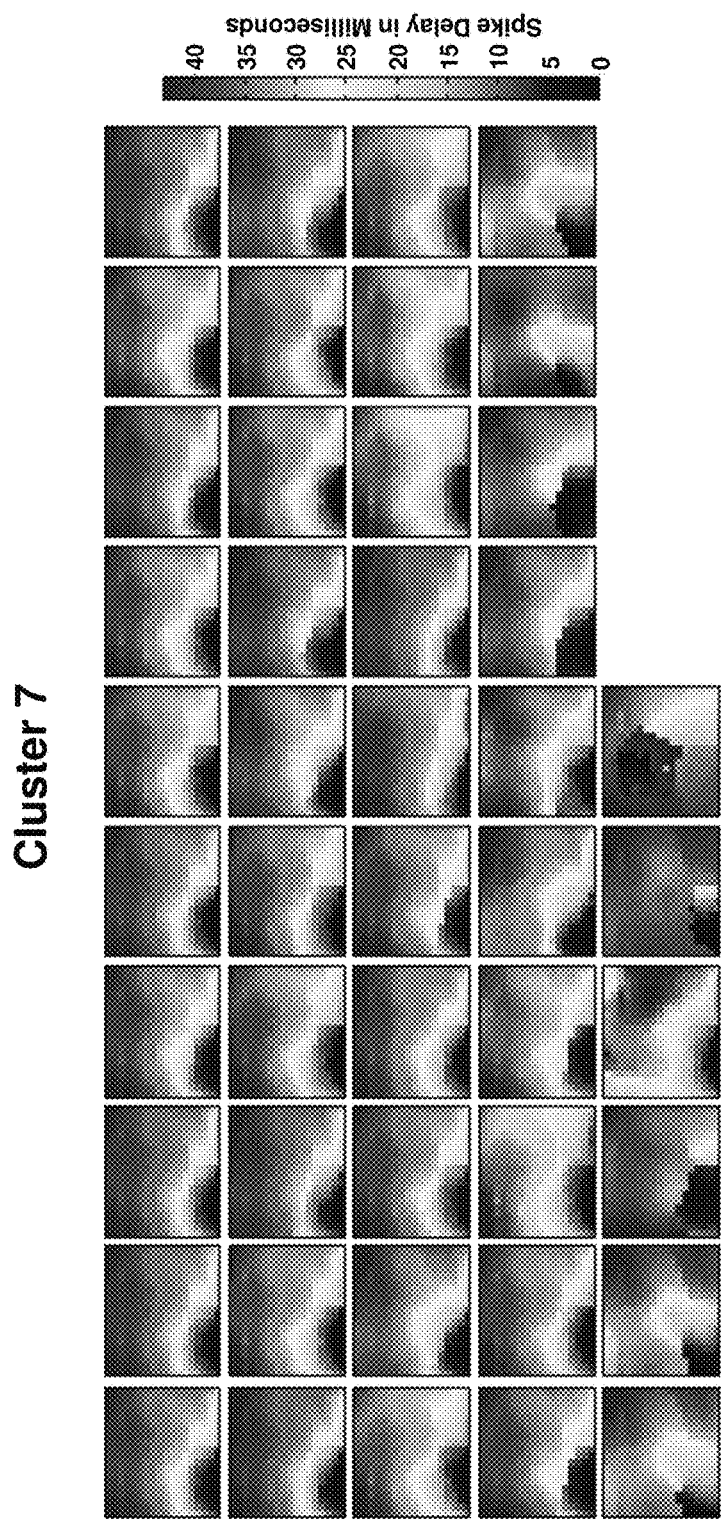
Figure 14A:
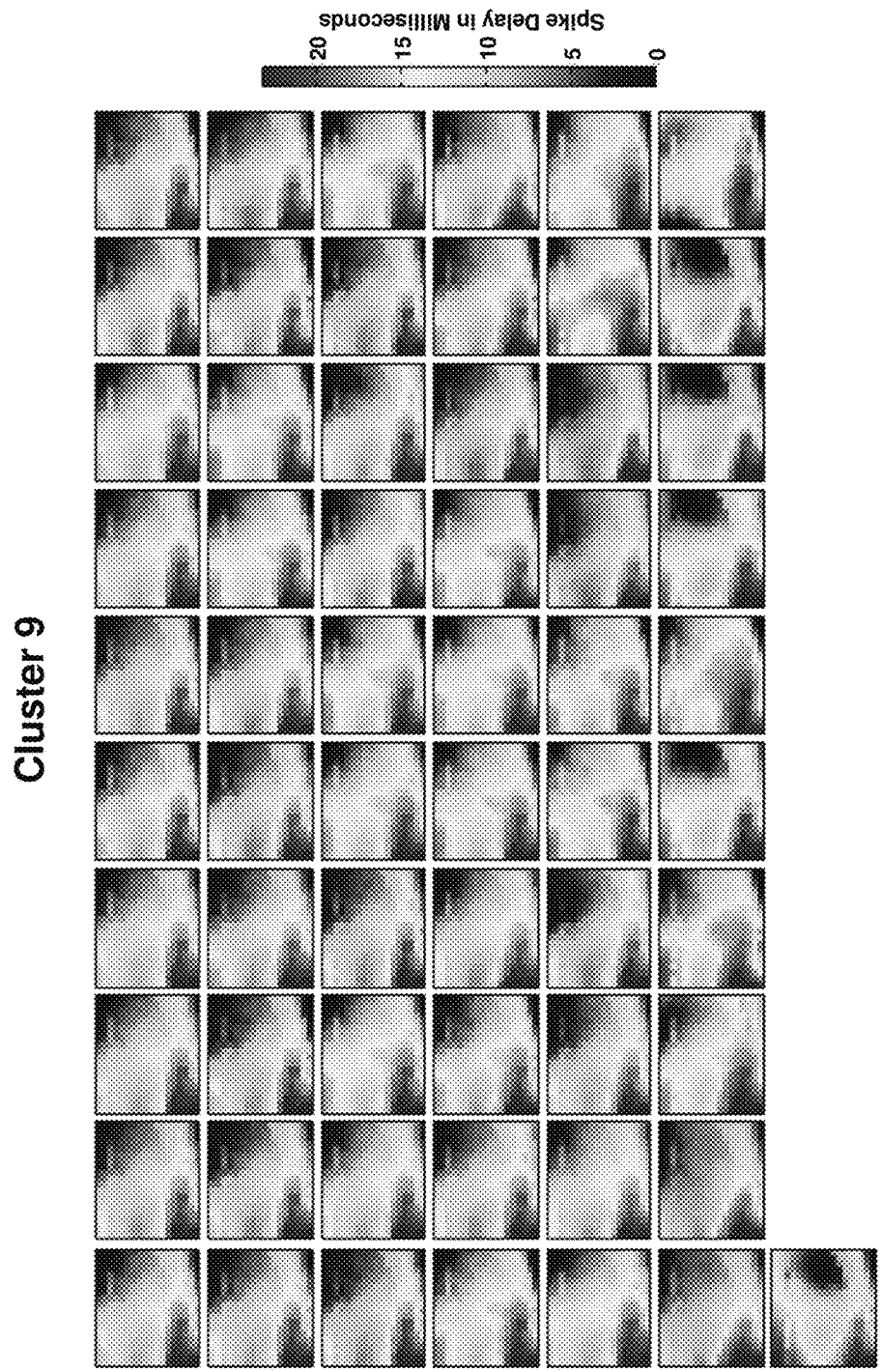
Figure 14B:
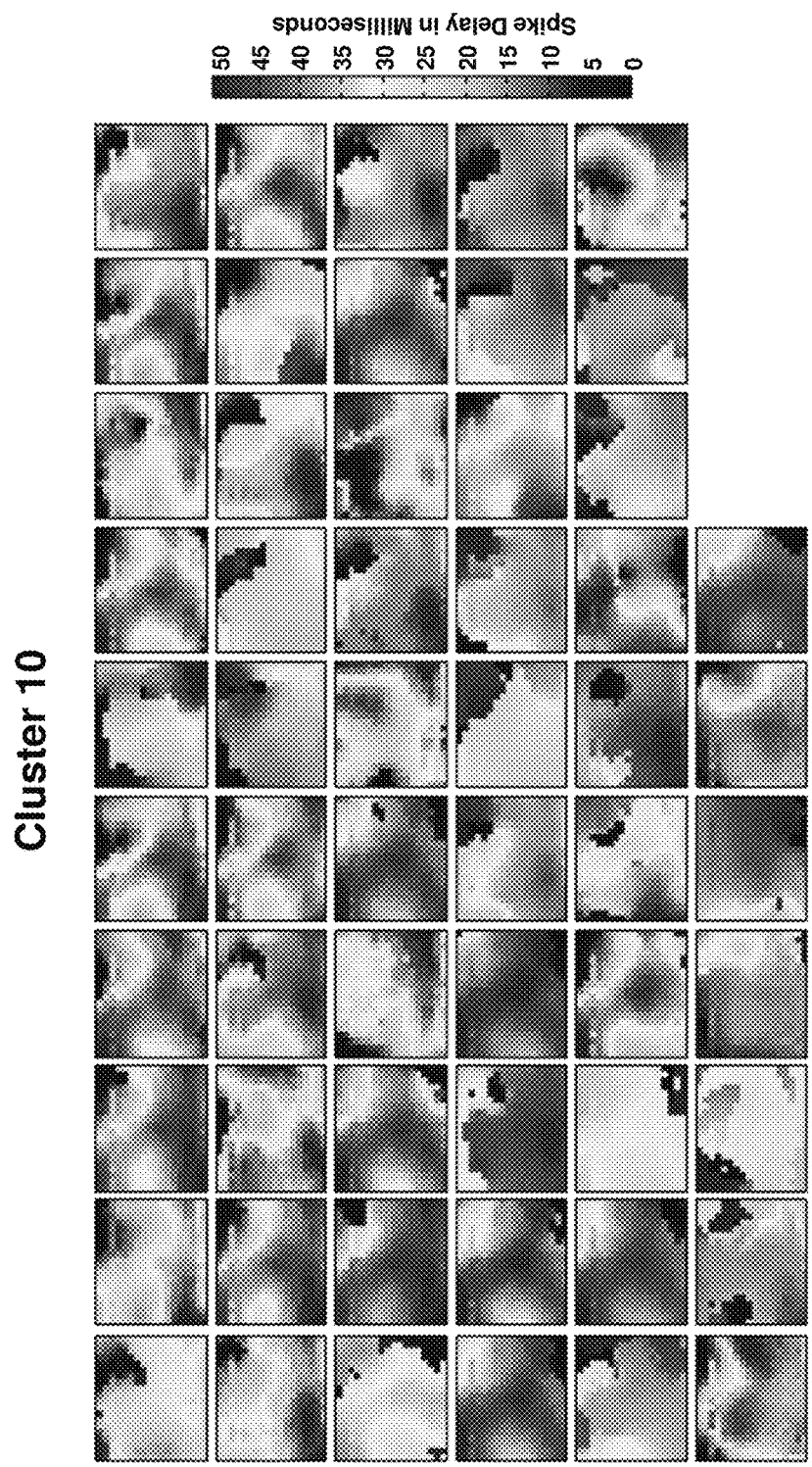
Figure 15A:
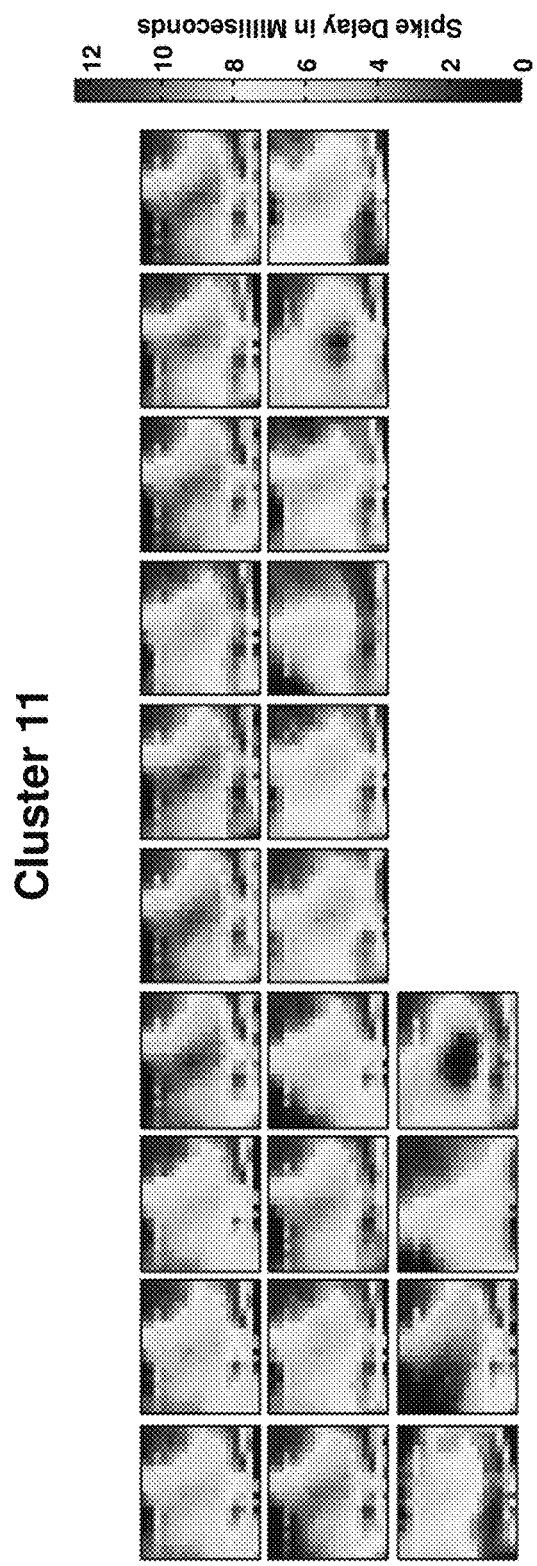
Figure 16A:
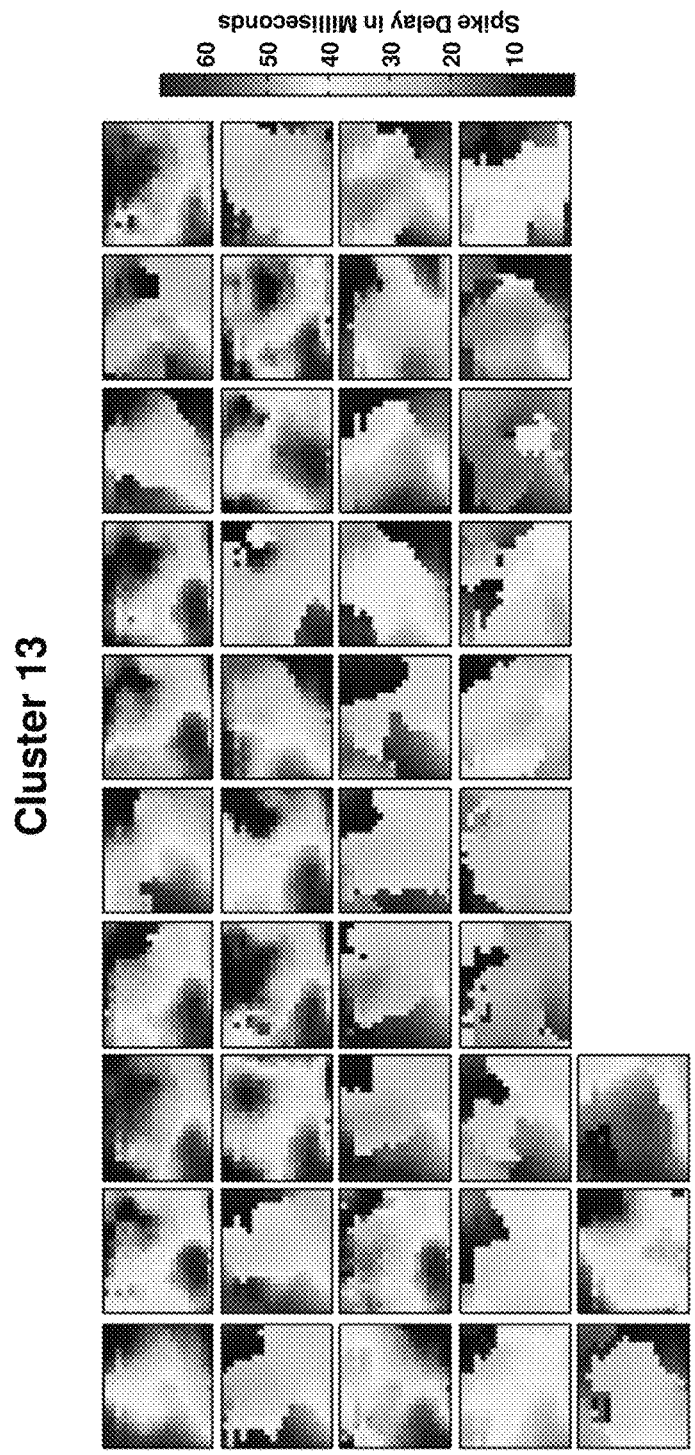
Figure 16B:
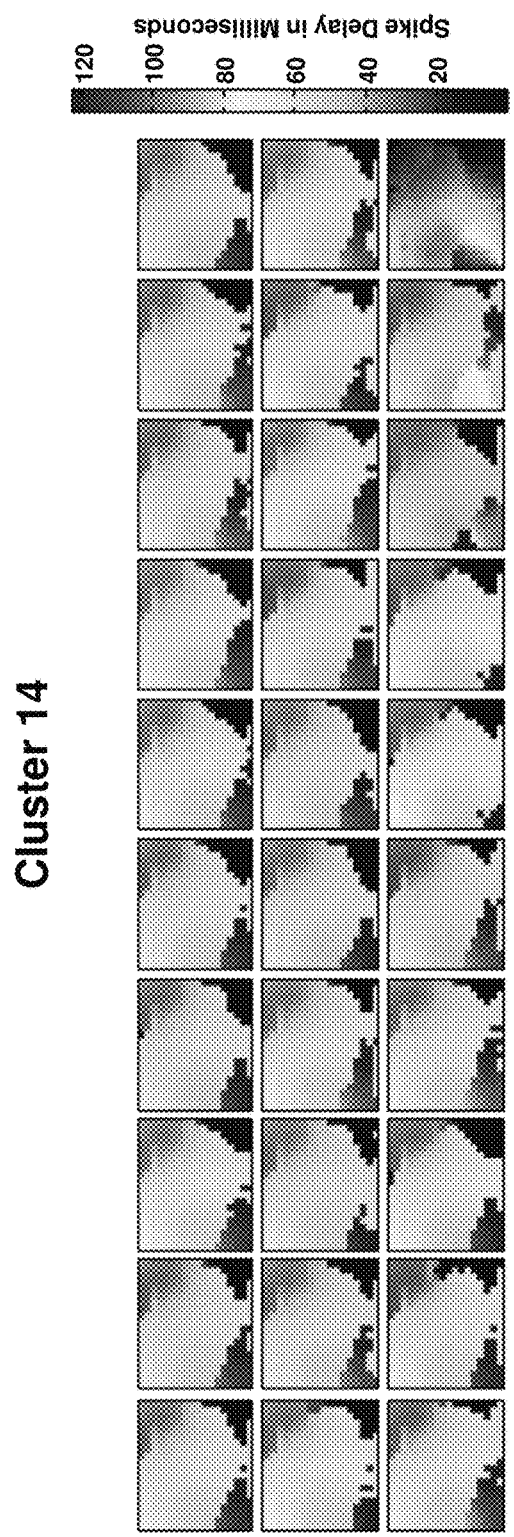
Figure 17A:
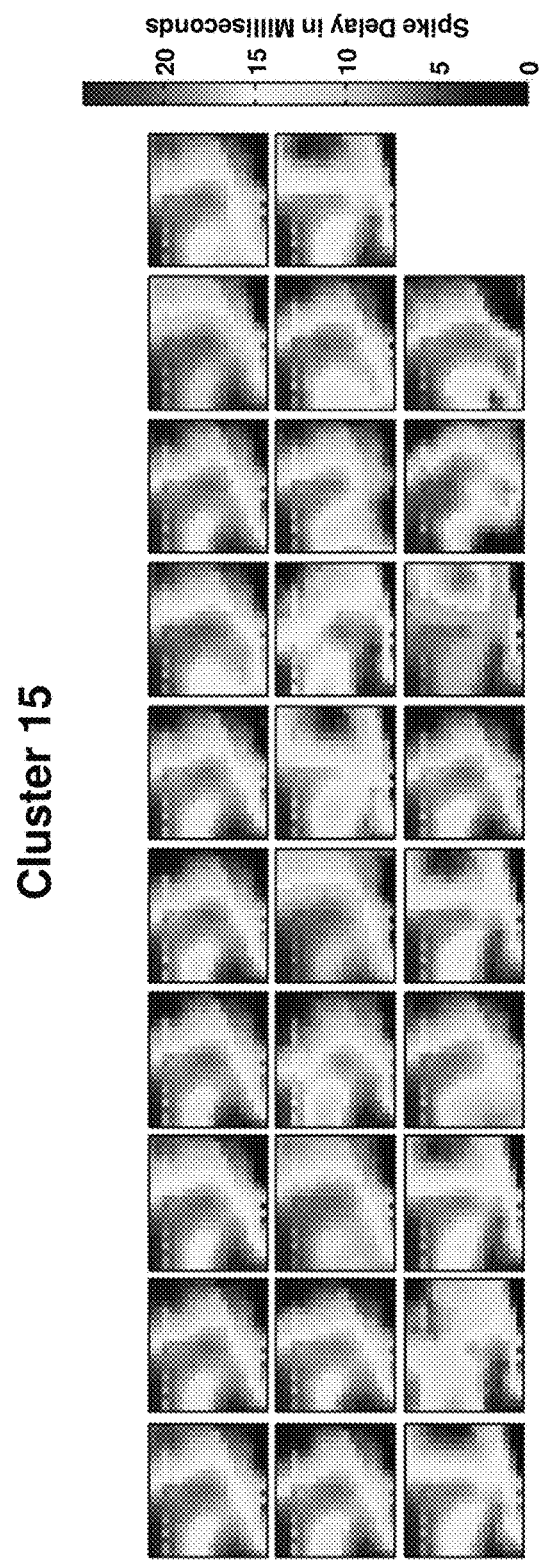
Figure 17B:
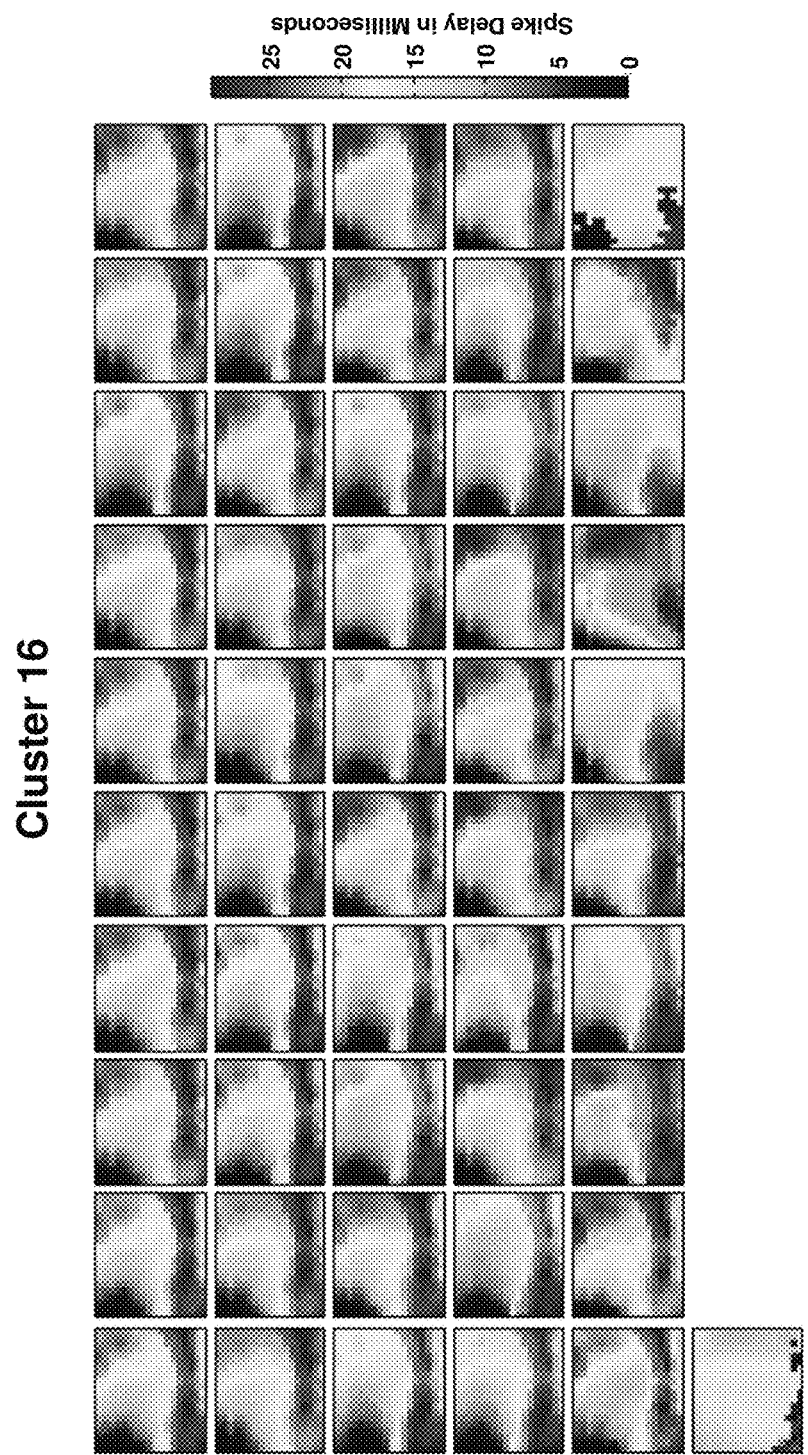
Figure 18A:
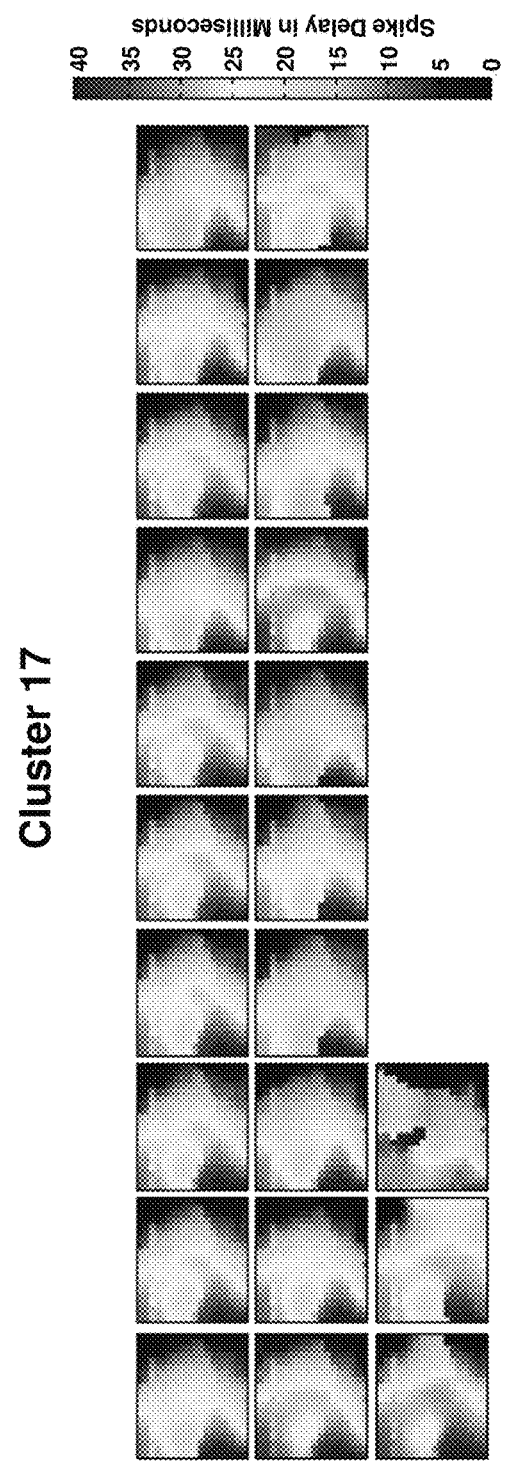
Figure 18B:
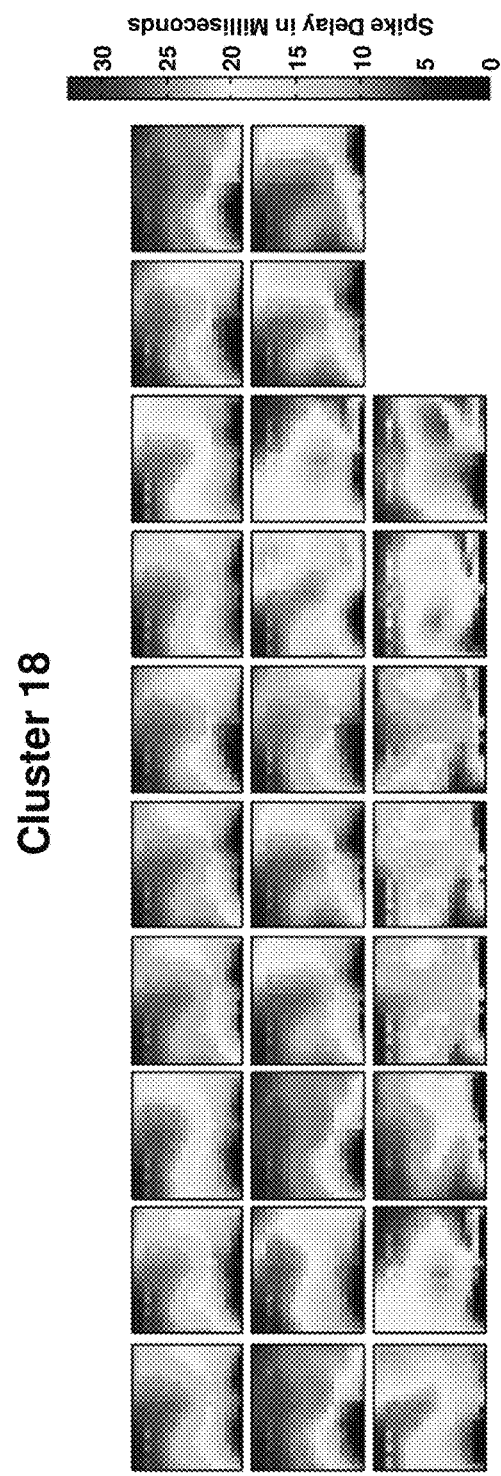
Figure 19B:
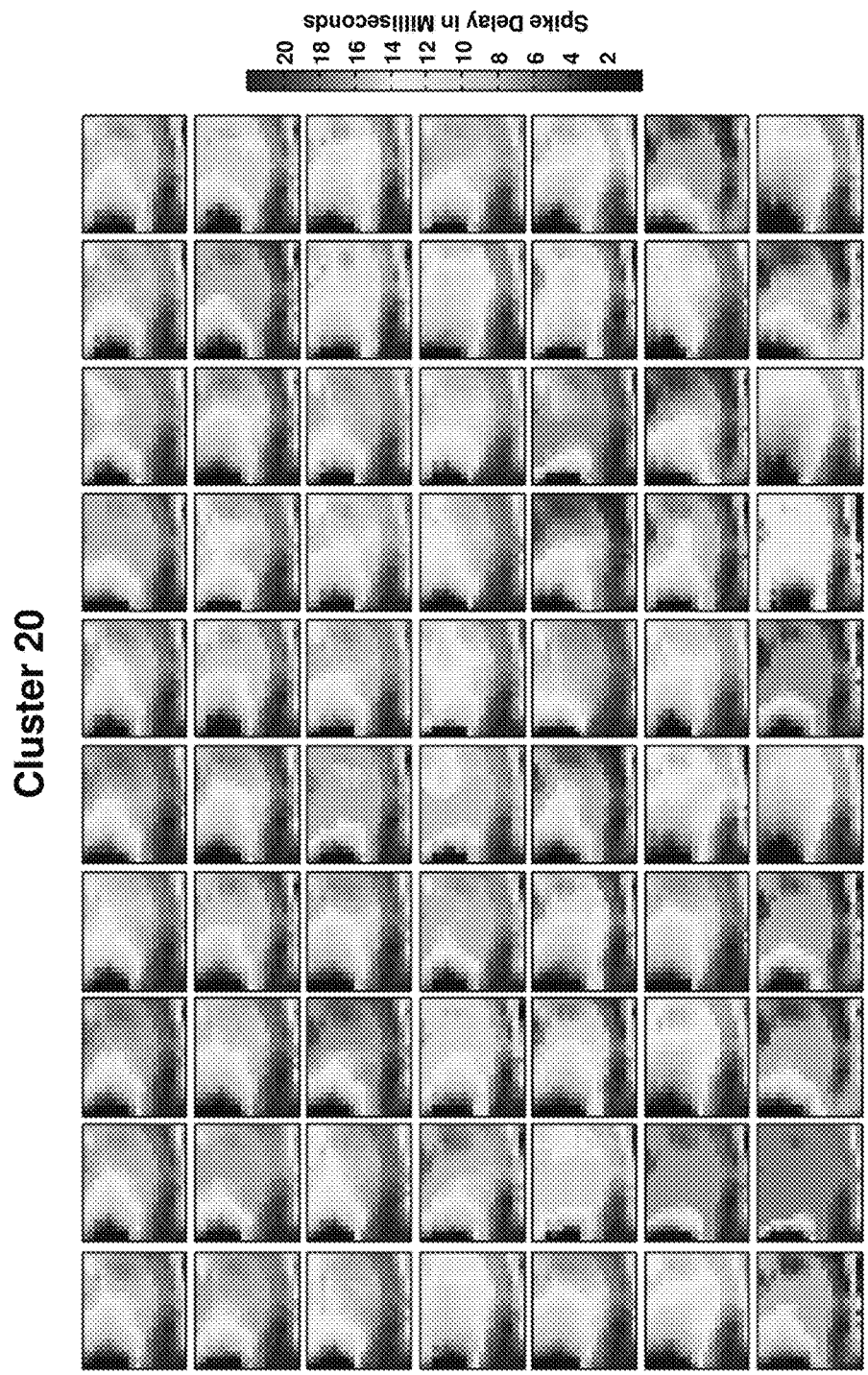
Figure 20:
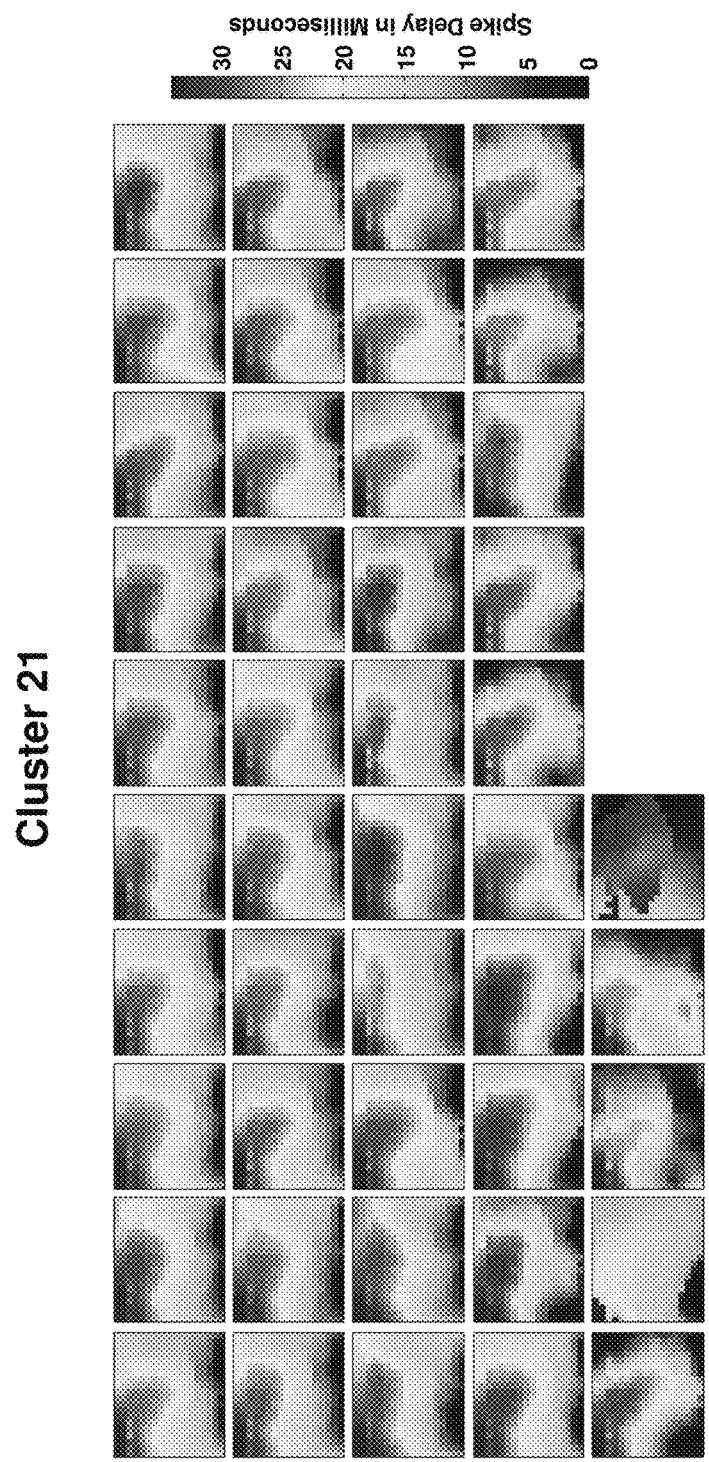

Band-pass filtering the spiral wave data to investigate only the primary frequency component (as in previous analysis[40-42]) yields delay plots that are consistent with spiral waves. The primary frequency of the counter-clockwise spiral during the seizure is 6 Hz (see FIG. 9). Spiral wave data is band-pass filtered from 4 to 8 Hz using a 6th order butterworth band-pass filter in the forward and reverse directions, resulting in zero-phase distortion digital filtering (and effectively doubling the order of the filter to a $12^{th}$ order filter). The relative delay for each electrode is calculated by first upsampling by a factor of 12 and then taking the index of the maximum cross-correlation between each channel and the average of all 360 channels. The resulting delay image map (FIG. 6C) shows a singularity as if forming a counter-clockwise rotating pinwheel. Clockwise motion is also demonstrated by the delay plot (FIG. 6D) albeit with a less clear singularity.

In addition to the spatiotemporal patterns analyzed above, the large SNR of the electrode array facilitates pattern analysis of single ictal and interictal spikes. Stereotyped, repetitive spatiotemporal patterns of single spikes are frequently observed throughout the dataset. We develop a clustering algorithm to test whether the spatiotemporal patterns of single spikes can be classified consistently. First a standard, threshold-based spike detector is run on the average of all 360 channels to provide event detections. The threshold is set at −500 μV with a refractory period of 160 ms. Data from all 360 electrodes are band-pass filtered from 1 to 50 Hz in the window 60 ms before and 100 ms after the threshold crossing. The data is then upsampled by a factor of 12 and cross-correlated with the average of all 360 channels. The relative delay of the spike on each channel is calculated using the index of the maximum correlation value. In addition, the magnitude of the spike on each channel is calculated using the RMS value of the zero-meaned signal within the same window. The 360-element delay and RMS vectors representing each spike are normalized by dividing by their maximum respective values and concatenated. Using these two features, relative delay and RMS, the speed and direction of the wavefront, as well as its amplitude, is encoded.

To lessen the computational burden before clustering, principal components analysis (PCA) is used to reduce the dimensionality of the spike data from 720 to 81—a number of coefficients that accounts for 99% of the data variance. Finally, k-medoids clustering[43] is carried out on 877 detected spikes. The potential number of clusters, k, ranged from 1 (i.e. no clustering) to 30 and the gap statistic[44] is then used to determine the optimal number of clusters[45]. 21 clusters are returned. Delay maps for all of the spikes in each cluster indicate a strong similarity within clusters (see FIGS. 10 to 20).

Example relative delay image maps for six different clusters are shown to illustrate their differences (FIG. 6E, left frames). The events in the six clusters shown are found both ictally and interictally. The representation of each event on a standard clinical electrode, based on the average signal, is plotted as a trace (FIG. 6E, right). They illustrate that vastly different micro-scale spatial patterns can be indistinguishable when detected with conventional systems on a macro-scale. This data explicitly demonstrates the functional benefit of the present high density, high resolution device arrays for recording a spatio-temporal profile from brain at high spatial resolution.

5 of the 21 clusters appeared to occur only during seizures. One example each from two of these clusters is shown (FIG. 6F). These results suggest that µECoG can differentiate ictal from interictal patterns that would show up as nearly identical spikes at the resolution of clinical EEG.

Discussion: Spiral activity is described by mathematical models of 2-dimensional excitable media[46] and is documented in brain and heart,[39-42] but until now a tool did not exist to record exhaustive spatiotemporal patterns of brain activity in a large mammalian brain, as we demonstrate here. Our results not only demonstrate the presence of spiral waves during seizures with unprecedented detail but also, and perhaps more importantly, offer a method to record such waves in a chronic fashion in awake, behaving animals and humans.

The significance of high density, active array technology is evident in the neural dynamics which emerge at a spatial scale 400 times finer than used clinically. This technology demonstrates complex spatial patterns, such as spiral waves, clustering of spatiotemporal patterns, and heterogeneity and anisotropy of sleep oscillations, all of which occur within the space occupied by one current clinical ECoG electrode. Whereas coarse spatial undersampling prevents current technology from resolving the micro-scale spatial patterns that occur in the brain, the high resolution of the active array technology enables us to distinguish intrinsic from pathologic signals efficiently, even within the same frequency bands.

We report that spindles are spatially punctate and temporally coherent, whereas electrographic seizures propagate as planar and spiral waves. Although prior investigations using voltage-sensitive dyes have found spiral waves in rodents during EEG epochs dominated by sleep-like delta frequencies[42], in contrast, we demonstrate activity which is spatially inhomogeneous and does not spiral, yet are present during delta-dominant states, and which appear as sleep spindles electrographically. While optical imaging has demonstrated spatial patterns such as planar waves and spirals in disinhibited rat cortex[41], high-density, active array technology enables us to show that these spiral dynamics in disinhibited cat cortex are electrographic seizures at the clinical scale.

Ultimately, the question of clinical relevance is whether there are spiral waves in human cortex, yet voltage sensitive dye recordings are infeasible for use in humans due to the requirement that the brain be optically exposed and subjected to toxic dyes. Our results suggest that technology incorporating flexible, high-density, active arrays of electrodes can provide equal or superior recordings in a fully implantable system. If spiral waves are demonstrated in human cortex, the clinical implications are profound. Seizure control may be analogous to the control of cardiac arrhythmias, which are also known to manifest as reentrant spiral waves of excitation[39]. Further, as learning tasks increase spindle activity[47], which may be due to consolidation and integration of memories[48], understanding the fine structure of spindles has implications for learning and memory efficiency, as well as thalamocortical networks involved in sleep and primary generalized epilepsy.

Finally, flexible devices such as those shown here hold the promise to enable neuroprosthetic devices that have been limited until now by the lack of resolution of the brain-machine interface and by the irregular topography of the brain. Utilizing the extreme flexibility of active electrode arrays, devices can be folded and implanted into currently inaccessible brain regions, such as sulci and fissures that can be simultaneously recorded and stimulated, along with surface regions to enable devices to facilitate movement, sensation, vision, hearing and cognition. These devices can also be powered remotely through wireless power transmission techniques[49].

Our work also has implications for treating disease. Disorders such as epilepsy, dementia, affective disorders, movement disorders and schizophrenia are all conditions that affect dispersed brain networks, rather than a single locus of brain function. Investigations of major depression, parkinsonism, and chronic pain with magnetoencephalography has identified "thalamocortical dysrhythmia," but increases of spatial and temporal resolution as with the recording method presented here would allow a more detailed characterization of these diseased networks[50]. Only with new approaches that can resolve micro-scale activity over large areas of cortex will we be able to begin to understand how the brain functions in both disease and health, and to develop better diagnostic and therapeutic options for those affected.

Methods. Fabrication of the Active Electrode Array: Doped silicon nano-ribbons on a silicon-on-insulator (SOI) wafer (Si(260 nm)/SiO$_2$(1000 nm)/Si; SOITEC, France) are prepared using a high temperature diffusion process (950-1000° C.) in a rapid thermal annealing (RTA) system. These nano-ribbons were transfer printed onto a PI substrate (12.5 µm, Kapton, Dupont, USA) using spin-coated, uncured polyimide (PI) as a glue layer. Once the PI is cured, gate oxide is deposited with plasma enhanced chemical vapor deposition (PECVD, plasmatherm, USA). Contact openings for the source and drain connects are made with a buffered oxide etchant (BOE, Transene, USA). Finally, metal (Cr/Au, 5 nm/150 nm) is deposited using an electron beam evaporator (Temescal, USA), creating n-type transistor arrays. Each unit cell contains 2 transistors, which are connected by metal lines. Subsequent layers of metal interconnections are electrically isolated with polymeric inter-layer dielectric (1.2 µm, polyimide, Sigma Aldrich, USA). Following two metal circuit interconnection layers, a water-proof encapsulation is formed with a photocurable epoxy (SU8, Microchem Corp), protecting the device while submerged in conductive bio-fluids. The completed active sensor array is connected to an interface circuit board through a flexible anisotropic conductive film (ACF, Elform, USA).

Figure 23:
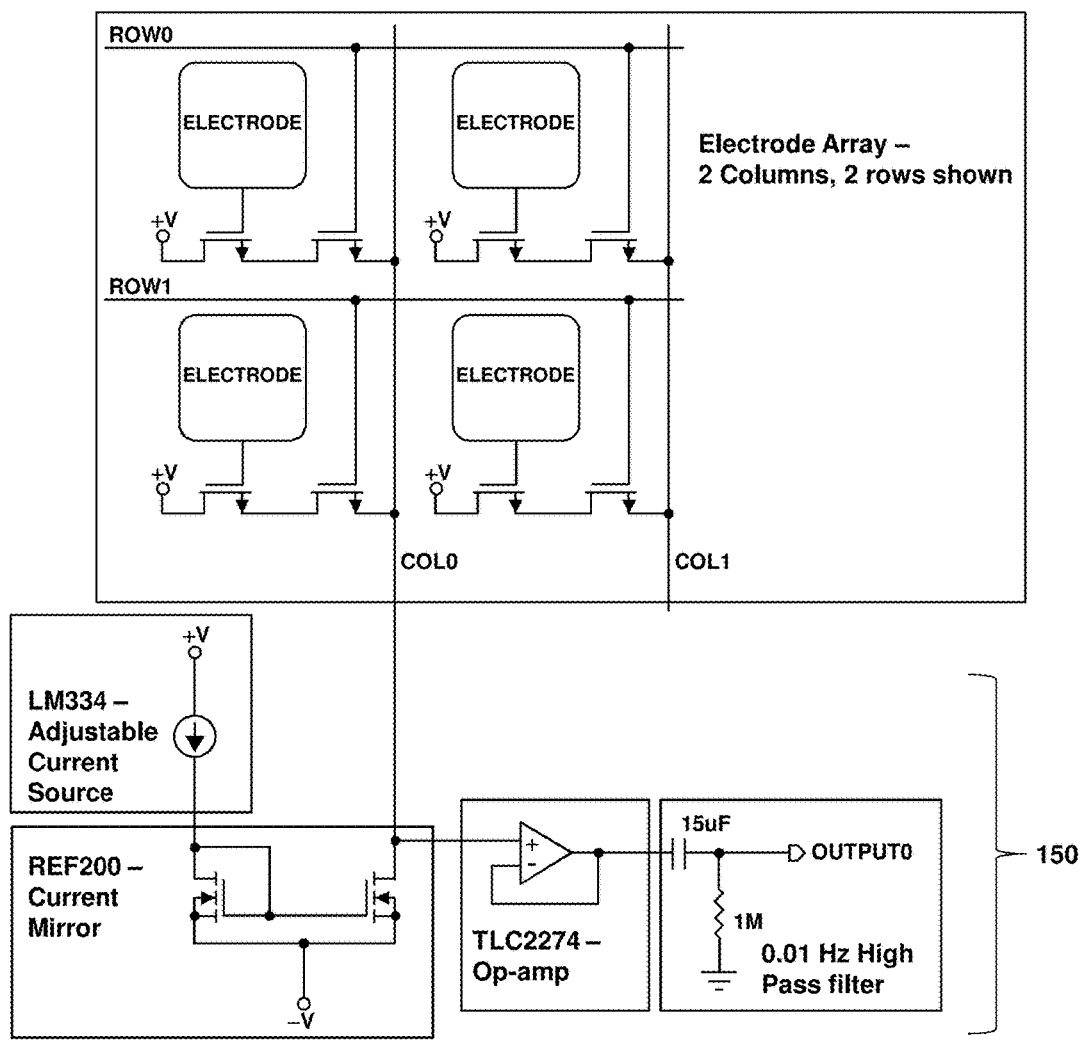
FIG. 23. Block diagram of constant current sink implementation. This circuit is repeated 20 times, one for each column of the electrode array.
Figure 24:
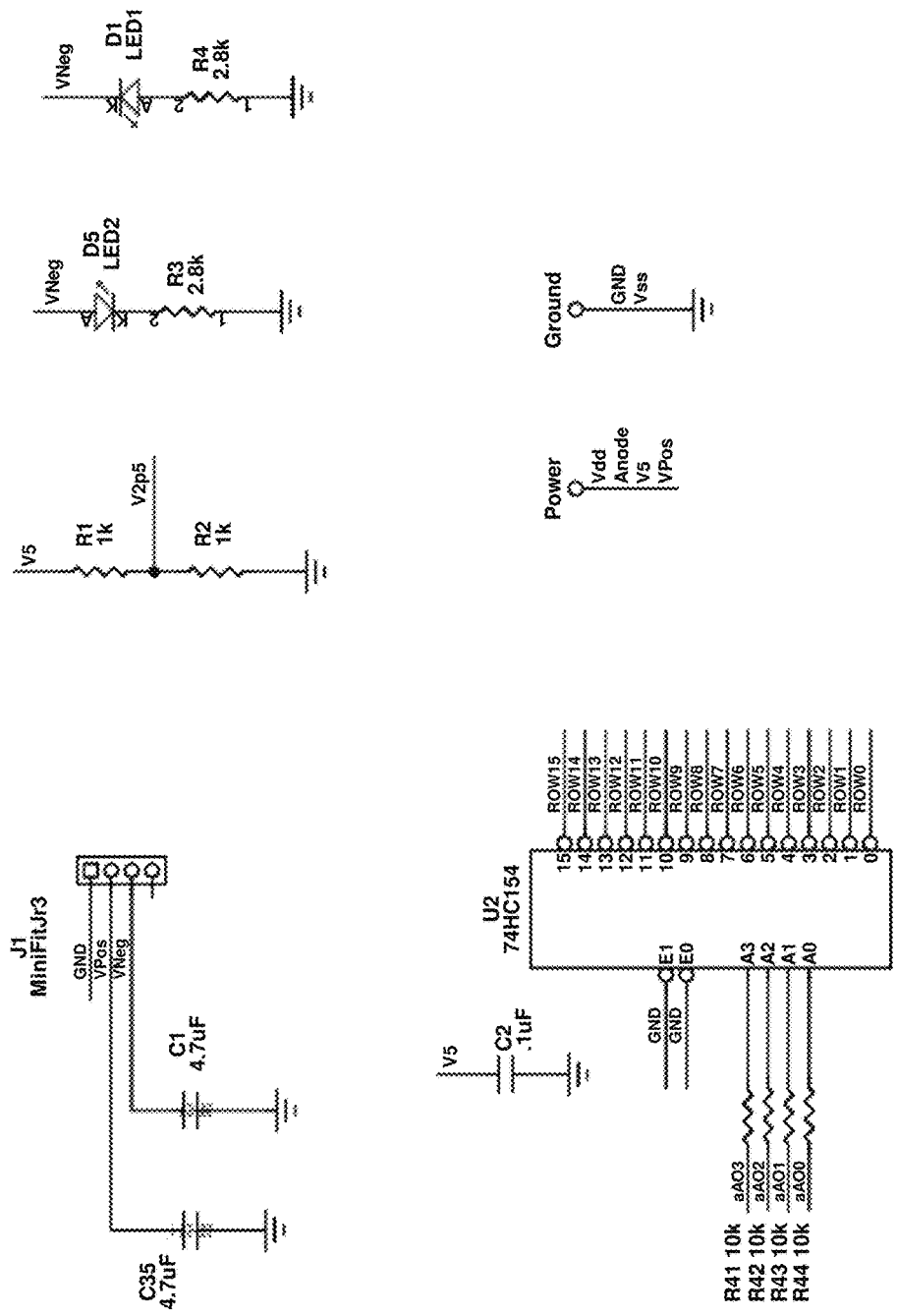
Figure 25:
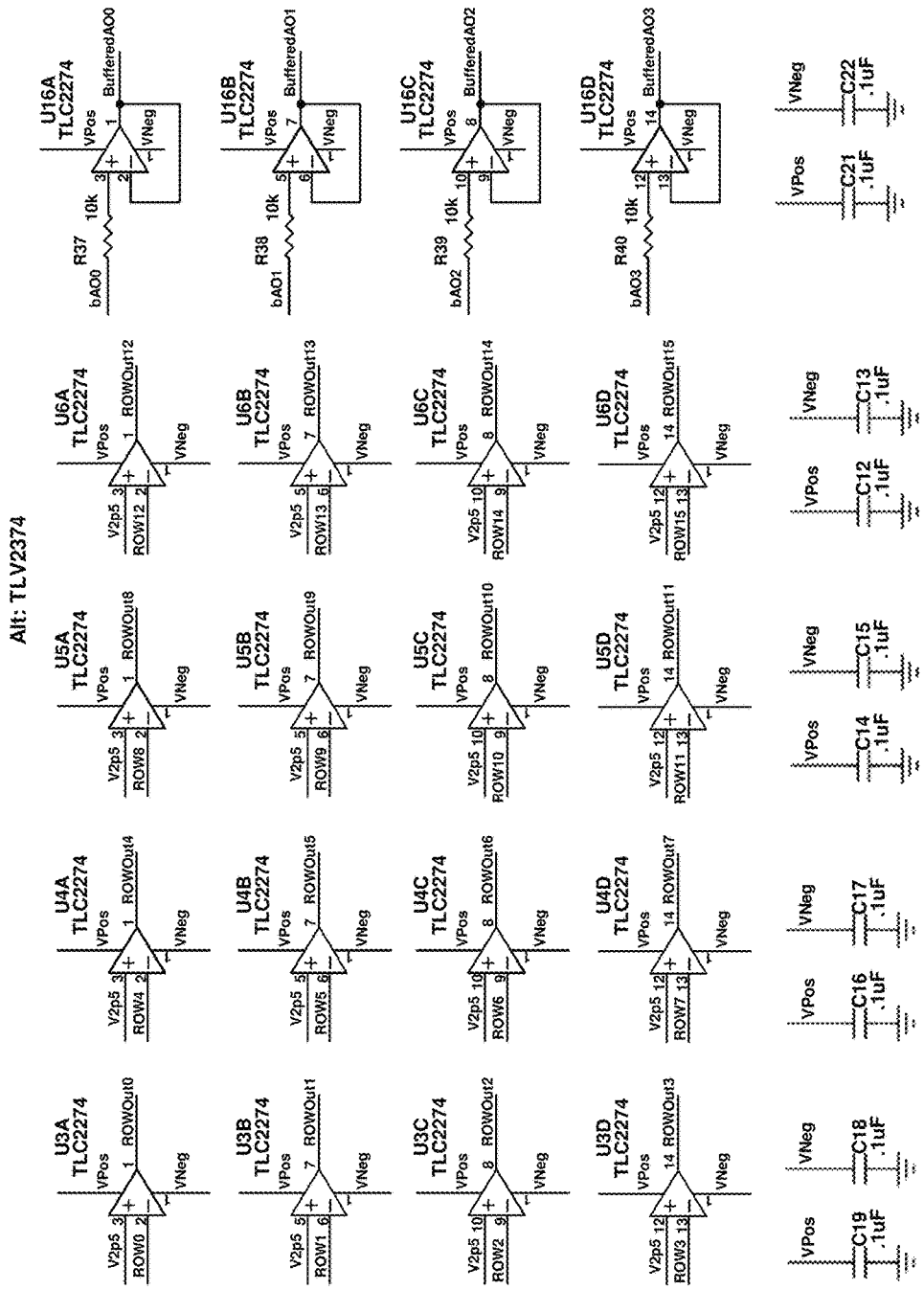
Figure 26:
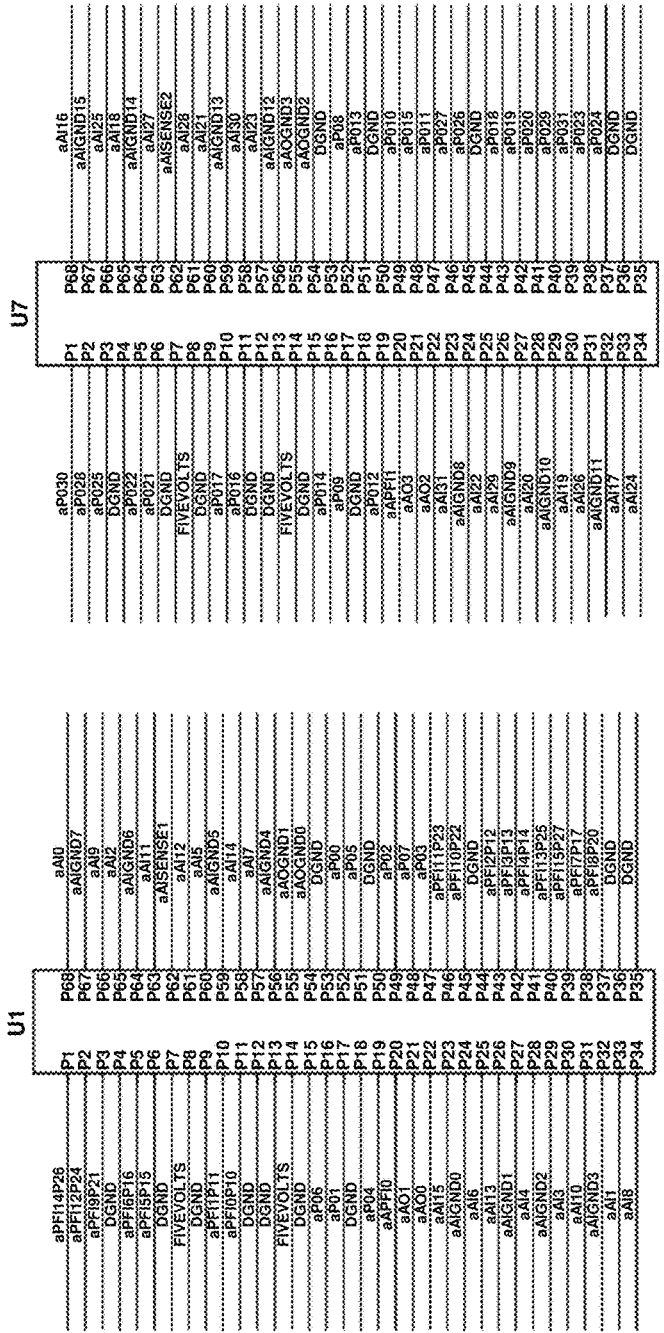
Figure 27:
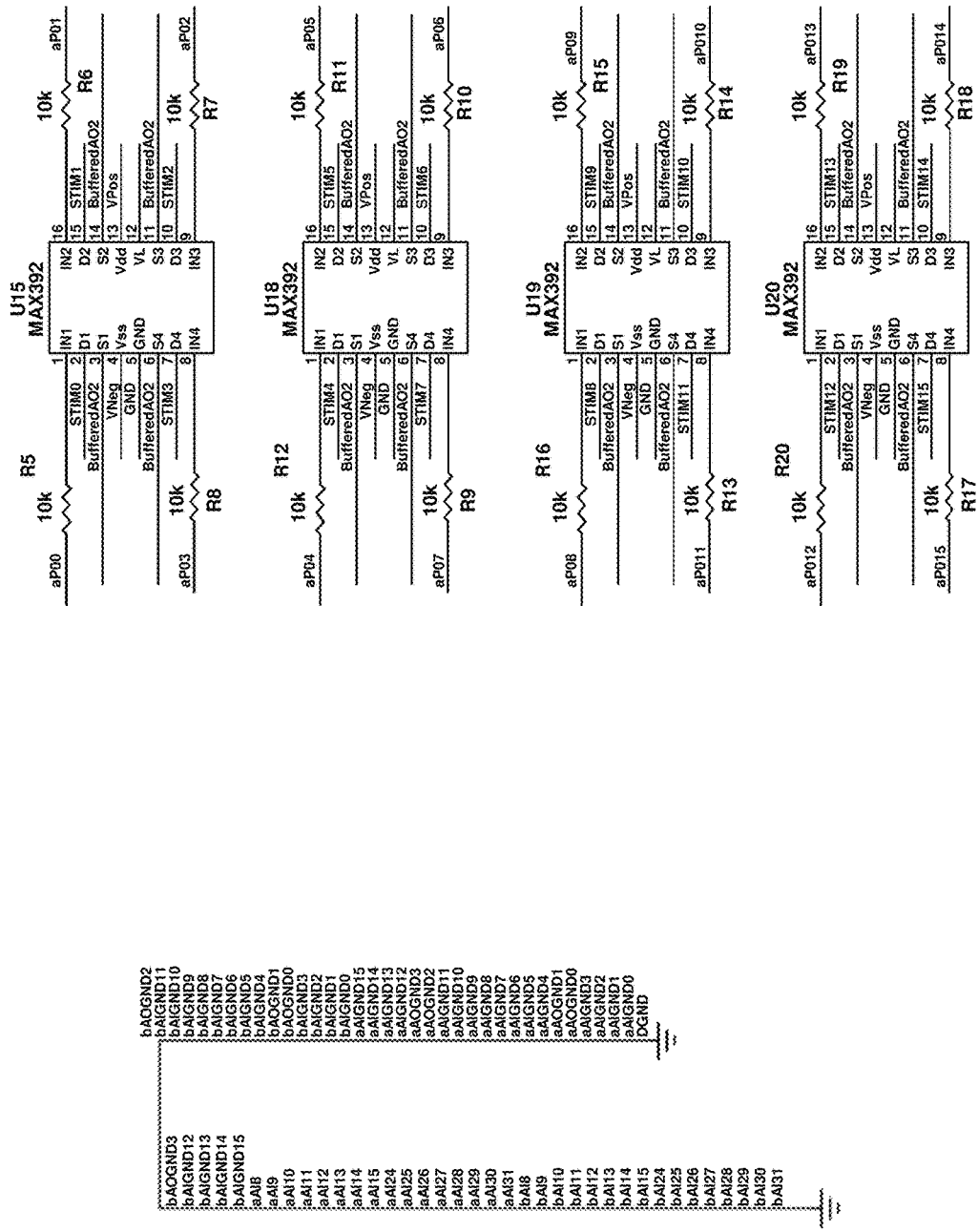
Figure 28:
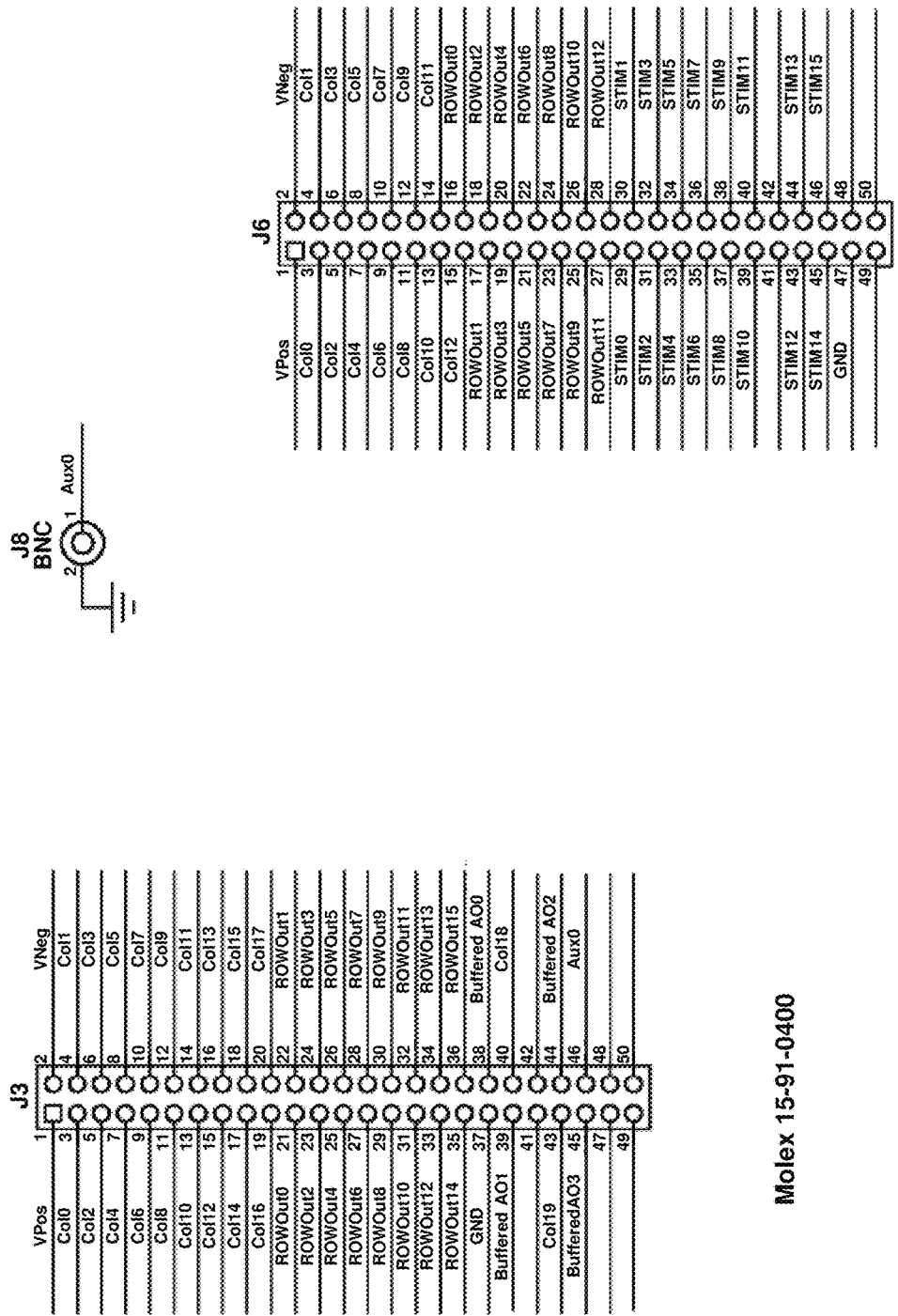
Figure 29:
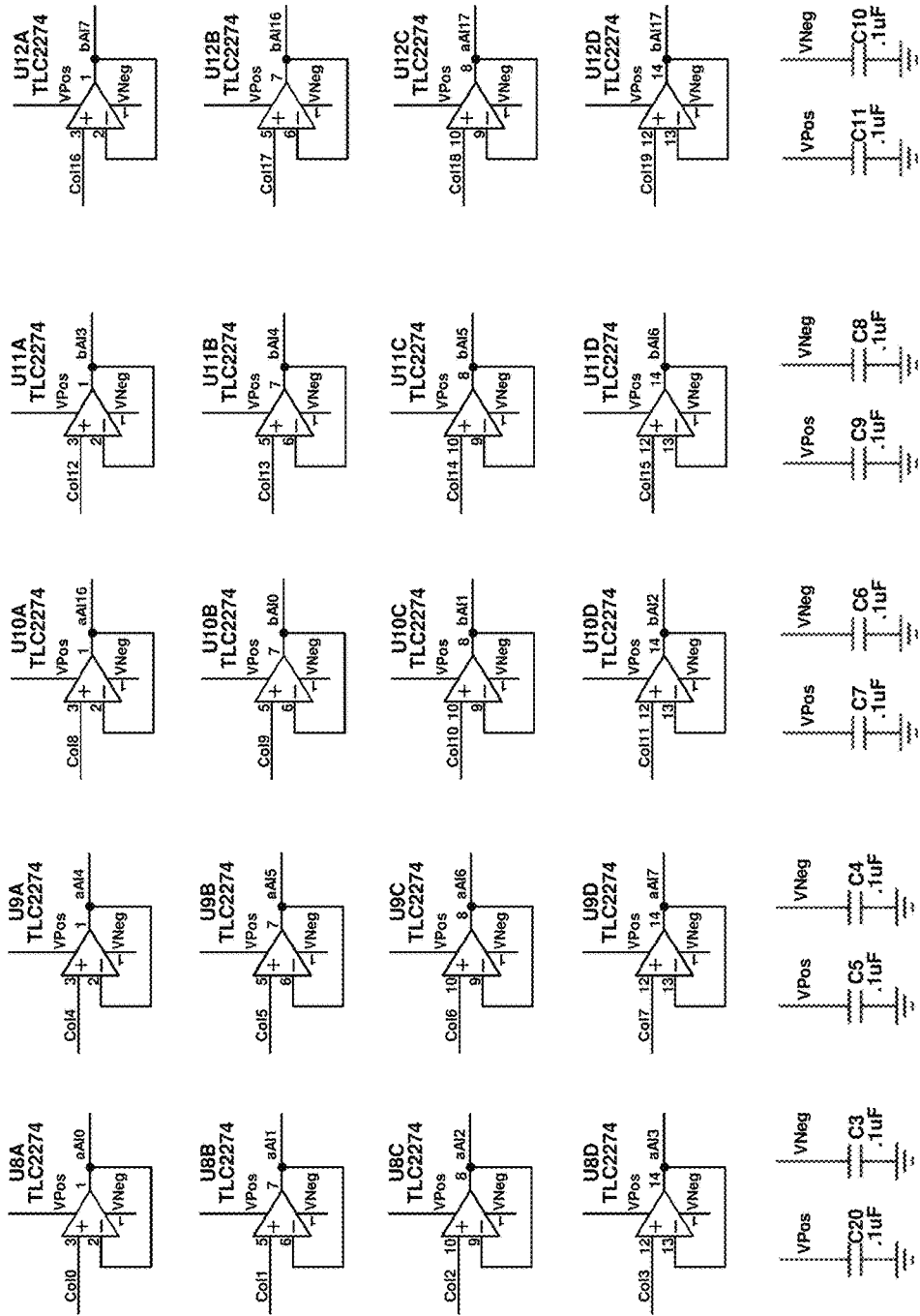
Figure 31:
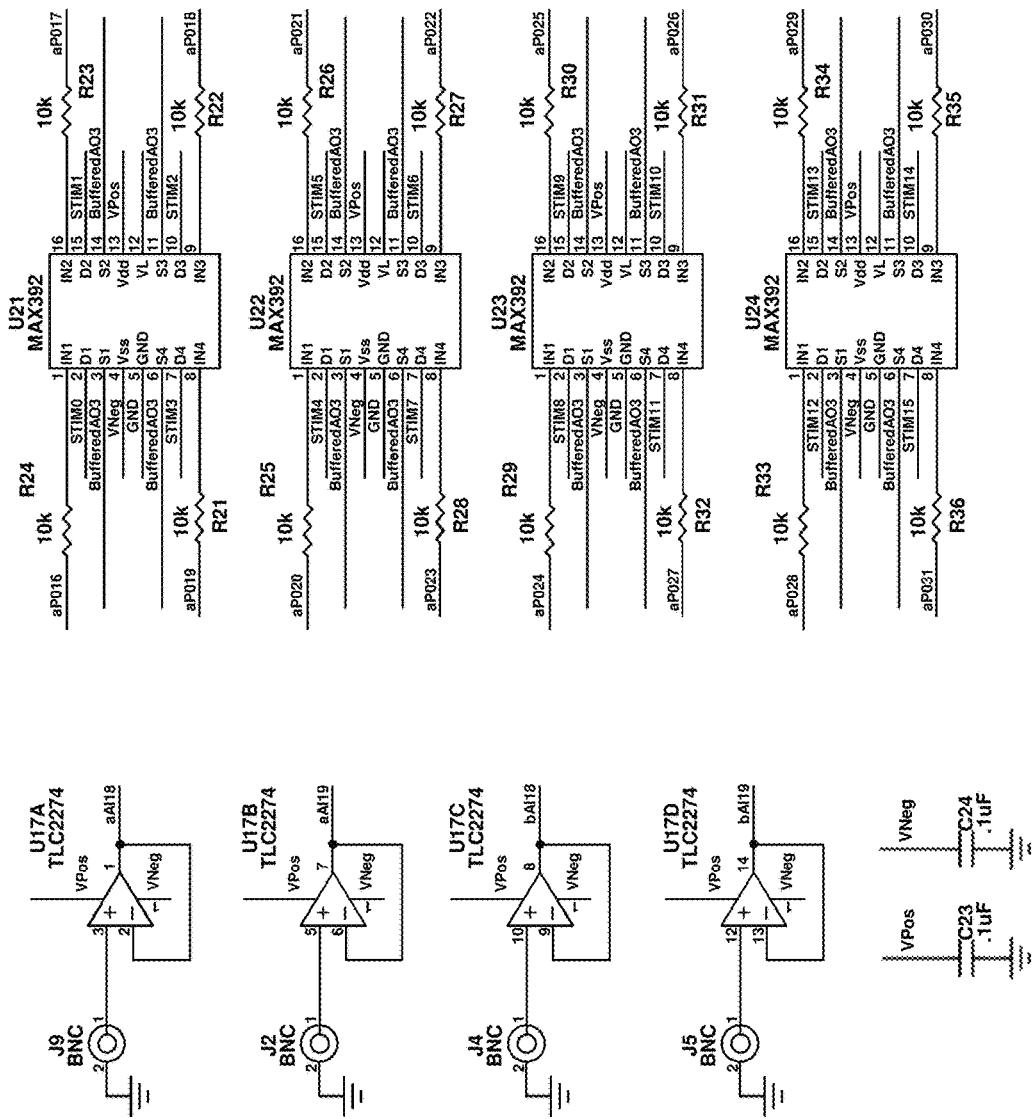

Multiplexing: The connections between four unit cells are illustrated in FIG. 23 (FIG. 1 illustrates any number of unit cells may be employed). When connected to an external constant current sink the selected unit cell completes the current path from +V to −V and forms a source-follower amplifier. The buffered voltage output is from the same circuit node that is connected to the constant current sink. The 18 row select signals of the multiplexed electrode array are cycled at 5 kHz to sample all of the electrodes on the array, yielding a sampling rate of ~277 Hz per active electrode, with all 18 electrodes in a given column sampled sequentially.

Data Acquisition: The multiplexed analog signals were synchronously sampled at 100 kHz using a custom data acquisition system (see FIGS. 22-31). 20 times oversampling per switch interval is used to improve the SNR (yielding the 5 kHz cycling rate previously stated). With faster analog to digital converters, the electrode sampling rate can be readily increased to 12.5 kS/s without loss of SNR[27]. Voltage data are recorded from all 360 electrodes of the active electrode array. The reference (ground) electrode for the acquisition system is clipped to nearby, exposed muscle. Except where otherwise indicated, the µECOG data for all experiments are band-pass filtered from 1 to 50 Hz.

Animal Experiments: Experiments are conducted in accordance with the ethical guidelines of the National Institutes of Health and with the approval of the Institutional Animal Care and Use Committee of the University of Pennsylvania. Surgical and stimulation methods are as described in detail previously[51,52]. Briefly, adult cats (2.5-3.5 kg) are anesthetized with intravenous thiopental with a continuous infusion (3-10 mg/kg/hr) and paralyzed with gallamine triethiodide (Flaxedil). Heart rate, blood pressure, end-tidal $CO_2$ and EEG are monitored throughout the experiment to assure depth and stability of anesthesia and rectal temperature was kept at 37-38° C. with a heating pad. The surface of the visual cortex is exposed with a craniotomy centered at Horsley Clarke posterior 4.0, lateral 2.0.

During visual stimulation, the corneas are protected with contact lenses after dilating the pupils with 1% ophthalmic atropine and retracting the nictitating membranes with phenylephrine (Neosynephrine). Spectacle lenses are chosen by the tapetal reflection technique to optimize the focus of stimuli on the retina. The position of the monitor is adjusted with an x-y-stage so that the area centralae were centered on the screen. Stimuli are presented on an Image Systems (Minnetonka, Minn.) model M09LV monochrome monitor operating at 125 frames per second at a spatial resolution of 1024×786 pixels and a mean luminance of 47 cd/m².

REFERENCES (EXAMPLE 1)

1. Campbell, P. K. et al. A silicon-based, three-dimensional neural interface: manufacturing processes for an intracortical electrode array. *IEEE transactions on bio-medical engineering* 38, 758-68 (1991).
2. Freeman, W. Spatial spectral analysis of human electrocorticograms including the alpha and gamma bands. *Journal of Neuroscience Methods* 95, 111-121 (2000).
3. Kellis, S. S. et al. Human neocortical electrical activity recorded on nonpenetrating microwire arrays: applicability for neuroprostheses. *Neurosurgical focus* 27, E9 (2009).
4. Kellis, S. et al. Decoding spoken words using local field potentials recorded from the cortical surface. *Journal of neural engineering* 7, 056007 (2010).
5. Kitzmiller, J. P. et al. Micro-field evoked potentials recorded from the porcine sub-dural cortical surface utilizing a microelectrode array. *Journal of neuroscience methods* 162, 155-61 (2007).
6. Schevon, C. a et al. Microphysiology of epileptiform activity in human neocortex. *Journal of clinical neurophysiology: official publication of the American Electroencephalographic Society* 25, 321-30 (2008).
7. Stead, M. et al. Microseizures and the spatiotemporal scales of human partial epilepsy. *Brain: a journal of neurology* 133, 2789-97 (2010).
8. Amunts, K. et al. Brodmann's areas 17 and 18 brought into stereotaxic space—where and how variable? *NeuroImage* 11, 66-84 (2000).
9. Branco, D. M. et al. Functional variability of the human cortical motor map: electrical stimulation findings in perirolandic epilepsy surgery. *Journal of clinical neurophysiology: official publication of the American Electroencephalographic Society* 20, 17-25 (2003).
10. Fox, P. T. et al. Location-probability profiles for the mouth region of human primary motor-sensory cortex: model and validation. *NeuroImage* 13, 196-209 (2001).
11. Van Essen, D. C., Newsome, W. T. & Maunsell, J. H. The visual field representation in striate cortex of the macaque monkey: asymmetries, anisotropies, and individual variability. *Vision research* 24, 429-48 (1984).
12. Hochberg, L. R. et al. Neuronal ensemble control of prosthetic devices by a human with tetraplegia. *Nature* 442, 164-71 (2006).
13. Ryu, S. I. & Shenoy, K. V. Human cortical prostheses: lost in translation? *Neurosurgical focus* 27, E5 (2009).
14. Polikov, V. S., Tresco, P. A. & Reichert, W. M. Response of brain tissue to chronically implanted neural electrodes. *Journal of neuroscience methods* 148, 1-18 (2005).
15. Schmidt, S., Horch, K. & Normann, R. Biocompatibility of silicon-based electrode arrays implanted in feline cortical tissue. *Journal of biomedical materials research* 27, 1393-9 (1993).
16. Griffith, R. W. & Humphrey, D. R. Long-term gliosis around chronically implanted platinum electrodes in the Rhesus macaque motor cortex. *Neuroscience letters* 406, 81-6 (2006).
17. Margalit, E. Visual and electrical evoked response recorded from subdural electrodes implanted above the visual cortex in normal dogs under two methods of anesthesia. *Journal of Neuroscience Methods* 123, 129-137 (2003).
18. Chao, Z. C., Nagasaka, Y. & Fujii, N. Long-term asynchronous decoding of arm motion using electrocorticographic signals in monkeys. *Frontiers in neuroengineering* 3, 3 (2010).
19. Yeager, J. D. et al. Characterization of flexible ECoG electrode arrays for chronic recording in awake rats. *Journal of neuroscience methods* 173, 279-85 (2008).
20. Yu, Z. et al. Monitoring hippocampus electrical activity in vitro on an elastically deformable microelectrode array. *Journal of neurotrauma* 26, 1135-45 (2009).
21. Andersen, R. a, Musallam, S. & Pesaran, B. Selecting the signals for a brain-machine interface. *Current opinion in neurobiology* 14, 720-6 (2004).
22. Mehring, C. et al. Inference of hand movements from local field potentials in monkey motor cortex. *Nature neuroscience* 6, 1253-4 (2003).
23. Ball, T. et al. Towards an implantable brain-machine interface based on epicortical field potentials. *Biomed. Tech.* (Berlin) 38, 756-759 (2004).
24. Wilson, J. A. et al. ECoG factors underlying multimodal control of a brain-computer interface. *IEEE transactions on neural systems and rehabilitation engineering: a publication of the IEEE Engineering in Medicine and Biology Society* 14, 246-50 (2006).
25. Brunner, P. et al. Rapid Communication with a "P300" Matrix Speller Using Electrocorticographic Signals (ECoG). *Frontiers in neuroscience* 5, 5 (2011).

26. Streetman, B. G. & Banerjee, S. K. *Solid State Electronic Devices*. (Pearson: 1981).
27. Viventi, J. et al. A Conformal, Bio-Interfaced Class of Silicon Electronics for Mapping Cardiac Electrophysiology. *Science Translational Medicine* 2, 24ra22-24ra22 (2010).
28. Yanagisawa, T. et al. Neural decoding using gyral and intrasulcal electrocorticograms. *NeuroImage* 45, 1099-106 (2009).
29. Besson, P. et al. Small focal cortical dysplasia lesions are located at the bottom of a deep sulcus. *Brain: a journal of neurology* 131, 3246-55 (2008).
30. Stieglitz, T. Flexible biomedical microdevices with double-sided electrode arrangements for neural applications. *Sensors and Actuators A: Physical* 90, 203-211 (2001).
31. Stieglitz, T. Flexible BIOMEMS with electrode arrangements on front and back side as key component in neural prostheses and biohybrid systems. *Sensors and Actuators B: Chemical* 83, 8-14 (2002).
32. Thompson, S. E. et al. A 90-nm Logic Technology Featuring Strained-Silicon. *IEEE Transactions on Electron Devices* 51, 1790-1797 (2004).
33. Kim, D.-H. et al. Dissolvable films of silk fibroin for ultrathin conformal bio-integrated electronics. *Nature materials* (2010).doi:10.1038/nmat2745
34. Padnick, L. B. & Linsenmeier, R. a Properties of the flash visual evoked potential recorded in the cat primary visual cortex. *Vision research* 39, 2833-40 (1999).
35. Tusa, R. J., Rosenquist, A. C. & Palmer, L. a Retinotopic organization of areas 18 and 19 in the cat. *The Journal of comparative neurology* 185, 657-78 (1979).
36. Hinton, G. E. & Salakhutdinov, R. R. Reducing the dimensionality of data with neural networks. *Science* (New York, N.Y.) 313, 504-7 (2006).
37. Larochelle, H. et al. An empirical evaluation of deep architectures on problems with many factors of variation. *Proceedings of the 24th international conference on Machine learning—ICML '07* 473-480 (2007).doi: 10.1145/1273496.1273556
38. Anderson, W. S. et al. Studies of stimulus parameters for seizure disruption using neural network simulations. *Biological cybernetics* 97, 173-94 (2007).
39. Witkowski, F. X. et al. Spatiotemporal evolution of ventricular fibrillation. *Nature* 392, 78-82 (1998).
40. Prechtl, J. C. et al. Visual stimuli induce waves of electrical activity in turtle cortex. *Proceedings of the National Academy of Sciences of the United States of America* 94, 7621-6 (1997).
41. Huang, X. et al. Spiral waves in disinhibited mammalian neocortex. *The Journal of neuroscience: the official journal of the Society for Neuroscience* 24, 9897-902 (2004).
42. Huang, X. et al. Spiral Wave Dynamics in Neocortex. *Neuron* 68, 978-990 (2010).
43. Hastie, T., Tibshirani, R. & Friedman, J. *The Elements of Statistical Learning*. (Springer-Verlag: New York, N.Y., USA, 2001).
44. Tibshirani, R., Walther, G. & Hastie, T. Estimating the number of clusters in a data set via the gap statistic. *Journal of the Royal Statistical Society: Series B (Statistical Methodology)* 63, 411-423 (2001).
45. Blanco, J. a et al. Unsupervised Classification of High-Frequency Oscillations in Human Neocortical Epilepsy and Control Patients. *Journal of neurophysiology* (2010) .doi:10.1152/jn.01082.2009
46. Paullet, J. E. & Ermentrout, G. B. Stable Rotating Waves in Two-Dimensional Discrete Active Media. *SIAM Journal on Applied Mathematics* 54, 1720 (1994).
47. Gais, S. et al. Learning-dependent increases in sleep spindle density. *The Journal of Neuroscience* 22, 6830-4 (2002).
48. Tamminen, J. et al. Sleep Spindle Activity is Associated with the Integration of New Memories and Existing Knowledge. *Journal of Neuroscience* 30, 14356-14360 (2010).
49. Sekitani, T. et al. A large-area wireless power-transmission sheet using printed organic transistors and plastic MEMS switches. *Nature materials* 6, 413-7 (2007).
50. Llinás, R. R. et al. Thalamocortical dysrhythmia: A neurological and neuropsychiatric syndrome characterized by magnetoencephalography. *Proceedings of the National Academy of Sciences of the United States of America* 96, 15222-7 (1999).
51. Cardin, J. A., Palmer, L. A. & Contreras, D. Stimulus feature selectivity in excitatory and inhibitory neurons in primary visual cortex. *Journal of Neuroscience* 27, 10333 (2007).
52. Cardin, J. a, Palmer, L. a & Contreras, D. Cellular mechanisms underlying stimulus-dependent gain modulation in primary visual cortex neurons in vivo. *Neuron* 59, 150-60 (2008).

Figure 7B:
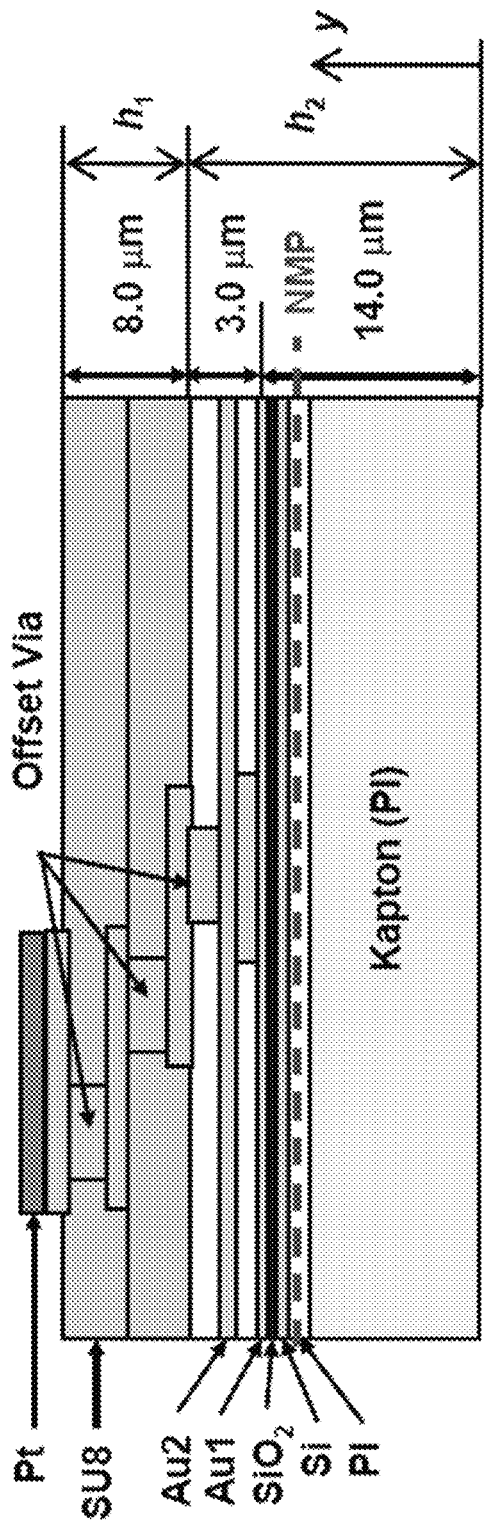

Bending Stiffness and Bending Strain:

The cross section of the electrode array is shown in FIG. 7B. Since the Au (500 nm and 150 nm), Si (260 nm) and SiO$_2$ (100 nm) layers between the top SU8 and bottom Kapton® are very thin, and are very close to the neutral mechanical plane, their contribution to the bending stiffness can be approximated by polyimide (PI) within 1% error. Therefore the complex multilayer electrode can be approximated by a two-layer structure, composed of PI of thickness $h_2$ and SU8 of thickness $h_1$. The distance of neutral mechanical plane from the Kapton bottom is $y_0$, and is obtained as $$y_0 = \frac{1\bar{E}_{PI}h_2^2 + \bar{E}_{SU8}h_1(2h_2 + h_1)}{2\bar{E}_{PI}h_2 + \bar{E}_{SU8}h_1}. \tag{S1}$$

where $$\bar{E}_i = \frac{E_i}{1-v_i^2}$$

relates to Young's modulus $E_i$ and Poisson's ratio $v_i$ (i=PI for PI layer, i=SU8 for SU8 layer).

The bending stiffness of the electrode is $$EI = \bar{E}_{PI}bh_2\left(\frac{1}{3}h_2^2 - h_2 y_0 + y_0^2\right) + \bar{E}_{SU8}bh_i\left[\frac{1}{3}h_1^2 + h_1(h_2 - y_0) + (h_2 - y_0)^2\right], \tag{S2}$$

where b=10 mm is the electrode width.

For the electrode bent to a radius of R, the strain at position of distance y from the Kapton bottom is $$\varepsilon = \frac{y - y_0}{R}. \tag{S3}$$

Mechanics of Electrode Insertion

Figure 32A:
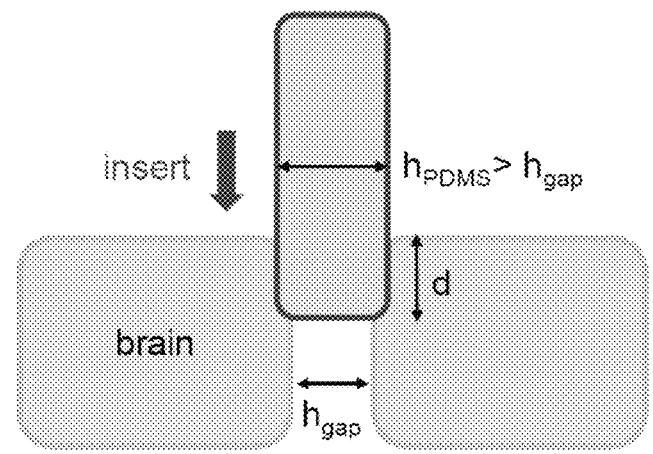
FIG. 32A-32B.

The electrode is folded around a soft PDMS of Young's modulus $E_{PDMS}$=100 kPa, width B and thickness $h_{PDMS}$, and is inserted into the gap of thickness $h_{gap}$ between the hemispheres of the brain. The insertion depth is d (see FIG. 32A). Since the thickness of brain (>10 mm) is much larger than that of the folded electrode (~0.7 mm), the two hemispheres of the brain are modeled as semi-infinite solids, of Young's modulus $E_{brain}$=3 kPa and Poisson's ratio $v_{brain}$=0.35[1]. For a semi-infinite solid subject to uniform pressure p at the top surface in the circular region of radius a=$\sqrt{Bd}$, the surface subsidence w at position of distance r from the circular center is w=[4(1-$v_{brain}^2$)p$\sqrt{Bd}$]/($\pi E_{brain}$)$\int_0^{\pi/2}\sqrt{1-r^2\sin^2\varphi/(Bd)}d\varphi$, whose average over the pressure region is obtained as $$\bar{w} = \frac{16(1 - v_{brain}^2)p\sqrt{Bd}}{3\pi E_{brain}}. \quad (S4)$$

Since the electrode array is much stiffer and thinner than PDMS, its deformation due to insertion is negligible compared to PDMS. Therefore, displacement continuity gives the relation between the pressure at the interface p and the average subsidence $\bar{w}$ of the brain surface due to electrode insertion to be $$\frac{p}{E_{PDMS}}h_{PDMS} + 2\bar{w} = h_{PDMS} - h_{gap},$$

which gives $$p = \frac{h_{PDMS} - h_{gap}}{\frac{h_{PDMS}}{E_{PDMS}} + \frac{32(1 - v_{brain}^2)\sqrt{Bd/\pi}}{3\pi E_{brain}}}. \quad (S3)$$

And the maximum compressive strain in the brain due to electrode insertion is obtained as $$\varepsilon^{max} = \frac{-(1 + v_{brain})p}{E_{brain}}\left[1 - 2v_{brain} + 2\left(\frac{2v_{brain}}{3}\right)^{\frac{3}{2}}\right] \quad (S6)$$

$$= \frac{-(1 + v_{brain})\left[1 - 2v_{brain} + 2\left(\frac{2v_{brain}}{3}\right)^{\frac{3}{2}}\right](h_{PDMS} - h_{gap})}{\left[\frac{E_{brain}}{E_{PDMS}}h_{PDMS} + \frac{32(1 - v_{brain}^2)\sqrt{Bd}}{3\pi^{3/2}}\right]}.$$

Figure 32B:
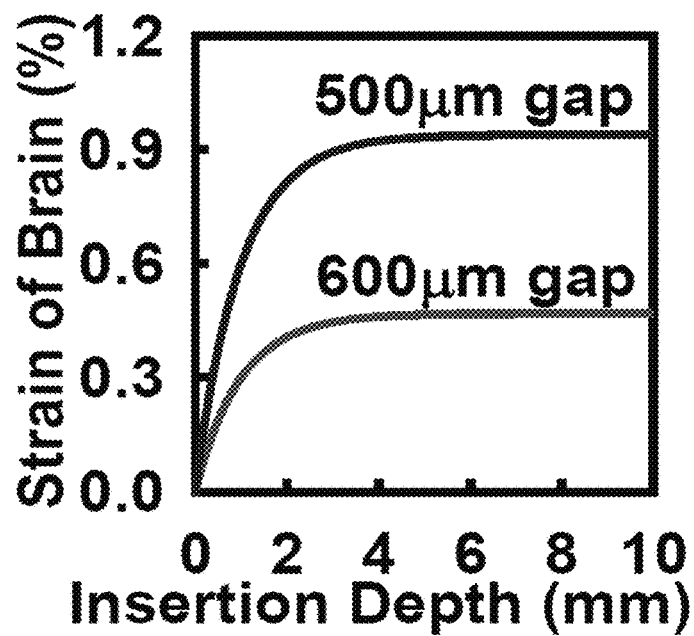

As the folded electrode inserts into the brain gap (insertion depth d), the gap $h_{gap}$ between the left and right brains decreases and approaches an asymptote $\bar{h}_{gap}$ (i.e., minimal gap distance). The brain gap $h_{gap}$ can be generally written as an exponentially decaying function of the rubber insertion length d, $h_{gap}=\bar{h}_{gap}+(h_{PDMS}-\bar{h}_{gap})\exp(-d/1\text{ mm})$, which defines zero insertion length as rubber first touches the brain (i.e., $h_{gap}=h_{PDMS}$). For $h_{PDMS}$=700 μm and B=16.2 mm in experiment, the maximum compressive strain in the brain versus the insertion depth of rubber is shown in FIG. 32B for minimal brain gaps $\bar{h}_{gap}$=500 and 600 μm.

Circuit Design: The dimensions of the two transistors in the unit-cell (FIG. 2B, left frame) are equal so that they will have matched performance. The width of both transistors is selected to be as large as possible at 200 μm while still leaving room for large interconnections between adjacent unit cells. The L is selected at 20 μm to be conservative for the processing technology. The resulting W/L ratio of 10 yielded reasonable levels of current output. The width of all metal lines and size of all VIAs was increased by 2~4× from prior designs to improve reliability and ease manufacturing. The electrode spacing is set at 500 μm based on prior work and to match well with the 500 μm spacing of the ACF ribbon cable, enabling a simple layout of the interconnections.

Figure 21:
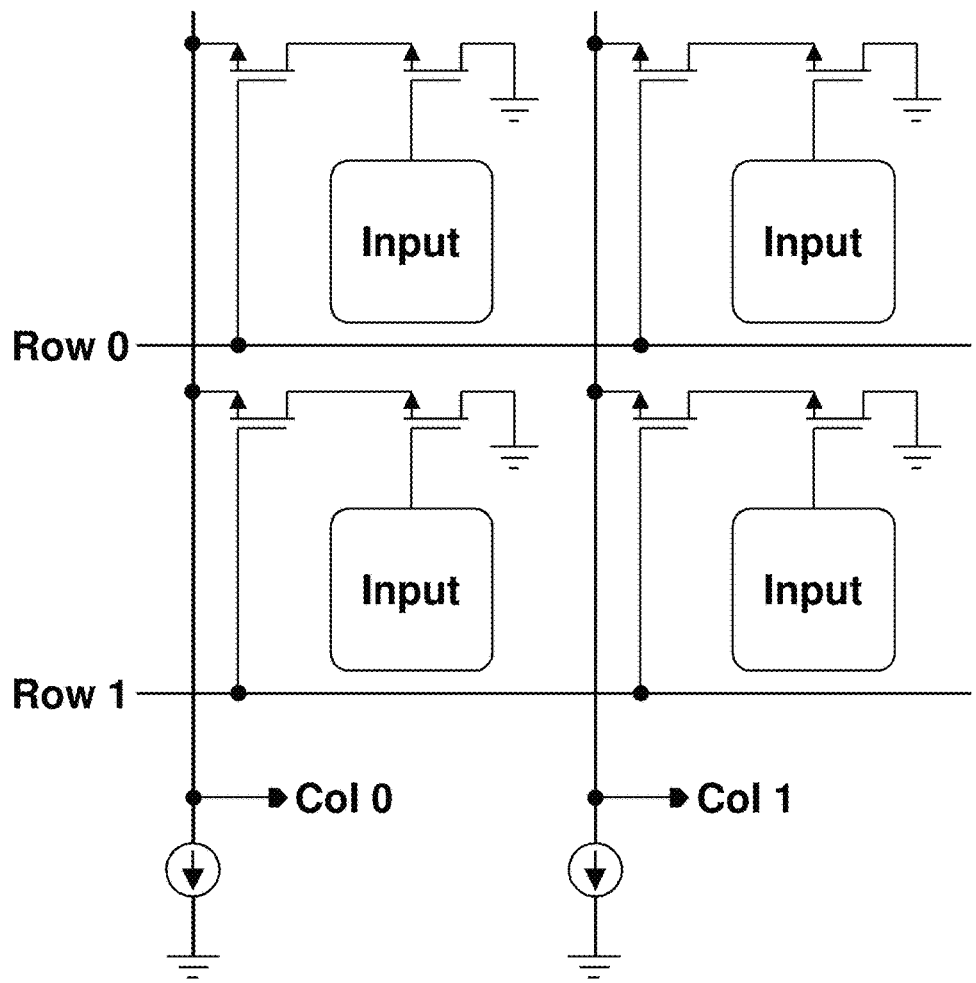
FIG. 21. Circuit diagram of four unit cells, showing multiplexing connections.
Figure 22A:
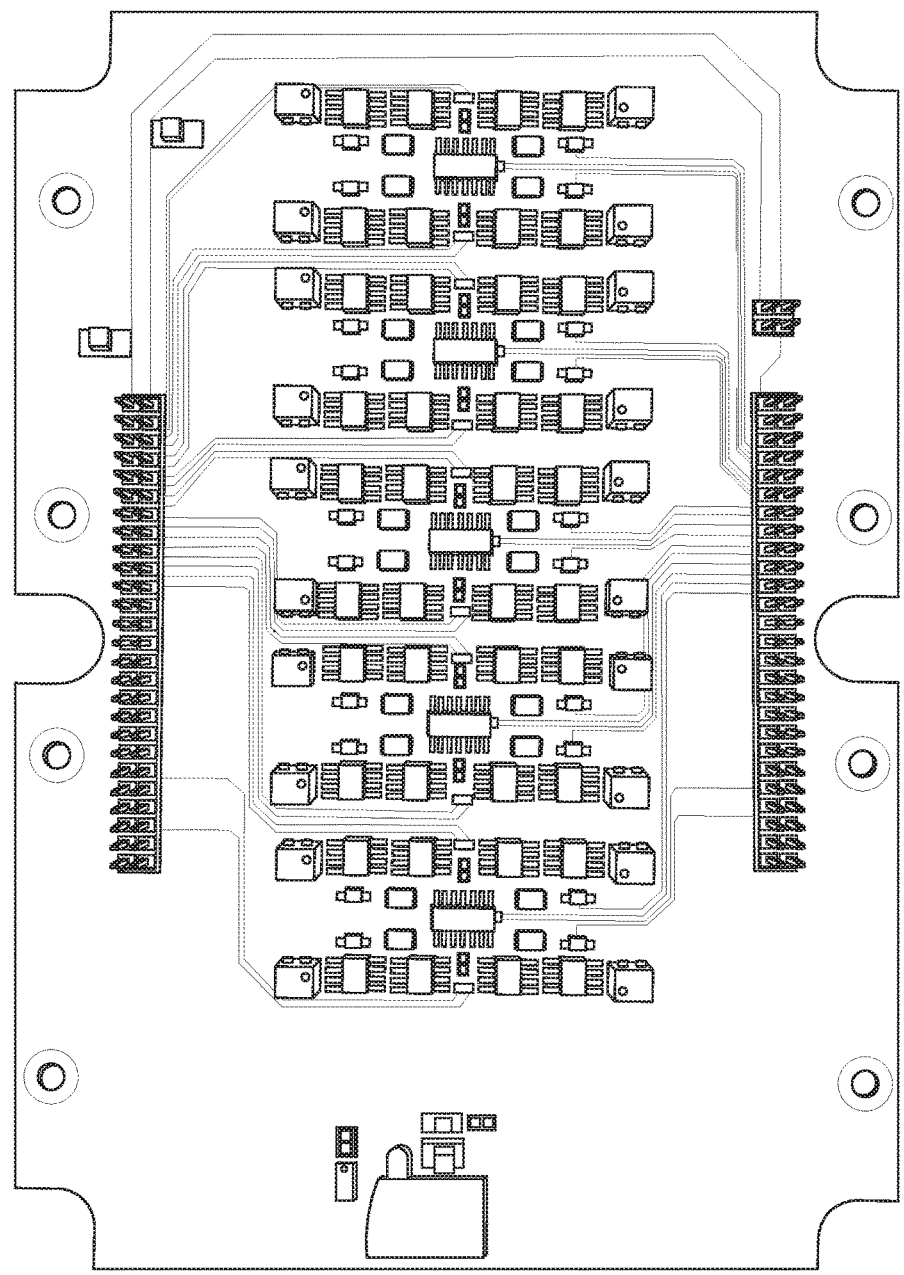
FIG. 22A-22C.
Figure 22B:
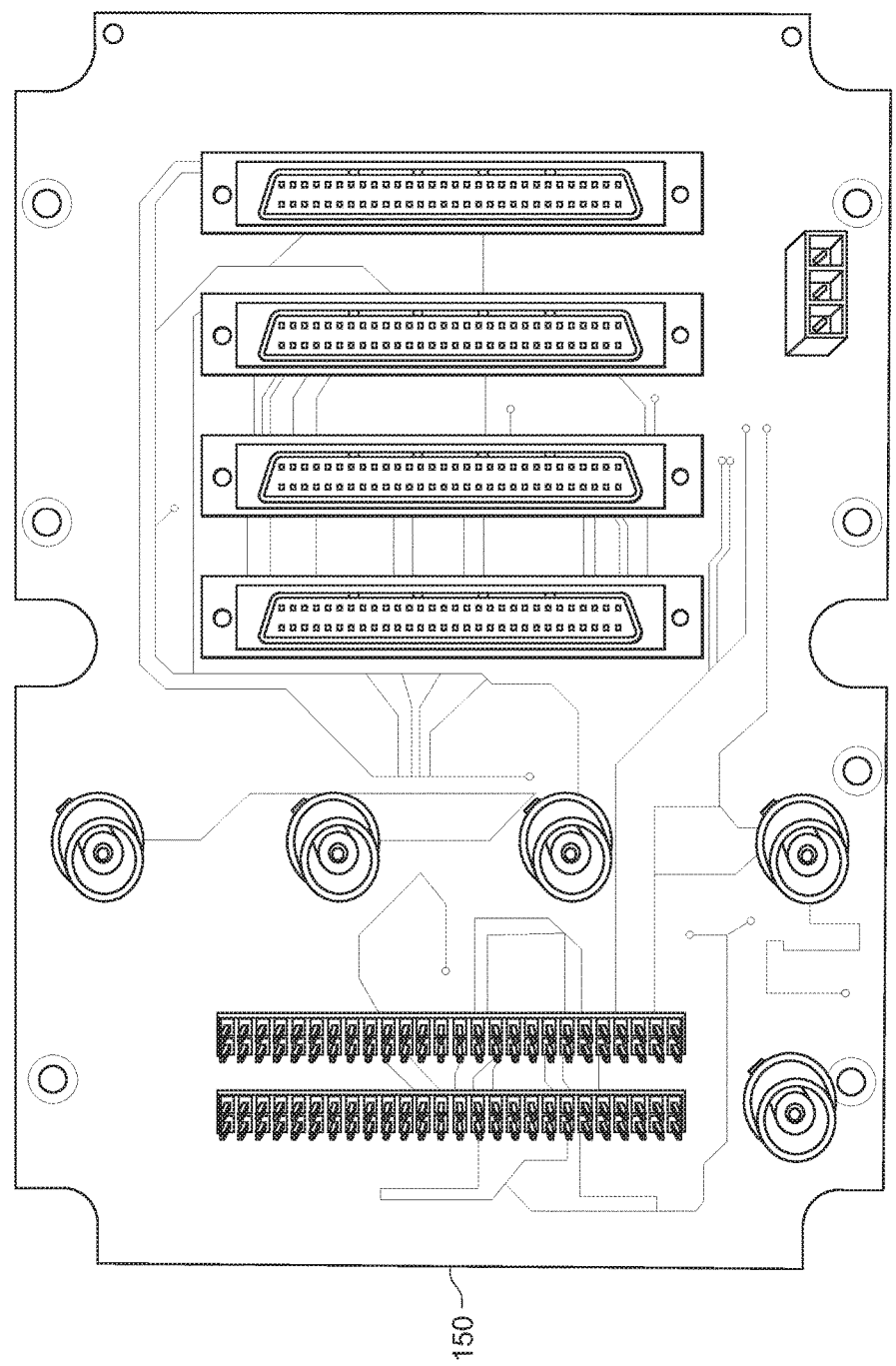
Figure 22C:
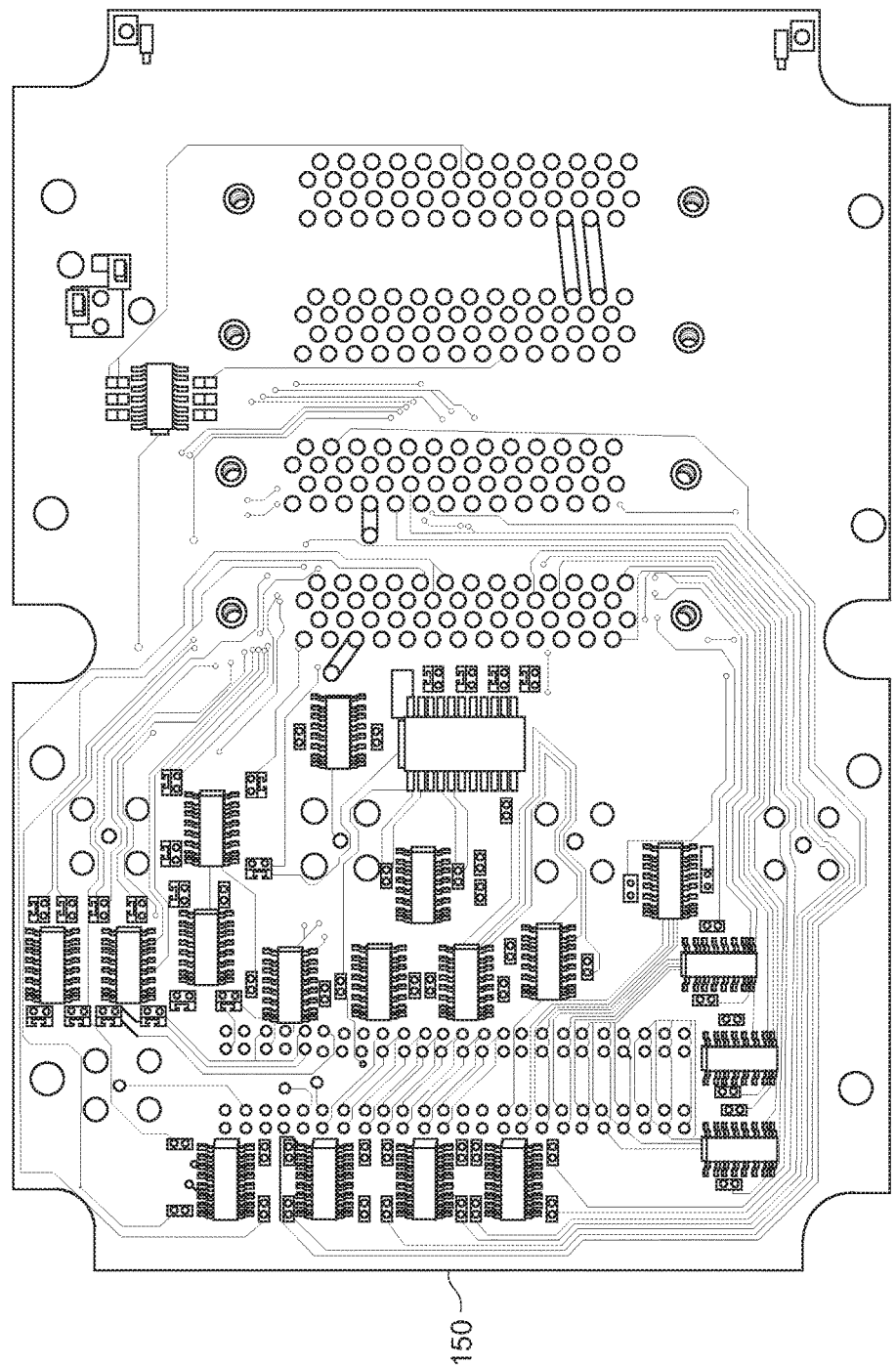

Current Sinks: The ideal current sinks shown in FIG. 21 can be implemented using commercially available semiconductors as shown in the block diagram in FIG. 23. This basic circuit that is implemented 20 times, one for each column of the electrode array. The circuit makes use of several commercial semiconductors. The first of which is the LM334 which is a 3-Terminal Adjustable Current Source (National Semiconductor). It is used to set the constant current for the source follower. The current is adjusted via a potentiometer on the third pin (not shown). The constant current generated by the LM334 is mirrored by the current mirror section of the REF200—Current Reference (Texas Instruments). The REF200 is used because the LM334 cannot respond to fast transients while supplying low amounts of current. The REF200 current mirror bandwidth is 5 MHz, to enable fast multiplexing. The REF200 also contains two 100 μA constant current sources, which are not used.

The output of a single column from the electrode array is connected to the current mirror and the non-inverting input of a TLC2274 Op Amp as shown. The TLC2274 Op Amp (Texas Instruments) is used to provide buffering for the output of the source follower amplifier. This op-amp buffers the signal before the high pass filter. Additionally, adding this op-amp allows the buffering to occur as close as possible to the electrode array, minimizing parasitic capacitance and maximizing the switching speed.

The output of the Op Amp is connected to a 0.01 Hz high-pass filter. This very low frequency high pass filter is used to remove the average DC offset introduced by the source follower configuration of the amplifiers on the electrode array. The high pass filter frequency must be very low because it introduces aliasing for signals up to ~0.1 Hz. Signals lower than this present on one multiplexed channel will be aliased onto the other channels. However, any aliasing that occurs can be removed by a subsequent 1 Hz digital high pass filter on the acquired data.

Data Acquisition System: The output of the high pass filter is connected using a short cable (2') to a custom data acquisition system interface (see FIGS. 22B, c and FIGS. 24-31). The signal is buffered again by another TLC2274 op-amp to drive the 15' cable from the acquisition system interface board to a set of four PXI-6289 data acquisition cards (National Instruments, USA). This second stage of buffering prevents any loading introduced by the long cable run from influencing the high pass filter stage. The data acquisition system, in an aspect, is considered a component of a controller 150.

Figure 33:
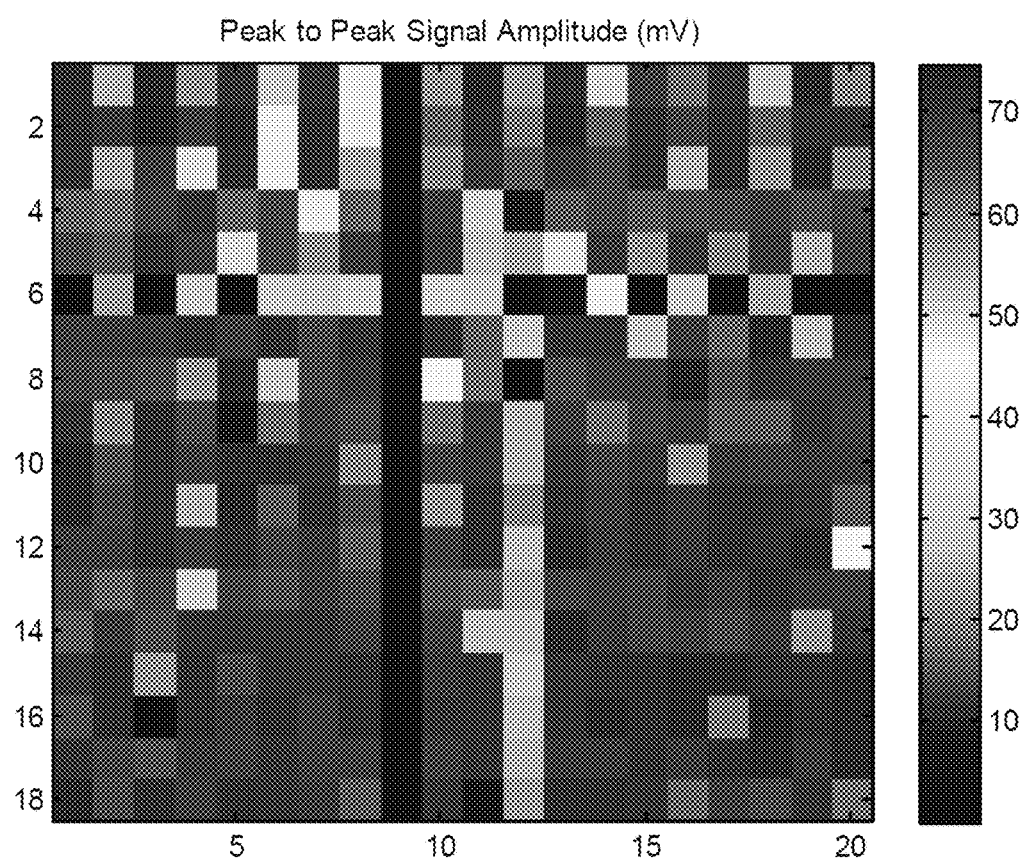
FIG. 33. Density map illustrating the spatial distribution of the electrode response to a 100 mV p-p, 3.14 Hz sine wave, demonstrating the spatial uniformity of the gain of the electrode array.

Gain: The gain of the electrode array is measured by submerging the array in conductive saline. A second electrode is submerged in the saline approximately 1" from the electrode array. The second electrode was connected to a 100 mV peak to peak sine wave at 3.14 Hz. This test presents a uniform signal for all of the electrodes on the array to measure. The recording duration of this test is 80 seconds and the sampling rate is ~277 Hz per electrode. The median signal level for all 360 channels on the array is 68 mV peak to peak, yielding a median gain of 0.68. The spatial distribution of the peak to peak amplitudes measured is shown in FIG. 33 illustrating the uniformity of the gain across the electrode array. ~83% of the electrode channels are operational for this sample. Channels determined to be not operational through this test are interpolated from neighboring operational channels prior to all of the analyses presented in the main text.

Power supplies: This electrode array design does not require symmetric power supplies. That is, the +V supply does not need to be equal and opposite of the −V supply. In fact, the source follower amplifier only requires that the +V supply is greater than $V_{in}$, the input voltage minus $V_t$, the threshold voltage of the amplifying transistor. Given that $V_{in}$ is typically within the range +/−100 mV for neural signals, as long as $V_t$ is greater than +100 mV (typical values are ~0.7 V, FIG. 2B, center frame), +V can be directly connected to ground (0V). However, if $V_t$ of the array is small or negative, the +V supply can be connected to a separate, small positive voltage supply, such as 0.5V.

Directly connecting the array +V connection to GND or at least minimizing the voltage of the positive supply has several advantages. The most important of which is that it reduces the potential for leakage currents through the gate of the buffer transistor (FIG. 1b, left frame) by reducing the voltage potential between the electrode (gate) and the silicon substrate. Another advantage is simplifying the power connections for the electrode array.

With the +V of the electrode array de-coupled from the +V of the acquisition system, the acquisition system power supplies can be increased without significantly increasing the potential for leakage current. The power supplies have been increased from +/−2.5V in prior experiments to +/−3.5V in the current experiments. This allows $V_{ds}$ of the buffer transistor (FIG. 2B, left frame) to increase, if needed, to allow the transistor to enter saturation and function properly in the source-follower amplifier. Increasing the acquisition system power supplies also improves the transient response of the buffer op-amps, which allows faster multiplexing.

Additionally, the row select signals are still generated by the acquisition system, so the high level logic (enabled) signal is approximately +V instead of 0V, and the low level logic (disabled) signal is approximately −V. This allows the $V_{gs}$ of the multiplexing transistor (FIG. 2B, left frame), to remain large, improving the conduction of the multiplexing transistor and reducing $V_{ds}$ when turned on.

Operation on batteries: Since the power supply rejection ratio (PSRR) of our system is very low, an ultra-low noise power supply is needed to reduce the noise of the ECoG recordings as much as possible. The PSRR is a measure of the ability of an amplifier to reject noise from its power supplies. It is a ratio of the amplitude of a noise signal presented on the power supplies of the amplifier, to the amplitude of that signal measured on the output of the amplifier.

Nickel-metal hydride batteries (NiMH) are chosen to replace the power supplies that power the acquisition system interface board and the electrode array. Batteries can provide a nearly noiseless power source and NiMH batteries in particular can provide very low output impedance, due to their low internal resistance. Since the power consumption of the electrode interface board is low (~35 mA) and the active electrode power consumption is very low (0.2-0.4 mA), simple AA rechargeable batteries were chosen. The AA batteries chosen had a charge capacity of 2650 mAh, which enabled the system to run for over 3 days on a charge, which is longer than our experiment duration.

The batteries are used in 4-cell and 6-cell configurations directly connected to the acquisition system interface board without any voltage regulation to keep the noise as low as possible. The cell voltage for the NiMH batteries that are used remained fairly constant between 1.2V and 1.3V through most of the discharge cycle. Therefore, the 4-cell configuration can be used to supply the data acquisition interface board with +/−2.4-2.6 volts, while the 6-cell configuration can be used to supply +/−3.6-3.9 volts. The 6-cell configuration is preferred because it increases the performance of the electrode array.

Switching Noise: Another large contribution to the noise in the electrode output is caused by the switching of the row select signals. Since the row select signals have a large amplitude (5V-7V) and fast rise and fall time (2 µS), they can easily corrupt nearby low-noise measurements through capacitive or magnetic coupling. This noise is not easily avoidable because of the nature of multiplexed sampling. The row select transistors require a large change in voltage to fully turn them on and off. However, this noise can be reduced by discarding the samples from the analog to digital converter that immediately precede and follow the transition on the row select signals. This dictates a minimum over-sampling ratio (the ratio between the analog sampling rate and the multiplexing rate) of 3. If an over-sampling ratio (OSR) greater than 3 is used, the samples that remain after discarding the samples adjacent to the row select signal transition can be averaged, further reducing the recorded noise.

Electrode Materials: The passive and active electrode devices shown previously utilized gold as the surface electrode material. In the current device, the electrode base metal is still gold, but an additional coating of flat platinum has been added to reduce the electrode impedance. Passive electrodes sized 250 µm×250 µm using the same dimensions and materials processing steps are fabricated to measure the impedance difference. Passive electrodes must be used to measure the impedance because it is not currently possible to measure electrode impedance while integrated in the active electrode.

The mean impedance of the 250 µm×250 µm passive electrodes is 84 kOhm±17% at 1 kHz, while the impedance of the same electrode design coated with flat platinum is 29 kOhm±9% at 1 kHz. Measurements were conducted with the array immersed in normal saline (0.9%). The reduced impedance provided by the platinum coating should increase the current output of the electrode and enable better signal transfer.

The electrodes in the active electrode array illustrated in FIG. 2A are 300 µm×300 µm. Based on linear extrapolation from prior measurements, we expect the impedance of these electrodes to be ~69% of the measured value (29 kOhm) of the 250 µm×250 µm electrodes or ~20 kOhm at 1 kHz.

SUPPLEMENTARY REFERENCES

1. Taylor, Z. & Miller, K. Reassessment of brain elasticity for analysis of biomechanisms of hydrocephalus. Journal of biomechanics 37, 1263-9 (2004).

EXAMPLE 2

Millimeter-Scale Epileptiform Spike Patterns and their Relationship to Seizures

Advances in neural electrode technology are enabling brain recordings with increasingly fine spatial and temporal resolution. We explore spatio-temporal (ST) patterns of local field potential spikes using a new high-density active electrode array with 500 μm resolution. We record subdural micro-electrocorticographic (μECoG) signals in vivo from a feline model of acute neocortical epileptiform spikes and seizures induced with local administration of the GABA antagonist, picrotoxin. We employ a clustering algorithm to separate 2-dimensional (2-D) spike patterns to isolate distinct classes of spikes unique to the interictal and ictal states. Our findings indicate that the 2-D patterns can be used to distinguish seizures from non-seizure state. We find two statistically significant ST patterns that uniquely characterize ictal epochs. We conclude that millimeter-scale ST spike dynamics contain useful information about ictal state. This finding may be important to understanding mechanisms underlying local circuit activity during seizure generation. Such information about spatio-temporal profiles permits investigation of seizure dynamics and their underlying mechanisms and inform new electrical stimulation protocols for seizure termination.

Introduction: In epilepsy research, many different brain recording techniques have been employed to understand neural dynamics between, prior to and during seizures. Electrophysiological studies employ techniques that range in size and scale from the Utah array [1], which records multi-unit activity from penetrating electrodes 400 μm apart, to scalp Electroencephalography (EEG), which records electrical potentials that are distorted by the skull, scalp, cerebrospinal fluid (CSF) and soft tissues, from electrodes many centimeters apart. Other studies utilize modalities ranging from Magnetoencephalography (MEG) and functional Magnetic Resonance Imaging (fMRI) to Voltage Sensitive Dyes (VSDs). MEG is a non-invasive technique that records magnetic components of potentials perpendicular to the EEG, and suffers from low spatial resolution, similar to EEG. Image-based technologies such as fMRI and VSDs complement standard electrophysiology, though each has its own spatial and temporal resolution limitations. In this study, we use a new, high-spatial density subdural surface active electrode array of 360 channels covering an area of 10 mm×9 mm to measure local field potential (LFP)-scale electrical signals in vivo from an acute feline epilepsy model. We examine spatio-temporal (ST) patterns of LFP spike activity recorded on a millimeter-scale that are unique to seizures.

Methods. Animal Recording: We analyze micro-electrocorticographic (μECoG) data from an acute in vivo feline model of epilepsy. Adult cats are anesthetized with a continuous infusion (3-10 mg/kg/hr) of intravenous thiopental. A craniotomy and durotomy were performed to expose a 2×3 cm region of cortex. The high resolution electrode array is then placed on the surface of the brain over primary visual cortex, localized by electrophysiological recordings of visual evoked potentials. Picrotoxin, a GABA-A receptor antagonist that blocks inhibition, is topically applied adjacent to the anterior-medial corner of the electrode array in an amount sufficient to induce abnormal electrical spikes and seizures from the covered region [2].

Figure 34:
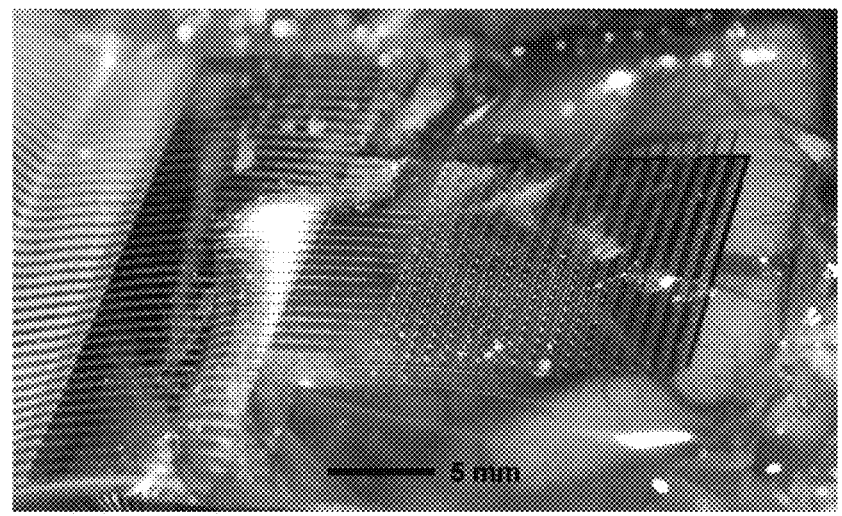
FIG. 34. Photograph of a 360 channel, high density neural electrode array used in a feline model of epilepsy. The electrode array is placed on the surface of visual cortex. The electrode size and spacing is 300 μm×300 μm and 500 μm, respectively.

The active electrode array placed on the cortex is used to record data from 360 independent channels arranged in 20 columns and 18 rows, spaced 500 μm apart. Each electrode contact comprises a 300 μm×300 μm square of platinum. Two high-performance, flexible silicon transistors for each electrode buffered and multiplexed the recorded signals[3]. The total array size is 10 mm×9 mm. Signals are recorded with an effective sampling rate of 277.7 Hz per channel. FIG. 34 is a photograph of the array placed on the surface of the visual cortex of a cat.

We analyze 13 minutes and 40 seconds of data for this study, containing 724 automatically detected spikes and 2 seizures, verified by expert review.

Pre-processing: All recordings are first band pass filtered between 1 and 50 Hz using a 6th-order butterworth filter in the forward and reverse direction, using Matlab's filtfilt function, to achieve zero-phase filtering.

64 of 360 channels are non-functional due to manufacturing imperfections. The missing data for these channels are interpolated from the surrounding electrodes using a 2-D averaging spatial filter of window size 3×3 pixels.

Small offsets in time that result from row multiplexing are corrected by upsampling and shifting the data in order to accurately align rows in time. Data are first upsampled by the number of rows within the array (18) via Matlab's interp function, which applies a low pass filter interpolation algorithm. Data are then temporally shifted by their respective row offset.

Spike Detection: We use a voltage-threshold detector to detect spikes on the signal obtained by averaging all 360 channels. The voltage threshold is set by visual inspection at about 500 μV. When the average signal crossed the threshold from above, a 160 msec segment of the recording is stored (60 msec prior to the crossing and 100 msec post-crossing).

Figure 35:
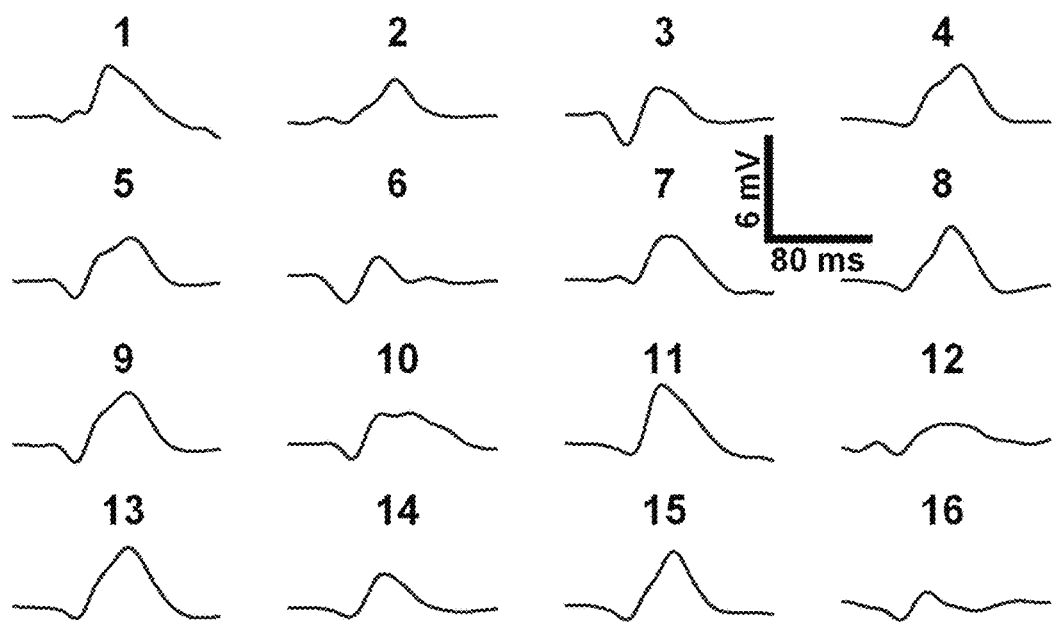
FIG. 35. Representative spike waveforms retained by the spike detection algorithm. Each of the spike waveforms is 160 ms clipped from the average voltage recording of all 360 channels. Within each window there is only one negative-going crossing followed by one positive-going crossing. These 16 waveforms are of the spikes closest (in the L1 sense) to each of the cluster centroids and correspond to the spatio-temporal delay maps in FIG. 36. Negative is plotted up by convention.

We analyze only single spikes (i.e. no poly-spikes) and retain only spikes which occur on a majority of the electrodes in the 2-D array in order to simplify the analysis of spike propagation. Specifically, the following quantitative criteria are used to retain spikes: 1) a single negative-going threshold crossing followed by a single positive-going threshold crossing within the clipped 160 msec window surrounding the triggering threshold crossing; 2) at least 50% of electrodes have a root-mean-square (RMS) value >40% of the maximal RMS across channels (within the 160 msec window). 724 average spikes met the above criteria. FIG. 35 shows 16 representative detected spike waveforms.

Feature Selection: For each of the 724 spikes, a 63-element feature vector is generated in the following manner: The average spike waveform is cross-correlated with each of the 360 single-channel spikes. This yields a single value per channel capturing the delay of the spike on each channel of the array. The zero-meaned RMS (i.e. standard deviation) for each channel is then calculated. This yielded a single value per channel capturing a representation of the power of the spike on each channel of the array. The 724×360 delay values are then normalized by dividing by each row maximum. The 724×360 'power' values are similarly normalized. The 724×360 matrix of delay values is then concatenated with the 724×360 matrix of 'power' values. The result is a 724×720 matrix representing 724 spikes, each with 720 features. Principal components analysis (PCA) is performed and a number of dimensions accounting for >99% of the data variance is retained. This results in a dimensionality reduction from 720 to 63.

Figure 36:
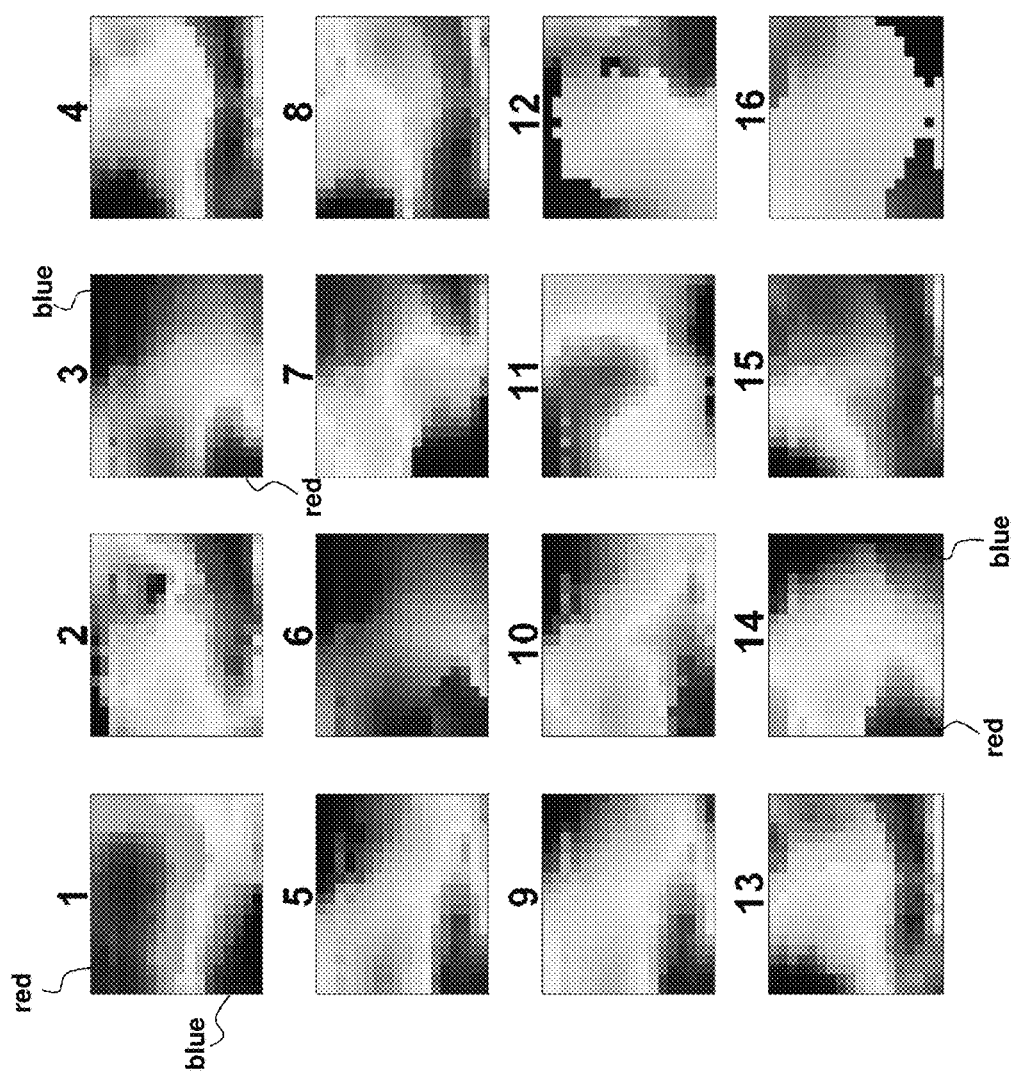
FIG. 36. Delay maps for the 16 clusters. Each of the above delay maps represents the spike within each cluster that is closest to its cluster centroid. Blue indicates electrodes with an early delay value relative to the average spike waveform and red indicates electrodes with a late delay value. Color shading represents relative timing of peak voltage in each spike, but not speed of propagation. As an example, the delay map for cluster 1 displays a spike ST pattern of propagation across the array of a spike that enters on the bottom left and proceeds in a sweeping arc until it exits the array in the top left. The corresponding RMS maps have not been included due to space constraints.

Clustering: k-mediods clustering [4] is performed and the gap statistic [5] is used to determine the number of clusters, similar to methods applied in other EEG classification tasks [6]. 16 clusters of ST patterns are identified. FIG. 36 shows delay maps for spikes clustered closest in L1 distance to the centroid of each distinct cluster. Blue indicates electrodes with early delay values relative to the average spike waveform and red indicates electrodes with later delay values. All analysis is performed in the Matlab® environment (The Mathworks Inc., Natick, Mass., USA).

Statistical Testing: We hypothesize that some ST patterns occur preferentially during seizure epochs. We use Pearson's chi-squared test to test the null hypothesis that the proportion of spikes occurring during seizure is equal across clusters (i.e. ST patterns). To address the issue of identifying a specific cluster which might account for a rejection of the null hypothesis, we conduct a permutation test. We hold cluster membership of each spike fixed while randomly permuting the seizure and non-seizure labels for one million permutations. For every permutation we record the maximum (over all clusters) of the proportion of seizure-spikes within each cluster to obtain the null distribution. We then compare the observed maximum to this null distribution.

Figure 37:
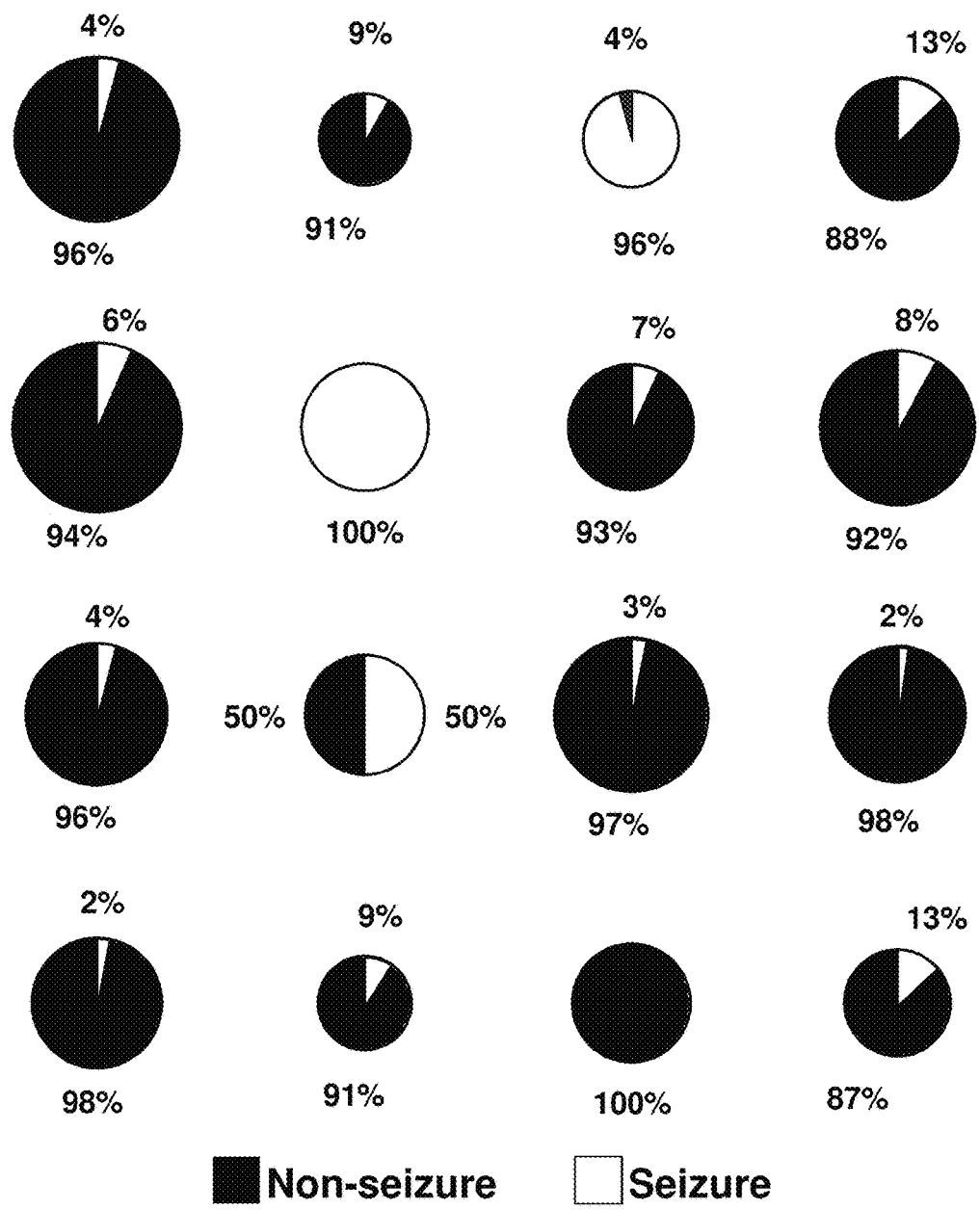
FIG. 37. Pie charts representing the 16 identified clusters and their proportion of spikes during and outside of seizures. Each of the pie charts represents one of the 16 different spike ST patterns identified. The whole area of each pie is scaled in proportion to the total number of spikes within the cluster. The blue section within each pie is the percentage of spikes associated with non-seizure epochs. The red section within each pie is the percentage of spikes recorded during seizures.

Results: FIG. 37 displays spike clustering and seizure analysis results. Each of the pies represents one of the 16 different spike ST patterns identified. Delay maps of representative spikes from each corresponding cluster are shown in FIG. 36. The whole area of each pie in FIG. 37 is scaled in proportion to the total number of spikes within the cluster. The blue section within each pie represents the percentage of spikes associated with non-seizure epochs. The white section within each pie represents the percentage of spikes recorded during seizures. Clusters 3 and 6 appear to have disproportionately large numbers of spikes occurring during seizure relative to outside.

We found a strong relationship between ST pattern and seizure state (i.e. within or outside of a seizure epoch). We reject the null hypothesis that the proportion of spikes occurring during seizure in each of the 16 clusters is the same ($\chi^2(15, N=724)=415.1$, $p<<0.0001$). Furthermore, we find the proportion of within-seizure spikes contained specifically in clusters 3 and 6 are significantly higher than would be expected by chance ($p<<0.0001$ for both clusters).

Discussion: Our analysis indicates that two specific ST spike patterns correlate with seizure epochs. In addition, we found other ST spike patterns that appear to be more loosely associated with seizures. We believe those patterns indicate periods of transition from the interictal to ictal states. We believe these patterns may hold information about the progression of abnormal electrical activity as seizures approach. Analyzing the brain's electrical activity using any of the electrode arrays provided herein provide new opportunities to increase our understanding of epileptiform spikes and their patterns of propagation. One possibility raised by these waveforms, is that spikes and seizures, when viewed at this resolution, may have features in common with cardiac dysrhythmias. In this sense it may be precisely their multi-dimensional ST appearance that could reveal re-entrant patterns and triggers in the same way that these types of events occur in cardiac tissue. We next plan to study the relationship among waveforms leading into ictal events, those occurring periodically during seizures, and the waveforms that occur immediately prior to seizure cessation.

Recordings at this spatial scale may be important to clinical patient care and evaluation for epilepsy surgery, as evidenced by studies in humans of high frequency oscillations and microseizures that are poorly detected by standard clinical electrode systems[7,8]. We anticipate that this new electrode technology, combined with novel methods for analyzing the large, high-resolution data sets arising from it, may lead to better understanding of spike discharges and seizure development, and more effective therapies for the more than 33% of epilepsy patients who remain medically refractory.

REFERENCES

[1] P. K. Campbell, K. E. Jones, R. J. Huber, K. W. Horch, and R. a Normann, "A silicon-based, three-dimensional neural interface: manufacturing processes for an intracortical electrode array," *IEEE transactions on bio-medical engineering*, vol. 38, August 1991, pp. 758-68.

[2] K. Morimoto, M. Fahnestock, and R. J. Racine, "Kindling and status epilepticus models of epilepsy: rewiring the brain.," *Progress in neurobiology*, vol. 73, May. 2004, pp. 1-60.

[3] J. Viventi, D.-H. Kim, J. D. Moss, Y.-S. Kim, J. a Blanco, N. Annetta, a Hicks, J. Xiao, Y. Huang, D. J. Callans, J. a Rogers, and B. Litt, "A Conformal, Bio-Interfaced Class of Silicon Electronics for Mapping Cardiac Electrophysiology," *Science Translational Medicine*, vol. 2, 2010, pp. 24ra22-24ra22.

[4] T. Hastie, R. Tibshirani, and J. Friedman, *The Elements of Statistical Learning*, New York, N.Y., USA: Springer-Verlag, 2001.

[5] R. Tibshirani, G. Walther, and T. Hastie, "Estimating the number of clusters in a data set via the gap statistic," *Journal of the Royal Statistical Society: Series B (Statistical Methodology)*, vol. 63, May. 2001, pp. 411-423.

[6] J. A. Blanco, M. Stead, A. Krieger, J. Viventi, W. R. Marsh, K. H. Lee, G. a Worrell, and B. Litt, "Unsupervised classification of high-frequency oscillations in human neocortical epilepsy and control patients.," *Journal of neurophysiology*, vol. 104, November 2010, pp. 2900-12.

[7] G. a Worrell, A. B. Gardner, S. M. Stead, S. Hu, S. Goerss, G. J. Cascino, F. B. Meyer, R. Marsh, and B. Litt, "High-frequency oscillations in human temporal lobe: simultaneous microwire and clinical macroelectrode recordings.," *Brain: a journal of neurology*, vol. 131, 2008, pp. 928-37.

[8] M. Stead, M. Bower, B. H. Brinkmann, K. Lee, W. R. Marsh, F. B. Meyer, B. Litt, J. Van Gompel, and G. a Worrell, "Microseizures and the spatiotemporal scales of human partial epilepsy," *Brain: a journal of neurology*, vol. 133, October 2010, pp. 2789-97.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

International Application Publication WO 2009/114689 and U.S. patent application Ser. No. 12/892,001 (filed Sep. 28, 2010), which are hereby incorporated by reference in its entirety, disclose flexible and scalable sensor arrays for recording and modulating physiologic activity. US Patent Publication Nos. US 2008/0157235, US 2008/0108171, US 2010/0002402 and U.S. Pat. No. 7,557,367 issued Jul. 7, 2009, all of which are hereby incorporated by reference in their entireties, disclose multilayer stretchable, foldable and printable semiconductor devices.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a size, sensitivity, temperature, a time, data transfer rate, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A device for spatio-temporally electrically interfacing with a brain in a biological environment, the device comprising:
    a conformable substrate;
    a conformable electronic circuit comprising a deformable array of electrodes in electrical communication with a plurality of deformable electrical interconnects, the deformable array of electrodes supported by the conformable substrate;
    a barrier layer encapsulating at least a portion of the deformable electrical interconnects, wherein the conformable substrate, conformable electronic circuit and the barrier layer provide a net bending stiffness of the device low enough that the device establishes conformal contact with brain tissue in the biological environment; and
    a controller connected to the conformable electrical circuit to monitor or actuate a spatio-temporal profile over a surface of the brain in electrical contact with the plurality of electrodes, wherein the controller is configured to:
        detect an electric potential of a plurality of individual brain surface locations beneath each electrode of the array of electrodes at a plurality of different time points;
        encode the detected electric potential to obtain an encoded spatio-temporal brain waveform;
        analyze the encoded spatio-temporal brain waveform to identify an abnormal spatio-temporal brain waveform; and
        actuate electrical activity over the brain surface with an output spatio-temporal profile from the deformable array of electrodes to disrupt or terminate the abnormal spatio-temporal brain waveform.

2. The device of claim 1, wherein each electrode is electrically connected to a pair of matched transistors, wherein the matched transistors comprise a multiplexing transistor and a buffer transistor.

3. The device of claim 2, wherein each pair of matched transistors are electrically connected to a common constant current source and a current mirror.

4. The device of claim 2, wherein the matched transistors are flexible and comprise single-crystal silicon.

5. The device of claim 1, wherein adjacent electrodes are separated from each other by a separation distance selected from a range that is greater than or equal to 100 μm and less than or equal to 1 mm.

6. The device of claim 5, wherein each electrode has an electrode surface area that is less than or equal to 0.2 mm².

7. The device of claim 1, wherein the deformable array of electrodes is supported by a top surface of said barrier layer.

8. The device of claim 7, wherein the electrodes are coated with an electrode coating layer, wherein said electrode coating layer comprises platinum.

9. The device of claim 1 having a thickness, wherein the thickness is less than or equal to 30 μm.

10. The device of claim 1, further comprising a support material, said support material having a first surface and a second surface opposed to said first surface, wherein a first portion of said electrodes are supported by said first surface, and a second portion of said electrodes are supported by said second surface.

11. The device of claim 1, further comprising:
a therapeutic device operably connected to the controller; and
a receiving passage through the conformable substrate for receiving at least a portion of the therapeutic device;
wherein the controller is configured to actuate the therapeutic device to provide a therapeutic intervention to the brain.

12. The device of claim 11, wherein the therapeutic device is selected from the group consisting of a penetrating electrode, a micro-syringe and an optical fiber.

13. The device of claim 11, wherein the receiving passage is centered at a center point of the conformable substrate, and the receiving passage has a cross-sectional area selected from a range that is greater than or equal to 100 μm² and less than or equal to 1 cm².

14. The device of claim 1, wherein said deformable array of electrodes comprises alternating columns of actuating and monitoring electrodes.

15. The device of claim 1, that provides electrical information at a transfer rate that is greater than or equal to 90,000 samples per second.

16. The device of claim 1, wherein the identified abnormal spatio-temporal brain waveform is a spiral waveform, and wherein the controller is further configured to:
actuate the electrical activity over the brain surface with the output spatio-temporal profile from the deformable array of electrodes to disrupt or terminate the spiral waveform.

17. The device of claim 1, wherein the controller is further configured to:
monitor or actuate the electrical potential of the brain tissue at a plurality of individual brain surface locations over a plurality of different time points;
analyze the monitored electrical potential spatio-temporal profile to identify an electrical waveform;
monitor the magnitude of electric potential at each brain surface location, a time course of electric potential change at each brain surface location, or both; and
calculate the relative delay of a spike in electrical potential at a brain surface location, wherein a spike is identified for any brain surface location having an electric potential that is greater than 50% of a peak root-mean square value over all brain surface locations.

18. A device for spatio-temporally electrically interfacing with a brain in a biological environment, the device comprising:
a conformable substrate;
a conformable electronic circuit comprising a deformable array of electrodes in electrical communication with a plurality of deformable electrical interconnects, the deformable array of electrodes supported by the conformable substrate;
a barrier layer encapsulating at least a portion of the deformable electrical interconnects, wherein the conformable substrate, conformable electronic circuit and the barrier layer provide a net bending stiffness of the device low enough that the device establishes conformal contact with brain tissue in the biological environment; and
a controller connected to the conformable electrical circuit to monitor or actuate a spatio-temporal profile over a surface of the brain in electrical contact with the plurality of electrodes, wherein the controller is configured to:
monitor or actuate the electrical potential of the brain tissue at a plurality of individual brain surface locations over a plurality of different time points;
analyze the monitored electrical potential spatio-temporal profile to identify an electrical waveform;
monitor the magnitude of electric potential at each brain surface location, a time course of electric potential change at each brain surface location, or both; and
calculate the relative delay of a spike in electrical potential at a brain surface location, wherein a spike is identified for any brain surface location having an electric potential that is greater than 50% of a peak root-mean square value over all brain surface locations.

* * * * *